(12) United States Patent
Frueh et al.

(10) Patent No.: US 10,428,118 B2
(45) Date of Patent: Oct. 1, 2019

(54) HUMAN CYTOMEGALOVIRUS COMPRISING EXOGENOUS ANTIGENS

(71) Applicant: Oregon Health & Science University, Portland, OR (US)

(72) Inventors: Klaus Frueh, Portland, OR (US); Scott G. Hansen, Portland, OR (US); Jay Nelson, Lake Oswego, OR (US); Louis Picker, Portland, OR (US); Patrizia Caposio, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 15/326,444

(22) PCT Filed: Jul. 16, 2015

(86) PCT No.: PCT/US2015/040807
§ 371 (c)(1),
(2) Date: May 16, 2017

(87) PCT Pub. No.: WO2016/011293
PCT Pub. Date: Jan. 21, 2016

(65) Prior Publication Data
US 2018/0282378 A1    Oct. 4, 2018

Related U.S. Application Data

(60) Provisional application No. 62/025,348, filed on Jul. 16, 2014.

(51) Int. Cl.
| | |
|---|---|
| *C07K 14/045* | (2006.01) |
| *C12N 15/86* | (2006.01) |
| *A61K 39/12* | (2006.01) |
| *A61K 35/33* | (2015.01) |
| *A61K 39/00* | (2006.01) |
| *A61K 39/39* | (2006.01) |
| *C12N 15/85* | (2006.01) |
| *A61K 39/21* | (2006.01) |
| *C07K 14/16* | (2006.01) |
| *A61P 35/00* | (2006.01) |

(52) U.S. Cl.
CPC ............ *C07K 14/045* (2013.01); *A61K 35/33* (2013.01); *A61K 39/0011* (2013.01); *A61K 39/12* (2013.01); *A61K 39/39* (2013.01); *C12N 15/85* (2013.01); *C12N 15/86* (2013.01); *A61K 39/21* (2013.01); *A61K 2039/5254* (2013.01); *A61K 2039/5256* (2013.01); *A61K 2039/572* (2013.01); *A61P 35/00* (2018.01); *C07K 14/161* (2013.01); *C12N 2710/16143* (2013.01); *C12N 2740/15034* (2013.01); *C12N 2740/16234* (2013.01)

(58) Field of Classification Search
CPC .... A61K 39/12; A61K 39/245; A61K 35/763; A61K 38/162; A61K 2039/525; A61K 2039/5256; A61K 2039/6075; C12N 15/86; C12N 7/00; C12N 2710/00011; C12N 2710/16111; C12N 2710/16143; C12N 15/869; C07K 14/005; C07K 16/088; C07K 14/045

See application file for complete search history.

(56) References Cited

U.S. PATENT DOCUMENTS

| | | | |
|---|---|---|---|
| 5,168,062 | A | 12/1992 | Stinski |
| 5,273,876 | A | 12/1993 | Hock et al. |
| 5,385,839 | A | 1/1995 | Stinski |
| 5,720,957 | A | 2/1998 | Jones et al. |
| 5,830,745 | A | 11/1998 | Hock et al. |
| 5,833,993 | A | 11/1998 | Wardley et al. |
| 6,033,671 | A | 3/2000 | Frueh et al. |
| 7,892,822 | B1 | 2/2011 | Koszinowski et al. |
| 9,249,427 | B2 | 2/2016 | Picker et al. |
| 9,541,553 | B2 | 1/2017 | Picker et al. |
| 9,783,823 | B2 | 10/2017 | Picker et al. |
| 9,862,972 | B2 | 1/2018 | Picker et al. |
| 9,982,241 | B2 | 5/2018 | Picker et al. |
| 10,101,329 | B2 | 10/2018 | Picker et al. |
| 2002/0176870 | A1 | 11/2002 | Schall et al. |
| 2003/0118568 | A1 | 6/2003 | Crew |
| 2003/0138454 | A1 | 7/2003 | Hill et al. |
| 2004/0086489 | A1 | 5/2004 | Schall et al. |

(Continued)

FOREIGN PATENT DOCUMENTS

| | | |
|---|---|---|
| EP | 0521427 A1 | 1/1993 |
| WO | WO-8810311 A1 | 12/1988 |

(Continued)

OTHER PUBLICATIONS

James SH, Prichard MN. The genetic basis of human cytomegalovirus resistance and current trends in antiviral resistance analysis. Infect Disord Drug Targets. Oct. 2011;11(5):504-13.*

(Continued)

*Primary Examiner* — Rachel B Gill

(74) *Attorney, Agent, or Firm* — Sterne, Kessler, Goldstein & Fox P.L.L.C.

(57) ABSTRACT

Human cytomegalovirus vectors comprising heterologous antigens are disclosed. The vectors derived from the TR strain, are ganciclovir-sensitive, include active US2, US3, US6, US7 and UL131A genes, and have a deleterious or inactivating mutation in the UL82 gene preventing the expression of pp71.

20 Claims, 19 Drawing Sheets

Specification includes a Sequence Listing.

(56) References Cited

U.S. PATENT DOCUMENTS

| | | |
|---|---|---|
| 2004/0110188 A1 | 6/2004 | Hahn et al. |
| 2004/0248300 A1 | 12/2004 | Preston |
| 2005/0064394 A1 | 3/2005 | Liu et al. |
| 2005/0118192 A1 | 6/2005 | Boursnell et al. |
| 2006/0019369 A1 | 1/2006 | Hahn |
| 2008/0199493 A1 | 8/2008 | Picker et al. |
| 2009/0148477 A1 | 6/2009 | Bruder et al. |
| 2009/0203144 A1 | 8/2009 | Beaton et al. |
| 2009/0297555 A1 | 12/2009 | Kemble et al. |
| 2010/0142823 A1 | 6/2010 | Wang et al. |
| 2013/0089559 A1 | 4/2013 | Grawunder et al. |
| 2013/0136768 A1* | 5/2013 | Picker .................... A61K 39/12 424/199.1 |
| 2013/0142823 A1* | 6/2013 | Picker .................... A61K 39/21 424/199.1 |
| 2013/0156808 A1 | 6/2013 | Jonjic |
| 2013/0202638 A1 | 8/2013 | Thirion et al. |
| 2014/0141038 A1 | 5/2014 | Picker et al. |
| 2016/0010112 A1 | 1/2016 | Picker et al. |
| 2016/0114027 A1 | 4/2016 | Hahn et al. |
| 2016/0354461 A1 | 12/2016 | Picker et al. |
| 2017/0143809 A1 | 5/2017 | Nelson et al. |
| 2017/0350887 A1 | 12/2017 | Picker et al. |
| 2018/0087069 A1 | 3/2018 | Picker et al. |
| 2018/0133321 A1 | 5/2018 | Picker et al. |
| 2018/0298404 A1 | 10/2018 | Frueh et al. |

FOREIGN PATENT DOCUMENTS

| | | |
|---|---|---|
| WO | WO-9604383 A1 | 2/1996 |
| WO | WO-9631241 A1 | 10/1996 |
| WO | WO-9906582 A1 | 2/1999 |
| WO | WO-02062296 A2 | 8/2002 |
| WO | WO-2003093455 A2 | 11/2003 |
| WO | WO-2006031264 A2 | 3/2006 |
| WO | WO-2006125983 A1 | 11/2006 |
| WO | WO-2010101663 A2 | 9/2010 |
| WO | WO-2011093858 A1 | 8/2011 |
| WO | WO-2011119920 A2 | 9/2011 |
| WO | WO-2011138040 A2 | 11/2011 |
| WO | WO-2011143650 A2 | 11/2011 |
| WO | WO-2011143653 A2 | 11/2011 |
| WO | WO-2012170765 A2 | 12/2012 |
| WO | WO-2014138209 A1 | 9/2014 |
| WO | WO-2016011293 A1 | 1/2016 |
| WO | WO-2016130693 A1 | 8/2016 |
| WO | WO-2017087921 A1 | 5/2017 |
| WO | WO-2018005559 A1 | 1/2018 |

OTHER PUBLICATIONS

Smith IL, Cherrington JM, Jiles RE, Fuller MD, Freeman WR, Spector SA. High-level resistance of cytomegalovirus to ganciclovir is associated with alterations in both the UL97 and DNA polymerase genes. J Infect Dis. Jul. 1997;176(1):69-77. Erratum in: J Infect Dis Apr. 1998;177(4):1140-1. PubMed PMID: 9207351.*

Lauron E, Yu D, Fehr A, Hertel L. Human cytomegalovirus infection of langerhans-type dendritic cells does not require the presence of the gH/gL/UL128-131A complex and is blocked after nuclear deposition of viral genomes in immature cells. J Virol. Jan. 2014;88(1):403-16. doi: 10.1128/JVI.03062-13. Epub Oct. 23, 2013.*

Heineman TC. "Chapter 71: Human cytomegalovirus vaccines." In: Arvin A, Campadelli-Fiume G, Mocarski E, et al., eds. Human Herpesviruses: Biology, Therapy, and Immunoprophylaxis. Cambridge: Cambridge University Press; 2007.*

Basta, S., et al., "Inhibitory Effects of Cytomegalovirus Proteins Us2 and Us11 Point to Contributions From Direct Priming and Cross-priming in Induction of Vaccinia Virus-specific Cd8(+) T Cells," Journal of Immunology 168(11):5403-5408, American Association of Immunologists, United States (Jun. 2002).

Besold, K., et al., "Immune Evasion Proteins GpUS2 and GpUS11 of Human Cytomegalovirus Incompletely Protect Infected Cells From CD8 T Cell Recognition," Virology 391(1):5-19, Academic Press, United States (Aug. 2009).

Borst, E and Messerle, M, "Development of a Cytomegalovirus Vector for Somatic Gene Therapy," Bone Marrow Transplant 25 Suppl 2:S80-S82, Nature Publishing Group (May 2000).

Borst, E.M and Messerle, M, "Construction of a Cytomegalovirus-based Amplicon: a Vector With a Unique Transfer Capacity," Human Gene Therapy 14(10):959-970, M.A. Liebert, United States (Jul. 2003).

Bresnahan, W.A and Shenk, T.E, "UL82 Virion Protein Activates Expression of Immediate Early Viral Genes in Human Cytomegalovirus-infected Cells," Proceedings of the National Academy of Sciences of the United States of America 97(26):14506-14511, National Academy of Sciences, United States (Dec. 2000).

Bresnahan, W.A., et al., "Replication of Wild-type and Mutant Human Cytomegalovirus in Life-extended Human Diploid Fibroblasts," Journal of Virology 74(22):10816-10818, American Society for Microbiology, United States (Nov. 2000).

Brondke, H. "Human Herpesvirus 5, Towne Strain," US3 (NCBI GenBank Acc. No. AAS49002), Dep. Apr. 8, 2004.

Brondke, H. "Human Herpesvirus 5, Towne Strain," US6 (NCBI GenBank Acc. No. AAS49004), Dep. Apr. 8, 2004.

Brown, B.D and Naldini.L, "Exploiting and Antagonizing MicroRNA Regulation for Therapeutic and Experimental Applications," Nature reviews Genetics 10(8):578-585, Nature Publishing Group, England (Aug. 2009).

Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.

Cantrell, S.R and Bresnahan, W.A, "Human Cytomegalovirus (Hcmv) UL82 Gene Product (pp71) Relieves hDaxx-mediated Repression of Hcmv Replication," Journal of Virology 80(12):6188-6191, American Society for Microbiology, United States (Jun. 2006).

Cantrell, S.R and Bresnahan, W.A, "Interaction Between the Human Cytomegalovirus UL82 Gene Product (pp71) and HDaxx Regulates Immediate-early Gene Expression and Viral Replication," Journal of Virology 79(12):7792-7802, American Society for Microbiology, United States (Jun. 2005).

Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society for Microbiology, United States (May 2003).

Chau, N.H., et al., "Transcriptional Regulation of the Human Cytomegalovirus Us11 Early Gene," Journal of Virology 73(2):863-870, American Society for Microbiology, United States (Feb. 1999).

Davison, A.J and Stow, N.D, "New Genes From Old: Redeployment of DUTPase by Herpesviruses," Journal of Virology 79(20):12880-12892, American Society for Microbiology, United States (Oct. 2005).

Dudek, T and Knipe, D.M, "Replication-defective Viruses as Vaccines and Vaccine Vectors," Virology 344(1):230-239, Academic Press, United States (Jan. 2006).

Dunn, W., et al., "Functional Profiling of a Human Cytomegalovirus Genome," Proceedings of the National Academy of Sciences of the United States of America 100(24):14223-14228, National Academy of Sciences, United States (Nov. 2003).

European Search Report for EP Application No. EP16200334, The Hague, dated May 18, 2017.

European Search Report for EP Application No. EP17197412, Munich, Germany, dated Apr. 23, 2018.

Prod'Homme, V., et al., "Human Cytomegalovirus UL40 Signal peptide Regulates Cell Surface Expression of the NK Cell Ligands HLA-E and gpUL18," J. Immunology 188(6):2794-2804, American Society of Immunologist, United States (2012).

Goodrum, F., et al., "Human Cytomegalovirus Persistence," Cellular Microbiology 14(5):644-655, Wiley-Blackwell, England (May 2012).

Gorman, S., et al., "Prior Infection with Murine Cytomegalovirus (Mcmv) Limits the Immunocontraceptive Effects of an MCMV Vector Expressing the Mouse Zona-Pellucida-3 Protein," Vaccine 26(31):3860-3869, Elsevier Science, Netherlands (Jul. 2008).

(56) References Cited

OTHER PUBLICATIONS

Grimwood, J., et al. "NCBI GenBank Direct Submission," Ace. No. AC146906, Sub. Nov. 5, 2003.
Hagemier, S.C., "Functional Analysis of the Human Cytomegalovirus UL82 gene product PP71 protein during Virus Replication," Doctoral Dissertation, The University of Texas Southwestern Medical Center at Dallas, May 2007, pp. 1-181.
Hahn, G., et al., "Human Cytomegalovirus UL131-128 Genes are Indispensable for Virus Growth in Endothelial Cells and Virus Transfer to Leukocytes," Journal of Virology 78(18):10023-10033, American Society for Microbiology, United States (Sep. 2004).
Halary, F., et al., "Human Cytomegalovirus Binding to DC-SIGN is Required for Dendritic Cell Infection and Target Cell Trans-Infection," Immunity 17(5):653-664, Cell Press, United States (Nov. 2002 ).
Hansen, S.G., et al., "Complete Sequence and Genomic Analysis of Rhesus Cytomegalovirus," Journal of Virology 77(12):6620-6636, American Society for Microbiology, United States (Jun. 2003).
Hansen, S.G., et al., "Effector Memory T Cell Responses are Associated With Protection of Rhesus Monkeys From Mucosal Simian Immunodeficiency Virus Challenge," Nature Medicine 15(3):293-299, Nature Publishing Company, United States (Mar. 2009).
Hansen, S.G., et al., "Evasion of Cd8+ T Cells Is Critical for Superinfection by Cytomegalovirus," Science 328(5974):102-106, American Association for the Advancement of Science, United States (Apr. 2010).
Hansen, S.G., et al., "Profound Early Control of Highly Pathogenic SIV by an Effector Memory T-cell Vaccine," Nature 473(7348):523-527, Nature Publishing Group, England (May 2011).
International Search Report and Written opinion for International Application No. PCT/US2011/036657, Korean Intellectual Property Office, Republic of Korea, dated Mar. 28, 2012, 12 pages.
Jones, T.R., et al., "Multiple Independent Loci Within the Human Cytomegalovirus Unique Short Region Down-regulate Expression of Major Histocompatibility Complex Class I Heavy Chains," Journal of Virology 69(8):4830-4841, American Society for Microbiology, United States (Aug. 1995).
Jones, T.R., et al., "Replacement Mutagenesis of the Human Cytomegalovirus Genome: US10 and US11 Gene Products are Nonessential," Journal of Virology 65(11):5860-5872, American Society for Microbiology, United States (Nov. 1991).
Kaech, S.M., et al., "Effector and Memory T-cell Differentiation: Implications for Vaccine Development," Nature Reviews. Immunology 2(4):251-262, Nature Pub. Group, England (2002).
Kalejta, R.F, "Human Cytomegalovirus PP71: a New Viral Tool to Probe the Mechanisms of Cell Cycle Progression and Oncogenesis Controlled by the Retinoblastoma Family of Tumor Suppressors," Journal of Cellular Biochemistry 93(1):37-45, Wiley-Liss, United States (Sep. 2004).
Karrer, U., et al., "Expansion of Protective CD8+ T-Cell Responses Driven by Recombinant Cytomegaloviruses," Journal of Virology 78(5):2255-2264, American Society for Microbiology, United States (Mar. 2004).
Kropff, B and Mach, M, "Identification of the Gene Coding for Rhesus Cytomegalovirus Glycoprotein B and Immunological Analysis of the Protein," 78(Pt 8):1999-2007, Microbiology Society, England (Aug. 1997).
Lilja, A.E., et al., "Functional Genetic Analysis of Rhesus Cytomegalovirus: Rh01 Is an Epithelial Cell Tropism Factor," Journal of Virology 82(5):2170-2181, American Society for Microbiology, United States (Mar. 2008).
Mahmood, K., et al., "Human Cytomegalovirus Plasmid-based Amplicon Vector System for Gene Therapy," Genetic vaccines and therapy 3(1):1, BioMed Central, England (Jan. 2005).
Marshall, K.R., et al., "Activity and Intracellular Localization of the Human Cytomegalovirus Protein PP71," The Journal of general virology 83(Pt 7):1601-1612, Microbiology Society, England (Jul. 2002).

Maussang, D., et al., "Human Cytomegalovirus-encoded Chemokine Receptor US28 Promotes Tumorigenesis," Proceedings of the National Academy of Sciences of the United States of America 103(35):13068-13073, National Academy of Sciences, United States (Aug. 2006).
McGregor, A., et al., "Molecular, Biological, and in Vivo Characterization of the Guinea Pig Cytomegalovirus (CMV) Homologs of the Human Cmv Matrix Proteins pp71 (UL82) and pp65 (UL83)," Journal of virology 78(18):9872-9889, American Society for Microbiology, United States (Sep. 2004).
Mohr, C.A., et al., "A Spread-deficient Cytomegalovirus for Assessment of First-target Cells in Vaccination," Journal of virology 84(15):7730-7742, American Society for Microbiology, United States (Aug. 2010 ).
Mohr, C.A., et al., "Engineering of Cytomegalovirus Genomes for Recombinant Live Herpesvirus Vaccines," International Journal of Medical Microbiology 298(1-2):115-125, Urban & Fischer Verlag, Germany (Jan. 2008).
Moutaftsi, M., et al., "Human Cytomegalovirus Inhibits Maturation and Impairs Function of Monocyte-derived Dendritic Cells," Blood 99(8):2913-2921, American Society of Hematology, United States (Apr. 2002).
Murphy, C.G., et al., "Vaccine Protection Against Simian Immunodeficiency Virus by Recombinant Strains of Herpes Simplex Virus," Journal of virology 74(17):7745-7754, American Society for Microbiology, United States (Sep. 2000).
Murphy, E., et al., "Coding Potential of Laboratory and Clinical Strains of Human Cytomegalovirus," Proceedings of the National Academy of Sciences of the United States of America 100(25):14976-14981, National Academy of Sciences, United States (Dec. 2003).
Wu., H.L., et al., "Cytomegalovirus vaccine vector 68-1 elicits universal, MHC-E-restricted CD8 T-cell responses against SIV," Journal of Medical Primatology 44(5):313, Wiley Online Library, United States (2014).
Olaleye, O.D., et al., "Cytomegalovirus Infection Among Tuberculosis Patients in a Chest Hospital in Nigeria," Comparative Immunology, Microbiology and Infectious Diseases 13(2):101-106, Elsevier Science Ltd, England (1990).
Onuffer, J.J and Horuk, R, "Chemokines, Chemokine Receptors and Small-molecule Antagonists: Recent Developments," Trends in Pharmacological Sciences 23(10):459-467, Published by Elsevier in Association with the International Union of Pharmacology, England (Oct. 2002).
Oxford, K.L., et al., "Protein Coding Content of the ULb' Region of Wild-Type Rhesus Cytomegalovirus," Virology 373(1):181-188, Academic Press, United States (Mar. 2008).
Plotkin, S.A., et al., "Vaccines for the Prevention of Human Cytomegalovirus Infection," Reviews of Infectious Diseases 12 Suppl 7:S827-S838, University of Chicago Press, United States (Sep.-Oct. 1990).
Powers, C and Fruh, K, "Rhesus CMV: an Emerging Animal Model for Human CMV," Medical Microbiology and Immunology 197(2):109-115, Springer-Verlag, Germany (Jun. 2008).
Redwood, A.J., et al., "Use of a Murine Cytomegalovirus K181-derived Bacterial Artificial Chromosome as a Vaccine Vector for Immunocontraception," Journal of virology 79(5):2998-3008, American Society for Microbiology, United States (Mar. 2005).
Rizvanov, A.A., et al., "Generation of a Recombinant Cytomegalovirus for Expression of a Hantavirus Glycoprotein," Journal of virology 77(22):12203-12210, American Society for Microbiology, United States (Nov. 2003).
Ryckman, B.J., et al., "Characterization of the Human Cytomegalovirus Gh/gl/ul128-131 Complex That Mediates Entry Into Epithelial and Endothelial Cells," Journal of virology 82(1):60-70, American Society for Microbiology, United States (Jan. 2008).
Schleiss, M.R., et al., "Genetically Engineered Live-attenuated Cytomegalovirus (CMV) Vaccines Improve Pregnancy Outcome in the Guinea-pig Model of Congenital CMV Infection," Retrovirology 5(1):1-3, (Apr. 2008).
European Search Report for EP Application No. EP11008462, Munich, Germany, dated Jul. 26, 2012.
GenBank Report, Accession No. NP_057850, (published Aug. 1, 2000).

(56) References Cited

OTHER PUBLICATIONS

Pietra, G., et al., "The Emerging Role of HLA-E-restricted CD8+ T Lymphocytes in the Adaptive Immune Response to Pathogens and Tumors," Journal of Biomedicine and Biotechnology 2010(9070921):1-8, Hindawi, India (2010).

Oxxon Terapeutics Licenses Rights to Xenova's DISC-HSV and DISC-GM-CSF Vector Technolgies, BusinessWire, Jan. 13, 2005.

Tessmer, M.S., et al., "Salivary Gland NK Cells Are Phenotypically and Functionally Unique," PLoS Pathogens 7(1):e1001254, Public Library of Science, United States (Jan. 2011).

Ulmer, J.B, "Tuberculosis DNA Vaccines," Scandinavian Journal of Infectious Diseases 33(4):246-248, Informa Healthcare, England (2001).

Wang, X., et al., "Murine Cytomegalovirus Abortively Infects Human Dendritic Cells, Leading to Expression and Presentation of Virally Vectored Genes," Journal of virology 77(13):7182-7192, American Society for Microbiology, United States (Jul. 2003).

Wiertz, E.J., et al., "The Human Cytomegalovirus US11 Gene Product Dislocates Mhc Class I Heavy Chains From the Endoplasmic Reticulum to the Cytosol," Cell 84(5):769-779, Cell Press, United States (Mar. 1996).

Altschul, S.F. and Gish W., "Local Alignment Statistics," Methods in Enzymology 266:460-480, Academic Press, United States (1996).

Altschul, S.F., et al., "Basic Local Alignment Search Tool," Journal of Molecular Biology 215(3):403-410, Elsevier, England (Oct. 1990).

Andre, S., et al., "Increased Immune Response Elicited by DNA Vaccination With a Synthetic gp120 Sequence With Optimized Codon Usage," Journal of Virology 72(2):1497-1503, American Society for Microbiology, United States (Feb. 1998).

Barsov, E.V., et al., "Transduction of Siv-specific Tcr Genes Into Rhesus Macaque Cd8+ T Cells Conveys the Ability to Suppress Siv Replication," PLoS One 6(8):e23703, Public Library of Science, United States ( Aug. 2011).

Do, J.S., et al., "Unexpected Role for MHC II-Peptide Complexes in Shaping CD8 T-Cell Expansion and Differentiation in Vivo," Proceedings of the National Academy of Sciences 109(31):12698-12703, National Academy of Sciences, United States (Jul. 2012).

Felgner, J.H., et al., "Enhanced Gene Delivery and Mechanism Studies With a Novel Series of Cationic Lipid Formulations," Journal of Biological Chemistry 269(4):2550-2561, American Society for Biochemistry and Molecular Biology, United States (Jan. 1994).

Gilicze, A.B., et al., "Myeloid-Derived microRNAs, miR-223, miR27a, and miR-652, Are Dominant Players in Myeloid Regulation," BioMed Research International 2014:870267, Hindawi Publishing Corporation, United States (Aug. 2014).

Gill, R.B., et al., "Coding Potential of Ul/b' From the Initial Source of Rhesus Cytomegalovirus Strain 68-1," Virology 447(1-2):208-212, Academic Press, United States (Dec. 2013).

Gish, W and States, D.J, "Identification of Protein Coding Regions by Database Similarity Search," Nature Genetics 3(3):266-272, Nature Publishing Group, United States (Mar. 1993).

Goodman-Snitkoff, G., et al., "Role of Intrastructural/intermolecular Help in Immunization With Peptide-phospholipid Complexes," Journal of Immunology 147(2):410-415, American Association of Immunologists, United States (Jul. 1991).

Wang, D and Shenk,T ., "Human cytomegalovirus UL131 Open Reading Frame is Required for Epithelial Cell Tropism," Journal of Virology, 79(16):10330-10338, American Society for Microbiology, United States (Aug. 2005).

Hancock, M.H., et al., "Rhesus Cytomegalovirus Encodes Seventeen Micrornas that are Differentially Expressed in Vitro and in Vivo," Virology 425(2):133-142, Academic Press, United States (Apr. 2012).

Hansen, S.G., et al., "Broadly Targeted Cd8+ T Cell Responses Restricted by Major Histocompatibility Complex E," Science 351(6274):714-720, American Association for the Advancement of Science, United States (Feb. 2016).

Hansen, S.G., et al., "Cytomegalovirus Vectors Violate CD8+ T Cell Epitope Recognition Paradigms," Science 340(6135):1237874, American Association for the Advancement of Science, United States (May 2013).

Hansen, S.G., et al., "Immune Clearance of Highly Pathogenic SIV Infection," Nature 502(7469):100-104, Nature Publishing Group, United Kingdom (Oct. 2013).

Higgins, D.G and Sharp, P.M, "Clustal: A Package for Performing Multiple Sequence Alignment on a Microcomputer," Gene 73(1):237-244, Elsevier/North-Holland, Netherlands (Dec. 1988).

Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).

Huang, X., et al., "Parallelization of a Local Similarity Algorithm," Computer Applications in the Biosciences 8(2):155-165, Oxford University Press, England (Apr. 1992).

International Preliminary Report on Patentability for International Application No. PCT/US2016/017373, The International Bureau of WIPO, Geneva, Switzerland, dated Aug. 15, 2017, 8 pages.

International Search Report and Written Opinion for International Application No. PCT/US2015/040807, European Patent Office, HV Rijswijk, dated Oct. 28, 2015, 6 pages.

International Search Report and Written opinion for International Application No. PCT/US2016/017373, Korean Intellectual Property Office, Republic of Korea, dated May 23, 2016.

International Search Report for International Application No. PCT/US2012/041475, Korean Intellectual Property Office, Republic of Korea, dated Dec. 14, 2012.

Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).

Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).

Malouli, D., et al., "Reevaluation of the Coding Potential and Proteomic Analysis of the Bac-derived Rhesus Cytomegalovirus Strain 68-1," Journal of Virology 86(17):8959-8973, American Society for Microbiology, United States (Sep. 2012).

McGregor, A., et al., "Expression of the Human Cytomegalovirus UL97 Gene in a Chimeric Guinea Pig Cytomegalovirus (GPCMV) Results in Viable Virus with Increased Susceptibility to Ganciclovir and Maribavir," Antiviral Research 78(3):250-259, Elsevier, Netherlands (Jun. 2008).

Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).

Murrell, L., et al., "Impact of Sequence Variation in the UL128 Locus on Production of Human Cytomegalovirus in Fibroblast and Epithelial Cells," Journal of Virology 87(19):10489-10500, American Society for Microbiology, United States (Oct. 2013).

Myers, E.W., and Miller, W., "Optimal Alignment in Linear Space," Computer Applications in the Biosciences 4(1):1-13, Oxford University Press, England (Mar. 1988).

Kim, S., et al., "Human Cytomegalovirus MicroRNA miR-US4-1 Inhibits CD8(+) T cell Responses by Targeting the Aminopeptidase ERAP1," Nature Immunology 12(10):984-991, Nature America Inc, United States (Sep. 2011).

Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).

Oxford, K.L., et al., "Protein Coding Content of the UL)b' Region of Wild-type Rhesus Cytomegalovirus," Virology, 373(1):181-183, Academic Press, United States (Mar. 2008).

Pearce, E.L., et al., "Functional Characterization of MHC Class II-Restricted CD8+CD4- and CD8-CD4-T cell Responses to Infec-

(56) References Cited

OTHER PUBLICATIONS tion in CD4-/-Mice," Journal of Immunology 173(4):2494-2499, American Association of Immunologists, United States (Aug. 2004).
Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).
Pearson, W.R., "Using the FASTA Program to Search Protein and DNA Sequence Databases," Methods in Molecular Biology 24:307-331, Humana Press, United States (Feb. 1994).
Hanley, P.J., et al., "Controlling cytomegalovirus: helping the immune system take the lead," Viruses, 6(6):2242-2258, MDPI, Switzerland (May 2014).
Picker, L.J., et al., "New paradigms for HIV/AIDS vaccine development," Annual Review of Medicine 63:95-111, Annual Reviews, United States (Feb. 2012).
Pietra, G., et al., "HLA-E-Restricted Recognition of Cytomegalovirus-derived Peptides by Human CD8+ Cytolytic T Lymphocytes," Proceedings of the National Academy of Sciences of the United States of America 100(19):10896-10901, National Academy of Sciences, United States (Sep. 2003).
International Preliminary Report on Patentability for International Application No. PCT/US2015/040807, The International Bureau of WIPO, Geneva, Switzerland, dated Jan. 17, 2017, 8 pages.
Joosten, S.A., et al., "Characteristics of HLA-E Restricted T-Cell Responses and Their Role in Infectious Diseases," Journal of Immunology Research, 2016:2695396, Hindawi Publishing Corporation, Egypt (Sep. 2016).
Wu, F., et al., "Role of Specific MicroRNAs for Endothelial Function and Angiogenesis," Biochemical and Biophysical Research Communications 386(4):549-553, Elsevier, United States (Sep. 2009).
Sambrook, J., et al., "Molecular Cloning: A Laboratory Manual," Second Edition, Cold Spring Harbor Laboratory Press, United States (1989).
Schuessler, A., et al., "Charge Cluster-to-Alanine Scanning of UL 12B for Fine Tuning of the Endothelial Cell Tropism of Human Cytomegalovirus," Journal of Virology, 82(22):11239-11246, American Society for Microbiology, United States (Nov. 2008).
Schuessler, A., et al., "Mutational Mapping of UL130 of Human Cytomegalovirus Defines Peptide Motifs within the C-Terminal Third as Essential for Endothelial Cell Infection," Journal of Virology, 84(18): 9019-9026, American Society for Microbiology, United States (Sep. 2010).
Smith, T.F. and Waterman, M.S., "Comparison of Biosequences," Advances in Applied Mathematics 2(4):482-489, Academic Press, Inc., United States (Dec. 1981).
Michaelson, J.S and Leder, P., "RNAi Reveals Anti-Apoptotic and Transcriptionally Repressive Activities of DAXX," Journal of Cell Science 116(Pt 2):345-352, Company of Biologists, London (Jan. 2003).
Nicholson J.P., et al., "Properties of Virion Transactivator Proteins encoded by Primate Cytomegaloviruses," Journal of Virology, 6:65, BioMed Central, England (May 2009).
Ulmer, J.B., et al., "Heterologous Protection against Influenza by injection of DNA Encoding a Viral Protein," Science 259(5102):1745-1749, American Association for the Advancement of Science, United States (Mar. 1993).

Cranage, M., et al., "Carriers for the delivery of a vaccine against respiratory syncytial virus," Expert Opinion on Biological therapy 5(7):939-952, Taylor & Francis, United States (2005).
Antonis, A.F., "Vaccination with recombinant modified vaccinia virus Ankara expressing bovine respiratory syncytial virus (bRSV) proteins protects calves against RSV challenge." Vaccine 15(25):4818-4827, Elsevier, Netherlands (2007).
Kovarik, J., et al., "Induction of adult-like antibody, Th1, and CTL responses to measles hemagglutinin by early life murine immunization with an attenuated vaccinia-derived NYVAC (K1L) viral vector," Virology 285(1):12-20, Elsevier, Netherlands (2001).
Welter, J., et al., "Mucosal vaccination with recombinant poxvirus vaccines protects ferrets against symptomatic CDV infection," Vaccine 17(4):308-318, Elsevier, Netherlands (1999).
Guillaume, V., et al., "Nipah Virus: Vaccination and passive protection studies in a hamster model," Journal of Virology 78(2):834-840, American Society for Microbiology, United States (2004).
Wyatt, L.S., et al., "Development of a replication-deficient recombinant vaccinia virus vaccine effective against parainfluenza virus 3 infection in an animal model," Vaccine 14(15):1451-1458, Elsevier, Netherlands (1996).
Kenjiro, I., et al., "Long-term protective immunity to rinderpest in cattle following a single vaccination with recombinant vaccinia virus expressing the virus haemagglutinin protein," Journal of General Virology 81(6):1439-1446.
Grey, F., et al., "A human cytomegalovirus-encoded microRNA regulates expression of multiple viral genes involved in replication," PLOS pathogens 3(11):1593-1602, Public Library of Science, United States (2007.).
Ojha, M., et al., "Spatial and cellular localization of calcium-dependent protease (CDP II) in *Allomyces arbuscula*," Journal of Cell Science 116:1095-1105, The Company of Biologists, United Kingdom (2003).
Powers, C.J., et al., "Signal peptide-Dependent Inhibition of MHC Class I Heavy Chain Translation by Rhesus Cytomegalovirus," PLOS Pathogens 4(10):e1000150, Public Library of Science, United States.
Powers, C., et al., "The US2-11 region of RhCMV is both necessary and sufficient to counteract CD8+ T-cell immunity during re-infection of rhesus macaques," 34th Annual International Herpesvirus Workshop, Jul. 25, 2009, Ithaca, New York.
Smith, M.S., et al., "Roles of Phosphatidylinositol 3-Kinase and NF-B in Human Cytomegalovirus-Mediated Monocyte Diapedesis and Adhesion: Strategy for Viral Persistence," Journal of Virology 81(14):7683-7694, American Society for Microbiology, United States (2007).
Bentz, G.L., et al., "Human Cytomegalovirus (HCMV) Infection of endothelial Cells Promotes Naïve Monocyte Extravasation and transfer of Productive Virus to Enhance Hematogenous Dissemination of HCMV," Journal of Virology 80(23):11539-15555, American Society for Microbiology, United States (2006).
Fruh, K., et al., "CD8+ T cell programming by cytomegalovirus vectors: applications in prophylactic and therapeutic vaccination," Current Opinion in Immunology 47:52-56, Elsevier, Netherlands(2017).

* cited by examiner

Fig. 17B

```
SEQ ID NO:4 HIVgag    MAARASILSGGKLDAWEKIRLRPGGKKKYRLKHLVWASRELDRFALNPSLLETTEGCQQI 60
SEQ ID NO:5 #3D6 p4   MAARASILSGGKLDAWEKIRLRPGGKKKYRLKHLVWASRELDRFALNPSLLETTEGCQQI 60
SEQ ID NO:6 #3D6 p5   MAARASILSGGKLDAWEKIRLRPGGKKKYRLKHLVWASRELDRFALNPSLLETTEGCQQI 60
SEQ ID NO:7 #3D6 p6   MAARASILSGGKLDAWEKIRLRPGGKKKYRLKHLVWASRELDRFALNPSLLETTEGCQQI 60
                      ************************************************************

SEQ ID NO:4 HIVgag    MNQLQPAVKTGTEEIKSLFNTVATLYCVHQRIDVKDTKEALDKIEEIQNKSKQKTQQAAA 120
SEQ ID NO:5 #3D6 p4   MNQLQPAVKTGTEEIKSLFNTVATLYCVHQRIDVKDTKEALDKIEEIQNKSKQKTQQAAA 120
SEQ ID NO:6 #3D6 p5   MNQLQPAVKTGTEEIKSLFNTVATLYCVHQRIDVKDTKEALDKIEEIQNKSKQKTQQAAA 120
SEQ ID NO:7 #3D6 p6   MNQLQPAVKTGTEEIKSLFNTVATLYCVHQRIDVKDTKEALDKIEEIQNKSKQKTQQAAA 120
                      ************************************************************

SEQ ID NO:4 HIVgag    DTGDSSKVSQNYPIIQNAQGQMIHQNLSPRTLNAWVKVIEEKAFSPEVIPMFSALSEGAT 180
SEQ ID NO:5 #3D6 p4   DTGDSSKVSQNYPIIQNAQGQMIHQNLSPRTLNAWVKVIEEKAFSPEVIPMFSALSEGAT 180
SEQ ID NO:6 #3D6 p5   DTGDSSKVSQNYPIIQNAQGQMIHQNLSPRTLNAWVKVIEEKAFSPEVIPMFSALSEGAT 180
SEQ ID NO:7 #3D6 p6   DTGDSSKVSQNYPIIQNAQGQMIHQNLSPRTLNAWVKVIEEKAFSPEVIPMFSALSEGAT 180
                      ************************************************************

SEQ ID NO:4 HIVgag    PQDLNVMLNIVGGHQAAMQMLKDTINEEAAEWDRLHPVQAGPIPPGQIREPRGSDIAGTT 240
SEQ ID NO:5 #3D6 p4   PQDLNVMLNIVGGHQAAMQMLKDTINEEAAEWDRLHPVQAGPIPPGQIREPRGSDIAGTT 240
SEQ ID NO:6 #3D6 p5   PQDLNVMLNIVGGHQAAMQMLKDTINEEAAEWDRLHPVQAGPIPPGQIREPRGSDIAGTT 240
SEQ ID NO:7 #3D6 p6   PQDLNVMLNIVGGHQAAMQMLKDTINEEAAEWDRLHPVQAGPIPPGQIREPRGSDIAGTT 240
                      ************************************************************

SEQ ID NO:4 HIVgag    STPQEQLQWMTGNPPIPVGNIYKRWIILGLNKIVRMYSPVSILDIKQGPKEPFRDYVDRF 300
SEQ ID NO:5 #3D6 p4   STPQEQLQWMTGNPPIPVGNIYKRWIILGLNKIVRMYSPVSILDIKQGPKEPFRDYVDRF 300
SEQ ID NO:6 #3D6 p5   STPQEQLQWMTGNPPIPVGNIYKRWIILGLNKIVRMYSPVSILDIKQGPKEPFRDYVDRF 300
SEQ ID NO:7 #3D6 p6   STPQEQLQWMTGNPPIPVGNIYKRWIILGLNKIVRMYSPVSILDIKQGPKEPFRDYVDRF 300
                      ************************************************************

SEQ ID NO:4 HIVgag    FKALRAEQATQDVKGWMTETLLVQNANPDCKSILKALGSGATLEEMMTACQGVGGPGHKA 360
SEQ ID NO:5 #3D6 p4   FKALRAEQATQDVKGWMTETLLVQNANPDCKSILKALGSGATLEEMMTACQGVGGPGHKA 360
SEQ ID NO:6 #3D6 p5   FKALRAEQATQDVKGWMTETLLVQNANPDCKSILKALGSGATLEEMMTACQGVGGPGHKA 360
SEQ ID NO:7 #3D6 p6   FKALRAEQATQDVKGWMTETLLVQNANPDCKSILKALGSGATLEEMMTACQGVGGPGHKA 360
                      ************************************************************

SEQ ID NO:4 HIVgag    RVLAEAMSQAQQTNIMMQRGNFRGQKRIKCFNCGKEGHLARNCRAPRKKGCWKCGKEGHQ 420
SEQ ID NO:5 #3D6 p4   RVLAEAMSQAQQTNIMMQRGNFRGQKRIKCFNCGKEGHLARNCRAPRKKGCWKCGKEGHQ 420
SEQ ID NO:6 #3D6 p5   RVLAEAMSQAQQTNIMMQRGNFRGQKRIKCFNCGKEGHLARNCRAPRKKGCWKCGKEGHQ 420
SEQ ID NO:7 #3D6 p6   RVLAEAMSQAQQTNIMMQRGNFRGQKRIKCFNCGKEGHLARNCRAPRKKGCWKCGKEGHQ 420
                      ************************************************************

SEQ ID NO:4 HIVgag    MKDCTERQANFLGKIWPSSKGRPGNFPQSRPEPTAPPAELFGMGEGIASLPKQEQKDREQ 480
SEQ ID NO:5 #3D6 p4   MKDCTERQANFLGKIWPSSKGRPGNFPQSRPEPTAPPAELFGMGEGIASLPKQEQKDREQ 480
SEQ ID NO:6 #3D6 p5   MKDCTERQANFLGKIWPSSKGRPGNFPQSRPEPTAPPAELFGMGEGIASLPKQEQKDREQ 480
SEQ ID NO:7 #3D6 p6   MKDCTERQANFLGKIWPSSKGRPGNFPQSRPEPTAPPAELFGMGEGIASLPKQEQKDREQ 480
                      ************************************************************

SEQ ID NO:4 HIVgag    VPPLVSLKSLFGNDPLSQ 498
SEQ ID NO:5 #3D6 p4   VPPLVSLKSLFGNDPLSQ 498
SEQ ID NO:6 #3D6 p5   VPPLVSLKSLFGNDPLSQ 498
SEQ ID NO:7 #3D6 p6   VPPLVSLKSLFGNDPLSQ 498
                      ******************!
```

Fig. 18

Next generation sequencing of RhCMV 68-1.2 SIV-gag ΔUL36 viral DNA

Premature Stop codon due to G → T substitution in SIV gag in 37.9% of the population

SEQUENCE LISTING

```
<160> NUMBER OF SEQ ID NOS: 7

<210> SEQ ID NO 1
<211> LENGTH: 244443
<212> TYPE: DNA
<213> ORGANISM: Human cytomegalovirus

<400> SEQUENCE: 1
ggtggtgttg cctgcggcgg ggacgggggt tgcgctggga tcgggggtgg cgccggggac      60
gggggctttt cgcagcgggg aacacacacc gcctatttaa cctccacccg ctacaacaca     120
cacatgccgc acaatcatgc cagccacaga cacaaacagc acccacacca cgccgcttca     180
cccagaggac caacacacgt tacccgtaca ccacagtaac acacaaccgc aagtccaaac     240
ctcggacaaa cgcgccgccg aagaccaccg cacgcagatg gagctcgacg ccgcggacta     300
cgctgcttgc tcacaggccc gccaacacct ctacggtcaa acacaacccc aactacacgc     360
```

```
ataccccaac gccaacccac aggaaagcgc tcattttttc acagagaatc aacatcaagt    420
cacgcatcta cttcacaaca ttggcgaggg cgcagcgctc ggctacaccg tcccccgcgc    480
ggaaatccgc cgtggcggtg gcgactgggc cgacagcgca agcgacttcg acgccgactg    540
ctggtgcatg tggggacgct tcggaaccat gggccgccaa cctgtcgtga ccttactgtt    600
ggcgcgccaa cgcgacggcc tcgctgactg gaacgtcgta cgctgccgcg gcacaggctt    660
tcgcgcacac gattccgagg acggcgtctc tgtctggcgt cagcacctgg ttttttttact   720 cggaggccac ggccgccgtg tacagttaga acgtccatcc gcgggagaag cccaagctcg    780
aggcctattg ccacgcatcc ggatcacccc cctctccaca tctccacgcc caaaaccacc    840
ccagcccacc acatccaccg cctcgcaccc acatgctacg gctcggccag atcacacgct    900 cttcctgtc cttccacac cctcaaccac ggttcacaat ccccgaaact acgccgtcca      960
acttcacgcc gaaacgaccc gcacatggcg ctgggcacga cgcggtgaac gtggcgcgtg    1020
gatgccggcc gagacattta cgtgtcccaa ggataaacgt ccctggtaga cggggtaggg    1080
ggatctacca gcccagggct cgcgtatttc gccgccacgc tgcttcaccg atatccaata    1140
aacccatccc ctcgccacga cgtctccgcg tatctttgta gcctcaggaa tccgtcccca    1200
cgtccaccca tcccgagcac tccacacgct ataacgacc acggacacgg caaatgcatg     1260
caaacttctc atttattgtg tctactactc tgtgttgcta caggggtga aggcaaagaa     1320 aaaaaaaagg aacaaaataa tagattagca gaaggaataa tccgtgcgac cgagcttgtg    1380
cttcttttct tataaggagg caaatatact agggaaaaca taagaatagg aagaaaccga    1440
ggtttgggag aaaagctgag ataaaatagc gcattttcca tacagaggtt gttgttttg     1500 tggatcctaa gaggtttcaa gtgcgaatct taaagttctc acgagaatat tgtcttcaag    1560
aatcgacaac tgtggtccaa gattttttt tggtcttttt aggttctgcg agggacatca     1620
cgatggatcg ttgcgatgaa gtcacgcgta cgcctctggt gtggcgcggt gtcgtgacag    1680
gagagtgtgt tttcagtgca gagctgtctt gattcctata tccgagtatc tgttttctcg    1740
taaggacggt aatcttcttt ggtgtaagta catctaaaag ctgcaaacta tattttaagg    1800
gctgtctcta ggtgtacttt gatgctggag ttttcgctg tgttgatgtg aataaatcta     1860
ctactactat tatatgcaga aagagtgatt atgccgagac aagattgcat ggctgaact     1920 gtttcaaaaa cgcctacact ctacttatcc gtaaacctaa ggtaatacta tgtgtaagtt    1980
gttttttttt tctttttgta gtaaaatggt gatacgtgca attaaaactg tattccatgt    2040
ttccatcctt tcatttcaac tttaaaggcg gctttgagag cgaagaagtg cgaggataaa    2100
aatggatgac tccttcgtgt ccagggagtc gactactgca acgctgattg attaaaagat    2160
ggtctccgat gatgatgttg ttattgatcg aatcatggtg cagaacggcg acggagagga    2220
gcgtgtccgc cgccgggaag gtggtctctt tctcttttct ttttcaaga aatcttccat     2280 gtgtttatcg tagtgatcga aatcgactga tctcgggttc ttttttgttgg tttcttttcg   2340 gttaatcatg tattgttttc tttttttaca gaaagatact ttttttcatga gcaattcctc   2400 gcccggcgcc ggcatgccga ggtggggcca ctgcgatcag cggcatgccg acgccgaccc    2460
ggggatcttg gattcaccgt tttctctctt ctctctctac atacagaccg ggtggcagga    2520
gcggtaagga atcatcgtcg tctttcattc ttcgatgatt atggtaatac taaatcttat    2580
ctaggagcat atacatctaa gattggagta ctagtagtcg tttgtggttt ctattttttt    2640
ttatatttat ctatgacagt ttttctgttt ttcgttttga taataatata ataaaaactc    2700
atggacgtga aatctggctt ggttgtggtg atttcattct cattattgtt gttttctttc    2760
```

```
cgtcttgcgg atgaagatgt tgcgatgcgg ttgttgttgg tgttgctata caccgagaga    2820
gatgatcttt ttgttcttct ggttcatttc ctatgattgt ttggctgctg accgacgcgt    2880
caggatgtgc agggcatgcg gggaatcagg accggacacg ggataatttc atctacctat    2940
acggagatcg cggtcctcgc catgaggatc gcgacaggcg cgtcgagggg gcaggaacac    3000
ccttgcggat tgacattctt ggtggtgttt cgttgttgtc ggtagttgtt gttgacgatg    3060
aggataaata aaaatgacct tgttttttgtt ctgttttctc ttgttgggaa tcgtcgactt    3120
tgaattcttc gagttatcgg aaagctgagg tacccaaatg tctgtagctt ttttctttttt    3180 accctcttgt ttatcatctg cgattcgtgg taggtaggag agggaaatga taatccgaga    3240
ttaaggaaag gagaagataa aataaaaaaa aaataaaaca gaagccgacc ggccgccgac    3300
ccgttcccca ggaccagcct acgaggaacg gataacgcgg tggcgacggc agcggtggtg    3360
gcgctggggg tggcggtagt ggtactgctg atggtagtcg ggacggagga gagacgatgc    3420
atacatacac gcgtgcatgc tgcatggggtg gatggtccga ccgggagacg cggaagagaa    3480
actcacataa aaaggtgaca aaaagagcgg ttgaaaaaag aaaacgagat tcgaccagac    3540
agaagaggag gaccggggct tggcgaccct tccacgactg ctgttgtcat ctcggctcct    3600
ccgtcttctc ccggccacgg gcggctaagt caccgccgtt ctccccatcc gtccgagcgc    3660
cgaccgacca gccggccgat tcgcccgccg gggcttctgg agaacgccgg ggcagcagcg    3720
atctggagaa gccgctaaac ccctgcgttt ttatatggta gctctgccga gcgcgggctg    3780
acgcgttaag taagcggaaa gacgtgtgtg acgaaaaggg gtcccatggt atttcacgtg    3840
acgatgagga gatgcggttt ggagcacata cggtttagaa aaagggagtt gtcgtgacaa    3900
gggctgaggg acctctgtct ccatgtgtgt ataaaaagca aggcacgttc ataatgtaaa    3960
aaagaacacg ttgtaaacaa gctattgctg tatcattcgg ctgactatgc ttcattcgga    4020
ctgattttct tttcctaacg gcgtaactta aagtgattaa cgtatgatat tgttccccca    4080
gagttatact atagtcatca tcctaaaatt cagatataaa tgaacacatg tcgtatgaga    4140
ttattaagaa accgaaacca cccatagttc accatcctct tcatcattca gccgatgacc    4200
cactccgtac aacgactcag tctgcttcgt catattgcaa agcacaagcg acgtatgtga    4260
acaacttgaa acacagactg tgttattaat gaccgttgta ccattactag tcacattgca    4320
taaagatcct ccgccgtcgt cccatctttt ccactcggtg gaaaaccggt cgctatcatc    4380
aactatggtg agattttcac cctgcgtggt attcagtttc ttcatattca taccttggat    4440
tccattatta aaccccaata ttaagcacgt tattagtacc ccccccccc accaaggaat    4500 gtgactggac cggttcctag cagctctggg agccatgttc aggttgaacc acagctacag    4560
cgaaaccgag tccagtgacc ggtaaccacg tccagcccct gcgtatgtac cagtccaagc    4620
acgtccggtc attgttctac acaggaaatc taactaggtc aacgtaattt tattccaccg    4680
ttacgcagaa tactaacaaa aaactacaca aatgtaacgg attacacata atttattacg    4740
tgaaaactgt aagaaagcca attcaccaag cgatacattt atttgacttc caagtgccac    4800
acatcaccac tatattcatc catgttttca ccgaaccaac gagacagatc gaagaagcca    4860
gaatcttccg actttaaatt acataaatcc aacgtattat gaccacagct cgacacacaa    4920
atagttgcgt tactattcac agtggcatta cctatacccg taacgttgca caaccactga    4980
tcaccattgt caccaaaaac ggttttccac ttagttgtca acggatcttt cctatgcgta    5040
atggtaaaat tactaccagt cgtcgctttt agctcattac gagtattatc cgcatccaca    5100
```

```
tatatcaacg tcatagctag gcacgctata agtaccccccc ccccacaatg gaatgttgcc    5160
aaaccggttc tttcccgtta tagccatagc gttcccaggc aaaagcaaac gccgaaccta    5220
atgcagtaaa aagcgcttgc agccagaacc agcttatgta ccagccacga taacatccgg    5280
tcactgtttc cacaggaaac cctaccaggg tagagcccccg cttgtttttt cctgtctatc   5340
ttgtttagca actcgtaaac tgtcagtcta gccacgtccg tttagatcaa aagtcacgta    5400
tactgcgacg ttgttttccac ccgtttcccc gtcccgccgt ttccgaacaa cccacccggg   5460
ttcagacaac cgaccaccaa cagaaatata cacacagacc accgggagtt cagttaaaga    5520
tttcatcagg tttattttgg ctgctgctag tcttttgctt cttagaaaaa aaatacccat    5580
atagagaaat aatgatagtt tgacaacaca tatggcaggg atttcttctt catcaataag    5640
atatgcaatt cccccaggga gagactttca acaattgaat ttacaaaaac aaaattacat    5700
caggagaaag agaggataca ttaataaata tattatatct ggtgtatata ctgaatgctg    5760
ctggttcata agtaacgat gctacttttt ttaattccaa gatggttttt ctttgttagt     5820
cttttgttga cttgctggtt cctaaaagtt ctcaaaaacg attgtgtgaa gattttatga    5880
cgttggttga ctagttcatg agattctgct gtacgtgtga tggttattcg ctggttcgtt    5940
ctaagatgag tatcgtactg tgtctgcgat ggtcgtctct tactggcatt ctctcggctg    6000
cctcttgctt tcatgattga aaaggaaaaa aggactccga gggcgcggtc atcttttact    6060
tttcggtttt ttcgttggcg ggtcagaggt agtcagatca tgagactgtc gtggtcgatg    6120
aaactgtgtc tgctcaagtg acgtccattt cttgtacgga gaaaaagtc atcgggataa     6180
ataaggctat acaaggcgtt gtcaagcgtg cggctctaaa caaattaagc gatacaaaat    6240
tacagtaata cgaataataa gttacccccct ccccctgtgg tcccccccgag acgagagcca  6300
cccatcgtgt actctcgcac cacccacgac cacagaggga gacgggacga agagacgacg    6360
cagagcgcca tctccttctg gaggccggcg gcgttaactg ctacagctgc ggcggcgaca    6420
acagctgcga tttgtcggcc gacatgccga tggtatgggc ggcggcggca gtggccgcgg    6480
cagcggggag gagaggagag agaagaggag cggggcgtcc gaaggcgagg atggcatggt    6540
ctcgccggag cgcccggctt ttatggaacg ctcgcgtccg gtcgggcagc gcccacagga    6600
agatgagtca aaacttttaa accatcctga gacccgagta gcggtttaca ggccgcacgc    6660
cagtcttagc taaaaacagc ggacagtccc acgctgtttc tgttgtggct ctctccagtt    6720
tcctcatcgc cgtcccgatc tccgtcgtca tcggaagaat accaccgcct ctcatgcggc    6780
agtcgatcga cctcgacgaa cgagacgcgg cgacgcctct ctacggccga ctggttgtgg    6840
tggtgaaaga agagcaccag caatcccagg aggagcaaca agccctcaca tgtccaggag    6900
gtcggggaga gggcctgtcg gagatggccg tgaggcatca cgtacggcag ctgaggagaa    6960
acggagaaga aaggaaaatt accgtcaggg gccggggttc ttattagaga aacagcacgt    7020
aggtcaggat ccagatgcta atggcaatca tgatgacgat gatcatgcag gccaagacgc    7080
ggcgcaccaa tgccgaatcc aatagccgcc gtgcctccgg ttggtggccg gcggcatcta    7140
gagacatgat ttgggggga ccggcggcgc gaaaagacag ggagatggac agtgtcacgg     7200
tgttttgtta tgattaggac atggggaccg gaagccgaga cagagtacta cagggtgttg    7260
aagggtaacg tgagggagat catgtcatgg gcgggctgaa gaccgtgcgg ggaggattgg    7320
cgtgtgcggt gcttgtggaa cacggtgttt taatatgtat ccgcgtgtaa tgcacgcggt    7380
gtgcttttta gcactcggct tgataagcta cgtggccgtt tgcgccgaaa acacggttac    7440
caccaactgt ctcgtgaaaa cagaaaatac ccacctaaca tgtaagtgca atccgaatag    7500
```

```
cacatctacc aatggcagca agtgccacgc gatgtgcaaa tgccgggtca cagaacccat    7560
taccatgcta ggcgcatact cggcctgggg cgcgggctcg ttcgtggcca cgctgatagt    7620
cctgctggtg gtcttcttcg taatttacgc gcgcgaggag gagaaaaaca acacgggcac    7680
cgaggtagat caatgtctgg cctatcggag cctgacacgc aaaaagctgg aacaacacgc    7740
ggctaaaaag cagaacatct acgaacggat tccataccgg ccctccagac agaacgacaa    7800
ctccccgttg atcgaaccga cgggcacaga cgacgaagag gacgaggacg acgacgtctg    7860
ataaggaagg cgagaacgtg ttttgcacca tgcagaccta cagcaccccc ctcacgcttg    7920
tcatagtcac gtcgctgttt ttgttcacaa ctcagggaaa tttatcgaac gccgtcgaac    7980
caaccaaaaa accoctaaag ctcgccaact accgtgccac ctgcgaggac cgtacacgca    8040
cgctggttac caggcttaac actagtcatc acagcgtagt ctggcaacgt tatgatatct    8100
acagcagata catgcgtcgt atgccgccac tttgcatcat tacagacgcc tataaagaaa    8160
ccacgcatca gggtggcgca actttcacgt gcacgcgcca aaatctcacg ctgtacaatc    8220
ttacgattaa agatacggga gtctatcttc tacaggatca gtgtaccggc gatgtcgagg    8280 cttttctacct catcatccac ccacgtagct tctgccgagc tttggaaacg cgtcgatgct    8340
tttatccggg accagggaga gttgtggtta cggattccca agaggcagac cgagcaatta    8400 tctcggatt aaaacgccag tggtccggcc tctcactcca ttgcgcctgg gtttcgggac    8460
tgatgatctt tgttggcgca ctggtcatct gcttcctgcg atcacaacga atcggggaac    8520
aggacgctga acagctgcgg acggacctgg atacggaacc tttgttgttg acggtggacg    8580
gagatttgga ataaaagatg cgcgtcaacc gtcaaagacg caacaacctt acgtaccgac    8640
aaacggtata tgtaattctg accttctaca ttgtacatag gggcatatgt aacagcaccg    8700
ataccaacaa ttctacatct acttcaaata gcaccgtctc tgatactaat gtatattcta    8760
ctccaaatcc tcccagtgta tcttctacaa ctcttgatac atctaccgac tcacagatat    8820
caatcgcctc aaacaccata tccagcacta caaatacatt gaccgcatat tctataacta    8880
cgttaaacac ctcgacttca tcttcaactc ttactgctgt ctctagtacc catacaaagat    8940 cctcaatact ctccaacaac gcatcataca ccacatcatt ggataataca actacagaca    9000
taacgtccag cgaaagttca atcaacgtgt cgacagttta caacaccacg tacattcctg    9060
taacatcgct tgctattaat tgtactgcta caattaacgg aacaaataat tctagttcaa    9120
aaacttgcca acaagacatt gaaacaatac ctgtgaaatc aactccacta acggcagaag    9180
aaggaacaaa tattcaaata catggcaatg acacgtggga ttgtcccgac gtggtttggt    9240
atcgacatta taattggtct acacatggac accacattta tcccaataca cattacaaaa    9300
ctttgataca tcgacgcaag atcctaacgt cacatcctat atgttattct gatcgctcat    9360
cacctaccgc gtatcatgat ctatgccgtt catgtaataa aacagaacta cgcctttacg    9420
atttaaacac caccaattct ggtagatata gccgacggtg ttacaaacag taccatcacc    9480
agggaccaca cgaggatgaa aatttcggac taactgtaaa tcccaggaac aacactgaca    9540
attataccat cccagtatgt cccagatacg tagaaacaca atcacaggaa gatgaacaag    9600
acgacgatta tacactaagc actaccataa ataataatct tatgcgcaaa acaggtcact    9660
atgacatctc acatggcacg cacactacat gggctcttat actaatttgc atagcctgca    9720
tgcttctttt ttttgttcga cgagccctca ataaaaaata tcgtccacta cgagatgata    9780
ttagtgaatc tagccttgtt gtgcaatatc atcctgaaca tgaagactaa cgtttccgga    9840
```

```
catgcaacac ataaaattaa gtaacatatc taccatgaag tacagcaaat atctactaat    9900
gtctatccat ccaacagtga taccatgcac tggcatcttg cgattacatg gacggtaatc    9960
atatccacgt tttcggaatg ttgtaaccaa acttgtccgt gttcctgcgt ttgtgtcaat   10020
tctacaacag tcaacatatc cacaaatgaa acaacgtcta aagccatcac tccaactgct   10080
acgacaaata ccgcaaaaac aacgtcaagc cttgttatta ctacaccgtc atcagtaacg   10140
attagcaaag ccgtgtctac tgcagcttca tcaaccatac tatctcaaac caatcgcagt   10200
catacaagta atgtcatcac aaccccaaaa acgcggtttg aatataatat cacgggatat   10260
gttggccaag aagtgacttt caacttcagt ggatcatttt ggagctacat tgaatggttc   10320
cggtacagtt ctccaggctg gctttattcc tcggaaccaa tatgcaccgt taccaacagt   10380
tatcatcata ctttccctcg tggtacctta tgtttcgatt gtaacatgac aaaatttgtt   10440
atttacgatc taacgttaaa cgattctgga aagtacgttg tcaagagaac acgtcatgac   10500
aatcaatacg aagaagcatg ctacaatctc acggtaattt atgccaacac gacagccata   10560
gttaccaaca ggacgtgtga tagaagacaa acaaaaaata cagacactac taaccatgga   10620
atcgggaaac atattattga aactattaaa aaagccaaca ttcccctggg gattcatgct   10680
gtgtgggcgg gcatagtggt atcagtggca ctcatagcac tatatatggg taaccgtcgt   10740
aggcccagga aaccgcgtta taccagactt cctaaatacg acccggatga gttttggact   10800
aaaacctgat atgcacatca ataaactttt ttgtatcttt agttattaat gtctgtgtgt   10860
ttattcagaa taactcattt ataatataag acggaatatt catatacatt aaaaacatgg   10920
gtgtacaata taacactaaa ctgttattag ccgtattagc aattatccca gctggcattc   10980
tagtacaggc aatttcacat gagcaaaaaa catcctaccg gcaacttttg ctgcaaagtg   11040
aacgtgtgca ataccccatc acaacagtcg agggagatac aatttgcttt aacgttagta   11100
acaacccctg caacttttcc agttattgga atcacaataa ttgtgaactt gcggttgga    11160
caccgttttt ctttgaatat gctggatata ctgaaaacac gtcgtgtcac ccacgattta   11220
cctgtattca tgatactaaa ggtctaaaac tatacaatgt aaccatgaat gactcgggaa   11280
tttatacaca acacgtttat cactgtgata ttccatgtaa catcagcgat gatcgtaaat   11340
ataacgtaga tgacattgat aactgcaacg ctactataaa tgtaaccgac tatattatta   11400
ccgtgttgtc ttcacgttat tctaaacgca ccgattacca cgtagatact tacattggtt   11460
atgcaaccac tgtggtgaca atagtatttta tctgtgtttt aacttgcatt aacgtctcag   11520
caactctaag gcacagacta cgaactagaa acaacgttaa cagcataacg tgattacaaa   11580
gtatcaacgc tagtttatcc aagagaaact ttcatgaagg atcgcaataa agcattgcta   11640
tgtatcatct ttattttaat catgtacctc atttatattt attttaaacg tcgttgtatt   11700
cctactccgt ccccagacaa agcggatctg cgagtggaat ttccctcatt accccgtgt    11760
gtcggcatac agtgcgctgc ataagaacac gcatgacaca tagcgtacct ctggacggta   11820
cagtatatga taacatgatt caaggaaagt atggattcct accgacatgt tatgacagaa   11880
cacacaggtt ttctgcgtgt tttataaaag agcgtctcga agcagcttga gccacactac   11940
ggtccagata acgagcgttg caaaaaatat gccgcgcagt agtcgaaagc cgtactgagc   12000
gtgcgaagcg ggtagggtgc cgaacgacgg atatgcgccg ttgtcatctt cgactataag   12060
gatcgcgacc gagtcttcgg gcatggtaaa agccacacgg tgtggttgat atgtagcgta   12120
tccggtttgg aatcgttcgg ctccggctca ggggatagtg aggaattctc aggggacgat   12180
atgggaccca atgactggat aaaagaaggg ttttttccag taagatgatc cccgtatcac   12240
```

```
atgaggtctg gatatatata aatgaggagt gaaataggca aagggtatca gacaccagcc    12300
tcgtcatgca gccgttggtt ctctcagcgg aggaactatc gtctctgcta atttgcaaat    12360
acatcccacc ttaagcgacg agtccataaa gcaccgttgt ccgggtacgg tgaaagtgac    12420
ccggattgta gcacgtccct tttttgtttt tgcatcgttt atcgtcacca ctagtgcaat    12480
attttgatcg taaggctgaa agagtattgt tatgatgctt agaacgtgga gattattaca    12540
gatggtactg cttgccacgt actgttatta tgttttgcg aattgttcaa tcagcacgac    12600
gactgctcct gtggaatgga agtctcccaa ccgtcagatt cccaagaata ttacctgcgc    12660
taattactca gggaccgtcg gcggtaacgt tactttttcag ggtctcaaga ataaaacgga    12720 agactttta tcttggctac tcgggtctgg ctataagtcc atttgctcgt tcttcccaca    12780
actccctggt gattctaatg agcagcatta cagatatgaa gtaaccaacc tcacgtacaa    12840
ttgtacctat gaccgcctaa cgttactgaa tctgacaatg gaaaacagca ggaattacta    12900
tttcagaaga gaagatgcga attccacctt ctactactct tgttacaatc tgaccgtgtc    12960
ctagagaacg cacgtgaagt tccacagagc cgcgtggctg tagctattgt ttacgttgct    13020
tttgaaatgt taagcgtccc tacgcgcta acatgtttct aggctactct gactgtgtag    13080
atcccggctt tgctgtatat cgtgtatcta gatcacgctt gaagctcgtg ttgtcttttg    13140
tgtggttggt cggtttgcgt ctccatgatt gtgccacgtt cgaatcctgc tgttacgaca    13200
tcaccgaggc ggagagtaac aaggctatat caagggacga agcagtattc acctccagcg    13260
tgagcacccg cacaccgtcc ctggcgatcg cgccgcctcc tgaccgatcg atgctgttat    13320
cacgggagga agaactcgtt ccgtggagtc gtctcatcat cactaagcag ttctacggag    13380
gcctgatttt ccacaccacc tgggttaccg gcttcgtttt gctaggactc ttgacgcttt    13440
tcgccagcct gtttcgtgtg ccgcaatcca tctgtcgttt ctgcatagac cgtctccggg    13500
acatcgcccg tcctttgaaa taccgctatc aacgtctcgt cgccaccgtg tagctagtta    13560
gccagctgtg tatagtttgt tgtgttttgc ttttgcgtat ttgttttcag tcagagagtc    13620
tgaaacgggg tgggagggac ttttgcgggt aatgcatgct aaaataaacg ggtgggctgg    13680
ggtgtgcttg gtaactcact gtttgaatac gcgctcacgc acatatgtag cactcaacat    13740
gttagctttt gcccgcacgc cccgggcgt gccgagctgc cttttaata aagtctgggt    13800 ttccagatac gcgctggttc tgattttgat gatttgtgcc tctgaaagct ctacgagctg    13860
ggccgtgaca tccaatcgac tgcctaactg tagcacggta actacaacag cgggtcaaga    13920
cgctgaattg cacggtccgg caccgttaag ctgtaatgtg acccagtggg gacgttacga    13980
gaatgaaagc acaccgtat tatggtgcac tttatgggga tcacgcatgc gagtctcatt    14040
aggacaccgt gtagcgtttg gctgttcttg gaaaacattt tttatttata cgttttctga    14100
aagtagcggt ggcacttact atcaaaaagg ttacaactgc accgacaaac atataacact    14160
atcttgtttc aacctaacgg tggttcctcg agcggttcaa agcacaacca ccgtaatgac    14220
acccacggtg gttacaaact ccacattcag tgtgtcactt attgcgttga gactgacgac    14280
aaattccagc gcggttggac acgctagtta tcaacgacaa cagcgtgttg aaaacgggac    14340
gttatccaag aacataacta acttggcatt cacctatggc agctggggcg ttgcgatgct    14400
gctgtttgcc gccgtgatgg tgctcgttga tttgggtttg cctcaatcgg cttggcgacg    14460
ctggcaaagc cacgtggacg atgaagaacg tggtttgtta atataggaag taaaaggcac    14520
tgttttagca tgactgtttc caaaccgtaa cgtggtaaat aaatcatggc ttccgacgtg    14580
```

```
ggttctcatc ctctgacagt tacacgattc cgctgcagag tgcatcatgt gtacaataaa    14640
ctgttgattt tagctttgtt tgcccccgtg attctggaat ccgtcatcta cgtgtccggg    14700
ccacagggag ggaacgttac cctgatatcc aacttcactt caaacatcag cgtacggtgg    14760
tttcgctggg acggcaacga tagccatctc atttgctttt acaaacgtgg agagggtctt    14820
tctacgccct atgtgggttt aagcttaagt tgtgcggcta accagatcac catcttcaac    14880
ctcacgttaa acgactccgg tcgttacgga gcagaaggtt ttacgagaag cggcgaaaat    14940
gaaacgtttc tgtggtataa tttgaccgtg aaacccaaac ctttggaaac tactccagct    15000
agtaacgtaa caaccatcgt cacgacgaca tcgacggtga ccggcgcgaa aagtaacgtt    15060
acggggaacg ccagtttagc accacaacta cgtgccgtcg ctggattctc caatcagacg    15120
cctttggaaa caacacgca catggccttg gtaggtgttg tcgtgtttct agccctaata    15180
gttgtttgta ttatggggtg gtggaagttg ttgtgtagta aaccagagtt atagtaatgt    15240 gtttttatc agggagaagg ttttgtacca acaatgacta catcggggct atctgtgtcg    15300
gaaaattatg acgaaaatta tggactcacg gaaaccgcca atacaacgcg tacaaatagc    15360
agtgactggg taacgttagg aaccagtacg ccactgttgg gaagcacgga gactgcgatc    15420
aatttcggca acgcaactac ggttattcca caacctgtgg aacacccggc tggagaagta    15480
cagtaccaaa gaacgacaac gcattactct tggatgctga ttatcgttat cattttcatc    15540 attttatta tcatctgtct acgagcacct cgaaaagttt atgatcgttg aaagacagc    15600 agagagtacg gacaagtgtt tatgacggat acagaactgt aatatactat gatgtctaag    15660
aagtgtttgc ggttatttcc atggatgaca attttgtttt gcataccaaa agcacaacat    15720
tggaactata tgacaatacc atgcgttctt aaaattggac gcggcggtca aaatatgagt    15780
ttgcctcccc ttaacaattc attgtacgga aacgatattt tcaatggta tacagacaga    15840 ccgacagtca ccaacacgtt atgtctttat caaaacaatg agtactacac acaatccaat    15900
gaagatattt caaacatcaa atggcaatgt acaaaaaacc atacgttaat tcttattaac    15960
ctaaccgcaa catatagtag gaactattac tttcaatctc ttaaaactct tgggcaagga    16020
ataccgagac cgagcagctt atgttataat gttagtgtac accttaccca ccaaacacat    16080
tgtcatacaa ccacattatc cctgtatcca cctacacctg tacacaattc attaacaata    16140
tcaccgtcat tagcttcaac caactttaca catgttgcgg tccatcatgc cgcaggtaac    16200
gttgaagcac aacacaacac tgccactcca catacaacgt ggatcatacc cctggttatc    16260
attataacaa tcatcatttt aatttgtttc aaatttcccc agaaagcttg gaataaattc    16320
acacaatacc gatacaacag tatgctcgcc gccgcttaaa gaatcaccgt cgaggaaact    16380
aaaagctatg tacgtttatt tttcagctca ctgtttgaat accgtaaaca taatgacgta    16440
catatacgtg gttatacaac aggtgtttgt gttatgcggc gactgattaa ccatatcgtg    16500
aaccatgatc ttttccgatg gtctgtcgtg accgcaatga tattttacaa gtattccgaa    16560
acctgtatgg aggtcactgt cagagtaggt gatccagtta ccctcggtag tggacatggt    16620
tatcatccag gacaaaaagt acactggtat aaccagtcat gcgtcggcat cagcaacggc    16680
gaaaatacgc atcctatctg cacctacgac cctcctaaac ctggtagaca aaagacaatg    16740
aaaaccactc cgttgccatc accactgttg tatgaatgtc acaattccac attaagcatt    16800
cttcatgtaa acgtctcaga tcccagaaac tattgcaggc gaaaatgtcc accaagggt    16860 aactgtgagt ttcccacatg ttttacatta tcgctgattt ctagaacgac aaccaccaga    16920
agacccggac aaaaaactac gctgtcgcga ttaaaaacta cgccaaataa acatacgcag    16980
```

```
cacaaaagat ccacgcgaag aacgtcactt aaagattaca atgtaacggg tctgccgaaa    17040
ggctttgcgg actcgtttac cggtaacgta gaggcacata gagccaaaga tgccgcacac    17100
agcgcatgga ttctcattgt catcatcatt atcatagtcg tcattctgtt tttcttcaag    17160
attcctcaaa gactccgaga gaaatgggac accaagggaa acctttacaa agggaccgat    17220
ggcctgccca ctacggacta attatcgtga gcggacggat atgtccggtt tcaaactcac    17280
tgtttgaata tagggacagt ccctacgaaa cctgagaaca tgtggaaatc acctgtggta    17340
gaatgctgct caggtacatt acctttcatc gcgaaaaggt actttaccta acggctgcat    17400
gcatctttgg tgtctacatc agcctccatg atgcctgcat accggtggtt ggcaagatag    17460
gtaccaacgt tacgttgaac gcggtagatg ttctttcccc tcgcgatcaa gttcgttggt    17520
catacggtcc aggcgggcaa ggctacatgt tatgcatttt cactggcaca tcaacaacaa    17580
cgtttaacag cacgcgcttt aattttcat gtctgagtaa ttacagcctc ctcctcatta    17640
acgttaccgc gcagtatagt actacctatc gtactatgac atcgctagac gattggcgtc    17700
accaaaaaca taaccatggt tttcgatgga ctttagacac atgttacaat ctgacagtga    17760
acgaaaacgg tacattcccc actaccacca ccaaaaagcc cactacgact acgagaacga    17820
caactaccac aacacaaaaa acaaccacca cgagaacaac caccaccgcc aagaagacga    17880
cgataagcac tacccatcat aaacactcca gtcccaaaaa atccaccacc ctaacagtc    17940 acgtagaaca tcacgttggt tttgaagcca cagcagcgga aacaccgtta caaccaagcc    18000
cacagcacca acacgtggct acacacgccc tctgggtttt agcggtcgta atcgttatta    18060
tcatcattat cattttctac tttcgaatac cgcaaaagct gtggctgctc tggcagcatg    18120
acaagcacgg catcgtgctc atcccccaaa ccgatctgtg agcaagtcgc gtaggaaacg    18180
attgcatgaa atcactgtga aacgccaact ccgtgccaac tggcacggcg acaggcctt    18240 tgacgtattt gaagccaggc gcgctcttga taccgaaagg atccgagggg gctttccaaa    18300
gccgacgtcc ctgattccct tcataaagct gttgaccggc cctagaaaga ccaagagcat    18360
gctgtgggcc cactgcggtc gcttcttgcg ttatcatctg ctcccgctgc tgctgtgtag    18420
actgccattc ttactccttt ttcagcggcc gcagtgggcc cacggcttgg acattgtcga    18480
ggaggacgag tggctacggg agatacaagg agcgacgtac cagctgtcca tagtgcgcca    18540
agctatgcag cacgccggat tccaagtcag agcggcgtcg gtcatgacac ggcgaaacgc    18600
cgttgacctg gaccgaccgc cgctttggtc gggatcgctc ccgcatttgc ccgtctacga    18660
tgtgcgttcc ccgcggccgt tgagaccgcc gtcatcacag catcacgccg tatcacccga    18720
actgccgtcg cgaaacggga tacgttggca gtaccaagag ttgcagtata tggtggaaga    18780
acaacggcgc gaaatcagt cgcgtaatgc gattccgaga ccctcgttcc ccccccggga    18840
tccaccatcg cagccggcag aggatgcacg agacgcggac gcagaacgtg ccgaatcacc    18900
acatagtgca gaaagcaccg tcaggcacga cgcgagtgag aacgcagtgc ggcaacggcg    18960
cgaaagacgg cgctataacg ctctgacggt ccgcagccgg gactcgctgc tcctgacgcg    19020
aatacgcttc tccaaccaac ggtgtttcgg acgcgggcgt ttgagacatc ccgcgggaag    19080
tggtcccaac accggcggac cgcgaccegg cggtgcggga ctccgtcaac tacgccaaca    19140
actgacggtc cgctggcagc tgttccgcct acggtgccac ggttggacac agcaagtctc    19200
tagccagatc agaacccgct gggaggaaag caacgtcgtg agccagacgg ccacgcgagt    19260
acgtacgtgg tttgtggaaa gaaccacgtt ttggcgtcgc acgtggattc cgggacagaa    19320
```

```
cccggcggcc gaagcgcaag aactggccgt cataccgctg gcacccacgg tgctccagca   19380
gaacgaggaa ccacgtcaac agcttacggg agaggagaca agaaattcaa cgcacactca   19440
acgtgaagaa gtggaggacg tttcgagaga ggacgcgaga gaagggaatg atgggagccg   19500
agcaagtgga aacgacgaga gaaggaataa tgcgggaaga tatgatgatc acgaggttca   19560
agagccgcag gtcacttatc cagcgggaca aggagaactg aacaggaggt cacaggagga   19620
gaacgaggaa ggtggaccgt gtgaatcgcc gccaatgacg acaaatacgc tgaccgtggc   19680
ctgtccgccc cgcgaacccc cgcatcgtgc cctgtttcgt ctatgcttag gactgtgggt   19740
ctcgagctac ctggttcgac ggcccatgac gatttagaat acaccgagcc attcctttat   19800
ttccccccccc cccatccccg gtcgcttatg cgtgtcaaac actaccaata aagataatct   19860
gccaatagca ccttatatat aatatgtggt cgcgtgtggt cttttttaagg agccctgaaa   19920
cacagacagg tatgggcggt ggccggctgc cgccgctgtg gctgccgcta ctgatcgcct   19980
ggagcgagtg gggcaactgc tgcctcgatg cgcctccggt ggtgcgttcg ccctgtctgc   20040
agccggtgcg cgaccgcaac cgcgagcgga acccgggctc accgcagttg ctgccttacg   20100
gcgaccgtct ggaggtggcc tgcatcttcc ccgcgcacga ctggccagag gtctctatcc   20160
gagtccacct ctgctactgg cccgagatcg tgcgttcgct ggtggtggac gcacgcagcg   20220
gtcaggtgtt acacaacgac gccagctgtt acatcgccgg cgggcgctgg cgttttgagg   20280
acggcggcgc ggcgcagcgg ctgagcctct cgtttcgtct catcaccgag accgcgggca   20340
cctacacctg cgtgctgggc aacgagaccc acagcctggc gaccgagacc acggcgctgg   20400
tggccgacgt gcacgacctg cgccactcgg accgctcctg cgacctggct ttcggatcgc   20460
gctcacagac gcggtacctg tggacgcccg atccctccag gttgcgcagt ataaactgcg   20520
gttgggaggg tgaacggcac cgcgtagtcc actacatccc cggcacctcg ggtctgctgc   20580
cctcgtgcga ggaggacgag cgcgaactgt gcgtgcccct catcagccat agcatcgccg   20640
acaacaactg cagccgccgg catcgagtag acggcgctag gcggcgctat catctgcgga   20700
gggattactg gctgacggat ccgaagatcg ggctgctggc cgcgggatcg gtggccctga   20760
cctccctctg ccacctgctg tgctactggt gttccgaatc gtaccggcgc ctgaacaccg   20820
aagaggaaaa cgaggcggcg gaggaaactg ccgcgggaga agcctctgcg gtagcggcgg   20880
cggccgtctc tgaggaagag cagcagcggg agtaaacggg gagagccatg aagcggatga   20940
ttcgcagtca cggcaggaaa acggaatgtc agatgacggg cgccggcgag cgacgcggct   21000
ccgccgtcgg tgcgctcatc tgcgacacg gtacccgacg cggcagcggc gccaacgaac   21060
gccgcgactc cgacgtcggt cccatcgccc acagtagcgg taccagacgc ggttcggcaa   21120
atgaaacgtc cgcctgtacg cggaccgatc accagaaggc ggacattggg ctgtggttca   21180
tgtttctgtt ttttggactg tgttcgtggt tagcgatgcg gtatcgcgca caataaattt   21240
tgaatccata tcaaggaacg cgtgttttgt attttattgg gaatattggc ggggataaac   21300
cggtttcgga tgtttaccct taatcttacc ggggacctcg ttgtcctctc cccttcttc    21360
ctcggacacc gggcttcatg ctgacgtagg taccgactgg ggtcaaaagc ctgggtactt   21420
atggggagcg cgcacaaagg accgtcaggc gccggcatgg agcgtcgccg aggtacggta   21480
ccgctgggat gggtgttttt tattctttgc ttatctgcct cttccccgtg tgctgttgac   21540
ctgggtagca agtcctcaaa ctctacctgc cgcttgaatg tgacggagtt ggcctcgatc   21600
cgtcctgggg aaacgtggac gttacacgga atgtgtatct ctatctgcta ctacgagaat   21660
gtgaccgagg acgagatcat cggcgtggct tttacttggc agcataacga gtctgtggtt   21720
```

```
gacctgtggt tgtaccagaa cgatacggtg atccgcaatt tcagcgacat caccaccaac   21780
atcttgcaag acggactgaa aatgcgaacc gtccctgtga ctaaactgta caccagccgc   21840
atggtcacta atcttaccgt gggccgttat gactgtttac gctgcgagaa cggtacgatg   21900
aaaataatcg agcgcctcca cgtccgattg ggctcgctat atccgagacc gcccggatcc   21960
gggctcgcca aacacccctc cgtaagagcc gacgaggaac tgtccgcgac cttggcgaga   22020
gacatcgtgt tggtctcggc catcactctg ttcttcttct tgctggccct acggatcccc   22080
cagcgactgt gtcagcggct gcgcattcgc ctgccgcatc gataccagcg gttacgcacc   22140
gaggactgaa cggataaccg caaaggccac gtgcaacgtt cacgctgcta taagaaggcc   22200
atgtcccccg tggacgggtc tctttgacac gagcgcggca cgccgttgcc acgagcatgg   22260
atcacgcgct cctcacacac ttcgtcggcc ggccccgtca ctgtcggttg gaaatgttga   22320
ttctggacga acaggtgtct aagagatcct gggacaccac ggtttaccac aggcgccgca   22380
aacatctacc tcgacgtcgc gctccgtgcg gcccccagag gcccgccgag attcccaaaa   22440
gaagaaaaaa ggcggccgtc cttctgtttt ggcacgattt gtgctggctg tttcgacgac   22500
ttttctttcc tcgggaggac tcggagccac tgatgtcgga tccggcacgg tctcccgaag   22560
aggaggagta acaacacac ggctaagagg atacatcatc aaagaagata ggaggggtca    22620
aaacgcggac tgaaagtata taacgccgat catgtccgag gaactgttaa taaaacgcca   22680
tgatgacaat gtggtgtctg acgttgtttg tgctgtggat gttgagagtg gtgggaatgc   22740
acgtgttgcg ttacgggtac acggggattt tcgatgatac atcgcatatg acgttgaccg   22800
ttgtggggat ttttgacggg caacactttt ttacctatca cgttaattcc agcgataaag   22860
cgtcaagtcg ggccaacggt accatttctt ggatggctaa cgtctcggcg gcctacccca   22920
cctacctgga cggggaaaga gccaaaggtg accttatttt taaccaaacc gagcaaaacc   22980
tgttagagct ggaaattgcg ttgggttacc ggtcacagag cgtgctgacg tggacgcacg   23040
agtgtaatac cacggaaaac ggtagttttg tagccggtta cgagggattt gggtgggacg   23100
gggaaacttt aatggagctc aaggataacc tgacactatg gacgggcccc aattacgaaa   23160
ttagttggtt gaagcaaaac aaaacgtaca tcgacgtaa aattaaaaac atcagcgagg    23220
gggatactac aatacaaagg aactatctca agggtaattg cactcaatgg tccgtcattt   23280
atagcgggtt tcaaaccccc gtcacccacc cagtggtaaa gggcggtgtc cgaaaccaga   23340
atgacaacag agctgaagca ttctgtacat cttacgggtt cttttccaggg gaaattaata   23400 ttacttttat ccattacggt aataaggcgc ccgatgatag cgagcctcaa tgcaatccgc   23460
tacttcccac cttcgatggg actttccatc agggatgtta cgtagccatc ttttgcaatc   23520
aaaactacac ctgccgcgtt acacacggta attggacggt ggaaatcccc atcagcgtta   23580
cctcacctga cgacagttcc tcgggggagg tccctgatca cccgacagct aacaaacgct   23640
ataacaccat gaccatcagc agtgtcctcc tagccctgct tttatgcgct ttgctattcg   23700
cgttcctgca ctactttacc accttgaaac aatacctacg taacctggcc tttgcgtggc   23760
gctatcgcaa ggtccggtcg tcatgaccag caacgccctg tatgagctgt ttcgacgtcg   23820
gttaccgcgt gcccccgtca acacggtcat gtttctcacg cgacgcactc gtgatgggtt   23880
ctgcggtcgg ttgacgtcca tcgccacgaa ttcccactac actatgttcg tgttagatca   23940
cggatccgtg cgcatcgagc gaccgagtca gtcagaagtg gattgcgcca gtttaatgga   24000
aacgctgaag cggattcggt tacgaaattc gtgggtagcg tcagaagacg agctagatgt   24060
```

```
gagtcgcagg gacgcgtgac acgaaacgcg ttcaggatta acgtaggttt tcgaaataac   24120
ctacgtccgt gagtgacgcg gtttcgtgtt gaaacccgcg cccgcttctc acggtggttt   24180
atgatgaaac cggcgttgcg gatccacgcg ggttcctcat tcaacctgcg aaaagaggaa   24240
gttgcggtaa aaccacgtca ataaagacgt caatgacacc tcaatgttgc gttggaacgg   24300
tctttatata tacaaacgcc gttatgatca gtgtccggca agatgctcgg gatacgggct   24360
atgctggtga tgctggatta ctactggata cagttgataa cgaacaatgg cactcgaagc   24420
aacaataccg ataccatctt tgtatctctc cttaccgggc ccaacggagt tactcgcaca   24480
gccatcggag gtctgtattc aaactacacc aacttaactg gagcatttgg cttcacttca   24540
acaaatatgt cagcaaccaa ctcttccgct gaggataatt ggagcgtaac caacctgacg   24600
gagagttgca tcaaccgcgg tgagtcctat gtgactacca tctggcttct ggactgcact   24660
aaaaacgata cttattggta ctatggaaat gcctacaatc atacatgtga aggtacaatt   24720
tcgggatatc tcctgggcat gtgcaagcta tggaaaagtt gggtcaataa tattacttct   24780
tataacactg tcagagtcga atcgctggga aatgaaaaac ggtgcatgct gctccctaga   24840
cagtatactc tcaacgccac ggtggaatgg tacaacaaat ctgaaggtga cgtaccagaa   24900
gaattcatgg actatgttat cctgacccc ttggctgtgc ttacatgcgg actgcaggaa   24960
gcttatatac tcgacaaagg tcgtagatac atgtatttgt tttccgtgtc ctgcgtggga   25020
atcacaggta ccgtatctat tatactcgtc tccctatcgc tgctcatcct catctgttac   25080
tatcgctgtg gccggcttct gatatgccca cgcggctttg aactcttgcc agaattcact   25140
gaggaagagg aggaaaaaga aaaattgtta acgcataatg acattgaagt ccaagtgcct   25200
attcgcacgc ggcgactact cgtcccttgg atccgggaga gcaaaatgtg ggtactacca   25260
cccccgttgc ctccacgacc tccccactta atagaattcc cgccgtctcc tccgtcatcg   25320
cctgggccca tgcacatggt ggtctgcatg ccagcatgac gaactttgga ctctgagccc   25380
caagcggtac gaactacata ttttccataa atctacactg aacttgagca caaagatact   25440
gacaatagac tggatataca gacttttata tgatccctgt acagatgtaa ataaaatgct   25500
tttatttaaa actggtccca atgttcttcg ggaatcatgg ggtggggacg ggggacgcgg   25560
tagggagcaa aaccgggtac atggggggga acatcgtcca acagtagcac cagcggattg   25620
ggtaggggtt gctgcggagg tcggtcgatg acgatgtcga tctccatcgg cagatccggc   25680
aacatctctt catctcccct accgaccagc actcggcgct gttctggatg tatatgattc   25740
tggaaaagcc tccgacgagc tcgcggcgcg tagaaagcca agcggcgcaa gggccggcga   25800
gcccgaaagt ccatgcgcac agatggcatg agtccttgag tgacggtggt gagctgggga   25860
acagggctac ctcccatcgc gacggtgaca gtggatccat gagagaggcg ccgcacgctg   25920
catggctaaa taccgtgaat cccctgacgt cgtctttcgt cccgaacgcg tcatgttggg   25980
ggcgaggcgt aaaccgtcga ggttgaaaaa ccgcgtatct gcgacccgtc cggactacgt   26040
tgttttttag aagcggccac atgacctcga gatgtcgtca cccaaggtat ttaacggcac   26100
acagccagac gcgttcgtca gcagcgacgc cgacaagacc tcagcatggc tcggaggcta   26160
tggatcttga gcttactagc cgtgaccttg acggtggctt tggcggcacc ttctcagaaa   26220
tcgaagcgca ggtaaacgga atctggggaa ttcaacacag gtaagaaata taaaaaaata   26280
acgtgattgt gaacgcggtt atcgtgtttt tgcagcgtga cggtggaaca acccagtacc   26340
agcactaact ccgatggtaa taccaccccc agcaagaacg taactctcag tcaggggggg   26400
tccaccaccg acggagatga agattactcc ggggggagact atgacgtttt gattacggat   26460
```

```
acagatggag gtaaccatca gcaaccacaa gagaagaccg acgaacacaa gggagaacac    26520
accaaagaaa atgaaaagac ccagtagcag cagcagatcc caagggttaa agaccatgtt    26580
gactattttg ttttttatta aaaagctgta aggttttgct ctaaaaacac cccgcctccg    26640
gtcttttttc ttttgtattc ggcacgcgaa acacggtttc ttcccatagc ctgtctaact    26700
agccttcccg tgagagttta tgaacatgta tctcaccaga atgctagttt gtagaggcta    26760
tgcgggatgc tgcggcggcg cgaccttccc tctccaccca gccccgtcaa acacacgcg    26820 actcgagcgg ttcgtatgaa aaataaaaaa cagcttttta tttacaggaa cggggaaaaa    26880
aaaggcacac ggtccgtggg agacgcgggt tcacgcgtcg tcaaaaagtt ggtggtccac    26940
tccgtaagga caggtaggct tatttagctt ccgcatgctc ctggttccgt aataaatgcc    27000
gttttcgtgg cagcgtgtca tgccgcgagt cacaaactcc atcaaactgt cggccacgat    27060
gcaaacgtgc tgattgttgg cagcaaagac gcgcatacag tcgtccacga agaggttgat    27120
cacgtcgtag gggctcacca accagcctaa aggttccacg tggttactgc cgaccatgac    27180
cctccagtcg ttaatctcgc tccagtcgta cagccgaatc gtggagacgc gaatgacgct    27240
gtaatcaccc atgaccatga gtcggccgcg atacgtagca cgccactgcg cgaacgcgtg    27300
gatgtgcatg cagccggcca gcgctctaag cgaggcggtg tgcggcagct cctctgggac    27360
ggtgatgaag ttgcagcgtc gcaaaccgat gttgagaaat tcagtgatgc tctcggccac    27420
aaaggtcaac gagtcagagt agatgtggtc ggtccacagg tacatggcgc ccgaggcgcc    27480
caggtacagt tcagacggca cgttgtgatc gcccttgtgt ttaagaaagt tgtaggtgca    27540
gatgctgccg acgaaacgca gcggctcggg gcagcagagg tagctggcca gacgctgtgc    27600
atcccgtcct tcgtcgcgca ccaagcgcca gcgacgccgg ataacgaggc agcggtcttt    27660
gggccagacc agggccacgc gttgcccggg tttccacggt cgcgacgtct taggaggcct    27720
ccagcggtcg agcagattga gaaaacagtc cttgattacc gacatcgcgg tcgcgcgtcg    27780
gtggacaaaa agaaatcggg ccgatccaga aaaaaaaaa acgacagcga acaccgccg    27840 tgctcgagcg aagggtggcg gagggccaga agaggcggcc ttgacgacgt tggcagcgaa    27900
aaaattggca cgcgagtcaa acgggaagta gcgtcggtgt tttatgcccc aagcagcgtc    27960
gtcgtcactc gtggcgtcac agtcaacggt gctgacgtcc tttggggcag tcggcacgc    28020 gatcgtagat gccgttgtgg ccgctgaaac gtcggttttc aaacagcagg ttaagtccca    28080
gacacatgaa cgtgttcaga ttatctccca cccggatgta gcggtcgtcg cgcacgtcgc    28140
aggcgtagac ggccccggta taggcgacga cgatggggat aaggtcgacg gccagcgca    28200 ggtgaggaaa gggcgcgttc tcgcccttga ggctgacggt tcccaggccg agaacgcgca    28260
ttccgaaagc ggttttgatg ttgcgcagca agtgaccgcc ttccacgctg ttttcgaaac    28320
acctgaggtt gcatagacgc agttccgttc ccggcgggaa cgtcaatggc atgaactgcc    28380
cgtggtggcg gatgatgaat cgtgccatgg tatccaaacc gaggctccag gcgcgcaaca    28440
gcgggcgaaa gtagcgctta accaacgacg aggtcaggta gcgcatgcag tgcagggttt    28500
cgacggcgcg cagcccgacg cgcgcaaact ccatgaggtt gcgggccagg tagtagacgg    28560
cggtgtcctc gcgtacatag caaaagacat agccctcgtc cgagatgagg cacacggcgg    28620
tcttcttctg ctgatccggc gacaacacgg cctcgttcac gaagcgaccc acgaaggcca    28680
ggcgcgtctc gcagcacagg tagtgactcc aagctttcac gtcctccggt ttgaagtcct    28740
cgtccgtctc gatctcctgc agcactaggt tccagcccgg cggccagacc acgggcaaca    28800
```

```
cctggcctgc gttgatgcgc acgtaagctt ccagacagcc caggccgaac tcggccgtga   28860
gcgccaggct agccagatcg ctcatgtgac gcgccgagtc ggtgggcgag cccgggggcc   28920
cgtcgcacac cacgctccgt cttcttgtcc tcaccgcggc cagcgtggcg aggacacttt   28980
ccgcgcccga ggctgtatct tcggtttgcc cgccggagcc ggccctcact atataacgtc   29040
ccgcccgggt ctcctccatg tatgcaggta agcaactgag ccgaacgcac ctcagcagac   29100
gagaggatgt cgtcgcggcg tcgcagctcg tcacgtcgct ctggcgaacc ctcgacggtg   29160
atttatatcc cctcgagcaa cgaggacacg ccggcggatg aggaggcgga ggacagcgtt   29220
ttcacgagca cgcgggcgcg cagcgccacg gaagatctgg atcgcatgga ggccggtttg   29280
tcgccctaca gcgtctcctc ggacgctccg tcgtccttcg agctcgtgcg cgagaccggc   29340
ggcaccggcg ccgccaagaa accgagcgaa aagaaacgat cgtcgtcacg tcggcaaccg   29400
cagatcgcag cgggcgcgcc tcgggctcg ccggcgacac caaggccgg caagtcgcct   29460 aaagtctcgc gaccgcctag tgtgccctcg ctgcccgaga acggcgccgg cggcggtggc   29520
gacgataaca gcagcagcgg cggtagcagc agtcgcacca ccagtaacag tagcagaagc   29580
accagtcccg tggcgccagg tgagccgtcc gctgccgagg gcgatgagtt ttccttctgt   29640
gacagcgaca tcgaagactt tgagcgcgaa tgttaccggg tcagcgtggc cgacaatctg   29700
ggcttcgagc ccagcgtggt cgcgccgcag cacgtcgagt atctcaaatt cgtgctgcaa   29760
gactttgacg tgcagcacct ccgccgcctc aacgaatgca tacccatgcc ggccttcgcg   29820
ctcaccagcc tcgtcgaccc cgtcttaaac aacgtagcgc ctggcgagcg cgatctcacg   29880
cgtcggataa tcacgcacgc ggtgatcatc aactattact acgtggcgca aaagaaagcg   29940
cgccacatgg tggaggccat acggaccacc gtgcgggacg acacggtacg ccgggtagcc   30000
gcgcaggtca acaaccagag ccgttcgggg cgtgcgccg cgctagcgct tcactttctc   30060
acgtcacgaa aaggagtgac ggacggtcag tacgccacgt ctctgcggcg gctggacgaa   30120
gagctgcggc atcgcggcac gcccgaatcg ccgcggctca ccgaggtcta ccagacgcta   30180
cgcgattaca acgtgctctt ctataccgcc cactacacct cgcgcggcgc gctctacctc   30240
tatcggcaaa acctgcagcg gctcaacgaa aaccaccggg gcatgctccg gctgctttcg   30300
gtcgaagaga tatgcgaaga gcacacgctc aacgatctgg cgttcctagt aggcgtcgag   30360
cttatgatca cgcactttca acgcaccatt cgcgtgctgc gctgctatct ccagcaccag   30420
ctgcagagca tctcggagct gtgttacctc atctatgtac aactgccgtc gctgcgcgaa   30480
gactacgcgc agcttagtga cgtgctctac tgggccgtca gtcaaaacta cgactacgcg   30540
ctctacgcga gcacgccggc gttgtttgac ttttacgcg tcgtgcgtca gcaggacgcc   30600
ttcatttgca ccgactacgt gtactgcgcc ctgcgtctgc tggcctgtcc cgacagacct   30660
attatcggtg acaccggcgg cagcagtagc tcccaacgcc tcgtaggcga gtttatggtg   30720
cgcgatccgc tgttgcgcga cccgcgcgcc acccacctgc gccagaaact catcacccgc   30780
gacatatgcg tggcgcggtt gcaagcgcag ccctcgagtc gacacattcc ggtcgaacac   30840
acgggtgtct cctccgtcac cctgctcaag atctttagcc aggtccccc cgacgaacgc   30900 gaagaagaca cgttacgcga gatggctctt aaagcgttta tggaagcgaa cggtaatcac   30960
cccgaacaaa tctgccgatc cccaccaccc ccgctgccac cgcgcgacta tcctcaacgc   31020
gacgagcggg accgtcaccg tcgcgaccgc cgcgacagcg gggaatactg ttgctgatgg   31080
tgggacgaaa cagcagggcg gaacagttta tgatagaaag tcacaggaaa gtatgtgttg   31140
tttttttttt aatgtaccaa gaataaaaag tgcgtctacg accaaagcgg tgtgtggacg   31200
```

```
ctcgtcctct gtcttctccg gttttttttt atgtgtgtgt ttttcttttc cttcctattt    31260
tgttacggca acagcgctga tggcacgttg ccggcttcga acatcgcgtc ggtgatttct    31320
tgcttgcccg gcgtcacacg gtgacgcagc agcgcgcggc tcacgtagca ggccgactcg    31380
cggatgacct ggccgtcggc gtcgcgtcgc aggcccgagc ggttgccgtg acgcagtcgg    31440
ccctgcgcgg cgcgctccac gtcttcaaag tagctgtgta gcaggccgcg ctccagcagc    31500
tgcggcagcg agtcggcggc gcgcaccaca aagttctcac ggctgatctc gtagcacagc    31560
acgctgccgt cggctgccac gccggccacg ctgcggtccc aactgaagag gttggcgagt    31620
ccgatggtgc cgatgacgcg caactgaccc tgggtcacca ccagcagctt ccagtattct    31680
acgtcgcgcg gggtgaggat ggtctcctcc acgtcgcaga caaacaacgt gtagccgcgc    31740
ggatagggca gatccaggtg gcgaccgcgc tggcggcgca taaaatcgtc taaattcaaa    31800
ccgccgtcgg gtgcgcgcct gctcgtcatc gccgcgcctc gtcggtcgat gaccccacgg    31860
tgcttataac gcgccgccgc ggcttcatgt ggcgtgacct ccgacctcgt gaggccgaaa    31920
acggcgtaca tgaagacgct caaacttttg aatgtgggcc cggtagcgca ccgagggccc    31980
cggggcggcg acgacggcgg gtccgagttc agcgggggcc ttgcggcggc agcggttggc    32040
gtggttgctc agctcggcgt ccgagagcgc cgagctgaac tgcggcagcc gcgtgcgatc    32100
ctgcggcgcg tccccgtgtc gcagcgagtg ccagagcagg cgctggacgc gcgccgtctc    32160
gggcgtcggc ggcgcgcgac agccccggcg cagcttgaaa acgtgcaggc acagcagctc    32220
gcgcttgatg cgcagcgaca cgctgcggta gtcgggaatc cgctgcacca gctcgagaaa    32280
gtcgcagaag gtctccacga acgtgtcctc ggtgaagcga atgcgcttca gatcgtggac    32340
gtgtttgcga aaccgcgaca gttctcgacg ttgcacgggg ttctgagcga gtcccttgcg    32400
cagcagcgca gcctcgcctt taaacagcct gatgagccgc tgcacgtccc cgctcaacat    32460
acgtatacac gccgtgtact cgtgacgtat actggcgcgc agcagccgaa tgatacgcag    32520
ggccagcacg gcgttggagg ccaggtacat ggcgtagccg cgacgcgggt tggcacaggc    32580
ccagcccgcg gggagcagaa agtagtcgtc gaccagcgtc tgcgaccagt cggcgaagcc    32640
caggtcacgt gatacgctgt cctggacgcg ggccacgtcg ccggctgtga ggtggcggat    32700
cgccggcagg tgaaacgcgc ccaggtgtcg attgcgctcc agcctcagct cggcgtgctc    32760
caaacgggaa tggtgggacg ccaccgcgga gggcgacaaa gaggagtggt cgccgccgcc    32820
gtagttaccg ttgtgattac cgccgtcgtc gcgcccgtcg ccgcactcgc aaaaggccgc    32880
gtagaggtcc ttcaacgccg cttcggctcg cgccataaac gtggcgtgga aaaaacggc    32940 ggcgcggtgc gtccggtact tgacgggcaa cccgcggcac agggccgccg gcaggcagcg    33000
gccgatgagt tcgcgctcct cgggctccag aaacaggcac agggtgccgt ccaggcgcag    33060
gtacagctcc tcggtcatcg agcatagctg ccgcaagtaa tgggtgcgcg tcccaaaggt    33120
cttgtaatcg agcaacgtgc acaccacgta ttgccccgtg gccacggcca gagcgatgcg    33180
tttggcggcg cgactgatct ctggcaagta ctgcgcctcg tgcaccagac ggcggaaagc    33240
gccggcgttg agccagcgaa aatgctgcgg atcgggcggc aagggcacgc ctcgaagcgc    33300
ggcccagaca gcgaggtccg actcgagcgt cagaccgcgg atgtcgtact tgccgtgcgc    33360
cgtagcgcag gctgaatgga ccagacagct gcggcgaatg tacaccatgg cgtgcttggg    33420
atgtttgggc gccggcgttt tcttttttctg accgccggcg gccgcagat cctcgggcgt    33480 gcgacacaac aggccggcgc gcacagcctc ctgtcgatta cgaatcggcg tcaggtaggc    33540
```

```
gcgcaggaac tggtgacaaa actcctcatc atcacgacag tcgtcgagat actcgtacgt    33600
ggtgagcgga tcgcgaaata ggcgctcgtc accgtcgtca tggtcttctt tagcctgctc    33660
ctccggctgc tgggttggcg gtggaggcgg cggctgatcc acggggttca tgactgagag    33720
gaagaagaag gtggcggcga agcgacgcgg agcgacggcg gtaaagccag acaccggcta    33780
tatagctagt catcacagtc tcctccttca cgacgcccc gtgccgctca cgctatccag     33840
cacgctacgg cccgaaaaca cgtactcgct gacgtcgtac gcgggcgatg tatggctgct    33900
caccggtttc gcggcgacgg ttgcgctcga gtccaacggc gagaagcaaa acgccgtgg     33960 gcaacgaaac cagaaggagc cctgacggat aaaaccgcgc agcgtctcgg ccaacttaac    34020
cagcatcgta ccgtacagca gtacgtgaat gccgccgtgc gcgtccataa atacggcttt    34080
gtttacgggt tccatccatc cgatgactac aaagtgagcc tgttctagca cgccgatcac    34140
aaaattgttg gcctcgtcgg cctcggccac attccacgag ccgaaagtga agtacaagc     34200 gggcgagccg cccaggcgga ttttgctacc ggcgtggagc tgacatacgc gcagcagatt    34260
ggcgcggtcg tgcagtatct gggagagttc gtacatgccc gcgaaggtgt gcttaaacca    34320
cgcgccctct acgatttcat ccacgtaatc gcgctcaaag aagctataca cggcaaagag    34380
gccgttctca aaaaactcgc cgaacgagag ccccagcacg tacaccttgt cctcgccggg    34440
caggtacgca aaggcgtgcc cgtgcccgga gacccagatc tcgggcgccg tgtttgcgtc    34500
cggcacgcat tcgtacacac tgacgaggcc gataaagtac aagcggccag cctggcgcag    34560
gcacgagaag cgccggtagg tcttgtgatc gcgcaccacc ccaaagtact gagtgtcgcc    34620
cagcatgatg ccgtgcagcg gcggccagca cagcgggagc caacgacccg ccgtggcgcg    34680
cacgtagcgc tgcaggtgaa ccccgctcgc acgctcgcgc ggcttcgggc gcttgtgggt    34740
ccaggcatca cgcagaccgc gccagatgct gctgaacttg gctgcccgc gcagatagag     34800 cgacgagagc gagtcaaagt agcccacgac gagcctgtcg ggagacacaa gagcgcgaaa    34860
atcaaaccta gagcgacgac ggtgaaaaaa ccgattataa gcgcgtgtct caaacacgct    34920
actttcggtt ataaaaacac cgtcgcccta tttctgggcg tgtgtacact gatgactcac    34980
ctacgctttt tgaacggcag tctcagctcg ggattggcct cgtacagcga gctgcggtcc    35040
acggggccga tgctctcgta gcgaaagtcg tcgatgagca gcgccagccc cacgcgcacg    35100
aagcccctga ggtcgcgcgc cagccgcacc aacttatcct gccccaccag cgccgcgtac    35160
acggtacccg tgtcgccgca gagaatccgc acgcggtgaa agaaggtctt gtcctcggcg    35220
ccctcgatct cgcccagcgg catgacgggc tcgcgcgtgt acaacgaacg ttgaaagcgg    35280
cgcagcatcg aggccgagag ccccagatcg cgcgccgtgc gcagcaccag ggaatgcttc    35340
tcggccagsa tgagggtcag ctgcgcctcg cgatgcgcct ctacgtaggc gcagcgagcg    35400
gcggtgtcct cgcaagccag caactcgcgg aaagccagca gcgaacgtag gtagcggccg    35460
cgagcggagg cgcgcgagcg gcggcacagc tcggcccgat gatcgggatg caccaagggc    35520
acgttgggtt gcagacgcgc gcagatggat tcgtgcaccg ggtcgcagcg gatcatgccc    35580
ttggcaaaaa atccggccag atccgaggcc aactcgtaca ggcagtcctc ttgcgcgtcg    35640
taggcgaaca cggcgccgta cgcgtccacg aacacctggt accggcaggt ggcgtgcgag    35700
accgtgccaa tgagatgcag agctcggaat tcgccgaaaa agtcgttctg gcagtgctcc    35760
agatcgatct cggtcagcga gtgcggcgaa tgctcgcccc cgaccacgta gatgcactgc    35820
gagggccagc ccagcgacac gcacgagccc tcgaagcgcc gcaagtaacg ccgcaggccc    35880
tcatagtcgc gtcgcacgca caggtcggcc aagtcgcgcg tgcaaaagac ctcgggtacc    35940
```

```
aagcagcgtt tgcgacgcgg ccgacgcgcg tgcccgggca gaggaggaag gcgcgacggc    36000
ggcgacgacg aggaggaaga cgccgtggcc gccgagcagc ccttgcgacg gccggacatg    36060
ccggcagtcc gcgacgatcc acaggagaca aaaagcaga agcagcagta gcctcggcga    36120
cccgctccac cccgtcctcc acacgctcag ccgcgactga acgccggggc gcgccgctac    36180
ttgggttttt atagccatct gcccccgtc tcgggcaccc gggagcgatc tacggagacc    36240
tgacagcagt tgggcaacac aagatagggga aatacaaaga cacttttaat aaaaaacgag    36300
actactttgt gtgtgtgctc cgtaaactgt ttattctccc cctccgcttc gctctggatg    36360
ggctccgggc ccgtcaacac gcgactcgcg cggcaaaagg cacgctgttg acggcgcgag    36420
agcccgtcgt gatagtccat catgccccgg agatcgtgca caaagcagct gtcgccgcgc    36480
agaaaccgac gcagcgtctc cacgtgctgc agctgccggc gcgtatcagg agccgtcatc    36540
gctgatgtcg tcatcgccct gacaggcgcg tagatggctc cgcgagatca cgcgcgtttt    36600
caaccgccgt gacacatcag gtccatcttg agctggcgcc gggcctcgcg caggtgtcgc    36660
acgcgttgtg agcgggaggc gagttcggct tcttgctcga actcctgctg ctcactgtcc    36720
gagagggtgc gataaaaggc ggcaaagtcc tccaagtcgg ctacatgcgc cctgggtctg    36780
acgctccaaa gcgtacgcag tctgatgaag cggacccatc gagcgtcacg gcacgccgtc    36840
ttgaacgcgg ggcccgggaa gaggttcttc tccccggcgc gctcgggccg gcgaggccga    36900
cgcggtttat ataccgtc tcggacggcg ggacgccgag cccgcgccgc ggccgctcat    36960
ccggagacgg cggaaaccgc ggcgccgag gaaacgggga ccggcaacga cggcggtggc    37020
ggcgaccaga ttatggggga aaaacccacg cttgtaaccc tgttgaccgt cgccgtgtcg    37080
tcgccgccac cgtcgtcgcc gctgccgctt gtcagcttca cggagctgct gttaccgccg    37140
ccgtccgtcg ccgccgccgc ggtggcggcg acagcgacga gcgaggtggg cgagaaaacc    37200
gcggagcaag aggtagcggc tgcgggtccg gagaccggga atgagagaag agaaaacagg    37260
gagaacgaag gaggggagac gaggacgaca gacaccaccg cggtcaaaag gtcgcacgac    37320
ggtatccctc gccaactagc agagcgcctg cggctgtgcc gccacatgga ccccgagcag    37380
gactatcgtc tgccggcgca ggacgtggtg acctcgtgga tcgaagcgct acgcgacgcg    37440
gaccgcgata actacggtcg ctgcgtgcgc cacgctaaga ttcaccgttc ggcctcgcac    37500
ctgacggcct acgaatcgta cttggtgtcc atcaccgagc agtacaacac ggcctcgaac    37560
gtgacggaga aagcttcgta cgtgcagggc tgcatctttc tctcgtttcc cgtcatttac    37620
aacaacacgc agggctgcgg ctacaagtac gactggtcca acgtggtgac gcccaaggcg    37680
gcgtacgccg agcttttctt tctgctctgc tccaccagcg agagctccgt ggtgctgcaa    37740
ccgctcatca ccaagggcgg gctctgctcg tccatggcgg tttacgacga ggaaaccatg    37800
cggcagtcgc aggcggtgca gatcggtttt ctgcacacac aactggtcat ggtgcccttc    37860
gtgccgcacg cctgcccgca ttacgccgtg ccttcacga cgccgggaaa gccgggctgc    37920
ggcggtgctc cgagcggcgt tgcggggttg gaggaggcgg cgcccttgg acgggtcagc    37980 gtcacgcggc atggcgcgac gctgctgtgt cgcgtggacc atctgacctg gatcagtaag    38040
cgcgtaacca cgtacggaca caaaaaaatt acgcgctacc tcgcgcagtt ccgcggcacg    38100
atggacgacg acgaggcggc gctacccggt gaggacgaag cgtggatcgc gtccaaaaac    38160
gtgcagtacg aattcatggg tctcatttc accgtcaacg tggattcact atgcgtggac    38220
gcggaacagc gccaactgct gggcaccgtg gccacctcct tctgtcaccg cgtctcggac    38280
```

```
aagatcacgg cgcgcaacat gccgcgcgcc ttttccttct acctgctgac gagcgcgcag   38340
cgcgggtacg acctgcgatt tagccgcaac ccgtcactct tttttagcgg cgacgcgctc   38400
aactgtccgc ttctcaatga gcccaacgtg ttttcgctca cggtgcacgc gccttacgat   38460
atccacttcg gggtgcaacc gcggcagacg gtggagttgg acttgcgcta cgtgcagatc   38520
acagaccggt gtttcttggt ggccaacttg ccacacgagg acgcctttta cacggggctc   38580
agcgtgtggc gcggtggcga gccgctcaaa gtcacgctgt ggacgcgcac gcgttccatc   38640
gtgatcccgc agggcacccc catcgccacg ttgtatcaaa tcaccgaggg cgacggtaac   38700
gtgtactcgt acaaccacca cacggtgttt cggcagatgc acgccgccgg agcaaccacg   38760
ttctttctgg gcgacatgca attgcccgcg acaactttc tcacgtctcc ccatccctga    38820
ccctccgtcc gtcctccttt cccgacacgt cactatccga tggtttcatt aaaaagtacg   38880
tctgcgtgtg tgtttcttaa ttattcctcc gtgttcttaa tcttctcgat cttttggagg   38940
atgttctgca cggcgtccga cggcgttttg gcgcccccca tgccggcaga acccggttgc   39000
ggccccgtac cgctcttctg gggcgacgat aggtcgaaag ccaccgtttt catgcccgtc   39060
gtgctcttga cgggggaacc tacggcggcg gttcccgtcg agcggcgtga ttgcaaagcc   39120
gcgctcgccc ccggtttcag gatggaggga gaggccacag gcggcgcatt cgatacgctg   39180
cttttggccg tagacgacgg tgggtaaacg gtggttaccg cgggatacgt cggcgtggtc   39240
gaggcggccc ggctggtgcc ggacaggcga cccggcgcgc taccgctcac ggggaccgag   39300
ggcggtcgac ctaccaccgc tttgccgccc aaagtaggtt tcaaggaagg aacaacaccg   39360
acacggccgc cccggccttt caccggagac ggggggggcac tcttggccgg ggacggagag   39420
gctgacgaaa gcatggacag cggcgatgtg gcggggaca cgacatcatc ctccgtgggc    39480
gacaaaacgg acgccgaagc tgacggctgt cgagccgaag cggaagaggt tcccgcgcca   39540
gaagtcacgt tccttgatga cgtcgtttta gacgaagccg gttgaggttg caacagcgtg   39600
gcgggtaccg tcgacggcgt gcccgacacc tgtttctcta gccttccctg aaccggtgtc   39660
gacgtcaccg tctgcgctcg ggcggacgcg tgcggcgtcg cgactcgctt gcccagcacc   39720
ggtttctggc tcgtggatgt cgtcgtcatt ggagacgata acttagcttt acgtattctg   39780
gacggcgtcg actgctcggg cgtctgactg ggaggcgaaa tgacgtcgtt gtaatcggac   39840
gacggtgttg tgtgtcccag gctgacgacg gagccggtgt ccgaggagtc gtcgtcttcc   39900
tcctcgctgt cttcgaccgg tgactctgca gtttggtccc ttaaagccca aacctcatca   39960
gcggcgttct gagacgctgt ttgtgtcacc gcggcgcgtg gagtcgacgg cctccgaggg   40020
gtggtggaca cggtgttttg agaagccgtg gaagtcgtag gcatcctgaa gggattgtga   40080
gccaggtgag gattcttgag ggcccacgcg cgttcgcgcg gccagttggc ggggttcata   40140
tccccgggca acgcgccgt cggagcccag ggcgagttac cgttgaccgg ggtttgggta    40200
cccgcgaagg taggtgtcgg ggccggagcg ggggccgtgg aaggattgac aggcgtcggc   40260
gtgaggatgg cagtgccggc gccagcaggg acgttaactc cggcgccgaa cgtcaacgtc   40320
ggttgctcga acttgtacgc ggtggtgacg ggcggtttgg cactcgtctc ggtatccgtg   40380
atgtccacca gcgtgtcggt gaaacgcgga tcttgacggt tgggggata gccatccgag    40440 ctgtcggaat cctcgtcgcc cgagaaaaga tcccctctgg tctccgtgag cggcctcacg   40500
tcccacgcgc tgtcccgacg gacccttccc gggctggcct tggtcacctg cggggagacg   40560
agactgaaag ccgcgtgacg ctgttgttgc tgcgggatgt tcaagggacc gctggtcggt   40620
ttctgactgc ccgaggataa caggccgctg aaaacgctgg aaacaccgcc accactagcg   40680
```

```
acgcccttgc cgctagttcc cggtttcttg atgggcgtaa agatgttttt ctcgtcatcg    40740
tcatcgtcgt cgtcctcatc ggcactggag ccaaagagcc tccgggaggc gctcggttta    40800
cgtgccgggg gcggtggttg ctgttgacgt tgctgcaggt tctgctgcct ctcctcccaa    40860
gccttcagct gctgtttctc acgctgcacc acctcgtcgt ccacccgttt ctgccgctcg    40920
cgacgctttt cctcttcgtc gtaatagccg acggccgccg aacgggcggc gtgggcgtcg    40980
gcggccggtg ccagagaacc atgggcctcg aagcggaacg gtttgtgtcc cttccaggga    41040
ctggcgatcc agctccagcc gtccagcggc tgcgtgggga catgtttctt gggtaccgac    41100
gagaaggcca accgccgcc gagcgagagg agattggcgt catcatcaaa ctccaacgac     41160
ggcgagcgcg cgcccaaaaa ggtgtgcgcc gactgcggga agctgtccac gtagatgtca    41220
aagtcctcga tgagcagctc cagcagcgtg tcggccgagt cgccgttttc cacggcgtgc    41280
ttgaggatat tgcgacagta gttggaatca aaggaaaggc acatacgcag ctccttgacc    41340
agcagcttgc agcgctcctg aatgcgcgcc agacatttgc gctccagctc ctcccaagac    41400
ctacgcacgt tcatgatgag acggcccgtg tacacgagct tgttgacggc gttgaccagc    41460
gccgtgttgg cgtgccggtc caggttaagg tcgagcggtt tcacacagaa catgttacgg    41520
cgcacaccct ccaggttttc ttcaatgcgc tgcacctccg tatccttgag gtgcacaaag    41580
gcgatgggtt ccgtctggcc gatggctgtg accagcgtct cgcgcaccga catcttggcc    41640
agaatgaccg cgcttacgag cgcgcgctcg acgatctcgg catcgtggcg cacgtccgta    41700
tcgaattcgg tatggtctag cacagccagg tgatcgcgcg ccttaccacg atcaccgaac    41760
gggtaagtgt agccgcgacg cgccacggcc gcgcaacgca cctcgaactc ctcgagcacc    41820
gaggagaggt cggggttgtg gaaacgcagc tcgcggtagt atcccaacca aagcatgagc    41880
tcgttgaaca gcaccgtacg ccggtgcagg cgttttttcgc cacattttttt caggatcttg    41940 gggtgtgcct cgagatccac gtcgggcttt tgcgtgagat ggcgcagaaa gttgaccagg    42000
gctaccacat cgcgccgctg tagaccgata aactgcaaac tcatgctggc ttttctccag    42060
aacccggaag cgtcgtcgcc ccggactgcg cccgcggtct gctattcgcc cgcgatggac    42120
accatcatcc acaactcggt gagcgtccca cccaaaggga gggggggtag tttaatagcg    42180
gaggcggata cgcggttttc tttaagcgc cgctgacttg tttcttctgt tttttcgccc     42240
cgtgtgctgt tccgcccaga cccgcaacaa cactcctccg cacatcaatg acacttgcaa    42300
catgacaggg ccgctattcg ccattcgaac caccgaagcc gtactcaaca cattcatcat    42360
cttcgtgggc ggtccactta acgccatagt gttgatcacg cagctgctca cgaatcgcgt    42420
gcttggctat tcgacgccca ccatttacat gaccaacctc tactctacta attttctcac    42480
gcttactgtg ctacccttta tcgtactcag caaccagtgg ctgttgccgg ccggcgtggc    42540
ctcgtgtaaa tttctatcgg tgatctacta ctcaagctgc acagtgggct ttgccaccgt    42600
agctttgatc gccgccgatc gttatcgcgt ccttcataaa cgaacatacg cacgccaatc    42660
ataccgttca acctatatga ttttgctatt gacatggctc gctggactaa ttttttccgt    42720
gcccgcagct gtttacacca cggtggtgat gcatcacgat gccaacgata ccaataatac    42780
taatgggcac gccacctgtg tactgtactt cgtagctgaa gaagtgcaca cagtgctgct    42840
ttcgtggaaa gtgctgctga cgctggtatg gggtgccgca cccgtgataa tgatgacgtg    42900
gttctacgca ttcttctact caaccgtaca gcgcacgtca cagaaacaaa ggagtcgtac    42960
cttaaccttt gttagcgtgc tactcatctc cttcgtggcg ctacagactc cctacgtctc    43020
```

```
tctcatgatc ttcaacagtt atgccacaac cgcctggccc atgcagtgtg aacacctcac    43080
actgcgacgc accattggca cgctggcgcg tgtggtgccc cacctacact gcctcattaa    43140
tcccatcctg tacgcactgc tgggtcatga ctttctgcag cgcatgcggc agtgtttccg    43200
cggccagttg ctggaccgcc gcgctttcct gagatcgcag cagaatcagc gagctacagc    43260
ggagacaaat ctagcggctg caacaattc acaatcagtg gctacgtcat tagaccccaa     43320
tagcaaaaac tgcaatcagc acgccaaacg cagcgtgtct tttaactttc ccagcggtac    43380
gtggaaaggc ggccagaaaa ccgcgtccaa cgacacatcc acaaaaatcc cccatcgact    43440
ctcacaatcg catcataacc tcagcggggt atgagctttc ctgttactt attcagaaag      43500 caccagaacc cgtcgccatt tcccctcata tacggtacac gtccccctga tctgtcatca    43560
cggtacacag atttcgcccg actgcggacg ccgacggcca atcgcgtggc gtaggagtgg    43620
cgccccggct tcattataac gccacgtcgg agccctgcg cgccacaacg ccgtccggcg      43680
caacttctgt ctcggcacgg tacgataaaa acgacgtccc ccgtcgacgt tgttttctcc    43740
gagcggtgat cgttcccgtc cctatcctcc ctccgcggcc cccacggcgg cggcctgctc    43800
gcacggacct atactattac cgccccaccg ccgtcgtcgt catgaacttc atcatcacca    43860
cccgagactt ctccaacgac gattcagtcc tgcgagccgc cgagatgcgt gacaacgtgg    43920
caggctcgat ttccaaagcg tacaagggca cggtacgcgc cgaaggcaag aagaagctgc    43980
tgctgaagca cttgcccgtg ccgccggcg gctgctcgcg ccgcaacagc aacctcttcg      44040
ttttctgcac cgaacgcgac taccgcaagt ccaccagggg catcgcacag ctcaagcgcg    44100
cgccggccga actggacccc cacgagatcc agcaagtcac ggccagtatc cgctgccgcc    44160
tgcagcccag tctccgcgag ccgcccacgc cggccgacga gctgcagacg gctgtgtcgc    44220
gcgtgtgcgc gctcttcaac cagctggttt tcacggccca gctgcgccac tactgcgagc    44280
accaggacaa ggtggtgagc tacgcgcgcg acgagttgac caaacgctgc ggcgaaaaat    44340
cggcgctggg cgtggaggtg catcaactgg tagccttgct gccacacgag cgccaccgcg    44400
aactgtgcca cgtcctcatc ggcttgttgc accagacgcc gcacatgtgg gcgcgctcca    44460
tccgtctcat cggacacctg cgccactacc tgcagaacag cttcctacac ctgttgatga    44520
actcaggttt ggatatcgcg caagtcttcg acggctgtta ccacagcgag gcctaccgca    44580
tgctcttcca gatcggtcat acggactcgg tgtcggcggc cctggaactc tcacacagcg    44640
cggcggccgg gctgcccgag gccgatgaga caacgacga gggagaggag gacgacgacg     44700
agctccgtca cagcgacccg gcgccgcttc acgagtccaa gaagccccgc aacgcccgtc    44760
gtccccgcac acgcatgccg cctcacgagc aaaagcccga agaaacgag gaggaagaag      44820 aggagctgtt tccctcctgc aaggcaaccg cagcattcct gcgggcagaa ccctccgtct    44880
ccaacgacga cggcaacggc ggcgaacgct gcgacacgct agcgaccgcc ctgcggcatt    44940
gcgccgacga agaagacgga cctctagcca gccagaccgc tgtgcgggtc gccgcgaccc    45000
cctcaccttc agtcacccca gcccttaccc ccgtcacgtc cccataacc ccgttgtgta      45060 tttaacgtca ctggagaaca ataaagcgtt gatttctcaa gttccgctct ggttttggtt    45120 tcgtttcaa agggagcccc atcatggccc aaggatcgcg agcccatcg ggcccgccac      45180 tgcccgttct ccccgtggac gactggctca actttcgggt tgacctgttt ggggacgagc    45240
accggcgcct gctgctcgaa atgttgaccc agggctgctc caactttgtg ggctgctca      45300 acttcggcgt gcccagcccc gtatacgcgc tggaggccct ggtggacttc caggtgcgca    45360
acgcttttat gaaggtaaag cccgtggccc aggagattat ccgtatctgc atcctcgcta    45420
```

```
accactaccg caacagccgc gacgtgttgc gggacctgcg cacgcagctc gacgtgctgt   45480
actcggagcc gcttaagacg cggctgctta gagggctcat ccggctctgc cgcgctgcgc   45540
aaaccggcgt caagcccgag gacatcagcg tgcacctggg cgccgacgat gtgacattcg   45600
gcgtgctaaa acgagcgctg gtccggctga accgggtacg cgacgcgctg gggctgcgcg   45660
cgtctcccga ggccgaggcg cgctatccgc gcctcaccac ctacaacctg ctgttccacc   45720
caccgcccct caccacggtc gaggcggtgg atctgtgcgc cgagaacctg tccgacgtaa   45780
cacaacgtcg caaccgaccg ctgcgctgcc tcacctccat caaacgcccg ggctcacgca   45840
ccctggagga cgcactaaac gatatgtatc tgttgttgac gctgcgacac ttgcagctgc   45900
gacacgcgct ggagctacaa atgatgcagg actgggtagt ggaacgctgc aaccggcttt   45960
gcgacgcgct ttacttttgt tacacgcaag cccccgagac gcggcagact ttcgtcacgc   46020
tggtgcgtgg gctggaactt gcgcggcaac acagcagtcc ggccttccag ccgatgctgt   46080
acaatctgtt gcagctactg acgcaactgc acgaggccaa cgtgtacctc tgcccgggat   46140
atttacattt cagcgcgtac aagctgctga aaaagatcca atcggtctcg gacgcccgcg   46200
agcgcggcga gttcggggac gaggacgaag agcaggagaa cgacggcgag ccgcgcgagg   46260
cccagctcga tctcgaagcc gatcccacgg cgcgcgaggg cgagcttttt ttcttctcca   46320
agaacctgta cggcaacggt gaggttttcc gcgtgccaga acagcccagc cgctacctgc   46380
gccgacgtat gttcgtggaa cggcccgaaa ccctgcagat cttctataac ttccacgaag   46440
gcaagatcac caccgagacg tatcacctcc agcgcatcta tagcatgatg atcgagggcg   46500
cctctcggca gacgggcctg acacccaagc gcttcatgga actcctcgac agagcgcctc   46560
tgggccagga gtcggaaccc gagatcacag aacatcgcga tttatttgcc gatgttttc    46620 gccgtcctgt gaccgacgcg gcttcttcgt cgtccgcgtc ttcgtcgtcg tcctcagcat   46680
ctccgaattc tgtttcgctg ccgtctgcca ggtcgtcatc cacacgaacc accacgcccg   46740
cgtccacgta cacctcggcc gggacttctt ctaccacggg tctcttgctc tcctcttctt   46800
ccttgtcggg atcgcacggc attagctccg cggacctgga gcagccgccc cggcaacgac   46860
gccgcatggt cagcgtgacc ctcttttcgc cctactcggt agcctacagc caccaccgac   46920
gtcaccgaag acgacgcagc ccgccacccg caccccgagg gccggccac acacgcttcc    46980 agggacccga cagcatgccg agcactagct acggcagcga cgtcgaagac ccgcgggacg   47040
atctggccga aaacctacgg catctctgaa cgcggttttt cctcttttc tacgtgtctg    47100 tctcaggacg agacgtcgat atcaataaaa ataccgtcga cgtggttttt ttaacagtgt   47160
ggttttcttt attgactagc ggagtacaca gtttacgagt aaaaaagaca gggaaaggtt   47220
atataaaatg ctgtattata tacaaaaaca tgcacataaa cagacgggac caccgtgctc   47280
gtcatcctct cctcaatcag ttgttcatgt aggcgtgtgg cggggtgagg ggcggcatgc   47340
cgttggcggc gccgggaata atgtgccgtc gaccgacgtc gcacaccttg aaacgccgtc   47400
ggcgcacgca gcggtcgcag gacgggatat cccagaggaa gcccatgtag gtctcggggt   47460
cctcgtcgtg aaagcggtag gagagttcaa agtggtgcaa cgagcccgtc cgagctcgca   47520
gcttctggcg aacaccctcc acgtcatcgg tgcacaacga cagtgctggg ctctcacaca   47580
gggcctgaag ctcctgcggc acaggtgcg tggccagggg cgagtccgtc gtcaccagtt    47640
tgacgcagtg catcaggttc tcggtgatgg cgtcgtacag gcgactctca gcctcctcgt   47700
gcgtcatcac gtttcgaggc agcgacagct cgtcgtcgtc atcctcgtca aacatgatca   47760
```

```
tggggtcagg ggttttttg ggatgttgac aggtgggtgt cttttccaga cgcacgatgg    47820
cctcacgccg gccgctgaaa cggtggtttc ggtgtccctt ctttcccatg acgcaggtga    47880
acataaccac gtcctcggcc aaacggtaga cggcgtccat ggcggggtcg tagccgtaga    47940
cgacgccgaa agtgtccacc aagacgtact ggcgtacgag gaactctttg cgttctggca    48000
cctcgtggcc cagcgcgccc aacaactggt ggtaacaggt gatgcgcggc acggtacgga    48060
tcatgagctc catggtctgg atgctgccgc ccgcgcggac gacgctgaag gatgtttcct    48120
tgaacttcat aacctctgtg ttgtgggtcc agaaggcgaa atgggtgtcg ggacactcat    48180
cgaaagggtc gtcgatggtg taggaagcgt agccccgctt ggtcacctcg ccgacaggc     48240
tctccacgtc accgcggtag agcatgacgg cgttccagta atcgtcgtac tgcaccatgg    48300
gccgctggta gtcgcgcata gtgtggaagt ggtcgcagtg acgaaagcca tgccgcagaa    48360
agtccttcat ggtggatgcc agctcgtaga cgcagtcgcg caggtcatcg tagcagtaga    48420
tgccgccgcg ctgcccgatg agcacgatga gttggtagcg cataaagccc ggaccctcga    48480
cgaagccaaa ggggtgcagg tattcctgac agcacacgta agcacctggt ggagaaataa    48540
gaaaaatcca cgcacgttga aaacacctgg aaagaacgtg cccgagcgaa cgtcctcttt    48600
ccaggtgtct tcaacgacgt ggggcttacc ttgcgaacag acggtgccca tcttgcccac    48660
gaagggcccc agggcgttgc gcgaacggag ctggatgaag cagcgttcgg gccaggccac    48720
gtgcagccgg gtgccgcatt cctgctccag aaagtcgttg agaccgttaa agtccccggc    48780
tcgaatggcg atgcagccgt aggccatcag cgtgtcccgt aggtcgtcca tgacggactc    48840
ctctaccttc gctcgccgac gctgcgcttc tccagccacc gctgcggtcg acagactcct    48900
tcgtccgcct tcggagaact acggcgcggc ggcacggcct ttatagacac tatcagcgtt    48960
gacgtcagac gatccgatga acgtcgtttt ttgtgctgga acttccctcg tcccgacaaa    49020
tgtagcggaa atcttcaagc aaatcgcgac gaagtccgat gaggaggatg caaaagaggc    49080
tgagcaacgc gatgctgccc gccgccacag tacatatgct caacaacgcc cagtgtccca    49140
acgcgcgact tttggctcgg agcagagccg aacggcggtt tctccacatg acagataacg    49200
tggtccagta cgtccatcct ttgcattccg gcgtccagac gggaagcgtt gtcatgttag    49260
ttcccgtaaa ggtcgtgttt tgtcttgttt tgtttctcat gagtttaaca gtccttttta    49320
gaaaccgcgg gcacatgtct tgtagaaaga tgtaatcact ctccgcgtat gtcgctaggg    49380
ttgacatcac agtggtagtg ttttccgaag aagtgacgtt gtcagtgata ttgtcagtga    49440
cgttaatttc ttcccagtgt acggataact cgaacggtgt cgtatgcgcc accgctctca    49500
acacgtaact acggccggtg aggttaagtg ttagttgtcc cacggtcaca ttggtgtcat    49560
ttgtaaaaca cgcgatttct ccgcgaactt ccgtgacgtt ggtttcacgg gtctcgttga    49620
gaacacgcag aggaaaccag ccttccagat gatactggaa accaaacgta agcatgacgc    49680
tatgccattg tctccgtggt tgccgaaacg ttacgttcag aggcagtttg gcttcggctc    49740
ctgcgcaagg cccgttatag atttgcgtgt cattgcgcgt acagtttaac cggcagttca    49800
tactcgtggt gttagaagtg atgttaacac ccgtgccgtg gtacgtgcat cggaccgaaa    49860
caccgtgtcc cgtgctccaa aacagcgtca acaacagcca cacagacacc tacgtggaga    49920
cgacacggga cttttattg acggagactc acgtttctac cctcccctttt cccgtaggta    49980
aaacccacg tttatcacac acgttgtttt tacctgaaac ccgcgcagcc cgtggacgcg     50040
acaaaaaacc gcggcactag aaagaaaatg aaacaagtat gttttattaag cagcatgtgg    50100
ggctaatagg ggggataact gaggtatagc aactatgaaa aaatactaca aaaaaaaag     50160
```

```
ctgaacatgg tcatctagca gcaaagttct ccttctagac cacgaccacc atctgtacca   50220
cgtcgccctc cccggtcgtg tacatcacat ccttcaccac gaccggtggc aacggcggcg   50280
acgaggacaa ctcgctctcg acggaggccg ggacgacaga ggacgggggg gtggtggcgg   50340
cggaggacgg aggggtggcg gcgacagcgg ggtcttcttc cgacacgggc gacggcaggc   50400
tcggcggcgc ggacagcacc cgttgcgccg gggcgtgaga aggctgagcc ccggtggcct   50460
ggatgtgggc caacgaattg gctcgcagcg agtcgcgatc cacgaaggtc ataggaattt   50520
tcccttcgcg gatccgccgc tcagattcca ggatggcgcg cacgtagctg ttcaccgact   50580
tggcaaaagt gcgcggccct tccgtattct tgtcgcgacg cgcttccagc acctgctttt   50640
cgtagtccag ctggtggaag accatcacca ggtcgtccat agtgtgcgcg tgctgacgga   50700
cgtgggagcg cacctccacc gggaacaaag cgttccaata ctccagcacg atggcaccgt   50760
gccagaactg cgccatgctg ggcgccagga aaaacaggat accggagtcg taggcgaaca   50820
cgtcccactt gggcgtcatg aacaacacca gctgacgcgt gggccgcacc gaagcttcct   50880
cccaggcctc gatgaccccg aacatgatga gctcctggtc caacgggggg cagtgtcgct   50940
ccagccaact gatcttgctc aggttcatct gcagaaactc gtaagagggg tcgcagatgc   51000
acacgtagag acccgagtcg tgccgcagcc tggctccgcg cttcatcagt ttcctcaccg   51060
cgtagcgaag cgccaccttg cccaacgccg acgcctggat cagtccccc acgtccatct   51120
gcgtctgtcg ccactcggcc tcgtccagca ggctcgtgat agcggaagtg ctatgcgtgg   51180
tcgtagtcat cctttctatc cttctctatg aatagcagca atagcggtaa agtcccttct   51240
tatactatcc cggagtctgt ggttttttt gtttacccct gcttactggt gagactgctg   51300
ggggccgttg tgctgcagca gctgagctcg tcgccgccgt tgccacagga accggtgcct   51360
ccgcagggcc tttttgaggg cctcgcaggc ttctcgcgca agtcctgaga ggccctcggc   51420
gtcgatgggg ttcacctcgg gcgtccgagc ctcgtttct tcttcttcat cctccctttc   51480
ctcctccgtg tcctcccgct ctgtgtcctc cgttacgctc tcctcccgg cctcggccaa   51540
gagcgcagcc accaagtcca cggaccgctc ggtctccgag ttctcaccgt caattacgcc   51600
atgttggcgg cgtaaccggt gccgagaacg ccgggtgagc gcacatgctt ttttctttct   51660
taaccaaggc gggagaggat cttcaaggcg ttttcgctgg atccagcggt agctaaagta   51720
ccaaaaggcc agcaggccca cgctacctaa cagattcacg tagactggag acataattaa   51780
agaaagaagt gaaacccgcg tgtgggtctc acgtcgtctt gaaacaccgt cttatataca   51840
tgaagatgcc ggacatgacg cgcccaagac acgtggggtt tccccttag gggacccggt   51900
ttcttaagat gttttcatc ttcgcacgcg atgtactaca tcaaagggtc ggctgaccga   51960
ccgcattgac gcacagtttc cgagtacgcg cgtctcggag cacctgacgg tgagccaccc   52020
agctcacgcg gataggggac aacactgacg tgaggggcga ttcacgtcac tgacggctga   52080
cgggaataag acgggtgagg gatttccacc tttttcttaa gtgtgactct ccttacggta   52140
aatcgcacct gtgacctctt aaccctcct ccctggtacc caataacagt gaaaaacaca   52200
caccacacgt cacgacaccg atcgattttc tttattctta gtgtgatgat aggtaagggc   52260
actcgtgagg atgtgcagtt atcattatca agccttcttc aaggcgtagt gatgatcgtt   52320
gggcagaacc cccaagctcc tagcgatctg ggaatagaag gaggagaacg accccagggc   52380
cagaatgccc acagtgtaca tggcccaggt ctccagaccg aacgtggcgg gtcgcagctt   52440
cagatggtag gccacccgct ccgagagttg tgaatgctcg ttcaggcaac aggactgcag   52500
```

```
gtgggtgagc ccaaaagcgc tttcgtttac gccgcgcacg tgcaccgtct gggccgggca    52560
atcctggtgt tgcgcgcgaa aatggtcctg acaggagatt ccgtctacgt ggcggcgcgt    52620
gttgttaccc acttcgatca gcaacgtgtt atcggcagga tgatgcgaga acgcgacgac    52680
ggtgttgctg gaggtctggc ggcagcagta cacgtcgagc gtcatgaggg ccatgtcgcc    52740
ttggtggtac acggcgtacg cccaaccctg gaacacgagc ggacatcgcg gaccgtgagc    52800
ggacatcgcg ccggcggttg ttaccgtcgt ctcggcagga gaacacaata aactcctgat    52860
cctcatacac aggagtccaa gcgtcagaat taaagtccgc ggagccataa ccgcgcaagt    52920
gaagccgata cgagtgttgc tgaatttgtt cattctgccg actgttgctc acgagcgttc    52980
ggaggcggtg ccacaggctg ttggccatta aaaagtcctg gcccgaatga cgacgagaca    53040
gagcccgagg cgaagaaaaa ggcgcccgtc atgaagacgt aggcagggga attcccatat    53100
ttttatggct tcttttaaaa gtctgtatcc gactccatcc ggcgcttttc ccaaaccgtg    53160
gtctcctcgt cgtccgactc ggtacccagg aggtggtaag tcttttgccg cacgtagaaa    53220
gctttcaacg tggagcaaaa aatgagaata aagaccccga aaacgaaaca aaccacgccg    53280
atcatgccga tgcagacgtt catgtcgacg tagccggcgg tgctgttggc ggtgcggcaa    53340
aagagtgtca tgtcgtgcgt gcacaaaaaa caacacacac cacaggccag gtcgtagcgt    53400
agttattatt ccgtagcagc aatgatggta cagtcaagca catgctctat ttcccgttac    53460
cccgatgatg atgatgatgt tgtccccgtt gcagtggaat tgtcccggtt aatcaccacg    53520
gtgaacacca cggccaagaa aatgatccct aatatagcga ccactaagag agcaaaagtc    53580
catttccagc cgttgtcaaa gtacgccccc gtggtgggat gcatggtggc gggcatttcc    53640
atcatatcca tgtcgaacgt gtgtcgcggc gacggcgaac taaccaggca gtacgggggt    53700 cgataggggcg gtgggctgca gtcggtggt ggcggcggtg gcgtggaaac cgtcgtcggg    53760
cacagaccca tggcctgctc gtaggtgggg ggcgcgtcgt cgtgatcccg gtcgcggagc    53820
atcggcgtgg gctccatgtc ggtggcagtg acggcgacgg tggtaactgt ggtggagacg    53880
gtaccgacgg cgtccgcggc tcaccttcga gcaaagagcc ccttcttttt gcgcaaacga    53940
cggcaaaaca gttctctggg acagccgtg gcgcggtaag cgggtgccac gctttcaggg    54000
tgggtaaaac agtcgcgggc gaagcagtag ttgttgcaga accgcaaaaa cccgacgcga    54060
aagaagccca ggagtccgcg cgccagaaag tgcgcctgcc gcgtctcggg atgcacgccg    54120
aagacggcgc cgctctcgtt caccagtatg gagatgtcca ggcgctgctg cgactccacc    54180
ggcacggccc gcaccacaaa tacctgcagc acgttcagcg agcacgtctc ttttaaccag    54240
ttgccgtggg ccggatcctc gtaagtctgg ctcccgttca agacgaccgt cgtcagcgcc    54300
tcattaccgt ctcgccagct gaagatggaa ccctcgcgct tcatgcacag gcgccacagg    54360
gccagcaggt cgcgcgccaa catgaactcg cgacccacgt cgccgccggt ctcgaagcgg    54420
acatagccca gttcttcgcg cagcggcgcg tagttgcgca ggccctcctg cacgaagccg    54480
cggaaaccgg accgcgacac caggtacagc gattccacca cgggcgagta gacgtagacg    54540
cggccgccct cgccgatgag tacgggtagc ggtgggcggc cgatggcttc gcaacgactc    54600
acagtgccca ccggcagcag gaacttgtcg cagcacagga aggtcttctc caaacctta    54660 atattgagat gtccaaagta gccgacgcgt aacaggtcgc agtaggtgaa aaaccaaccg    54720
ttcggccagc tgagacgcag caccgtgccg ctgacgcgac gaaccagctt ctgcaggtcc    54780
ttgcgggcgt cggcggtgac agagcagcgg aaggtctcgt tgaccagctc gacagccagc    54840
gcgtcctcca gcgtacgttc cttcatctcg tcgttgatgc tctggcggcg ccgccggatt    54900
```

```
tcgtcgaaac gagccgcgga ggcggcgacc gacgcggagg tcgtccgaac gccctctgtg   54960
acgctgtcgt ccggccagtc aagaaagcta aggctggcgc tgcgccgcct aaagtgtccg   55020
atccgcgcgg gacgtcgctg agggacggtg gctggtctgc tggggcgggt acggccgcgg   55080
gtgtccgcgg acacgttagt tatacacgga attgagtcac gtggcacgtt gccagctgaa   55140
accgccgtcg tctccgccgg cgttttctcc atcacgggac cgcgccgtgc gcgcgttccc   55200
aggcacgcgg cccacgctct acccgcactt ttgcttcttg gtgttaggga cgaactcgaa   55260
cgttacagaa tcctcgctgt cgctctcctc tttcgcgtcg ttaaagtaat tgccggagtt   55320
gcgatccaaa ccgccgcctc ctcctcctcc gccgccgccc gatccaccct tggacgtcag   55380
gtagctggtg atcttgtgct gctcgtattt ttccttggag gaaagaccgt ggtcgtgatc   55440
accgccgccg ccaccgctgc tcattttccg cgtaccggaa ccaccgccac caccgcggtc   55500
gtgcttcttg ccgccaccgc cgccaccctc tcccagaccg ccgagaccca tgggttcgtt   55560
catgagatcg ttatccagac ccgggccgtc gtcgtgcaga ccgccggcat tggccagcga   55620
agagaggctg ccgccaccac cgccgccgcc acgcgacttg ccgctgttcc cgacgtaatt   55680
tttatcgaag ggatcgccac gctggaaagg ttcctcggtg agaaaattct ccacggcgaa   55740
cagaccgttg cgactggcca cgtacaacag cgtgtcgtgc tccgtaacta tacgcaacgt   55800
gcacggcagt ttggtgacgg cgcaattgag cagcgtctgg tagaagttct tcagctgcac   55860
gttgatacgc atgttttta cgccgtggaa actgacgcgg ttattggccg tgaattccag   55920
ctcgctgccg ttggtcagga tgaatttgat ggccggcgga ccggcgtgca ccagaatctg   55980
cacggtgccc gtagggcagg gcgctttttt aacgttacgc ttgacgcggg tatgcggccc   56040
gatccactta agcaggtcgg ccaccacgcc gaaatctaga tccacgtgca cggccgaatt   56100
ctcgctttcg cgcacaatgt cttggccgtg cacgcaggcc gagctgaact ccatattgaa   56160
atcgggcgcg cacatggaga tcttggccga aaggtccgag atgtcctgca cgtagaactt   56220
ggtcaggtcc ttgctggaag tcaggtacat gaaattaccg agcagcggcg tggaattgtt   56280
aatggtcttg ggctgaaacg acttgtcagt gatgtagaga catgagctgt taaaagtgat   56340
ttttgacacg cagtgactgc gtaccgtttg caagataagc gacggcgtgg gcaagaaggt   56400
aaccgtggtg ttctccttga gcgcacggat cacagatcgc agctgctgga tagccgtctt   56460
gtacggcttc agccgcagcg ccagcgtcgg cggctccgag aggcgcgtct tgcgatccat   56520
cccggacagc gtgcaagtct cgactaagga gcgggcgcga gcgagcgaaa gttttataga   56580
gagcacacac gacgaccggg aacgctgcga agacgcccgg cgtctaataa tacagccgcg   56640
ccgagccagc gggcccccga ctaagaggca cagtacttat atactccgac cttaaagcgc   56700
cagtggtacc acttgagcat cctggccaga agcacgtcgg gcgtcatccc cgagtcatag   56760
tagaaaacca gggccacgca ctggtccaca aacacgctca ggttcacggc cgccatttcc   56820
acgtcgtttt ggatcgccgg cgccgcctgg aacagacact cgctcgcctt accctcctcc   56880
tggtgctgct ccaaccacgc gtaattcacc acgggcacgc gcagcggcct ccgcaccacg   56940
gtggggaagt aacactcacg gttgggcggg cacaatgacc acaccgtctc ctcctcgaac   57000
acggtgccgc gcgaagccca cactgacggc gtcacgcccc acagatgcgc cacctcgtcg   57060
tcgggaccca ccgccagaaa ctgacagttg cgcaatccga actcgagcat gtcggcgcgc   57120
agcgcttccc agcgcgcgct ggcgatagag agccgcggca accgatacaa ttcgaaaatg   57180
aatttgccct cttgatagat ggtgcgttcg aaccactcgc agcgcggcaa acccgacttg   57240
```

```
cacaaatcga cgctagcgcg caccgcggca aagtacatgt gctcaaagat gcgctcgatc    57300
aagtcccaag aggcaaagta cgtgaaccct aaccgcatga gcgccgtgtg caagccggcc    57360
acgccgatgt gcagcggacg cagttttcc agcgcgctct ctacccacca ttcggacgct     57420
gacattagcg cgtccaggcg cgcgttgccc caaaccaccg cctcggtcac caactcgcgc    57480
agcacgctca aatcaaagta acgtcgcgtg ttccccaaaa ccacgtcggg tagatgcagc    57540
ttctgctcgt cgctacgcgc aaacacgcag cgagccacgt tcaccgtcag ccgctgcacc    57600
ggcatgtcac actcgccaaa gtggcacgac gccatatcgg gactcaagca cggcggcagg    57660
cacacgctgt cggccataat cgagtacttg actacgtgat ggacaaagac caccgaggca    57720
cggcccttga gcgcgcacag caacatcttt ttcagaaaat cgtccgtgtt cacgatcacc    57780
ttggggcacg attgctcgca gcgcgaatac tctttctcga aagccgactc ctgacccagg    57840
tccgagagcc gccgggagac aggccgcccg aacagcgagt agcgctgctc acgcgcacgg    57900
tatcgcttca ttaacacgct aggcacgttg aaagcgtagc aaaccccgt caactccgac     57960 gtgctttctt tgagaataaa gttaatcacg cggatagcgg ccacgtccca catgtccaca    58020
aacacacgta ccacgggtcg atgcacctcc ttctcgcgta tcaaatcgca gtatcccccc    58080
aggcaacgaa tcacgctgtt cacatcggcg ttaagtcgcg ttacgttcac cgacacagaa    58140
acgccgcaac tcaaggtgct catccatttg cacatagccg cccaactggc gtcacgcgaa    58200
aaagggtcgg ccgagatcag aaagtcgtac tgcggcacgc gatcgaaacc cacggtagac    58260
atggtgaagg tggacagcga cagctgccca tcgcgacagc gcttcaacac cgattccaac    58320
acctcgcctt cgaaacgcgc atccagatgg aaacgataga tgcgcgagtg cctactgttc    58380
tcgatagccg ccgtcaacgc cacggcgatg cgcaaaaaca cgccgcccgg actctcgtcc    58440
tgtccgtgca gttggcgaca caccttatcc aaacacaaaa tggccgcgta caagcccag    58500 caaccggcca attccacaaa acgcgccgtc tcctcggcca gcttgggtag atcctccatg    58560
tgacgcagca caaaacggcg caccgactca tcgcacagct ccgaagcgta acacagtggc    58620
gtgcggcttt cacgcgccca gttggctttg aaataaaagc gacccaacag cagatcgcaa    58680
cgcggcgagt gacgaattag acagggaccg tggcgcatga taagctgaaa cagcctgaaa    58740
ctgcccaaac cggcactgtg ccgcgacacg gtgtccatct cgcgccacag cgcgttcctg    58800
tcggacggca gctcccgtgc cggctcctgt acgccgcaaa agcgaaactt gccccaatag    58860
ccgtgacaat gacactttt gcccatcaac atgcgcgtag cctgtatcgg cggcgatact     58920
ttgcagagcg aagccccgaa atcgtcctcc tcctcgacac tgtccagctc catcctggtc    58980
gcgccggtcg gattgaaggt gctcaaaccg ctactcacgc gtccaccgcg actgggcacg    59040
gcggaaccgc tgtcacgcgt caacgacagc acagacggcg tgccgtcagg agacggcgac    59100
tcgggacgcc aactgacgac gccgccacca ctcgtaaaac ccgctacaca cgctacgccg    59160
ctcgacatgt tagtattttc agcggatgct tccttgtcac ccccgggcag cggcccttcc    59220
tcgagctcgc tgtcatctcc cccggtagta tcagcgacgg cctctgccga cgattcctcc    59280
gtctcggttt ccgcgccgcg gctcggaatc ctacctggcc ggcaccgatg tgcgggcacc    59340
gaggacaccc gctgttcctc gtccgcgtca gccgagtca taagtttacg aggaaaagaa     59400
caaagaaatc aggtagattt caataaagtg agtctagatg gcgccgataa ctacggttta    59460
taaagtctgt gtgcgatgtg tttatttttt tcttctgtgt ctcctccccg tatgctgtca    59520
gcgccgctca gacgaattct cgaaagtctc ccaattcgac gctaaagttg tccaaacgga    59580
cgacggacag tttgagttct ttgtgtacca ggaacgaggt gtgaatgtcg tcagccaggc    59640
```

```
accagcccag cttttgtatg accccggtac acagagggat ctggcgtggg cgcgtgatgc   59700
gacggttgac aaagctacag cgctcgcggg cgaactttcc gcgtgcaacg tcgaccaggg   59760
tctgccagtg tgcgatgctg gaggtgagca cgtagatgcc gggacgtgtt tcgggcccgt   59820
catagtcata gacgatgatt aaatacacgt attgcagccg tccccgggtc tcttcccacg   59880
tcagatacat gtctttcggt atcatcaacg cgaacacctc cgttttgagc gtgttgtaaa   59940
ggtagccgcg catgacgcag gtgagcaacg aggtgatgcc cagcgagacg tcttgacgc    60000
agcccagcgt ctcgaggcgg cggtgcagca gatgcgggcc cagatccagc cactgcagcg   60060
cggcgcgcgc ggccgaggcc gtgtacacgc tttcgagcag gcagcgcgtg ctggccgaga   60120
cgttggaggc gcgaatgcct aacaggtaga ggctaatgta gaggtgtcgc ggcgagtcgc   60180
aacccgtctc catgcggatg agcagcgcgc ccggctgcgc ctcgaactct accaggccct   60240
cgggcacgaa gaaacgcgcc gtgagcgcct ggtgatcggc gtggtagagg tagcgcaccg   60300
atatagtatt tacctcgcgt ttggctttga gcgccgtcac tagttcattg tcctcgtcgg   60360
ccgggtcgcg cggccgtttg gccaccgcgc gcgcgtccat gatggcgagg cgcacggtag   60420
atttcaaaaa gttgatagag cagctgcggg cacgggccac ggacaaagcg gaggcgttaa   60480
ataccgtgag ccaattggag atcggcgcgg tggatgccca ggacgtgacc gcgagcgccg   60540
tgcgcgcctt cgtgggtgcg ttgccgagct cgggctacca ctttggcttc gtgcgtcaga   60600
acgtggtctt ttacctccta agccacgcca cggtacagac ggcgcgcgac ccgctgtacg   60660
ccgccgagca gttgcacgaa cagctggacc gcttcctgcg acaccagcac gacggcggcg   60720
gggacgagga ccggttgccg ttctaccaca acggggccac actgacggct ttccagaagc   60780
tgttgcagac cctgcgcgag atccagaccg taatagccga acagagcggc ggcaccgcgg   60840
cagcggcgga cttgatcgcc agtaacaacg cgtcgaccga gcgccgcggc aagaagggcg   60900
gttcgagttc cggggggccag cagccgctgg tccgccgggt gatcacgcag ctggaaacgg   60960
ctgccacgga ggcgcggccc tacgtcaatt gtcgcgccgt ggccgaactc ctggacctga   61020
cctaccagcg gctcatctac tgggcctgca cgctcatgcc ctacgtgttg tttcggcgcg   61080
acaccgacac cgaactggac acggtgcttc tgatgcattt tttttacaca cactaccgtt   61140
cggttaacgg cgatttggcc gtggagtttc aaaactacgt caagaacagc gtgcggcaca   61200
tgagctcttt cgtcagttcc gatatcgacg gcgaccagaa gcccggtgcc gaacacatgc   61260
gtgacgtcag ctacaagctg ttcgtgggta atctgcaggc gcgtgacgcc agcggcctca   61320
tgtttcccat cattagcacg cgcatctcca ccgtgaacct ttacctgtcg cccgaacgta   61380
tgttttccca cccgggtctg atctcgcgtc tgttgagtga ggaagtttcg ccacgcgcca   61440
acctagacgc ttacgcgcgc gtgtgcgatc gcgtgctgga agaccacttg catacgccgc   61500
gacgcgtgca gcggctactg gatctgacgc agatggtaac gcgactggtg gaactgggtt   61560
tcaatcacga tacctgcgcg gcctacgcac aaatggcgct gatccagccg ccagtcaga    61620
agagctcgct ctttgtcagc gagattcgcg agaaactcat acagatcatc tacaatttt    61680
acacgttttt catgtgcctc tatgtgtaca gccccacgtt cctgttcgac caccggcggc   61740
ggttgatttt ggagcagcat cgatccacgt tgatcggctc caaggaggaa ctacagcacg   61800
tctggagcaa cgtgatactg aacgtcaata cgcactttgc ggttcagtac acggaagaag   61860
actttgaggc acatacgaag ggtgccacgg aggcggagcg cgagtacctg tatcgggacc   61920
tgcacagcaa gtggggcgtg cacctgtttta ccttgcgtcc gtctcgcggc gcggccggcg   61980
```

```
cggcctcgcc tttgcctccg cttgacggcg tcacacgctc cgacatctta cgcgaatgcg   62040
cgctcgttaa tctgaacgaa ggccgcgtca actacgcctc cctgctagcc ttcagtcatc   62100
atcccgagtt ccccagcatc ttcgcgcagt tggtggtggt aactgaattt tcggagatct   62160
ttggtatccc gcagggcctg tttcaagccg tgggttcgcc gcgtcttttt gcgctcattc   62220
agctgtgtcg tgtattgttg cccgagcagg tgacgctgta ccagaacctg gtctccatct   62280
acaacctgac caccttttgtc aagcacatcg acgccgcggt ttttaagacg gtacgcgatt   62340
gcgtcttcga catcgccacg accctcgagc acctcagcgg tgtacccgtc acgcccaatg   62400
tggacctgct ggccgagctc atggcgcgct ccgtagcgca taacctgtac accaccgtca   62460
acccgctgat cgaggacgtg atgcgcagca gcgccggcag tctgagaaac tatctgcgac   62520
acacgcgact ctgtttcggt ctggcgcgtg ggcgggcgcg cctctcggag gacggcgtga   62580
cggtgtacgt ggaggtacag ggtcagtacg gactgcgcgt acctaccacg cgtttcgtag   62640
aacagttgcg cgagctggtt cgccgcgatc ggctgttggc cgagaatctg cgcggcttga   62700
atgagcgcct gctgagtgtt cgcgtgcgcg tacgtcagat cagcagcgac acagaggaag   62760
taagccgaca cgccaagggt caccgcacgg tggcccagat gagcaaggcg ctcaaaaaga   62820
cggcctccaa aatcaaagtg ttggaaacac gcgtgacatt ggcgctcgag caggcgcaac   62880
gttccaatgg cgccgtcgtt accgcggtgc aacgcgcgct agccgtctttt gacgtactaa   62940
gtcgcgagaa cttggaacgc cgcggcgcac agctctgtct gacggaagcg acgagcctac   63000
tgcaccgaca tcgcgcgcta gcgccgatga cctggcccgc gggcacgggc gttgcggcgg   63060
cggccgaagc ggatcgcgcc ttacgcgagt tcttggaggc gccctgggaa tcggcgcccc   63120
aaccgccgcg actccgcatg acgcccgaca ccgatcacga agaatcgacg gcaggcgcga   63180
cgtccgtacc ggaggtcctg ggtgcgcgct acgaacccgc acacctggcc gcgagcgacc   63240
tattaaactg gtacatcgtc cccgtaagcc aggcgcagca ggacatcttg tcttcgatcg   63300
acccgcccgc cggctcgaca tcggtgtccc tgccgccggc ctcgccatga aagtcacgca   63360
ggccagctgc caccagggcg acatcgctcg ctttggagcg cgagcgggca atcaatgcgt   63420
ctgcaacgga atcatgttcc tacacgcctt gcacctgggt ggaacgagcg ccgtcctgca   63480
gaccgaggcg ctggacgcca ttatggaaga gggcgcgcgt ctggacgcgc ggctagagcg   63540
cgagttgcaa aagaagctgc cgccggcgg gcggctgccg gtctaccgac tgggcgacga   63600
agtgccgcgc cgcctggagt cgcggttcgg ccggaccgtg cacgcgctct cgcggcccttt   63660
caacggcacc accgagacgt gcgacctgga cggctacatg tgtccgggca tcttcgactt   63720
tctgcggtac gcgcacgcca aaccgcggcc cacctacgta ctcgtcaccg tcaactcgtt   63780
ggcgcgcgcc gtggtcttca ccgaggacca catgttggtc tttgatccgc acagctccgc   63840
ggaatgtcac aacgccgccg tgtatcactg cgagggtctc catcaggtgc tgatggtgct   63900
cacgggcttc ggcgtgcagc tgtcgcccgc tttctactat gaggcccttt ttctctacat   63960
gctggatgtg gcgaccgtgc cagaggctga gatcgccgcg cgtttggtct ccacctatcg   64020
cgaccgcgat atcgacctca ccggcgtcgt ccgggaaagc gcggacacgg cggcgacaac   64080
gaccaccgcc gcaccttcct tacctccgct gcccgacccc atcgtcgacc cgggctgccc   64140
tcctggcgtg gcgcccagca ttcccgtcta cgatccctcg tcctcaccca aaaaaacacc   64200
cgagaaacgc gcaaggacc tcagcggtag caaacacgga ggcaaaaaga aaccccccgtc   64260
cacgacgtcc aaaacactgg ccaccgcctc ctcctcctcc tcagcgatag cggcggcctc   64320
ttcttcgtcc gcggtaccac cgtcctacag ctgcggcgaa ggggccctgc cggccctggg   64380
```

```
ccgctaccaa cagctggtcg acgaggtaga gcaggagttg aaggctctga cgctgccgcc    64440
gttgcctgcc aacaccagcg cctggacgtt gcacgcggcg ggtaccgaaa gcggcgctaa    64500
cgcggcaacg gccacggcgc cgtccttcga cgaagctttc ctcaccgatc gtctccagca    64560
gctcatcatc catgccgtca atcaacgctc gtgtctgcgt cgcccctgcg gcccgcaatc    64620
ggcggcgcag caggcggtac gcgcctatct gggcctatcc aagaaactgg atgcctttct    64680
gctcaattgg ctgcaccacg gcctggatct gcggcgcatg cacgactacc tgagccacaa    64740
gaccaccaaa ggcacgtact cgacgctgga tcgcgcactg ctggagaaga tgcaagtcgt    64800
cttcgatccc tacggacgtc agcacggccc ggcgctcatc gcctgggtgg aggagatgct    64860
gcgctacgtg gaaagcaagc ccactaacga actgtctcaa cgactgcaac gtttcgtaac    64920
caagcgaccg atgcccgtta gcgacagctt cgtctgcctg cgacccgtag actttcagcg    64980
tctgacgcag atcatcgaac agcgacgtcg ggtgttgcaa cgtcaacgcg aggaatacca    65040
cggcgtttac gagcacttgg ccggcctcat caccagcatc gacattcacg acctagacgc    65100
cagcgatctg aaccgacgcg aaattctgaa agcgctgcag ccgttggacg acaacgccaa    65160
gcaggaactc tttcgcctgg gcaacgccaa aatgctagag ttgcagatgg acctggaccg    65220
tctgagcacg cagctgctga cgcgcgtgca caatcacatc ctcaacggct ttttgccggt    65280
agaggaccta agcagatgg aacgcgtcgt cgagcaggta ctgagactct tttacgacct    65340
gcgcgacctg aaactgtgtg acggcagcta cgaagaggga ttcgtcgtca tacgagaaca    65400
actgagctac ctcatgacgg gcactgtgcg cgacaacgta ccgctactgc aagagatcct    65460
gcagctgcga cacgcgtacc agcaagccac gcagcaaaac gagggtcgcc tcacgcagat    65520
ccacgacctg cttcatgtca tcgagacgct ggtgcgcgac ccgggcagcc gcggctcggc    65580
gctgacactg gccttggtac aggagcagct agctcaactg gaagcgctag gcggcctgca    65640
gctacccgaa gtgcagcagc gcctacgaaa cgcgcaactc gcgctaagcc gcctctacga    65700
agaggaagag gaaacgcagc gtttcctcga cggactctcg tacgacgatc cgcccaccga    65760
acagaccatc aagcgacacc cacaattacg cgagatgtta cgtcgcgacg aacagacgcg    65820
tctgcgactc atcaacgccg tactgagcat gttccacaca ttagtgatgc gactggcgcg    65880
cgacgagtcg ccgcgaccga cgttttttga cgccgtcagt ctgttgttgc agcaactgcc    65940
acccgactcg catgaacgtg aggatctgcg tgccgccaac gccacgtacg cgcagatggt    66000
caagaaactg gagcagatcg agaaagccgg taccggcgca tccgaaaaac gcttccaagc    66060
gttacgggaa ttggtttact ttttccgtaa ccatgaatat ttctttcaac atatggtcgg    66120
acgactgggc gtcggacctc aggtaacgga actctacgag cgatatcaac acgagatgga    66180
agaacagcac ctgaacggc tagaacgtga atggcaagaa gaggccggca agctcacggt    66240
aacttctgtg gaggacgtgc agcgtgtctt ggcccgggca ccgagccatc gtgtcatgca    66300
tcaaatgcaa caaacgttaa ccaccaagat gcaagacttt ttagacaagg agaaacgtaa    66360
acaggaagaa cagcaacggc agctactgga cggctaccaa aaaaggtgc agcaggattt    66420 gcaacgcgtg gtggacgcca ttaagggcga gatgctctcc accatcccgc accaaccact    66480
ggaggccaca ctcgagctgc tcttgggcct agatcaacgc gcccaaccgt tactggacaa    66540
gttcaaccag gacttgctgt cggcgctaca gcagctgagc aaaaaactag acgggcgaat    66600
caacgagtgt ctgcacggcg tgctgacggg tgatgtagag cgacgctgtc acccgcaccg    66660
agaagcggct atgcaaaccc aagcctcgct aaaccacttg gaccaaattt tgggtccaca    66720
```

```
actcctgatc catgagacgc agcaggccct gcaacacgcc gtccatcaag cgcagttcat   66780
cgagaagtgt caacagggcg atccaactac agccatcacg ggcagcgagt tcgagggcga   66840 cttttgcacgc taccgcagca gtcaacagaa gatggaggga caattacaag agactagaca   66900
acagatgacc gaaactagcg agcggctgga tcgctcgctg cgccaggatc ccgggaacag   66960
ctccgtcacg cgtgtacccg aaaaaccctt caagggtcag gagctggcgg gtcgaatcac   67020
gccgccaccc gccgacttcc agcggcccgt cttcaaaacg ctgctagatc agcaggccga   67080
cgcggcccgg aaagcgctca gcgacgaggc cgatctgctg aatcagaaag tacagacgca   67140
gttgcgacaa cgcgacgagc agctgagcac ggcgcagaac ctgtggactg atctggtcac   67200
gcgccacaaa atgagcggcg gactggacgt gaccaccccc gacgccaagg cgctgatgga   67260
aaagccgctg gagacacttc gcgagctgtt gggcaaagcc acgcaacaac tgccgtacct   67320
gtcggcggag cgcacggtgc gctggatgct ggcctttctg gaggaagccc ttgcgcaaat   67380
caccgcggac cctacgcacc cgcatcacgg aagcaggacc cactaccgga acctacaaca   67440
gcaagccgtc gagagcgccg tgacgctagc gcatcaaatc gaacaaaacg cggcctgtga   67500
aaattttatt gcacagcatc aagagacgac tgccaacggc gcgtccacgc cgcgggtcga   67560
catggtccag gcggtggaag cggtctggca gcgactggaa cccggacgcg tagccggcgg   67620
cgccgcgcgt catcaaaaag tgcaggaact gttgcagcgc ttgggtcaga cgctaggcga   67680
cctagaactg caggaaacgt tggcgacgga atactttgcg ctgttacacg aatccagac   67740 cttcagctac gggctggact ttcggtcgca gttggaaaag atccgcgatc tgcggacccg   67800
ttttgcggaa ctggccaagc gacgcggtac gcgtctctcc aacgagggag ccctgcccaa   67860
cccccggaaa ccgcaggcga cgacttcgct gggcgccttt acacgcgggt tgaacgcgct   67920
ggaacgacac gtccagctgg gtcaccagta tctgctcaac aagctcaacg gctcatcgct   67980
agtctatagg ctggaagaca ttcctagcgt gcttccgcca acgcacgaga ccgatcccgc   68040
gctgataatg cgcgaccgcc tgcgtcgcct atgcttcgcg cgtcaccacg acaccttcct   68100
tgaagtggta gacgtcttcg gcatgcgaca aatcgtcacg caagccggcg aacccattca   68160
cctggtcacc gattacggca acgtagcctt taagtacttg gcgctgcgag acgatggccg   68220
gcccctggca tggcggcgcc gctgtagcgg cggaggactc aagaacgtcg tcaccacacg   68280
ttataaagcc atcacggtag ccgtggccgt ctgtcagaca ttgcgcactt tctgccgcga   68340
gatctcgcag tacgacctac gaccctacct cacgcagcat cagagccaca cgcacccac   68400 ggagactcac acgttacata accttaagct cttttgttat ctggtgagca ccgcctggca   68460
ccagcgcatc gacacgcagc aggagctgac ggccgccgat cgcgtaggaa gcggcgaggg   68520
tggtgacgta ggggaacaaa gaccgggccg cggtaccgtg ctgcgcctga gtctgcaaga   68580
gttttgtgta ctcatagcag ctctgtaccc cgagtacatc tacaccgtcc tcaagtaccc   68640
ggtgcaaatg tcactaccct ccctcacagc tcacctacat caggatgtga tacacgcggt   68700
agtcaataac acacacaaaa tgcccccccga ccacctcccc gaacaggtca aggccttctg   68760
tatcaccccc acccaatggc ccgccatgca gctcaataaa ctgtttttggg aaaataaact   68820 ggtacagcaa ctgtgccagg taggcccgca aaaaagcaca ccacccctag gcaagctatg   68880
gctctacgcc atggccacgc tggtcttttcc acaagacatg ctgcaatgtc tgtggctaga   68940
actgaaaccc cagtacgccg agacctacgc ctcggtgtcc gaattggtac agacgttgtt   69000
tcagattttc acgcaacaat gcgagatggt gaccgagggg tacacgcaac cgcagctccc   69060
caccggagag ccggtgcttc agatgatccg cgtgcgacac caggacacaa ccaccacaga   69120
```

```
cacaaacacg accacagagc caggactttt agatgttttt attcaaacag aaaccgccct    69180
agactacgcg ttgggctcct ggcttttcgg catacccgtg tgtctcggcg tgcacgtagc    69240
cgacctgctg aaaggccaac gtgtactagt agcgcgccac ctcgaataca cgtcgcgaga    69300
ccgcgacttc ctccgcatcc aacgctcccg ggacctcaat ctcagtcaac tgctccagga    69360
cacgtggacc gaaacgccgc tggagcactg ctggctacaa gcccaaatca gacggctacg    69420
cgattacctg cgtttcccca cccgcttaga gtttattccc ctagtcattt acaacgcaca    69480
ggaccacacc gtcgtacgcg tgctgcgacc gccctccacg ttcgaacagg accacagtcg    69540
gctggtgttg gacgaggcct tccccacctt cccgctgtat gaccaagatg ataactcatc    69600
cgcggacaac gtcgctgcgt ctggcgccgc tccaacaccg ccggtacctt caaccgcgt     69660
gccagtcaat attcagtttc tgcgtgaaaa cccgccaccc atcgcgcgag ttcagcagcc    69720
gccgcgccga catcgtcatc gagcggccgc ggccgcagac gacgacggac agatagatca    69780
cgtacaagac gatacatcaa ggacagccga ctctgcatta gtctctaccg cctttggcgg    69840
gtccgtcttt caagaaaacc gactgggaga acaccacta tgccgagatg aacttgtggc     69900
cgtggcgccc ggcgccgcca gcaccagttt cgcctcgccg cctatcacgg tgctcacgca    69960
gaacgtcctc agtgctctag aaatactgcg gctagtgcga ttggacctgc gacaactggc    70020
gcaatctgtg caggacacta ttcaacacat gcggtttctc tatcttttgt aaccgacact    70080
gacagtagcg ggtaataaaa acaagaggat tgttatcgtt tttttatgat aaaaaaacaa    70140
cgtgtcattt tcacggtgat ttattcttgc tattatttt ccccatgggc tgtcagcgtc     70200
gggtgcgcga cactgctacc atgcgcaaca ggtccagttt aaaggcgcac ttgtcgttaa    70260
acaggctgga catgcgtgta tatttgctca gcatggtggc cagcaccggg tgggtggcct    70320
ctgagatctc ggtcggcaac tccaaaacga cgttgacgac gtgacggtgt ttttcgtccc    70380
gcttgttggc caccgtgggt cccggcgcgg tgttagacat ggggcaggcc gtgggggag     70440
gacgaggagg aagtcgctgc taaaccgcca cgcgcctgct gcacaatgtg ccgccgacg     70500
tggcaggcgg tctgtttaac cagcgcgcag ccccgacaca gcgggcgcc gtcttcgctt     70560
tccaaacagc tgtcgcggta ctcgcccgtc tgacagcgcg cgcacagcag gccgtgcccg    70620
tgcgaagtga ggcgcaggag acgcgggacc gtcacgccgc gtaccaccac agtggagtcg    70680
caggtgcgtg ccgcgcaggg cagaatgacg tcgaaagcca ccggtgatc gtacacggcg     70740
caagccgcgt tgaggcccag cacggctttc cagcccacgc gtacgcagcg ctgtccaaag    70800
agcgtctcgg agacgagctc gtagacgcgc tgccgcacca cccgctgact gccgcagagc    70860
gagcagtgta cgagctcggc gtgcgtgttg aagatgacgc tcttttcttg acggtcccga    70920
taatagaaca tcgagttgag cggaaaattt tgctggcagt gtagcttttc cttacccagg    70980
ttgaggcagt gtccgcactg ccgacagacc acggccacca gcgagcgcgc gtccagatgg    71040
cgctcgcact tgagtcgaca cagacaccag agcggcaggt cgatgacgct gccgatgagg    71100
ccgccgcgca gcgcggcgct gagtgcaaag aggacgatct tggtgggctc tacgtgacgc    71160
gcctgctgtc cggcgcccgc gtgtcctacc gccgcagctg ccgccgtcga gcctcctccg    71220
cgcgtctcgt cgtgcagacc cagtgcccgc aacggcacca ggtatcgcgg acacgtgtcg    71280
caaaacgtct gcaccgcttg tcgggccagt acgtagagcg ggtttccgca gggtaccttc    71340
ccagcgtgcc ggcgcaaggc tgcgatgagg ccccgcagct gcggcgaccg cggctgccgt    71400
tggtgacacc actggttacg gtggtatacg gccaaatcag cgcgggcgtc gaagcgcttg    71460
```

```
gcgcgtagta gtgctaggca cggcgagctg gtggggtgaa gcacgggcag ccgaaggtcc   71520
accccgaaaa ggaaacggtg aaggtcacct agcagcgagg cggtgacacc gtccaacaac   71580
gcgtgcagcc gctcgggcgg gtagagccgc agacggcgca gcaggtagtc ggtgtcgtag   71640
cgttcgaaac gcagaaaggc catcgtgcgg acggccacgg tgtgcagaca gtccatgctg   71700
tagacgtaag cgagaaacac aaagtagggc ttggtcataa ccatacgctg aaagagcgcc   71760
gtcaccgcct cccgctcggc ctgccgacac accagccatt cgcgcaggaa gcgttggtag   71820
agacggtcgc ccagctcccg attcagaaag cgcttatccg tcacgaagag atgaaggacg   71880
caagaacgtg gcacgtgatg caccagctgc tgctggagga ccgccgacgt ctgcgccgca   71940
aactgcgccg gtggctgcga cgtttctacc gccgcttcct ccggctgcag cgcaccgcgg   72000
ccgatcacca gctgcacatg gaaatggtcc tcgtgaacgc agaggggcgc gaagagacgg   72060
cgcagagcct ggtggaactc atcagtcgcg gtgtgcggag cgtgtcggag acgacgactg   72120
gccatgaccg cgccacagca gagccagcac cagcagaaga gccagcacca gcgggcccag   72180
agtcgcaaag cgcgcgggca gccacggccc agactgcggt cgcgatggcc cggagcgcgc   72240
tcgccaccac gatgacggtg cccaacgata accagtccgc tccaaggacg gcgcgcacgg   72300
cggagacggc ggatgacggt gatgggtcga cacccctcgc cgacgactca cgtgctcctc   72360
cagaggccga cgcgcggacc ctccgacgtc ctggcccgcc gctgccgccg ccgccttccc   72420
ttctcccgcc agagccagca actcctcctc ctcttcatca gcgtctccct cgcttgcgca   72480
tccgcatcgt cccatacagg cctcacaacg acacagccgc cacgaccccg ccgccatggg   72540
tggcggcggc ggccgaggcc cggcagcggc gccgccagcg gcgaccatgg tgggagagca   72600
actcggatga cgaggaggag gaggaggagg gggagatgcg gtccgagagg accgctttcc   72660
cgccgttcgc gtgagcgcgg ccgacatgcg ggcgcgccac agggacggac cgctgccgct   72720
gtgactgctt acggtgacgt ggttccggac cgccaacgac gtcgacgcgg cttcttggc    72780 gtacagctcg cgcagcagat tctcgtactc gccctcgttt cgggtccga aggcgatgag     72840 ctcgatgttg aagaccgacg ccgaattgga tttgcgcacc acgcacttcg tcagcactcc   72900
gtaggccgag ggcttgatct cctcgatgtc cttgagcgtg acgatgagcg actcgttcac   72960
cttaagcaca ttgaactcac ctacgtggcg cgccggcgag acgagcttga cgggcgctcg   73020
cacaaaacag cagagggaga cggcgcagcc agtgttttta aagataaaac aaggcacgtg   73080
gtctgtgcgg ctctcccagt agctgagcag atactcgaca caatagaccg tgtctgtctt   73140
gagcatggcg tcgcacaccg agtaattggg attttttacag ataaggccgg cgtcggtgac   73200
gcgcagctcg ctgggaccca acttgaggat acgccgcgtg gcctgcacca gatcctgatg   73260
gagaaccttg ttcatctcca tcgcaccgac gccaccgccg atttatttac ccggcgccgg   73320
ctcgtctttt ccctccagga ttccgttaat gtccatgagc ttgctgacga tcgccgttaa   73380
tagttgcgtc ttctcacgga ggatctctcc gtgactgcag gtcgcgcagt cgccgtgcac   73440
gtacttgagg aaggcggcgt acttctgacc cgcgttcacg aaatttaagc gcgcgtccag   73500
ggagggcagc aacagatcgt agacgcgcgg cagcatcggc tcgaactgta atagcagatc   73560
gtcgtcaaga tcgggtagcg cgtgcccgtc ttcaccgtcc tcgtcgtcac cacctccccc   73620
ctcgagccca ccgctcgtac cagccgcggg ctccgcgtcc tcgtcgatca ccagcggtcg   73680
cgtcggcacc ggagaatcca cgtcatcctg cacgtcgttt tcctcctctc cgtcgtcatc   73740
gtccagaaac ggcacccgct gcttagccca ggacattctt tctccgcgtc ctcaatcagc   73800
ggcgccgatc gccatgaatc cgagtaccca cgtgagcagt aacggcccaa cgactccccc   73860
```

```
ccacggggcc cacaccacgc ttcttccccc gaccagcccg gccccgtcca ccagctccgt    73920
cgccgccgct accttgtgca gtccgcaacg acaggccgtt tcgcgttaca gcggctggag    73980
caccgagtac acccagtggc actcggactt gacaactgag ctgctatggc acgcgcaccc    74040
gcgtcaagta cctatggacg aagcgctggc cgccgcggcg gccgcctcat accaggtgaa    74100
tcctcaacac cccgccaacc gttaccgtca ttacgaattc cagacgctca gcctcggcac    74160
ctcgggggta gacgaactgc tcaactgctg tgcggaagaa accacgtgcg gcggcacgca    74220
atccaccgta ctcaccaatg cgaccaacac caccaactgc ggcggagccg tcgccagcag    74280
tagcaacgca ggacctgccg gcgcttcggc cgcctgcgac ctagatgcgg aactggccgg    74340
cctcgaaacc tcggcggccg actttgaaca gctgcggcga ctgtgcgcgc cgctggccat    74400
cgacacgcgc tgtaacctat gcgccatcat cagcatctgc ctcaaacagg actgcgacca    74460
aagctggctc ctcgagtaca gcttactgtg cttcaagtgc agctacgcac cccgtgcggc    74520
gctcagcacg ctcatcatca tgtccgagtt tacgcatctg ctgcagcagc acttttccga    74580
cctgcgcatc gacgacctgt tccgacacca cgttctcacg gtcttcgatt tccacctgca    74640 cttttttcata aatcgttgct ttgaaaaaca agtgggcgac gcggttgata cgagaatgt    74700 caccctgaac catctggccg tggtgcgggc catggtcatg ggcgaagaca cggtgcctta    74760
caacaagcct cggcgccacc cgcaacagaa gcaaaaaaac aacccttatc acgtcgaagt    74820
gccgcaagaa ctgatcgaca actttctaga acacagctca cccagccgcg accgcttcgt    74880
gcagcttctt ttctatatgt gggccggcac cggcgtcatg agcaccacgc cactcacgga    74940
actcacgcac actaagttcg cgaggctaga cgcgttatcc acggcctcgg aaagagaaga    75000
cgcaaggatg acgatggaag aagaggagga tgaagaaggg gaagaaaaag gaggagacga    75060
tccgggccgt cacaacggca gtggcaccag cggggggttc agcgagagca cgctaaagaa    75120
gaacgtgggt cccatttacc tatgtcccgt acccgccttt tttaccaaaa accaaaccag    75180
taccgtgtgt ctgctgtgcg aactcatggc ctgctcctat tacgataacg tcgtcctgcg    75240
cgagctgtac cgccgcgtcg tctcgtactg tcagaacaat gtgaagatgg tggaccgcat    75300
tcaactggta ttggccgatc tgttgcgcga atgcacgtcg ccgctcggcg cggcgcacga    75360
ggacgtggcg cgctgtggac tcgaagcacc cacctcgccc ggaggcgact cggactatca    75420
cggcctgagc ggcgtcgacg gcgcactggc gcgacccgac ccgtattttt gccacgtcct    75480
gcgtcaggcg ggcgttacgg gcatctacaa gcacttttc tgcgacccgc agtgcgccgg    75540
caacatccgc gtcaccaacg aggccgtgct cttcggacgc ctgcaccccc accacgtcca    75600
ggaggtgaaa ctggccatct gccacgacaa ttactatata agtcgacttc gcgacgtgt    75660 gtggctctgc atcacactct tcaaggcctt tcagattaca aaacgcacct acaaaggcaa    75720
agtgcacctg gcggactta tgcgcgattt cacgcagctg ttggagagtt gcgacatcaa    75780
gctggtggac cccacgtacg tgatagacaa gtatgtctag cgtgagcggc gtgcgcacgc    75840
cgcgcgaacg acgctcggcc ttgcgctccc tgctccgcaa gcgccgccaa cgcgagctgg    75900
ccagcaaagt ggcgtcaacg gtgaacggcg ctacgtcggc caacaaccac ggcgaatcgc    75960
cgtcaccggc cgacgcgcgc ccgcgcctca cgctgcacga cctgcacgac atcttccgcg    76020
agcaccccga actggagctc aagtatctca acatgatgaa gatggccatt acgggcaaag    76080
agtccatctg cttaccctc aatttccact cgcatcggca gcacacctgc ctcgacatct    76140
cgccgtacgg caacgagcag gtctcgcgca tcgcctgcac ctcgtgcgag gacaaccgca    76200
```

```
tcctgcccac cgcctccgac gccatggtgg ccttcatcaa tcagacgtcc aacatcatga   76260
aaaatagaaa cttttattac gggttctgta agagcagcga gctactcaag ctctccacca   76320
accagccgcc catcttccaa atttattacc tgctgcacgc cgctaaccac gacatcgtgc   76380
cctttatgca cgccgaggac ggccggttgc acatgcacgt catcttcgaa aactccgacg   76440
tgcacatccc ctgcgactgc atcacgcaga tgctcacggc ggcgcgcgaa gactacagcg   76500
tcacgctcaa catcgtgcgc gaccacgtcg ttatcagcgt gctgtgtcac gccgtctcgg   76560
ccagcagcgt caagatcgac gtgactattt tgcaacgcaa gattgacgag atggacattc   76620
ccaacgacgt gagcgagtcc tttgagcgct acaaagagct cattcaggag ctgtgtcagt   76680
ccagcggcaa caacctatac gaggaggcca cgtcatccta cgcgatacgg tctcccctaa   76740
ccgcgtcgcc gttgcacgta gtttccacca acggctgcgg ccctcctcc tcctcgtccc   76800 agtccacgcc gcctcatctc cacccgccgt cgcaggcgac gcagcccac cactactctc   76860 accaccagtc tcagtctcag cagcatcatc accgtcccca gtcaccaccg ccgccgctgt   76920
ttctcaacag cattcgtgcg ccttgacact gtacggcaga aaagccggct ccaagtgcaa   76980
gcgccgcggc agcaccatgt gcaaaaactt gtccttgcgc gcggtttcgc cgccgggaaa   77040
gacgggcgac agcacgttgg ttacagcctt gagaacctgc tcaaagtact tgtcggtgtg   77100
aatgggcacg ccgtgctcgc gcacgtagct cggatcttcg gctacctcgt agttgcacac   77160
ggccgacggt ggtttccgcg ccctcttctt tgccggctct cctcctctcc tgttgctctc   77220
ctctaccccg ccgccgtcag cgtcgtcgtc cgtgccatca atcgcgtccg accgggaaac   77280
cacgccggcg gttacagaat caccgttgtc ggaggaaccc tgcggcgccg tccggacacc   77340
gggcgccgtc aggacgtaaa agacccgatc cccgaccgag ggtagctcct cagaacgggc   77400
cgccagtcgc ttaatgacgg caatgtgcgg caggttagat tgacggtaca acgagatgtc   77460
cttagaaagc accgacgaaa gcaccaggtc ctcgacacgc acacggtgca ggtacagatc   77520
gtcgcgggcc tgcaccaggc ggcgcaagat acgccagaaa ccgcgtggca cgccgtattt   77580
cttgacttca tcgagtgaga ggcgcgacag gcgcacggct gcttccgaga cctcgcgatc   77640
ctcaaagagc agcgagagga cgtcacgcgt gacgcccttg acgaactcgc aggccgtctt   77700
gcgcaccaga tccacgccct tcatgctcag acccgaggcg ccctccactt tgccgatgta   77760
acgtttcttg cagatcatca taagagagac gaagacccttt tcaaactcca gcttgacggg   77820
ctccacaaaa agacaggccg tcacgtagtg cgccaggctg ggcccacgcg ccaccagagc   77880
ctgcggcgtc aggccacgaa agcggacaaa cacgctgtcc gtgtcccgt agatgacccg   77940 cgcctccacc cgccgttcgt ccgagccccc tgacgatgtt tcgagcccct ccggtaacgt   78000
gctgctctcc tccgaatccc cctctcgcgt tctcactaca tagtcttcct gattaaaaaa   78060
attgtgcaaa aaacacggct ctgaaaaatt gtctttgatg aaccgcgccg tgcgctctag   78120
catgtcgcga ccgatgcgcg tgatgctggc ggcgatgggc agacacggca tcatgccgtt   78180
gaccacgccg gtaaaaccgt agaaagcgtt acacgttact ttgagtgcca tctgttcctt   78240
atcgagcagc atacggcgca cggggtcttg acactcgcgc atgcattcgc gcacggcacg   78300
gcgctgcgaa acccacttgt tgagcagttc cgaaagcacc gagacgcgca ccgaagcacg   78360
cacaaagcgg tgagtcacgc cgttctctag cgtgacgctg tatacgtcgg cggggtccac   78420
ggggtactcg ccacccggca ccagcagggt ggagtagcag aggttgtgag ccatgatgat   78480
ggaagggtag aggctggcaa agtcgaacac ggccacgggg tcgttgtaat aacccacctc   78540
gggctcaaac accgtggcac cctggtacga aaccgccgca gtaccgccgg cgccgtgact   78600
```

```
gtcgttggaa acgccgacgc tgccactact gccggagccg acgctgaaaa cgccgacgct   78660
gctactactg ttactgccag agccgggtaa aacgccgtcc tgactcgacg gcgcagattg   78720
caagggcggc gacatctgaa acatggccgc cacagaaccc gcgtcgccgg gcacggcagc   78780
ggtagagatg atagcggcgt taggtgacac ggcaacgcta ttcgtttcgg gcaccgtcgt   78840
acctttgctg tagtggttgg gcaggataaa atcgcggcag gcgcactcgt ccagcagcga   78900
ggtgtagata cggatctgct gtccgtcaaa gatgacacgc cgcaacggaa ttttagccag   78960
ccgcgcgatg gccccggcct cgtagtgaaa attaatggtg ttgaacagat cgcgcaccaa   79020
tacggcgtcc tgcagacagt aacggcctac ctgggcgcgg ccctcggcat tagccacgaa   79080
acaacgcggg atgtccttgt aggacaggtc atccttgcgt tgccgcaggt aaagctcggc   79140
catagtgttg agcttatagt tgggcgagtt agtcttggcc atgcatacgg ggtacatgtc   79200
gataaccacc gaacccgcaa tatacacctt ggtggcggcc gtgctggccg gattgttgtg   79260
agaagccgag ggaaaggcgg cggcgtactg ccgcttaaaa cccacggcgg ggctgtgtaa   79320
aaagaaacgg ccgccctgcg ccgtgggcaa cttgcagaag cgctgcgagt ccaccttata   79380
caggtactcg aggcgcgtga ggatgtactt caagtcaaaa gagttgatgt tgtaaccggt   79440
cacaaaggcc ggcgcgtacc gttgaaagaa aagcataaag cccagcagca gctcgtattc   79500
ggaagggaac tcgtagacgt ccacgtctgg gcccacctgc ccgcaggtgc cgatcgtaaa   79560
gagatgaaga cccgagtgcc caaagatcac accctccgaa gtgcagcccc gaccatcgtt   79620
cccgtttggg atcccctgat ccacggcggt gtttccccccc gtctcgtagc acacgcacga   79680
gatctgaatg acaatgtcat cggacttctc ggcgcaggga aaaccaccct cgccgctcat   79740
gcactcgata tcgaaggaca ggcatcgata gcgcggccac gagctgtcgt cgggcacggc   79800
caccaggtca gagacatcgc agtcgacctc gatatcacaa gtcgacgcgc gaccctgctg   79860
ccgccagtcg taacgattca cggagcacca gccgaacgtg gtgatccgcc gatcgatgac   79920
caaacgcgtc agcggatcca cacggacctc gtacacggga aaaccctgct ccagcagata   79980
ctcgccgatt tttctggcca tggtccagtt gctgatagac acacactgca aatcgggcac   80040
gggtcgcgtc ccgtacccgt agatggaggt cttggtggcc ggcgtgacag acacggcgta   80100
tggcgtccgc ggctcgggca ctagttcgcc cacgctggca atgacctcac gcagcctatc   80160
ggtgtcgctg tactcacagt aaaagtagct gcgctgcccg aaaacgttga cgcagatact   80220
gtagccgtgt tctgtggccc cgaagaaacg caacacgttc cccgaaggca ccagatgctg   80280
acgatagcgc ggcgacacgt tttcgggcga gtcgaagaag agcacggcgt ccgtctgatc   80340
gtaggtgtga aaacgaatag gtcccaccac gcgacccacc agggtctcgc gccaaggaca   80400
cggccaaacc atgtcatgac tcaacaaatg tttaatctct cgatagaaca tgagaggcag   80460
ccgtcccgtc ttatgcttga tcaaccccgt ctgaccgtcg aacatgacgc ctcgcggcac   80520
gatctgcaaa aactgtttct gtggcggccg cttcccgag ccctgcgcgg agccgggctg   80580
cgaacgctga cgccggccac ccgcgaccgc accgccggtc acgccgccgc tcagatacgg   80640
gttgaaaaac atagcggacc gtgagaggct gacagcttac gaagcacaat cacaaagaaa   80700
atacacatgc agcacctaga tatccagttt gaccccgtat atcacaagtc tctgtgtcac   80760 ttttttttgtc tgttttttttt ttcttctcct ggttcagacg ttctcttctt cgtcagagtc   80820
tttcaagtgt cggtagccgt ttttgcgatg tcgcagtcgg tctagcaggt tgggcttctg   80880
tcccttgtcc tgcgtgccag tctgtccgtc caaagaatct gtaccgttct gctgcgctcg   80940
```

```
ctgctctgcg tccagacgga ccagggccag aagcatctgg taagcctgct cgttggtgta    81000
aggcggagcc gccgtggatg catcagacga cggtggtccc gatcctttgc gaccagaatt    81060
ataaacactt tcctcgtagg aaggcggagc ctgtaacgac gtgtctttgg tgttgcccga    81120
cgtcacggtg gtcccgttgg cggacaccag atagggaaag aggttctgca gcggctgcat    81180
gcagagacgc cgctgtcgag tatagatcaa ataagtgata atgactacgg ctatggccac    81240
gaggatgatg gtgaaggctc cgaaggggtt tttgaggaag gtggcaacgc cttcgaccac    81300
ggaggccacc gcgccaccca cggccccaat ggctacgcca acggcctttc ccgcggcgcc    81360
caggccgctc atgaggtcgt ccagacccct gaggtagggc ggtagcgggt cgactacctt    81420
gtcctccacg tactttaccc gctgcttgta cgagttgaat tcgcgcatga tctcttcgag    81480
gtcaaaaacg ttgctggaac gcagctcttt ctgcgagtaa agttccagta ccctgaagtc    81540
ggtattttcc agcgggtcga tatccagggc gatcatgctg tcgacggtgg agatactgct    81600
gaggtcaatc atgcgtttga agaggtagtc cacgtactcg taggccgagt tcccggcgat    81660
gaagatcttg agactgggaa gctgacattc ctcagtgcgg tggttgccca acaggatttc    81720
gttgtcctcg cccagttgac cgtactgcac gtacgagctg ttggcgaaat taaagatgac    81780
cacgggtcgt gagtagcagc gtcctggcga atccttcacg ttcatatcac gcagcacctt    81840
gacgctggtt tggttgatgg tcacgcagct ggccaggccc aagacatcac ccatgaaacg    81900
cgcggcaatc ggtttgttgt agatggccga gagaatggct gacgggttga tcttgctgag    81960
ttccttgaag acctctaggc tgcgccgttg atccacacac caggcttctg cgatttgcgc    82020
cagcgcccgg ttgatgtaac cgcgcaatgt gtcataggtg aactgcagct gggcgtagac    82080
cagattgtgc accgattcca tgctggataa atgagttgca ttgttgccat ctgcacttct    82140
tttggttcta ctatgagtaa gattcagact ggagcggttg gccaaacgtt cgagttccac    82200
cagagatttt tgcttgatac cttgccagaa caccaccaaa ccaccagtgg tttcaaacac    82260
ggacacgttt ccatattttt catatgtttg attgtatgaa gtattgaaaa tctgctgtaa    82320
cttatttatg gcctcatcac gtacgcagtc cagcgcagag tcggacatgt tcacctcttg    82380
cttcttagat aagaaagtgg cggtcatttt ggcagaagaa aagtgatacg agtcctcggc    82440
ttcggaacga atggtgcgtt ccgaggcttc ccagaaagtg agttgacaag taacattctt    82500
ctcgtcctgt atatcccagg agatcactga gtccgcacgt tcaagaaaag ccaccaacct    82560
gtgggtctct aacgcagaat tcggtcttcc aaagtcggag acgatagtgt agttcggaaa    82620
aatgaaaaac ttgtcggcgt tttctccaaa atagctggca ttgcgattag ttccgttgta    82680
gaaaggagaa atgtcaacca catcacccgt ggaagttgcg aaaaaatgat agggatactt    82740
ggagcgcgca gtagtgatgg tcaccataca attcagatta caggtctcac gatagagcca    82800
ggtgctgccg cggctgtgcc attgatcctt gaccgtcacg taacgggtac tgtgggtgtt    82860
ggaataatcg tcgggcatta attgcatggt tttgttttca tagctgtccc tatgataagc    82920
cacgaaaacc gtgcctgcta taacgcggct gtaggaactg tagcactgac tgtggctgtt    82980
gatatgatga atctcccaca taggaggcgc cacgtattcc gtgttgctgc ccagcagata    83040
agtggtgtgg atgtaagcgt agctacgacg aaacgtcaaa accttctggt agactcgtac    83100
cttaaaggtg tgcgcgacga tgttgcgttt gtagaccacc atgatgccct cgtccaggtc    83160
ttcattgata ggcttcatcg aggtgcagac gatattacgt tcaaagcgaa taagatccgt    83220
accctgtgcc atagaacaca cgcgatagag gtacttggtg gtattgaccc ccaccacatc    83280
tccgtacttg agggtagtgt tgtagatggt ctcgttaaca ccatggctga ccgtttggga    83340
```

```
agaagttacg cgttgagaga ctgaaccgga tcgagagtga gcagcagacg tcgtatgaga   83400
ggaatggtga ctgtgagtag cagaagttcc acgagaagta aagatgagg  aaaccgcagc   83460
acccagacag acgatacaca agttaacgca gactaccagg caccagatcc tggattccat   83520
gttcgtcgcg ggccaaatcc agcagcgatg aggcgcgtcg tggtctcttg cgtgttcgcg   83580
ggaccctccg ggaaacgccc gcggtcgagg aggagggta  cggacttggc agccaaggtc   83640
ggtccggctc cctgaaggca cccgagacgg ccgcggcggc cgttagggtg gagggcttgg   83700
ccacgggagc tgttggcacg tcgccactct catccggtct ggacagatgc ctgtagagga   83760
ggagatatag atctttggac ttataaagac ttccttcgtg acgaagcagc agcggccact   83820
ctttgttata cgtgagaatc acatctctgt ccgggtgcag ttcgtcgcgc aggcacgcga   83880
tcgagagttg ttcccgaaa  gtttcattat atagtgcgac ggagagcacg agctcccgca   83940
cgtgcatcca catctccttc tgcagcacgt ttaggtcctg acagtccgaa aaattgaaaa   84000
aacccatgta cttcaccacc atccactcac tgggatacac ggtaccttcc gcgcatttga   84060
ccaaatcgtc cttgacgtgg ggtagtacgc ccgcgttgtc gcaggcatag gccatgtcca   84120
cattgtgaga gaggggatag cgatcggtac agtgtgtgaa gaggggcccg ttacacaact   84180
cgtagatctg ctgacccagt agcgggaggg attccacagg cagactcttg tggatcaggt   84240
tattgaccac atacaggtgc tcatcgtacg tgaactgatc ccccacgtcc accacgtctt   84300
ggtcctggtg gtattggctg cggtatagaa acccattcat gagcttagag ataaagtcca   84360
gacacaaggg ccccactagg ttgacatcga tgagtttgct agtcagacgc tcctgcgttt   84420
tgatgcaacg gatcaccttg ccatagccca cctctgagac cttctgcagg taggcgcgtt   84480
tgcgcacgtt cacctcgcgg gtgacgttgt ggatgcggga acgcgcgtcc accaagtcga   84540
gagcctcgtg ttcgtcgcag ttgcgcaccc gtaagccgtt ctcgccgccg tcgccgtcct   84600
gcccattcgc ccctccccct accgctttct tgcctcctcc acgggccgg  ccgccgccac   84660
cgttattcct ctgactgtga gtactgctgt tgctgctgtt gctggccgtc atcaaagtcg   84720
tacccgtccc cgacatcgcc tcccgtccac gcaggtgaat agcctcgccc tcggggccgt   84780
cgccccccgt gccatcgggc agcggacgtc gaatctcctc gagaatatgc ttgattttgg   84840
tgtacatctc gttgctttcg tggagcttgt tgaacaccgg gttgtcctcg aaagcttgaa   84900
tgctgaggga tgtgatgagg tcgatgatcc tgttggggc  ggcaaagacc gaccccacga   84960
acatgcgctc ctccccgtcc aacgcctttt ccccgagcac gaagatgtcc tccacgtcct   85020
ccccgtacag atggcgactg atgccgttca tgagcgcccg gcacagctgg tgatacacat   85080
ttagctgctg gatggtgatg cccacccgct tgacgataac ctccgaggta cgggaccagt   85140
aggtaaaatc cgacaaggaa tatattcgtt ccggtatatc cgtaaacagg ttgtactccc   85200
tcagcgcctc ctccgcctcc tggatgtagc tgtggtaggc cgatgaagaa gagaataggc   85260
ttttgagggc cgaaaggact ccagccaagt ggggatgcg  cgttgtcagg tccagcaggt   85320
cctgctccac cgtctggata ttcacatcgg actggcttga cggacggtgg accgctatat   85380
ggttgcacag caagccctgc agccgcttgt tcagcgagcg gccctgattc gggatgatgg   85440
tcagctcctc gtagcattgg gcgcatgtcg tcccttcgac gtacacttcc tgacgcgcca   85500
ccggcgagat gccgcatagg cgacggagga gctccagcag ctgcgcgcag acctccaggc   85560
cggcctccgg cgccaggatc ccgtacacgt agttcatttt gcacaggaag cgctcgatgt   85620
cgttgagtgt ggccagactg acgctgaaac ggacgttgtc cgtaaactgg agctccacgg   85680
```

```
tgtgatggcg atcgcagcga tccaaacgga ggacggtacg gtagaaggcc gcccggtccg    85740
gctggcgcga gtaggccatc agcgcccgat ccagcaaagc cgtatcctcg tgcagcgcct    85800
tcagcagcat ctccagatag agcgtcagca gcgaactctg cgtacgattc tgcgccacca    85860
cctccgggta gatcttccgg tacagataca ctatagccgc cgcgtttctc ttgaacggcg    85920
tggactccgc cagtaacacg ttcggatcgc agtactttag acactccagc tccatggcgt    85980
attcgttgca tttcgaacac actacgcata gtttctgtaa caaattcatc tccatgactc    86040
gactcgctca cgtacgagac gctgtcgtcc ggtctggcgc cggccagaga catggagtcg    86100
gtgcacaaat aactcgcggg ccgctcgcta tgccgactga cgttgacgtt aatatataac    86160
gacgtcgtcg acgacgcggg ttctgctccc gaagctgttg ccgccgcttg cggcgcaacc    86220
tcctccacca ccgccgccgc cggctcctcc gcctcgggcg acggggggctc ggagatgacc    86280 ggctgtgtct gacactcctc cccttcctca ggcggcccgg gcgccgacgc gaatgtcgga    86340
gtttgccagc gcggcggcgg tctctgtctc tggtgccgcg gcgctaacct tcggggctgt    86400
tgctgctgtt gatgatgcga cgccgtctgt cgccgctgtt gcggcggtag ctgatacggt    86460
gtcgcctggt gctgctgtgt cggtggctgc tgttgctgct gttgttgcgg tctgaaaagc    86520
ggccacgggg gctgcgactg ttgctgctgt tgttgcgatg ctcgtggctg cggcggccgt    86580
tgtcgcggcg tttgctggcg gttacaaccg gctgcgtttg gccggcaata acccgctgcc    86640
cccgccgccc ccgctgctcc cgccgacgcc gccagcctcg tcttcgccgg cgttcacgag    86700
aaagcagcca cctcccgtct cgccgggcac gccgaagcaa atggagttgc ccgcgacgga    86760
ctcgccgaga agaagaccgc cacccccgac gccggacgcc gcgccgacgc cactgggcgc    86820
gaagagcgcc gacaggtcgt gcacctcccc cccggcggcg tccgttaatc gctgggcgtc    86880
ggcgtccagc acgcgtcgca agttctccag cgaaaagtcc tccacgccct gctcctgcaa    86940
cgcggcaaac ttgtccatca gcgacgcggc cagcgcctcg cagccatcca cgaagaagag    87000
cacatcgtcg gacgcgggga tctcctcgcg cacgctcaga atctcgtaca cggccatcac    87060
ttcggggtcg caatccaagt tctcggcgtc cagcgccagc atgacgcggt ttttttataag    87120 atccgcgtca aaaagcacgt tctcgcggcg cgagcgtttg atgagcacgt cggccagacg    87180
cgtagccaag aggtagcgct ggcgcatgaa acgataatct tggccgctca tagagctcac    87240
gttaaggctg cgttccacac cgttgcccga aaagtagccg atctgcccaa actgatagat    87300
ctccttgctg ttgttgatac ccgcatactt ttccacgctc acgggcacgg tcaccaagga    87360
acgatgctca aaaacgctcc gtaccaacga ttcacgcgcc acagtggcgg ccatgggcgc    87420
cggcacgcct gcggtcttca agcccttgac atgcaacgca aattcggcgg gcgacgagaa    87480
acgcggacta gcacctaaca cgtgaggaaa ctgcgcgtgg ttctgcgtcg ttaagcgcgt    87540
cgtcaacccg tgcagcgagc caatgtagtc tttgaagccg tagtagcaga ggaatttgtt    87600
atggaaacgg ctttccacgt aactcagcac acagtctggc gccacatcca gcagatcgtg    87660
ctcctgatag tcagccgtca cagccaccag aaatttgacg aaagcattga actcgcccat    87720
gtcacctatg ggcacattct tgggcaacgc gttggaacag accttctgcc aaaactgtaa    87780
gcaggggaga ccacattcag gaaagagtcg ctcgtgatgt cgatacagca gaaatcccaa    87840
gcagccctta gccggattac gacgcggaac gtgatcgcgg cgaaaaaaca cgctacccgc    87900
gttgcccttg cccgcgcggt agatgggtcg gttttttcact cgcaccatga tcaacgtggg    87960
taccgacagc cgcgagagct tgatctccat gggcaccacg gcgtacgtgc cctgcgcgta    88020
cagcctaaag tccagcaggc ggtcgtgatc cgaattcttg gacgacttga tctgcttggt    88080
```

```
gaagagaaag cccttgcgcg acgacgtggt ggagaacgcg ccgtgaatgg attgaaaatg   88140
ctgcgtcatc catttggata ccaagttggt ggtcaacgga ttgtccacaa tgtatgaggt   88200
agcggtaata agcgccacgt tctggatcac gtaaaagacg gatctgaaat aggcgtaggc   88260
cagcagcggc tggaaggcca cggcgtaggg attcagatcc aggttgaagg cctgcgtggc   88320
gcccgccacc tcgtcgcggc tgctcttgag gcgcacctcc gaaacgaaac ccagggcctc   88380
gtcgtccaca aacttgttga gcgccgaaaa gacggccaca aagtcgcttt tgccgtgcgc   88440
gctaaaggta tcctcgcccg tcacggggtc gatgagccgc atcttgcggc agtaatccaa   88500
gatgcgattg agccgatagg tacggtccac gctagcgccc agcatgcgac cgccgcgccc   88560
catcattccc ccggaatccc cgccacccccc accaccacga ccgccgccca gaccgtcgct   88620
cgggcccccg ctcacgtccc gtccaccacc cccgccagca ccgccgcccg gaaccccgtc   88680
gtcacctttg ccgtccaaac ccccgtcctt ggcgtcgacg ttgtaacgcc gaccgaagct   88740
gcccaaaata tccacgtcgt tgagaaaacg cgactgcacg gtgatcacgc agggctcctt   88800
cttgggctgc ttgggcacca cgggcaagcg ggtgcgcacc cgcacgaagg ccgtctgata   88860
acacgtgtgg caacaagtac ccccacaggc ctcgcacagc cccgcggcgc agcccaccag   88920
gtgattcgtg agcgtcgacg aacccgacaa gcccgtgtta tacaccgaga cacgatttag   88980
ataccagacg aagcccgaaa ctagctgcgg acacgtgcca cacaccaacg ccaaatgctg   89040
cggcccatag cgttcgtcct tgagcggcgc gccttgaaat ttgagcacct tgcgcgcgtc   89100
gttgtagacg tcttcgcagg ccgccgacaa cccgttggtg aactgaatag ccttgagcaa   89160
cgtctcctga ctggccgtac cgccggcgct gggatgccgc gccgacgact ggagatacac   89220
cagcctgtgc tggtagagca ccgaattagc gctgaagacc aaggcggcca cgtgcgtcga   89280
gagatgcaac ttgagctcgg tcagcgcgcg gatcagatcg cggtgatcgg ttgcgttggt   89340
cactaaaggc cactcggaaa agagcataga ctcggcaggt tggtaggccg aatcgaaaaa   89400
taccgaggca aaactgaagg ccaactcgca aaccaccgcg tcactcagca tcagatgatc   89460
cttttccaga ctgctgagtc gctggctcat gtaccccaag tagcgcttat gtggcgccag   89520
cttcaccgac tgctgactgt cgtgcacaaa ctgccgcaac gccgcctcga tcagcacacg   89580
cggctccgag aagcgcagcg attgacacca tgacgtgtac acgtagtaga aaagcgtctc   89640
gcttacggcc ggcacgtaga gccctcgcgc ctccacaaaa gcgctgcgcg catccagcga   89700
gacctcgtcg gcttcggcgt caagctgcag cgaattaaag agcgtaggcg ggtacaacgg   89760
cacgcgcacc gcctcgccgc cgtacagtcg caccgtggtc gcctcctcca cgcatggaat   89820
cagctgaccg gcaaagagaa actccttcaa gccgttgccc accaccacgt gcacagtcgt   89880
ctcggacgcc tgacagccca ccgccgcgca caacgccgac agatcggtag gcacgcgatc   89940
cgcctcgggc gtgtaggcct ccaacgcgta cttctggcgg gcgtcctcgc acaaccgatg   90000
cacgtctccg tgatcctcgg taaaagccac gatgccttgc gtatgatgaa agtagagcgc   90060
aaaaggacag aaggacgtga ctttcgtgag caccccgccg tcgtaacaaa gcacaggcgt   90120
gcgcacagag acgccgaaat ccgcctccac cgtcagcccc gccaacagag gagcgatcac   90180
cacgctcgag gaacggtcgc atagcgagag agtggccaga atctcctgcg tttctgcgtt   90240
caacctgctg aagtagagaa aagccgcggg ccccaccggc gctagcgcgg ttagttcctc   90300
gtggctcatg gtggatgaac ggaagacaat ggctacgccg ccactgagtg aattttatac   90360
caaggaaaag ttcagcacgt catgtttgac gcacgacgtc tgatacacca ccgtggccac   90420
```

```
cactgcggtc tggctgcggt tgcggaccac caaaggcgac aaccgcaacg atcccagcaa   90480
ttcgtaagaa aagctaaccg ttacggtcgg gcagcctctc gcagccagac cgctagccga   90540
cgcacccgcc cgcgaaaata gcgtgatgtt cgggacggct tcgcgtcacc gcaaactaac   90600
gtcggtagtc gcgcacgtcg tttatcctca gcacaccgtc cgatcacaac ccgttttccc   90660
actcagtcgc acaagcagca cataaaaacc ccacacagtg cacgtgaaaa caacgtccct   90720
agaaaacggt gttttctgtc ctaccgtcac cgggccacac aggcaaatcc cgagcccgat   90780
ccccgaaaac accgtacggt gtttgtggcc tccaaaatca catcagataa caaaccgtga   90840
aaagtcacgt ttcacgaaca cggtgttttt aaatcacaaa gaaccacctg acggtttaca   90900
agcagaaaca ccgcaccacg gtggtacaag cgcggtggat ctggtctcgc aacctcaatc   90960
gccgctatca ccaccgactt tcgctgcgct ccgccgacaa aacgccgtat aagctacaca   91020
ccccaaaaac ccgcacgcct atgggcgcca aacgtgtgta ttatctcaac gtcacgacac   91080
gacacaaaca gcgtaacgtg gtttcccgaa cacgtacgcg gcacagaccc ccgacacgta   91140
ctcgaagacc ttacagttta cgagtcaata aaacaggaaa agatccgaac tttaaaattg   91200 tgtatttta ttttcccatc cccctctttt taccaaaaaa cacattttc gtcttgtaaa   91260 aagtaacttt cgcccattgc catgaaacac cgtgatgggg aacggtgttg tgtgtcgact   91320
gacgtcacta cggcgatcag tatcgacgtc gtgtatacat aacggtgccc ggtgttttta   91380
ttcggggcgt tgtcgcgtct tgatgtaatg taacctgaaa ccgccgtgtc caagaatgcg   91440
gaagccagcg tgtaatcata acggggtttt gggtacaatc tgacgacatc tggcggcgag   91500
cgtacaccat cgaatgtggc gatcgccggc tctacgtcac aatgacgcaa aaacacactg   91560
taaaacacgc gtagacagct ttcctggtca acgagcgcca tctggtgtcg gcataagaac   91620
aggcatcaac cccgtggccg gcgaggcggt gagcactttt gctggtcacg tgaccatcag   91680
cgcaggaagc gaggcccgta gaaccgccca agaggcggtg ccagatgcca acgtcataat   91740
cacaaggtga tttgttacgt cacgcgcgcg cacgcacgcg cgcgcggtag aatacagcga   91800
tccctagtga agccacaccc attacgtgta gccatatccg cttacgtata cagccacacc   91860
cctaggtacg ccaccttatc taccaatcat agaaacggat atacaatgac ccctccctag   91920
actccacccc ttgtacggaa atttcagata ggtggaaccc gttagggttc caccgtcctc   91980
ggtgtacgta caggcttctc cgtctaccgg aaatatacac ctgctgacgt agacgctact   92040
cccggatacg cgtcataagc tactggaccc taggggggag tgtctacagg gctacgtgca   92100
cgccccctta cttagggtat ccgcccccctt cctctgtttt ggcctagtaa acttaacgcc   92160
gccgcttctc acgtgaccc tggcaagcct acgtcacact cgcgtgacca cacccactcc   92220
ggatatacgt catcctgtgg aattccggac atacggtgac gtagcgagcg tagcgagcta   92280
cgtcacgtat gcgtacgtca cctccggcgg aaatcatctc tgatgacgta gcgagcgaag   92340
cgagctacgt catcagtccg ttttacgtat accgggtgct aggcgacgcc ccgtagggc   92400 ggagcctagc ttccaccct aggatgcata ccctatatag cataattctt ctaacgaaac   92460
gttctacgaa aacggactgg cggaacggga accaccgtaa ccccccccc tcaccccccc   92520 ccttctcctc cggaaccggg ggggcaaat ttttaccaaa tttgggcaac catgttttcc   92580
aatgggacgg cgtttccgtg cgcatgcgca gtcggggcga atttttggtt gtcagggcgt   92640
tgccacgcgg attatgggat gggggctcga gtgcgcatgc gccggggatg ccgcatggaa   92700
agcctatata taaggagggg tgaaccaggg gccccggtgc gcatgcgcgg accaggcccc   92760
gcgggagggt cgccctgcgc atgcgccggt aaaattccac tgggtgtgtg tcgtgcgcat   92820
```

```
gcgccagtat ttttccactg gaggcggtca gtgcgcatgc gtcggtaaaa ttccactgga   92880
tgtgcaccgt gcgcatgcgc cggtattttt ccactgggcg gccgcaccta gggagcgcga   92940
gccccgtgcc gggcatgggc cgcggcggtg gaaaattacc gctccgccca cctaggcggg   93000
gcatcttaaa acctataaaa cccggcgtac ccgccgcccc ccggcgcagt ccgcggcagg   93060
gttccggccg tgctgcggtc cgcacgctgc gcccgctccc gcctgcctcc cgccctaccc   93120
cccaccctcc ccggccgagg cccggcgccg gtccgtccgc gggcccgtcc caccgccctg   93180
gagcaccatc cggggccgtg ggccgggcac cgggcgcggc ccgctccgga cctcggccgg   93240
gggtccctcc cctccccccg ctcgaccccc ccatccgacg gcccggccgg gctgggaccc   93300
ccgcaccggg gtcccggttc ccgtccgcgg cccggggggga cccgagcggg ggcttcccac   93360
ccccaccccg ctcctccccg ggctccggcc cgggatccct cgctgctccc ggcgacctcc   93420
gccggcttcc cggtccaccc gccgcggaac ggacgggacc cggggtccgc gcccttcccc   93480
tcccccacg gggggctggg tcacggaccc cggttcctag gctcgttccg cggtgggcga   93540
ccggggatcc cccacccagc tccccttccc ggcccgcccc gctggctttt gggcccctcc   93600
gggctttttt tccggctggg ggtcgcgcg ctcggccgac gacgacggta ggtgggccgg   93660
gtggacggtg gtggggacgg gcgacgcccc ggctcgacgg cagtcggtcc cggaaggttg   93720
ggggctgggg gcccggtcag gagctccggg agcggggtcg accgcgacgg cttccgggtc   93780
tcgcggcggc tccctctcgg cggctccggt tgggctcccc tcccccctct cgagggtccg   93840
gccgccagtc gtgaccgggg gtccctcggc ctagccgccg gctctcggtc cgccttatcc   93900
tgggcgttgg ccggtccgt gacgctcccc tccccgctg ctccccaaaa aactccgccc   93960
gaaccgtcgc ggcttgctgg ccctgggcgt ggtcccccac tcccctcccc ccatcggccg   94020
cccagccggg gtcggcgcct cggacccac caggctgtgg cgtgtgtgct ggccgatgcg   94080
gcggcgaggt tgggtgtggc cggaagcgct cggggtcgac ggtgggccgt catgacacct   94140
caattgccgt cagtacgccc ctccacaatc accgtcccta cacgatgggc ccggcaggtc   94200
acccaacgtt ggttcaggcc cagtcgggtt tttccccggc acaaacgcac gtccccgtgg   94260
gctccacgcg ttttccaccc tttcctggag gggtccggaa caccgtgaat ccgcggggag   94320
ggtctcggca cgggccgagg agaccacgac cgtcccaccc ggcgtgtcga cccgtccgag   94380
acccgggaag ggaacaggcc ccacccttttt ttttcccttc tccgatttgc cgtggaaaac   94440
ccgtgaaccg atacgggtac agacggccga aaaaattcga gacgacaata cgacggcagg   94500
gcgtgatttt cttccccatc cgacaaaacc gtgtccctca aaattcccca cctttctctg   94560
ttcaaatggc cccgaaactg taaaacaccg ttcgaccgca ccccaaccgg cgccatcttg   94620
gtgaccttct cgacggttct ctcgctcgtc atgccgttct gagctccgac atggcggacg   94680
agagaaaatg gcgtcgagag cataggagcg ttttcgctcc aggcgggtaa aagaatagca   94740
cgataacttt tctgtgcttt ttttgagacg ttttagaaga gcttttttc tgctcagagc   94800
gaaaaaatga tagccctgaa aatctcgacg agtctggccg agcggcgcca tcttggagga   94860
ggggcgagtc gcgggcaccg cctcggtacc cctggccga ggcgagtccg cggtcgccgc   94920
ctgttccgtg atgctaccta gagggcgccg tcgaggcgac tcttcctgtt ttcgccctga   94980
gggctaacgg tcgctgacgt caaaccatct cgtgctcgct gagtcacatc cggttgttga   95040
caagcgatga aggaccgcac ccaaagtgcg ccctctagtc atcgcgcctg acccctttta   95100
taaactgctc gaagaaaaga acaccttatg tgaaaaaata cagaatgatg acaagttcat   95160
```

```
ccaacacaac cgctcaacaa cgccatatct atcagtgtcc aaaaactatc ttctatcctt   95220
tgaaactata aatgctgcct atatacatat ttagtatcca agactcttac cacgtagacg   95280
aaaagaagtg atacaatgat cttgacgtgt atcgtctata tcgtgctaga tatattcaga   95340
taagacgcgc aaaccataga tttctcatca gtatcatgaa agacctatag ctctatatac   95400
gaacctagtc attttaggac agccgccgga gaagccgacg agggatcggg cgggtgcagc   95460
cagaacctca cgcccgatcc cgcctccggt aggcgatttg catctgtttg gtaaaaagct   95520
cataagtctg tatgtgacct atatatatat tatacgctat gtacaccgaa ctgtcgctgt   95580
tgtataagaa gaaaaaactc tccatattta tatcgtctga attttttgctt gatagacacg   95640 tgtttggaac tctgtccccc cacgttttca ctgtgtataa caaaaatatg tgtttctcaa   95700
aagatcttga ggtgtttgaa aacgggggaa accgcgtttt gggtgcgcta agccccggac   95760
tgggacgtag ccggcgtccg gcacctatat ttttctattt tttttacaaa atatatgatg   95820
aaccaagaat aaaactctag ctctcgtcta ttttaatat gctctactta gaacctttt    95880 aatgacagaa tgaactccat gttatacgct ctttatatag tttctctgca ctaacccttta  95940 aaatcgtatc cttccctgtt gtacaaatca tcttttgata cacaatgatg acctgatatc   96000
cctccatata tatgatcgga tattattccg ttagacttgt cctccttttt tttcctcatc   96060
tcctgtatct ggagatatat gttgaccacc accgccatga ccaccaaaaa gctagccgtc   96120
acgactagaa atgtgtagga ttcggacttt ccgttcgaga agaaagagac cgcgtctctg   96180
gacgctcttt ttgtcggtct gaatcgaccc gggatacgta agagagcggc cctacatcgg   96240
ggggcgctcg agaccgacga cgttccatct gaccagaaaa aaaaaaggca cccctcggta   96300
gcgacctctc accatcgttt gcccgtccgc ccgtccttcg tagccatcat catcatctca   96360
ggctctatcg gtaccatcgt tgtcatctga aaaaaaaaaa ctgcctcacc cacctgcgta   96420
aaaacaccat ctttccggag gtgcggtaag acgggcaaat acggtcgtgc cgaggcaaaa   96480
aaacgcacca tcgacaccac accctcatga gcaccacctg tcggtgttgg tcgtcctcca   96540
tcgttctcta cgaacatctc gacgcccggg tgacggacga cggcaagacg tcccggagaa   96600
gacggtgttc tctcgggcgg tacgctctct ggatctataa tatctatagt agctaaacga   96660
gactgtgagt acgacgaacc acatcatctt ttttttatgt tgctccttta gaaaatgact   96720
tatgtcgacg acactcggca tcagccatct cgtgaaacac gctcgctttt cgtctctcca   96780
aggaacactg ggtccgctga aagggaccgt gtaccgacca aagcaaaaaa cacacacgta   96840
gtaacatgat caaccacgtc tgaatgacac gaaaacacaa tcgtataacg ctctattcat   96900
ggaacgaact tggaataaaa aaaccatcgc aggccagagg ctaagccgaa accgtccggg   96960
gaagcgggcg cgagttttcc gacttagtct ctggtgctcg ttgagcctct tttttttcc   97020 tgattctctg aagaatcacc gtcacagccc tatgacgcga aatcaattgc tagaacataa   97080
acgttctcaa caggtatgaa atgaacaaac tagatgatgc tataacctta tattgtgtgt   97140
atatagatag gtgtgaaatt tgtaggataa aaagtgtcgt tgtatgatgc acaacgatcg   97200
tgaaactgga gactgtagct ctctaccgaa tgcaaataca caaatgacat cgattcccgt   97260
ccccacataa agaaatgtgc tttactgtga aagaatgaag aagattcttg ttcctcgtac   97320
gacggggccc tcgctcgtcg tacctcttcc cccctccggg agaggggacg tcggggccct   97380
ccgtcgcacc gggccgaagc cagtgaaatg tttactacac tgtcatcaga atatatgatg   97440
tatattattt cctccaaact cctcaccata gccaccaatt cgcatcactt aagaaagtag   97500
tagcaaccgc ggcggcggcg accggccggt cgtcgtctcc tcgtcctcaa atgttgtaca   97560
```

```
tgtgcagaaa aatgtgtaaa tacgtgttat ttatcccatg cgtcttgtac atagatatat   97620
gtttttatat acgctattta tactttatat atccttttgc ataaccatag acagtcaagg   97680 atttttaatga tttgctcatc cgcctttgag ccatcgctta ggagttagtt cctctatgtt   97740
ctcggcccac ctttccgact acagtagcaa acccttgtac taccaccccg ataaaaacca   97800
catcatcatc gtcaccacga cctggaaacg acacacgttc ccccccaatc ttgggcatgt   97860
gtatatatat aaagaatggg agggagagga cgtggggctc gagaagaaat aaacgccaag   97920
ctcgattcga accaaaaaac cacatgtgta ttgtgctttt tttgttttta cggtggggaa   97980
aaggaggggg ccgtcattaa cgaaaaccgt gtatggggtc cggacacgaa cagtacacag   98040
cttatgggga aaaagctca cagagagaaa aaaacaccaa gctcaggcac gcgtacatca   98100
ttatcatcat cggatatctc accacgagtc atagtagtac caaggagtgt gtaacaccat   98160 ttttctttt ttctttgtaa cgggataagg gacagcaatc atcacgcaca acacccttca   98220 ctctctttt agtcatccat atcatcgctg taacacagca tgtcctcgta atcgggcgtc   98280
tggcagcgca ttaccaccga gtcgtcttct tgcggtaccg gtggtggcgg cggcggcggc   98340
ggctgctgct gggttaccgt cgtactgtga ttaccgttgg cggactgcac cgggatgata   98400
ggctgcttgt ggggaacctg gggtggactg ccgccgtgag aaggcgacgg cgtcatcaag   98460
ttaagctcac cacggtgact ccggacaccg gcgaggggcc ccgggggact gggagggacc   98520
gcggtcgtct tgtagacgac ggtgtccccg tgtcgatccg tggctcgtac cagatcttga   98580
ctgctagcgt cgtcactgtc ttcgtcctct tccagctcgc cctcagagta gtgctgctgc   98640
ggttgcgacg gtggctgggc gggaggagcg gcggcgatca ttggagaggg atgtcgatga   98700
ctcccttctc tgtcctttt atcgtaggct gtcagcgttg ctgggtccgt cctgcttcc   98760 atatttgcgc attgctcatc ggtgggatga atttggtctc ctccccgctg ttgtccgccg   98820
gcagtggcgt ggttgctggc ggttgtcgtt gtcgtaccgg caaagacggt gagatccaat   98880
agtgactgct cgtcgaaggg acagtacgct atcatgaaac gatagggtgc caacgcgcgt   98940
tggatgcgca gttcgcacat ctcgttctga cactcgtggc actgcagggc gcctaggatc   99000
aggtccgaga cagcgccgca gcggtaggta cccatgcgt tgttagtatc gaactggtca   99060
aaaaattggg gcgtaccggt gacttgcaac gcgcgacggc gtagcgagac ggccacgcgc   99120
gagaaagagc acacgtaggc catggcgcgg tgcatgggtt gcgagaaggt ctcgggcgga   99180
cgcttctgca gatcgcagac gtcgtcgcgt agccaggcgc tcatttgacc tggcttttg   99240 actagccgtt tgagcgtgct gcaatggtcg ccccagccgt cctggtggtc caggatgcag   99300
cccaggtcca ggttgttgag tttgttgaag agcagctgac gcatgccgcc caccgtctcc   99360
agatagggat cgtgcgggtt gacgggtagc ccgtgcaggt ggtggtactt catgtagctg   99420
agcgtttcgt cgatgatggc cagcaacgtg tgcaagttgg gagcgttgta cacggcgaag   99480
atcttttcca ccaccagctt gcgcagcaac ggttcctcca gccaatcgaa ctgttgacgg   99540
atgtgcaaca ggtagtcggt gtgcatgagc tcgtcgtgtg acagcaggat gcgaccgcgc   99600
ggctgatgat cttgcgggaa ggcggtgggg accttgagat cggcggggta gggtgccaga   99660
cgtagactct cggccgtgta gcgctgaagg tcgtagacgg gcgaggtaga actcggtgag   99720
gtacccgacg aggcggcgcc gcgctgcaga cgcgctcttt tcttctttc gatcaaacgg   99780 ctgagttgct gtagttcgtc ctcgtccatg gcgtccagtt cgtcgtcaat aagcgccagc   99840
atctgttgtt gttgcggtcc ggtggacgat ccgtgatgat tattggctga agaggggtga   99900
```

```
gaagaaccga aagtcgtagg acaactggga actcggcgac gaagatgcgt cgaatcgccg    99960
ccgtgatggt gcggttcgcc gtcatcgttg tcgtaagact taccgtagtg ggggttaagg   100020
ggcaccgagg cggacgcggc cacgcgtcgc ttgaaagagg aggacgccct atgtccgcca   100080
cggaagcccg cggtgcccat gatgatgtgt ccgccggtgc ccccgagtgc gtggcgggag   100140
gagggtggaa ggggaggagg atagtggtcc ggatcgcctt cggtatcatc gtctttgctg   100200
tagcggggtc gtcgtgcggg gacgcagggt cggtgatgat gcgaggcggc gccgacggta   100260
tcttccgcga gatggtattc gctggcggct gctccgttcc gtgtcgacgg cgaggttgga   100320
cttcgctcgc gtcggaactt ccgtggcacg ggttcgtaat ctagacagaa gcgccgtgcg   100380
cgacgggcgc ggcgttcgcg ctcgctcagg gaagataacg acggagcgtc gtgacggccg   100440
cgtgagtgca gctccatggc cgccgtcgct aggaaggtca cgttcgggca cgctgatgta   100500
tatatagatg agaccgctgc cggggggcgg gtcaccggcg ccgtggaaag tgaggctcag   100560
acggcggtcg ccggcggcat gggcgcgtcg ggcggtctga ttttgatgga aatgtggacg   100620
tttttggcgt tggagtgaca cttttttggtg aaacagcggc tccagaggct ggcccagagc   100680
gcgtagctgt gctcggtgcg caggtcgatg aacacctgca cggtctcttg cgggttgcgg   100740
tgcgtgtagt tgagacagcg aaaatcccgc gtgcgcgcgc cgtcgcgccg cttgacggcc   100800
acgcagcagg cgccgtgggg ctgaaagagg aggacgtggg gtgcggtaaa ctgctcgctg   100860
acgtgcggct cgtagtgttg cgtgaggtgc tcgagcagcg cgggccacac gcgggtgacg   100920
acgagccgct gcaagtccgt gtcggaaatc gcagcggcag tggcgccgtc gccaccgtac   100980
aggtgatagg cgagcacctc ggtgagaccg cggcgtcgat aacgcgtcac gttaagcgag   101040
cgcgtctcga taaagttggc ttcggtcgag gggcagattt tgtcgcgcac gctgagaatg   101100
acgcgtggcg gcgcgacag gggcaacgcg ggcaggtcgt gcggcgggtg gtggtgaagc   101160
aggttacgca gatccagttg ggcgcgcaca aagcctagcg ggtgttcgcg gtaggcgtcg   101220
ggcacgatga acagcggcaa cagacggcga tgcatgaaat agccgtcgtc ttggtccatt   101280
ttatacatgt agggcagacg tacagagcgt ccatggtggt agatgcctgt gtctaggctg   101340
ctctcgggat gcgagatggg gtccagcagc gtgtgcagtt cggcgtcgag acagacggcg   101400
tgattgagca cctgcgccac ggcgcgtaaa acgctggggt gtacggctac ggtgcaggcg   101460
gggaacggcg tgatgatgcg cagccccagt ttgcccttgc agcggcagta agggggtgac   101520
gtgtcaacgg aggacgttgg ttttttgaaaa acgccgttat cagggacgtt attttttgtcc   101580
tctttcccgt cttcgtcttc ctctgtgtcg cgctcgtccc ggtaatcgag atagtcgtcg   101640
tcatcgaaag gcgcgccggc cgcgtccacg ggcacgctgt tgggtgggca cgcgcttttg   101700
aagaaataga ccgggtgccg gtcggggtgc gtgtagccaa agaggctcgc ccatacggtc   101760
atccagacgc gtcgtagtcc gcgacataat tcaaagacgg tgtgtcgcgc cagaccggag   101820
acgccgtcgc gcagtcgtaa atcaaagtcg gccacaaaat tgaagacggg cagacgttcg   101880
ttgaagactt cgtgtcgcgt gtagtagaac tgtgtctcgg ggctggtgct ggccacgtcg   101940
tcgtcgtgta gccacacggt ctcggtcagg gcctcgtccg agaaacggct gtcgggtacg   102000
tgacggagca ggtcgcgcgg aaagaggctg cgatgccagg tttcggaggc cacggcgcag   102060
aagacgtgct ggtcattggg caggtgtacg cggtagacgg gcagcggtcg ctccagcagc   102120
ggtgccagcg cgggctcggg tagcaggtag cgacgttgcg agtaacgcgt tagcgtgccg   102180
gtggtgtagg tctgggctgt gcgcagcgag gcgcatagac gtaacaagcc ggacagggag   102240
cgttccagtg gcgagaagac agactcggaa agcgtgttga tgcgttcgag ctggcgcgcc   102300
```

```
agctgcgtgg aggtgccaaa gaagcccgcc aggtgcgtgc cgtcgatgcg gccgccgtag 102360
ccggccagcc ccaggccgtg cgggctggtc gccgagtggg gggattcgtc gagacccagt 102420
aggtgcgtct ccacgtagtc gtgcagaaag ttgtcgagcg agaagtattt ttgcatgacg 102480
tccagcagct cggtggaaag ccggcggccc agaaaacccg gttcgcgcgt gcactgcgct 102540
tcgggcgccg cgtcagcgtc gtaagccacc acgcgccggt actcgagcaa ccgcgcgcgt 102600
gccagcgccg tgcggtaggc caggtagacg tagtgcacgc agaccgtgtc gggcagacgc 102660
gcacgttcgc ggaacgcgtt gatctgcgtg tccacctgct ctagctcggt gtagtcgcgg 102720
cggttgcgcg ccacgcgta cgccacgaaa gcggacacgc gctgacgaaa gggcgagccc 102780
agtagcagac gcgcgaactc gcccatggag gcgtgcgtgg ggatgatggt gcccaggtcg 102840
cgcgtgcaga agctgcgcac gtactcctcc acggtggaga tggtgctgta ctggccctcg 102900
aataggtagt aggccatggt cagcagcacc tggccctcgg tgtgcccgaa gacgctgatg 102960
aaccacgagg gcgaggtggg gcagaggaag acctggttga gatgacgtag cacggccgcg 103020
tggtgaaagt acaccaggtg cttgaattcg cgcacctcgc cgccgtgttc gggcgagagc 103080
acgggcgtgc ggaagagatg ccggtagagc ggttgcgtct cggcctcgtc cagactggcg 103140
atgagcgccg agaggggat gggctggcgc gcggccaggt agcgcgagag ctgcagcgtt 103200
tcgttgttca cggcgaagac gggcgccacc cgccgcgagt ccgagcactt ttgcgtttgt 103260
aggcagaaat aaacacgtcg cgagacctgg tgtttgacca gcaggggaa gacgcagtgg 103320
tccgtcggtg tctgcgagag tacgttggcg actatatgag cagaatcata ctctgttgcg 103380
aacagaacga gcgtcatcgt cgcgccggca cgatgcagct ggcccagcgc ctgtgcgagc 103440
tgctgatgtg ccgtcgcaaa gccgcgcctg tggccgatta cgtgctgctg cagcctagcg 103500
aggacgtgga gctgcgcgag ctgcaggcgt ttctggacga gaactttaag cagctggaga 103560
tcaccccggc cgacctgcga acctttctc gcgacacgga cgtggtgaac cacctgctga 103620
agctgctgcc gctctatagg caatgccaga gcaagtgcgc gttcctcaag ggctatctct 103680
cggagggctg tttgcctcac acgcggccgg cggccgaggt ggagtgcaag aaatcgcagc 103740
gtatcctaga ggccctggac attctcatcc tcaaactggt ggtgggcgag tttgccatgt 103800
ccgaggccga cagcctggag atgttgctgg acaagttctc cacggatcag gcctcgctgg 103860
tggaggtgca gcgcgttatg ggcctggtgg acatggactg cgagaaaagc gcgtacatgc 103920
tcgaggccgg cgcggctgcg acggttgcac caccgacgcc accggcggtc gttcaggggg 103980
aaagcggcgt ccgcgaggac ggggaaacgg tcgccgccgt gtcggccttt gcctgtccct 104040
cggtttcgga ctcgctgatc cccgaggaaa cggggtcac gcgtcctatg atgagtttgg 104100
ctcacattaa caccgtctcc tgtcccaccg ttatgaggtt cgaccagcgg ctgctggaag 104160
agggcgacga ggaggatgaa gtgaccgtga tgtcgccgtc acccgagccc gtgcaacagc 104220
agccgccggt cgagcccgtg cagcagcagc cccaggacg cgggtctcac cgtcggcgtt 104280
acaaggagtc ggcgccgcag gagacgctgc ctacgaatca cgaacgcgag attttggatc 104340
tcatgcgaca cagcccccgac gtgcctcggg aggcggtgat gtcaccgacc atggtcacca 104400
tacctcctcc ccagataccc tttgtgggtt ccgcgcgtga actcagggc gtgaagaaaa 104460
agaaacccac ggcggcggcc ttgctgtcct ccgcgtgaac agcctggcac gttttggaaa 104520
acgtacgtga tcacggacac gacgagcacg gggtttctca tagacgtact ttattaggtc 104580
agggatgacg gggaggtttc gggccgacgt caaaaataac gtcactcgtg ttgacagggc 104640
```

```
tttctgcgtc ggagctctttt tcatcttctt ctgtctcgtc gacgtcatcg tctaccggcg   104700
agggtgtccg ttgcagcaac gcgtgctcgg gcgtgtgggt gaaaccgatg tcggggtgg    104760 gcggcacgat catctgtcct aggggggtgac tgcccaccgg cagataggta aagcggtggg  104820
tggtaaaaac cgctttggct acggtggtgt gtggggagat gcagacgtg  gtgtgcgaag   104880 tgttgaccac cgtcacgccg gccgcggtac ccgggagcca gatggtgggt cgaatgatga   104940
gatccgattg actaaactgg cgcacgccca ctatgagggc gcagataccg ggcgcgtgca   105000
cgtaggccgc gtcaaaatag acggtttgcg tgtgacccgg accgatcacc agcgtctgac   105060
gggtacgtaa tgaaaagaaa cggtgttcgt tgggcggcgg caagttcatg agctgccagg   105120
gttctggcac aaaacagggg aaaacgccga tatcgccttc gatggtgccc ggaaagatgg   105180
actgaaaagt gtcgttgagg ttgacgacat ccaactgcgg gacttgcagc ccggattcca   105240
gcagctcggg catgcaaacg aattgcgcgt ccaggcattt gtaaaaggta atgccaaaaa   105300
aaccttcggg gatatagagg ctgactccca gcgaggtggg cactttgcgc tcgcgtgata   105360
gccaaatgat gtgtttattg taaaaagcca gctgcgtgtg gcattgttta acgatgaaac   105420
tggaaggcat ccacttgtag ggaactttga gcggcgacgg taatggcgac gacgcttcat   105480
cctctcccgg atgctgctct ttgtcgtatt tctcctcggt cgattgggc agcgtaaatg    105540 tggtttgaaa atcgctatcg ctagcgaaac gcacgcagta acgcatgttg acggatttct   105600
cggctaggat gatggagcct gatgacggtg cggactcttc cttcattatt aacgtagggg   105660
tctcccagaa tcgctgaaaa cgggagcgcg gcagccgcga cagtaccagt tgagagtcga   105720
ttctgtcggt caacattgta agcatcgtgg cggtggtgtg atggagtgga aaacagtgat   105780
actaggtgtt tttgttttat cggtggcagc ggggagttct ggtaacagct catccacgtc   105840
aacctccgca actacgttaa aatcgtccag ttctagcgtg tcaacaagca aattgacgac   105900
aactgcgaca actacgacaa ctacgatgag tacgacctca tcgacaacta ccactaaacc   105960
aagttccact actcacgacc ctaatgtgat gaaacgacat actcacgatg attttttacaa 106020 ggcacattgt acatcgcata tgtatgagct ttcactgtcc agcttcgcgg cttggtggac   106080
tatgcttaac gctctcattc tcatgggagc tttttgtatc gtattacgac attgctgttt   106140
ccagaacttt actgcaacca ccaccaaagg ctattaaggg tggacagatt tacagctcga   106200
cggtgttccg gcggggtaag gtttccataa gtgggtgact ggagactaaa gttacggatc   106260
tcatctagaa atagcagcga gtctagatag tcccacaggg gatctataaa cgttctctga   106320
aatcccgttg atggtgacgt aggtgtagtt tcggaagccg ttttgttttc cacgaacatg   106380
gtttcgttgt aatataagga gctcatatca agagtaccgt aaatagtgta cggtgtttca   106440
ttacggatta gtacatgcgt gtttttcata aattctgata cggcggttcg gttgcggctt   106500
gattcacaaa aagggttttg ccggtaacgt agagtggtat acacccacgt cgctaggtcc   106560
cttaattgcg tggtcataat ggacttcata aagctactat caggacgata agcaattgta   106620
gacgtggaaa cccgccttgc ggtggtagta acactataag ttgcgttagt agtgacgttc   106680
agagcggttg acgttgtata gggagaatat ggcgtagtag tactttgaga tttcttactc   106740 ttttttttctg attgttcttt gactggagct tgtttacgct tgagttttcg catagtgttt   106800
ttcaacttag taccgttaat atacttaggg acgcgaaata aatttcggct catggcgtta   106860
accaggtaga aactgtgcgt acagttgcgt tgcgcgtaac gtagaagcaa ggcggttagg   106920
cctaaaaagt agatcgtttg actatccacg tttactttct tggaacctac atataacttc   106980
gtgttccaac gtggcacatt gaaaaacatg gggttgaacg tggtgaaatt gccgcagcct   107040
```

```
tgttcgccag tatcattacg tttggaaacg tttagcattt cggaaagaca agtcatggaa  107100
ggcaccgtac cgcaagatgg gggtctgaat gttattgttt tagccgtatg attgtattct  107160
gagaaaacgt acttagccgg ttttcgaagc tgagtgctat aaaaatcgaa ccaaagatag  107220
gtaacactgt tattttgaat gggtcccgct aaaatgtaat accgtggaaa ctcggtcatg  107280
ttcatagtca gattttttaat gtgttgtctg gtcatattaa agtattttgt atagatatcc  107340
ttttctagtt gtttcaaaat ctctaatttg aacttgtcta gtctttgctt gcctatcgta  107400
gacagtactt tacctgacca gtaacgtcct acggataatc gtaccgcagc cctacagttt  107460
atgaaagaga atagcaggaa agttagcgac ataaggaaga ataaattaaa aacacctctc  107520
atctctcctt ttctccccat gacagaggag gagaccccgc accgtccgtc tgccttgtgg  107580
tttggcttgc ctgcgtgtac tcactgctga ttctggtcgt tttgctgctc atctaccgct  107640
gttgcatcgg cttccaagac gacctagttt cccgcacctt ggctgtgtac cgagcttgta  107700
tccagggacc gatatgtaac cagacccaca acagtacctc gtaaataaag acgcacacac  107760
ctcacgcata tagtaccatc acaccgtgtg gcgtgtactt tattacaacg agcaagagtg  107820 cccctaact attggggccc gtaccgtttt agaaggtttt gtgtgaatgt ctttaacttc  107880 tctgtcccctt ttctcataaa ctgtcaggtc ctacagtcag catgtcttga gcatgcggta  107940
gagcagatag atgccgatga tggccgatag cgcgtagacg gacatcatga ggagacgact  108000
gtcggtggcg tccacgacaa cgtcagttac ttctaggacc gtaccgttttt tcaaaagcat  108060 gaggtagtga gttcgcggag atgagaccac cacttcgttg tagggatcca gggcgaaaag  108120
gacgtcgtcc gagtcgtgca tgtacatgat gttgatgacg ccttgcgtgt cgtcgtattc  108180
tagcagggcg ctttggcaaa aggcgcagtt ttctagggaa atgttgagcg ccgctgtgat  108240
gctgtgtgtg gtatgcatgt tgcgcgtcag ttcgcattta gtttgactgt ccgtctgggt  108300
gatgatgagg ctttggccta cgacggtggt ggagacaggg taggagatac ctttgatcag  108360
gtactggttt gttacgacat aactgacgtg ttcggagacg gtcagcgcgg agaaggattc  108420
gcctagtggc agacaaaaca ggtcggggaa ggtttccaac gtgcttggtt gcatggtaga  108480
taggatggag agggcggcgg gaacggtagt ggggacggtg gcatcgggga agagacgtgt  108540
gaggcgttcg agcgagtgat cgcgtcgccc gctactggaa cagggtgtgt acaggtcgct  108600
gaggtattcg tggtgcggat gagctagcaa ctgcgtaaag tgtgatagct cggccaatga  108660
acagaggccc gtttctacga tgaagatttc gcgtctctcc gtcgtatgta ccagcatgga  108720
gtggacgagg ctgcccatga ggtagagttc ttgacgcgcg aaggctgaaa gaaaagaggc  108780
caggtgcgtt ttgtgtagtt ttagggcaaa gtcggcgatc tgtcgtagtg cccactgggg  108840
gatgagatgt tgctgattct gtttagagag tatgtagacc aggcgtacga ggctggtgat  108900
gtcggtgatc tgattcggtg tccaaagggc tcgtttggcc aggtccacgg ccgtgggata  108960
cagtagcaac gtggtgcgtg gtggtgtttg tgagaggcag gtgatcataa attcttgtat  109020
ttgtaagagt gcggcctggc ggtctagggc ccgtgggacg gagacttggg cgccggcctc  109080
ttcttgtcgg gctgctgcga acagtgctaa tgcgtaggcg aaggccattt ctaccgtgcg  109140
gcggtccagc atctgacatc gaccgctctt gagtacatcc acggcgtaac ggtgaaagct  109200
gttacgtagt agtgcgctga ggtctaggta gttgaagtca agtgcggcgt caagaaagtc  109260
cgggtctttg agataagagt gacggttcag ttgatctttc ttaactagca ccaggagctc  109320
gtgtttttca gtttgtcgta gtataaagtt gtcgcgttga tagggcgctt tgaaaagtac  109380
```

-continued

```
gcgtggaaga tggccgaaga taagcagcat gggtgtgtcg tcgtctatgg acaccgtaac 109440
tacgaagaag tcctcggtca gtgtgatttt aacgtaacgt agttcgtcga tgaggtaaaa 109500
gccttggtgc aaacaaggtg tgacggtgct gaatagtaga tcgtgtccat caaagaggat 109560
acaggtctgg ttaaagtgtg gtcggtgtag tcctgaggtg gtatgtgatt ctgtccagcc 109620
gtgtggagtg gtttgcggtg gcatccaaac gtgaggtatt gacaggtcaa tgggcggtgg 109680
cacagtggtg ggctgttcac ctaggctgtc ttgtgccttt agctgctgcg aaaaagatcg 109740
gtagctggcc aggtctttgg ataccagcgc gtaagtgtta agtctctgtt ggtatctttc 109800
cagggtttcg gtcagatcta cctggttcag aaactgctcc gccagaggac ccgcaaaaag 109860
acatcgaggc atatggaata catagtattg attatagctt tggaaaaagt tgaaactgat 109920
ggcgttttcc ctgacgaccg tgctgttacg gaggctgctg ttgtaggtgc actgggtggt 109980
gttttcacgc aggaagcgga tgggtctccc gtaggtgttg agtagtaggt gaaacgcgtg 110040
agggtccagc gcttcggatg cggcgtctgc gccatatcgt tgcgaaggta ggtgactgag 110100
gaggtagacg gcgaagacgg tgaggtagga ggggaggccg ggccgcatag cgcggccgcg 110160
ccgctgggtt cagcggcgtg atccaggtgg tggttggcgt tacacccgag agaaggagaa 110220
aaaggatccc aggaaggagc acccgggtgc ggcgctacgg gttacaaaag tcgcgtctcc 110280
gtctatttaa tacgatgtca ttggccgctg cgaagggaga agaggggaca cgcgaataag 110340
ccatgccgtc cgggcgtggg gacgacgctg atttgacggg gaacgctctg cggagattgc 110400
ctcacgtgcg taagcgaatc ggtaagcgca agcacctgga catctaccgt cgtctgctgc 110460 gggtcttttcc ctcgtttgtg gcgctcaacc gcctgttggg aggccttttc ccacccgagt 110520
tgcaaaagta ccgtcgccgt cttttcatcg aagtacgatt aagtcggcgg attcccgact 110580
gcgtgttggt gttttaccg ccggactctg gtcgcgcgg catcgtgtat tgctacgtga 110640
ttgagttcaa aaccacgtac tcagacgccg acgatcagtc cgtgcggtgg cacgccaccc 110700
acagcctgca gtacgccgag ggcctgcgcc agctcaaggg cgcactggtg gactttgatt 110760
ttctgcgtct gccacgcggt ggcggtcaag tctggagcgt ggtgcccagt ctggtttttt 110820
ttcagcaaaa ggccgatcgc ccatccttt atcgggcttt ccgctcaggc cgttttaacc 110880
tgtgtaccga ttctgtcctg gactatctag ggaggcgtca ggatgagtct gttgcacacc 110940
ttttggcggc tacccgtcgc cgtcttcttc gagccgcacg aggaaaacgt gctgcgctgc 111000
cccgagcgcg tgcttcggcg gttgctggag gacgcggcgg tggcaacgcg cggcggggc 111060 tggcgcgagg acgtgctcat ggaccgggtg cgcaaacggt atctgcgtca ggagctcagg 111120
gatctgggtc acagggtgca gacttactgc gaggatctcg aagggcgcgt gtccgaggcg 111180
gaggcgttgt tgaaccagca gtgcgagctc gacgaaggac cgtcgccgcg gacgctgcta 111240
caaccaccgt gtcgtccgcg ttcgtcgtcc ccagggaccg gcgtggcagg agcttccgcc 111300
gtcccacacg gtctttatag tcggcacgat gccatcacgg gacccgccgc cgccccgtct 111360
gacgcggcga ccgcgtcagc ggccgccggt gcttcttcta cctggctggc gcagtgcgcc 111420
gagcggccgt tgcccgggaa cgtacctagc tactttggaa tcacgcagaa cgatcccttt 111480
atccgctttc acaccgattt tcgtggcgag gtggttaaca ccatgttcga aaacgcctcc 111540
acttggactt tctcctttgg tatctggtac tatcggctca agcggggtt gtacacgcaa 111600 ccacggtgga aacgagtgta ccatctggcg cagatggaca actttccat ttcgcaggag 111660 ctgctgcttg gcgtggtcaa cgcttttgaa aacgtgacgg tgtatccgac gtacgactgc 111720
gtactctccg atttggaagc cgccgcctgt ctgctggccg cctacggaca cgcgctttgg 111780
```

```
gagggccgcg atccgccgga ctccgtgacg gcggtgttga gtgagctacc tcagctgttg    111840
ccgcgtctgg ccgacgacgt gagtcgtgag attgccgctt gggaaggccc cgtcgccgtg    111900
ggtaacaact attacgcgta tcgcgactcg cccgatctac gctactacat gcccctaagc    111960
ggtggtcgcc actatcaccc gggcactttt gatcgtcacg tgctggtgcg gcttttccac    112020
aaacgcggcg tcctccagca tttgccgggc tacgggacga taacggagga gctggtgcaa    112080
gagcgtctgt cgggccaggt gcgcgacgac gtgctttctc tctggagtcg acgtctgctg    112140
gtcggcaagc tgggtcgcga cgtgcccgtc tttgtgcacg aacagcaata tctgcgttcg    112200
ggcctgacct gcctggctgg cctgctgttg ttgtggaagg tgaccaacgc ggatagcgtc    112260
ttcgctccgc gcacgggcaa atttacgttg gccgacctgc tgggttcgga tgccgtagcc    112320
agcggcgggt tgcccggggg gcgcgcgggc ggcgaagagg agggctacgg gggacggcac    112380
gggcgggtac gtaactttga gtttctggtg cagtactaca tcgggccgtg gtacgcgcgc    112440
gaccccgcgg tcacgctgtc gcagctcttt cccggcctgg ctctgttggc cgtgaccgaa    112500
agcgtgcgca gcggctggga tccctcacgt cgcgaggaca gcgccggagg tggcgacggc    112560
ggcggcgccg tgctcatgca gctcagcaag agcaaccccg tggccgacta catgttcgcg    112620
cagagctcca aacagtacgg cgatttacgt cgcttggagg tacacgacgc tctgctctt     112680 cactacgaac acgggctagg gcggctgttg tcagtgaccc tgccgcgtca tcgtgtgtcc    112740
actctgggct cgtccctctt taacgtcaac gatatttacg aactgttgta cttttagtg     112800 ttgggttttc ttccgagcgt ggcggtgttg taatttccac cacgtgtcgc tcgctgcata    112860
aagggcgagc gtccccggag agggtatatt cgtttggcga gagcgggcag cggtggtggg    112920
tatgtcccct tctgcggaga agactacctc agtcaccgat tccatcatgc tcgctatcgt    112980
gaatttcaaa tacatgggcc cgttcgaagg ctactctatg tcggccgatc gcgccgcctc    113040
ggatctactc atcggcatgt tcggctccgt tagcctggtc aacctgctga ctatcatcgg    113100
ttgcctctgg gtgttgcgtg ttacgcggcc gcccgtgtcc gtgatgattt ttacttggaa    113160
tctggtactt agtcagtttt tttccatcgt ggccaccatg ttgtccaagg gtatcatgct    113220
gcgtggcgct ctaaatctca gcctctgtcg cttagtgctc tttgttgacg acgtgggcct    113280
atattcgacg gcgttgtttt tcctcttct gatactggat cgtctgtcgg ccatctctta    113340
cggccgtgat ctctggcatc atgagacgcg cgaaaacgcc ggcgtggcgc tctacgcggt    113400
cgcctttgcc tgggttcttt ccatcgtagc cgctgtgccc accgccgcta cgggttcact    113460
ggactaccgt tggctaggct gtcagatccc tatacagtat gccgcggtgg acctcaccat    113520
caagatgtgg tttttgctgg gggcgcccat gatcgccgta ctggctaacg tggtagagtt    113580
ggcctacagc gatcggcgtg accacgtctg gtcctacgtg ggtcgtgtct gcaccttcta    113640
cgtgacgtgt ctcatgcttt ttgtgcctta ctactgcttc agagtcctac gcggtgtact    113700
gcagcccgct agcgcggccg gcaccggttt cggcattatg gattacgtgg aattggctac    113760
gcgtacccct ctcaccatgc gtcttggcat tctgccgctc tttatcattg cgttcttctc    113820
ccgcgagccc accaaggatc tggatgactc ctttgattat ctggtcgaga gatgtcagca    113880
aagctgccac ggtcatttcg tacgtcggtt ggtgcaggcg ttgaagcggg ctatgtatag    113940
cgtggagctg gccgcgtgtt acttttctac gtccgtccga gacgtcgccg aggcggtgaa    114000
aaagtcctcc agccgttgtt acgccgacgc gacgtcggcg accgttgtgg taacgacggc    114060
cacgtctgag aaagccacgt tggtggagca cgcggaaggt atggcttccg aaatgtgtcc    114120
```

```
tgggactacg atcgacgttt cggccgagag ttcctccgtc ctctgcaccg acggcgaaaa 114180
caccgtcgcg tcggacgcga cggtgacggc attatgagcg gcggcgctgt acgccagcgg 114240
ggagaaaagt ggcagataaa tcacgtcagg ttcacacgtc gttagccagc gtcggcatat 114300
gaagggcgcg ggcggccagt acggcctctg ggctgagaca ggacgaggca gggtgagaaa 114360
gaggaggatg gggggaccg gggtggtggt gctgctgctg ttgtgggtgt ggacggtgcg 114420
gatgccggga cagcgtgccg gcgaacgttc tgtaatcttc cataataaag gtaaaaatgc 114480
ccgtctcgtg tcgactccgc tggatctcga aggcgtcggg ggtaatgcgc atcttgccgg 114540
tgccgatgag ataaaagtac cacattttt gacagatgat gcgaatcaag ggttcgtacg 114600
cttcggcacc ccagtggcgc gtgaagaagg ccgccagacg aaacaagcgg tgtccgtaga 114660
gcgtgcctag ggagaagagg atgttgccgt tgcgcgccag gtcttcgggg aaaacgaccg 114720
gcaggccggt gtggcgctgc acaaagcgcg tcagcagtcc gccgctcaag cgcgggtgac 114780
acaggcgctg gctgagacgg gcggcgcgcg tttcatcgaa cacgccgcc tcaaagtcca 114840
gccccgggaa ggcctgacgc agttcgcggt acagatgagg ccagtagggt tgcggcgtct 114900
tgcgactaag cacggcgtgg tccgagacgc ccaggttgtt catggtttcg cgcagtagca 114960
gcgtttcgag accgcggtga agaggagga cgcagatgag gcgtacgatt ttgagttctt 115020
ccaaacgcag cgagctcagc ggctgtccgc gcgacatctt ctcgctaatc tgtaatatta 115080
gatgattggc gcaagtaaag gagaatttgc ccgtgcggac ccgcgggacg gcggggttct 115140
cttcgtcgcg ggccatcatc gttcgctcgg tgagcgggta gcgacggtga cgacaatgac 115200
gatggacgag cagcagtcgc aggctgtggc gccggtctac gtgggcggct ttctcgcccg 115260
ctacgaccag tctccggacg aggccgaatt gctgttgccg cgggacgtag tggagcactg 115320
gttgcacgcg cagggccagg acagccttc gttgtcggtc gcgctcccgc tcaatatcaa 115380
ccacgacgac acggccgttg taggacacgt tgcggcgatg cagagcgtcc gcgacggtct 115440
tttttgcctg ggctgcgtca cttcgcccag gtttctggag attgtacgcc gcgcttcgga 115500
aaagtccgag ctggtttcgc gcgggcccgt cagtccgctg cagccggaca aggtggtgga 115560
gtttctcagc ggcagttacg ccggcctctc gctctccagc cggcgctgcg acgacgtgga 115620
ggccgcgacg tcgctttcgg gctcggaaac cacgccgttc aaacacgtgg ctttgtgcag 115680
cgtgggtcgg cgtcgcggta cgttggccgt gtacgggcgc gatcccgagt gggtcactca 115740
gcggtttcca gacctcacgg cggccgaccg cgacgggcta cgtgcacagt ggcagcgctg 115800
cggcagcact gctgtcgacg cgtcgggcga tcccttcgc tcagacagct acggcctgtt 115860
gggcaacagc gtggacgcgc tctacatccg tgagcgactg cccaagctgc gctacgacaa 115920
gcaactagtc ggcgtgacgg agcgcgagtc gtacgtcaag gcgagcgttt cgcctgaggc 115980
ggcgtgcgat attaaagcgg cgcccgccga gcgttcgggc gacagccgca gtcgggccgc 116040
cacgccggcg gctggggcgc gcgttccctc ttcatcccg tcacctccag tcgaaccgcc 116100
atctcctgtt cagtcgcctg cgcttccagt gtcgccgtcc gttctccccg cggaatcacc 116160
gccgtcgctt tctccctcgg agtcggcaga ggcggcgtcc atgtcgcacc ctctgagtgc 116220
tgcggttacc gccgctacgg ctcctccagg tgctaccgtg gcaggtgcgt cgccggctgt 116280
gccgtctcta gcgtggcctc acgacggagt ttatttaccc aaagacgctt ttttctcgct 116340
acttggggcc agtcgctcgg cagcgcccgt catgtatccc ggcgccgtag cggcccctcc 116400
ttctgcttcg ccagcaccgc tgcctttgcc gtcttatccc gcgtcctacg gcgccccgt 116460
cgtgggttac gaccagttgg cggcacgtca ctttgcggac tacgtggatc cccattatcc 116520
```

```
cgggtggggt cggcgttacg agcccacgcc gcctttgcat tcgtcttatc ccgtgccgcc    116580
gccaccatca ccggcctatt accgtcggcg cgactctccg ggcggtatgg atgaaccacc    116640
gtccggatgg gagcgttacg acggtggtca ccgtggtcag tcgcagaagc agcaccgtca    116700
cgggggcagc ggcggacaca acaaacgccg taaggaagcc gcggcggcgt cgtcgtcgtc    116760
ctcggacgaa gacttgagtt tccccggcga ggccgagcac ggccgggcgc gaaagcgtct    116820
aaaaagtcac gtcaatagcg acggtggaag tggcgggcac gcgggttcca atcagcagca    116880
gcaacaacgt tacgatgaac tgcgggatgc cattcacgag ctgaaacgcg atctgtttgc    116940
cgcgcggcag agttctacgt tactttcggc ggctctcccc gctgcggcct cttcctcccc    117000
aactactact accgtgtgta ctcccaccgg cgagctgacg agcggcggag gagaaacacc    117060
gacggcactt ctatccggag gtgccaaggt agctgagcgc gctcaggccg gcgtggtgaa    117120
cgccagttgc cgcctcgcta ccgcgtcggg ttctgaggcg gcaacggccg ggccctcgat    117180
ggcaggttct tcttcctgcc cggctagtgt cgtgttagcc gccgctgctg ctcaagccgc    117240
cgcagcttcc cagagcccgc ccaaagacat ggtagatctg aatcggcgga ttttgtggc     117300 tgcgctcaat aagctcgagt aagagagacg ctatatttag ggtttccctc tcttttttt     117360 ttctacaccg tgataccta ataaagcaca ctgcggttat tatcaacgtc tctgtgtttt     117420
tattatttag aaataaatac agggaatggg aaaacacgc gggggaaaaa caaagaagtc     117480
tctctctact ggctcagagg atcgttgccg aacagggact tcagggacac caggggggc     117540 acctgctctc tgtccttctg ctcctgcttg ggcaggctgg cgatgccctc gcccatgccg    117600
aacagctcgg cgggaggggc ggtgggctcg ggtctgctct gggggaaatt gccgggtctg    117660
cccttgctgc taggccaaat cttgcccagg aaattggcct gcctctcggt gcagtccttc    117720
atctggtgcc cttccttgcc acacttccag cagcccttct tcctgggggc tctgcagttt    117780
ctggccaggt ggccctcctt gccgcagttg aagcacttga tccgcttctg gcctctgaag    117840
ttgccccgct gcatcatgat gttggtctgc tgggcctggc tcatggcctc ggccagcact    117900
ctggccttgt ggccgggtcc gcccactccc tggcaggcgg tcatcatctc ctccagtgtg    117960
gcgccgctgc ccagggcctt caggatgctc ttgcagtcgg ggttggcgtt ctgcaccagc    118020
agggtctcgg tcatccagcc cttcacgtcc tgggtggcct gctcggctct cagggccttg    118080
aagaaccggt ccacgtagtc tctgaagggc tccttggggc cctgcttgat atccaggatg    118140
gacacggggc tgtacatccg cacaatcttg ttcaggccca ggatgatcca ccgcttgtag    118200
atgttgccca cagggatggg agggttgccg gtcatccact gcagctgttc ttgaggggtg    118260
gaggtggtgc cggcgatgtc gctgcctctg ggctctctga tctggccagg ggatgggt     118320 ccggcctgca cggggtgcag tctgtcccac tcggcggcct cctcattgat ggtgtccttc    118380
agcatctgca tggcggcctg tgtccgcccc acaatgttca gcatcacgtt caggtcctgg    118440
ggggtggcgc cctcgctcag ggcgctgaac atagggatca cttcggggct gaaggccttt    118500
tcctcgatca ctttcaccca ggcattcagg gttctggggc tcaggttctg gtggatcatc    118560
tggccctggg cattctggat gatgggtag ttctggctca cttgctgct gtcgccggtg      118620 tcggcagcgg cctgctgggt tttctgcttg ctcttgttct ggatctcctc gatcttgtcc    118680
agggcctcct tggtatcctt cacgtcgatc cgctggtgca cgcagtacag ggtggccacg    118740
gtgttgaaca ggctcttgat ctcctcggtg ccggttttca cggcgggctg cagctggttc    118800
atgatctgct ggcagccctc ggtggtctcc agcaggctag gattcagggc gaagcgatcc    118860
```

```
agctctctgc tggcccacac caggtgcttc agccggtact tcttcttgcc gccaggcctc    118920
agtctgatct tctcccaggc gtccagcttg cccccgctca ggatgctggc tctggcggcc    118980
atggtggctg cgaaggcggg atgggggag  ggtcagggga tgcgcaaagg tgaacgggtc    119040
ttcgtgggag gtcgggaagg gttccggcaa ctgtcgcaaa tatagcagcg gcgacaggtg    119100
tggcgcccaa aagtcgcgtg tctgagtgga cgtgggtttt tatagagtcg tcttaagcgc    119160
gtgcgcggcg ggtggctcaa cctcgatgct ttttgggcgt cgaggcgatg catgcccgg    119220 gcagggcttc ttgccggtgg cggcgacgtt tgggttgcgc agcgggctgc catacgcctt    119280
ccaattcggc gaagatgcgg tagatgtcgt tggcgtccca gaagaactcc tggtacttca    119340
gattctgacc ctgaaccgta gccaccatgg gcaccaggtt gcgggccagg atgccggcct    119400 gccaggcgg  ccaggtgaac acggccggat tgtggatttc gttgtcggaa tcctcgtcgg    119460
tgtcctcttc gggcgcgacg gtggactcgg ccttaaggcg gccgcgtgtc ataacgcccg    119520
ccgtgcacgc cgtcgccgag gatgctgatt tgcgtttgcg gcccgcggaa gtggaggcgc    119580
ccgccatggc gccgccgccg gtaacgcggg gcgtcttgcg ctcggtggtt acgagttctt    119640
cgtcggagtc cgatccgctg gtccagacgt cgtcgtcgcc ctgggcggca ccctcgtcgt    119700
gccggtccca ggtgtgtcgg tactcaagct tgccctggat gcgatactgg ctggtgaagg    119760
tggggtgctc gctgtactga ggcccgcgct gcagcagcaa gtcgatatcg aaaaagaaga    119820
gcgcagccac gggatcgtac tgacgcagtt ccacggtctc gcgtatcgct tgtacctcca    119880
ggaagatctg ctgcccgttc atcaacaggt tacctgagat gctcaggccc gggatgctct    119940
tgggacacag cagcccaaaa tgctcgtgtg aggtaaaagc cacatccagc atgatgtgcg    120000
agatcttgcc cggtttgatt atcatatttt tgggacacaa caccgtaaag ccgttgcgct    120060
cgtgggggcg catgaagggt tgcgggttgc gggtcatcgt caggtcctct tccacgtcag    120120
agcccagcgt gacgtgcata aagagcttgc cggagggcac gtcctcgcag aaggactcca    120180
ggtacacctt gacgtactgg tcacctatca cctgcatctt ggttgcgcgc gtgttctcca    120240
tggagcaaac cagctcgtgc gcgcacacca cgtgccgcag tgccacgtcc ttggtgggaa    120300
acacgaacgc tgacgtgtag tagacgtcgg gctctttcca ctggttctgc tgacgcgtcc    120360
aggccagtcc cgagaccgtg agacgcgcct gccacatctg cttgcccgac gcgtgaatca    120420
cagcgtcagc tacgggcagg tgtcggtgtt tgcgctcggc cgccgacggg tagtggtgca    120480
cgttgatgct ggggatgttc agcatcttga gcggcagcgc gtacacatag atcgacatgg    120540
gctcctggct ggggcagatg cttcggcccg tggggttgtg cacgttgacc gacacgttct    120600
ccacctcgct gcccgtaaag tacgtgtgct gcacctgcag ctgattgtcg ccgcggtggc    120660
atggcgtcga gtcgggcgtg tactgcgaca ccaggatcag cgagggctgg ctcacgcgta    120720
cgtggatacc cgtctgcagg agtcgcgtct cgtgcggcag caccggcgtg tcgccgcgac    120780
taaacacggc tttcagcacg tgccccgaaa tgggacccag tacggatatc atttcgggac    120840
aacggcgacc gcgcgactcc atgctgcctg cgcgtacggg tgtaggcgac tgagcggcgc    120900
gccctttgcg gccgccgcct tacataggca ggcgaccaaa cgcggaaccc gaaataaaaa    120960
cgttctacac agagacaacc gcggattatt gagtgtcttt ttttattaca aaaaaaaga    121020 ggcaaagccc caccgtcacc acaccccatc acacaccacc accgattttt tttgttttaa    121080
ccccgtatcg cgcggacgcc tagtgtccgt ttcccatcac cagggtcctc tgtttagaga    121140
tcgccgcaga ccatggctaa agtgacagga ctcgttttct ctgtcgtatt ttccgtgagc    121200
ttacagtctt gcggttccgt ctccggggac gccagtcgca tgggcagcag gtcctccagc    121260
```

```
gcgatggaag cgcccagcac cgagagctgc tgttgcgacg gcgaatggga cgtggaccgc  121320
gagtgtagcg tggatttgac ttggtgcgtc attgctgaca ggcaaccgcg attcagcgta  121380
tgctttgacg agataaaata gaggcgtccc aggagcgcgt cccgtgggaa cgtggcgccg  121440
ttctcgtcgc tcaccagtac ggttaattcc aaccaggagc gcggtagcca gaccgtaacg  121500
ggcattttga gtccctgacg gttgtgtggt acaaaaacac ccagataagg cccgtaaaag  121560
cggcggtaga tacgtaacgt gtgcgagttt ttcagcgtca attcgtaagg gacgcgcacc  121620
tccagtccct cgtccgccgc accggagcgt ggcggtacaa agtaaggcag tggcgcgtcc  121680
gaaaagaagg gtcgtcgcac cgtttcgcgt cgcagccgca ggcgaaacgc cactgggtcg  121740
gctggcgcct cggtgcggtc gcaggtcacg ttgaaacgta acatgccgtc ttggtatagc  121800
gtgagtgacg acagcgtcag gtccggcggt gattcgttcg ggtctagctc caatcgtcca  121860
aagacggagg gtcccaatgt cttggcagtg gtttccgaga ggcgcgccga gatacggctg  121920
gtgagtccac gcggccccga gatgccgcct tccactcgat gccagcacag cgcgtgtcgt  121980
acgcgcaccg tcagcgtggg cgtcagatcc gcgtccgttg attccgcggt atcagcgacg  122040
gaagccgcgt tctccgttac gttgtttata tccagcgtcg gctcgaacgt gagttctggc  122100
agatgcagcg caagacagtc gtgtaacgcc gtgtgatgcg cggctttacg tcgtagcggt  122160
agccgtttca gcgcggcgt gatgatacgg agcgcgaaga gattgagtga taagcgcacg  122220
atggccatgc gcgtcagttg ctggtcgatt actgagcgca ggatatggca gcctgggcgt  122280
gcgggaaaga gagagaaggc cgggcgtacg tcagaatcct cgttagatac cacgcataga  122340
atgccgcgtt cacgatcgtc gttgcggtca tcctcgtcct cttctttttt cttctcttttt  122400 tccttttttt tctcgggctc atgggaagcc gccgtttctt cttcttgcga cgtcgcggag  122460
tcggtttgag actcgccgtt cgcttccccc aattgcagcg gcgtagagag cagaatctgg  122520
aagggatccc gcaattcttc gggtcggagg tcgaggtgca actggatcag atggtaggtg  122580
ccgcggtgca cccgaggctg acggatgtcg tgtttatccg tcagtgtgag gatggtctgc  122640
ggcgagccgc tgtgcttgtc cagctcgtcc ggcgttttca ggaggaggct gtcgtcgtcg  122700
gtactggcga cgcccatcat ggtcgtggtg gtagtggtgg cgaggaaagt gagcggcggc  122760
gctgacagag ctcggcgttg gcggcggcat ttgccgctgt gtcggctgct attgctgcca  122820
acgccaccgc cgccgcctcg tctggctcgt ggccggcggg cccgattccg aaggttgggg  122880
tcgacgcgtg gcatgcttgg tgtctgcggg cgcgagaggg ctggctcagc ctttaaatat  122940
gcaggtcgcg gatttgttat cgggtgaaac gtcacacacc gtgaagacga cctgttcgcg  123000
gatgaggtca tccagctgtc gcagcatgac gaaaagcgcc gacagccgcg cgatctcgtc  123060
gtcgggcgac acgtgctgcg gccgcgcggg cgtgcgcggc tcgccgacgc tgcgctcgcg  123120
gtccagccgc atcagcagct cctggcactt gacgagcagc atggagctgt cctctagcgc  123180
caacttgcgc acgtaggtca tggtcagctc cgaggctagg ttggccacca tggacatgga  123240
gaggcaggcg gtcttcatgt cgatcagcag gtgctggtcg atgaccggat cggggatggt  123300
gaaggtggcg tcgcgaaaag taatggtctg cagctgctgc acggcagcct ttacctcctc  123360
gtacgaacgg tcgagcgaga agaggcccat gatgagtagt cgctggttga tttccagcgc  123420
cagtggcatg ggtacgatcc agggcagcac cagctcccac tggcccagcg tcagcaggtt  123480
ctcgcgcgcc agcggtccgt ggaagagcgg cggcagcacg catagcgcgt cgcccttctc  123540
ccaagtcacg ggtcccgtgt tgaggacggt gtagagcagt ccgtgcgtcg gtacgtgtag  123600
```

```
gaggatctgg ttgccttcta cgcgccgcat caacgtcagc gtcatattgc gcagcaggcc   123660
gcgcagtcgt acgtagccgc gggtgtgatc tacgaactgg tgtaggccca gctggtagtg   123720
tttgatgaga tgtagacgct gcggaatggg cacaacggcc gctactagct tggtcagttt   123780
gcctacgtcg gcgatgctga gcttgtggtc gaaagtgcag aagatgttgg cctccatggc   123840
cgccatagcg gcggtgaaat cctggccgcg acggaggaga agcagagacg aacaacgtct   123900
gcaccgggcg cggcgtcaga gcgagcgtgg cgcgtccggg cccgcgtttg cgtctaggtg   123960
attcgccgtt aacctgcggt cgtcgccgtc ctcctcaccg gacggcctca cgagttaaat   124020
aacatggatt gctgtagcgg gatgatttcg cctacgacgt agttaccaaa gtgcgtttcg   124080
gacgtggcaa aagccccggc gccacccttg agtttggtct ccatcagcgc cagcgtggtg   124140
gtgctgagga tcggtagcgc ttcctgcgtc agacggcacg ggttttcgat gagttgttcc   124200
gtgccttcga cgcagacgta ctgcgtgtcc gtgtcgccgc ggatgcagtc cttggcgcgt   124260
agcaggtact cgtcgatggt tttgaagagc gttttgttgg ccgcgataat ctcttccgtg   124320
ttaaagtact gcgcgcaggg gctgtagaat ttggagttgt agcctagacg ttcgcgatgt   124380
cgggtgttgt agagtacgtc gctcagacag ccggcttgcg aggcccaggg gttgtgtgtg   124440
gccgcgaaag tctgtgcgtc cgcttcgcga tggtcgtaga tggccttggt ggcggcctcc   124500
gtgtcgtacg gatcgacggc cagcatgcag gaggcacgcc cgcgcgggtt gttgggatc    124560
ttaaagtaat taacgtccat cgtcaccggc gtaaggatta gttcgcacgc ggccttttgt   124620
ccgtgcaccg tggcggcggc attgcgctcg gacatgctgc cgaacgtcag catggagatg   124680
gtctccgtgt ctaacagttg cggccgttct acgccggccg cgtgccggat ccagcggtcc   124740
acctcgtcgt gccggtacac gttcataggg aagacgcgaa agaggtcctg cacgcggacg   124800
cccatgtcgg ttcgcacgcg gtttacgtag gctacgcagg tatttgacgt gtaacccaga   124860
cccatgtcta cggtgttaat gttctgcgtg acgtggtacg tggtgctgat gtcgcgttcc   124920
tccttggtca cgatagggtt gttgatgata actgacgtgc acgatttgcc gctgtagagc   124980
agcatgtcca cctcgaaggt gtcggtgcgt acggcgtga  gtgcgaatcc cgggtggatg   125040
tgcgccttgg tctgcagcac cagtgaaact ggtgagattt tgtataacat ggcggccagc   125100
gtcatgactg agtgcaacac gttgggacag gtggccgagt aacgcgaaaa gggcgagcgc   125160
agccagttgt ggtactcgtg tgcgaaggct gtgggtagcg ggaaaccacc gtcgtgacgg   125220
tgatagtgcg ggaactcggt cacgtagcgt ttaatgtcgt cgctcaacgc cgcgcagatg   125280
gtggggtttg agtagaaacg gtggaaaggt acgggtaggc tgtactcgat caacgtctta   125340
ggcgccgtca cgacgcagca gccgttgtaa agcacgtgct gacgtgagat aaagtccggc   125400
aggccctgac gttgcgcgtg gtccagaggc gcgcgcactt cgagcacctt gacgtgctcg   125460
cccacgaatt gcacggccaa aaacagttca cgacaggcct gcagcagcgg cgtgtgcgcg   125520
tcggtggcga cgtcctccac cagctcggtc agcatctcgc ctacggcttg acgttgcgcc   125580
gctatcgagt cttcggggt  gacgccgctt gtgctctctt tcgacgtcgt acctgacgtg   125640
gagaccgcgg tggcggccgg catcaggaga acgccggtc  ggtaaaagag gtctactagc   125700
agcgtcttga ggttgagtcc caggccgcag gcccggttgt tggtcatggc gggcatgagg   125760
cagagataaa agacctttg  taacgtccat tcgtcgtcgg tggcacggta atcgtccaca   125820
aacagcggct cgtcggcatc catggcgccc aaacgcggta cgtcagaaac gccgtggtgt   125880
cgcgcctcga tgttggccgg gttcaacggt tgccggtcgg ccactacctg tacgccttcc   125940
atgttacgcg gcaggtgcgt aacgaagggg ggccacagcc ggtggtcgtg cagcgcgttc   126000
```

```
acgtaagccg atagcggttc ctcagccagt tgaccgttgt taagtcccgg cagcgctgag  126060
atgcgcgtta ccagacgcag cacgcgacc  agattgcggt agtgaaagag caactgcggt  126120
ggtagggcgc catcagccag gtgttcggcg atcaacgtca ccagcgcgta gctgtgcgca  126180
aaaaccagca gctgacgtgt gtgaaacatg ttgacgatac aacgtgctac gaaagtgcgg  126240
attagcaaaa aagcgtcgac gttgccgtgt accagcacgt cgaccaggta gcagagctcg  126300
gggtaattgg ggcttgtcac ggtggttttg aaaagtcgca acgtctcttc gtagtcgggt  126360
ggtggccgca gtcgcatgtg ttccatgatc tcccaggtgc gcagttcgtg aagggggccc  126420
ggtgccagtc catctggcaa attaccgatg acgatacgcg tgtacacag  cgccaccgtt  126480
tcgctgtttt cctggcagtg cgtaaagtcg aagaaggggt gcagctcggt gtagagcgtg  126540
atgttgccca ccttgtagaa gtcggtgacc acaaagtcct gcttcatttc gttcaccgtg  126600
cgcgggacct cgcgtcgtac gcggtaaaaa tgcggtatgc ggcgcgccgc accgcccatg  126660
ggttcctgct gaaaacgaca ctcgagcagt cgttgcatgg cggttccga  gggcggtccg  126720
cgttccgtga aggtctgtag acagggcgcg ggctcgtgca gcaccgggtg gcacagcgtc  126780
ttgagcgcgt ccacaaagtc tatcttttgt acggcacggt cccggtttag caggtaggcc  126840
gtggtgggca acgcgttgcg aacggtgtcg ttaagcttaa ctttgctttc caccgtggtg  126900
taaccgcgat cctcgggcag atacagccct acggggaaga aaaacgtcag gtccacgtta  126960
cgttctagcg gatctttggt atcggtgttt ttgtagacgc gccgcaagtt ttccataatc  127020
accgtttttt cgcccagtcg gatcacgtcc atgctcagcg gcgttaagct gtgcgccccg  127080
gcctgcgaaa gcgagtcgtt gggcaaatgc ggttggcccg aagtcagatg agccttgtac  127140
gagttgaaat cggccaggat cgagtgatag gatatggcag tgacggcatt ttcgggactg  127200
agtacaaaat tgccgtaggt ggccggcgcc gagaccgttt ctttggtgat gtggcttgag  127260
agcagcgaca tgatgatctg cataacgttg gccgtgctta ccatcacgcc gctgatcttg  127320
gcccccgagc tcgtggtgta cgtcgtgggg ttgtctagga tgctatcggt ggccgcttcg  127380
gctagacgcg tgaggaactt gagcacatag tcgcgatcgc gcgtgcgatt cagcaaaaag  127440
agcgtggcca gcattttggc cttgaagctc tgcaagatgt tgcttcgctg gatgcggttc  127500
agcgcctgtc gcgccagcgt ggcgttctct accagcgtct gcactacaaa gtacggcggc  127560
gccttgcgta gcagtgtctg taaaaagctg tgaatcaagc gcgttccat  ggcgtcggcc  127620
gtgttttga  gcgcgcgcag caccgtgtgc atagcttcca cgttgaggat cttgtccagg  127680
atggtgcctt cgaacgtctc gcgcagatac gtgaggcagg ctgcgctgag ctcaaagggg  127740
atggtgatgg gggatttttc actgtatttg gtgaccataa tggtggtctg acgactggtg  127800
ggcaaaccgg cgccgctggc cacacgcggc acctgcacgt ggaacagcat ttttcccgta  127860
gtcagtttat tgaggtcgtg gaacttgatg gcgtgcgccg ccgcggccaa gccgctggtc  127920
aaaaaataaa cccattccag gcgattgcag aaggtgccga agatggcttc gaagtgaata  127980
ttgtaacgct cggggtcgtc gccgtagtag atgcgtaagg cctcgaacat ctcctcgccg  128040
gcgctggtct tgacgtgcgt cagaaagtca gtgggaatgc ctactttagg caggagctcg  128100
agcgccgacc agttctccat cgcggcgcg  gcgtgagcgc gaggcgtcgg agctcgggga  128160
aagcagcgcg accggagaa  tggccggcgc tgccgcgcgc cgcctcggct gtgacgctct  128220
aatagtcgtc ggcggctccg ctacgccgcg ccggggttta cacgtccccg tgcacgttcg  128280
cgcctgcaac ctcacccaag agctatcgac gggcgaggac gcccgcttct gtcgtccgcg  128340
```

-continued

```
acccgttaac gtcgaacggg tgcgcgctgt ttttgcggct ctctaccgtg cctgtccgat    128400
acacgtgagg accgagcccg agcgtgtcaa gctggtactg ggtcgtctgt tactgggacc    128460
cgtggccgta ccctgttttt gcgacggtga agtggagggc cacggtgaac atctggtacc    128520
tacgacgcag ttttgtcgcg ggccgctgct ctacgtgcac cgacgttgtt gttgcggatc    128580
cgtgaccgcc gggcgcgcgc tgtcctacca cgttctcgaa aaccacgtgg ccacgcatgt    128640
gctacgcgga ttgctctcgc tgacggaatg gaatcgagaa ttgccgagcc tcttttgcga    128700
ctgtcctggc ggcggtggcg cctcgggaac cgaggaacgc tacgccatgg cctgcctgcc    128760
gcgcgacctc agcctgcacc tggacgacta tccttacctg atggtggaaa tcggacgcgt    128820
actcagtgtc agcgaggtag acgactacgt aaccgccgtc tccggctacc tgggcgaggc    128880
cgcggcgccg cgcattcagg ttcactacaa gctgctcttt ggactcaacg tgcgtccgca    128940
agcgccgtgc gcgttggacg ctacacgcga ctttttctg ctggagctgc aaaagctttg    129000
gctgggcgtt gaatatcacc acgaagtgac gtcggagttt ttcggtcgcg tgctggccca    129060
gctgcatcgc gaccgcgccc gcgtcatgat ggcgcttcgc ttgcccgagc agacggtgtg    129120
ccacctgagc accttcgttc tcagtcgctt caagcgacag gtactgtact tcaagttaca    129180
ggtgagctac ggcaagtgcc ggactggcca cgctgacaga agtgggggag gggggaacgg    129240
tggaaatcag ggacaccaca acctactgtg ttatcgacgc cttagcgtca catttgccga    129300
cacagacacg gtgtggagaa accttttcta cgtttattac gaactagctc gggatctggg    129360
gtcccatggg acagagaacc gacccgtaaa ccgcggttac ggtgtttctt gcgctccgag    129420
gacgtcgcgg ctatcaccgt cagaatcgac ggtggtttcg gcgaacggac acgcgctgtc    129480
ttccaccgcg ctcccgacga cgagcgcggg tcacaagctg tcactgccgc gcgacccggc    129540
cgccgatcgc gttcgacgtt acgtgtgcat tatctcgcgt tcatgtacg ctcggtacgg    129600 ggagagatgg cgtaaacacc gtcaacggcg gtcggagacg ggagaagagg aggaggaaga    129660
gacgctggaa tcgggggaga ctgacgccac gccgccattt gactttacgg ggcagcagct    129720
gcgccgggcc tatcaggaac accgacgtcg taaacatcta gccgtgcagc gttacgcgcc    129780
gtgccgtcgt aagctcatcg gcgggatgga gtttgccgag gtgacgggcg tgagtctgga    129840
ccgcatcgcc gtcaacgctt tcaacaccaa ccgcgttatc aatatgaagg ccgcgctctc    129900
gtccatcgcc gcgtcgggtc tcggcgtgcg cgcgccgcgg cttcccaaga acatgaccca    129960
cagttttgtg atgtacaagc acacctttaa ggagcccgct tgcaccgtca gcacctttgt    130020
ttccaacgac gccgtctaca tcaactcgct caacgtcaat attcgcggtt cctaccccga    130080
gtttctgtac tcgctgggcg tgtaccggct gcacgttaat atcgatcact tttttctgcc    130140
ggccgtggtg tgcaatagca actcctcgct ggacgtgcat ggactggagg accaggcggt    130200
gatccgctcg gagcgcagca aggtgtactg gaccaccaac tttccgtgca tgatctcgca    130260
tactaacaac gtcaacgtgg gctggttcaa agcggctacg gccattgtgc cgcgcgtctc    130320
gggcgctgac ctggaagcca ttctgctcaa agaactctcg tgcatcaaga acatgcgcga    130380
cgtgtgcatc gattacggtc tgcaccgcgt tttcacgcaa ctagagctgc gcaattcgta    130440
ccagatcccc ttcctggcca agcagttagt gctgtttctg cgtgcttgcc tgctcaagct    130500
gcacggtcga gagaagcggc tgcagttgga ccgcctagta tttgaggcgg cacagcgggg    130560 tctcttttgac tacagcaaga acctcacggc gcacaccaag atcaagcaca cttgtgcgct    130620
catcggcagt cgtctagcca acaacgtgcc caagatcctg gcccgaaaca aaaagtcaa    130680 attggatcac ctgggccgga acgccaacgt gctgacggtg tgtcggcacg tggaagccca    130740
```

```
caagatccct cgcacgcgcc tcaaagtgtt agtcgaggtg ctgggcgcgt tgcagagtat   130800
cagcggtacg ccgcacacgc gcgaagtgat ccaccagacg ttgtttcgat tgtgctcggc   130860
ggccgcagcc acatcgggcc tgtgttcatc ccctccccca ttgtgtgtgt cctcatcttc   130920
ctccgtcccc tctgtcccaa cctccgtcag cgttgacggc agttctgaac ccacgtcgcc   130980
gcgagcgcgg tttgcatcac gatgatggaa gccgcggccg ctgccgccgc ggcgtttcgt   131040
ccggaggagc gtccgacgcc gggttggcac gacgcggcgt tgttaatgga cgacggtacg   131100
gtgcgcgagc acgcgtttcg caacggaccg ctgtcgcaac tgattcgccg tgtgttaccg   131160
ccgccgcccg acgccgaaga cgacgtggtt tttgcatccg agctgtgttt ttattgcagc   131220
ggtcgtttta accgcaggtc gtccgtcttc tccatctatt ggcagaagca tagcgatctg   131280
gtgtacgcgc ttacgggcat tacccattgc gccaagttgg tggtggaatg cggtcagttg   131340
gggagtagta ggctacggtg gcgcgacggt gatgcgagtg gtgaggagcg ccggggagac   131400
gacgacagca gggacgagct gtacgacgtg ccgggcattt atatgattcg cgtcaacgac   131460
ggcggcagca ccggtcccag acacgttatt tggccgggta ccagcgtgct ttgggcgccg   131520
gacgttgtga tcactacggt gcagcgacga atctcggcgg cgcgcgccct ggtgaacacg   131580
ttccgccaat attttttttt gctggaacgg cgctcgcacg aggagctggt tctttgtccg   131640
cccgagatgg aggagcgtct agcgccgttg ttgcagagtg ccacgcgcgg tgattcggac   131700
atgtttgacg gtgtggtggc cagcgcttat caccgtttgc gaatgagtaa tattccgcgt   131760
tcatccgccc gtctgctgga gcactgcgtg gggctggcgg gtgctaagaa gctgctcttg   131820
ctcgacgtgc cgcgtctgga gaactatttt ctttgtcagg tctgtcttta cgagctggac   131880
gaggacgaga tgggcgagga gatgctgggc atgttggccg gaaagcccga ggatgccgcc   131940
gtctcgggcg caagcggcgg ttttctgcta catcgcaaga cgatgaagct ggccgcctgt   132000
ctgtgtttgt tgctcaattc gctgcatttg caccaggagg cgctggaggc cttggatcct   132060
ccgccgccgc gcgtcgagga gaacgacctt gtcaacgtgg tgctgcgccg ttattatcgc   132120
agtcacggcg gcgtgcaggc gcggacgctg gcggcggccc gggctttgtt agccgactac   132180
gctgaaacgt tttcgccttt ggggagtttt acgcgcctgg gttacgatcg tctcgtttct   132240
gccgatgccg gcgtcagtcg ccggcacctg gtggctctgc tgcgtgccta gctgaccctg   132300
aaacggatgg cgtgtatatc gtcacacagg taggtggcca tgatgacggc gatgataaga   132360
tcgtccgaga tacgattctg gcgcttggcc gagtagcgtg ccgtcgtgcc ttcggccagc   132420
gtgacgcggt gcaggttctg aatctgctcc agaagatact cgatgggtc gtggctcagc   132480
ttgatggtgt aggagacgag ctcttgcgag gctttgatgt agcccgagtt gaaacgcgag   132540
atgaactgtt ccacgccagc gccttgtcg cggcccatga ggtagaaggg ctgttcgatg   132600
tggttctggt cgggcgtgtg gtagaagagc acgcggatga gcgtgctgct ctgcacgctc   132660
tgtcggatga ggcaggcgat gcgcacggcc gccgcctggt tggtgttgcc ctccacggcg   132720
atacgcagtt cgtccaggta agggtgcagg ctcagcaccg agatgatcat gtgcgccgcg   132780
cactcggcga tggctacctc agaactctcg gagaggtcgc gcaaaaagaa atgctctagg   132840
ccgtaaatga gaaactggtg tcggtaggcg cctacgccg ccacgcccgt gcccgaggcc   132900
ttgcggttgg tggtgaaggc cgggtccaga tacacgtaaa gcgtcttgcc gaaataatcg   132960
taggcgttgg tgttgagcgt gctgtaacgc aaaatatcga actcttcgcg gctctggtcc   133020
gtgatgagca cggtgttctg cgagatttta ttggtaccgc cgatgatctc gtccatgaaa   133080
```

```
gcgcccggca taaacatgtt ggccgtcttg cgcacctgcg agttgaggct gatgaaggtg    133140
ggcttgtgca gtcggtagca aggacacgcc gtggcgtcgc ccttctccgt gaagctgtgc    133200
aggtgctctt cgcacacgta agagaccacg ttgagcatgt caaagggcgc attgttgagg    133260
cgcgtcaaga aacacgtggc gtcactggta gtgttggtgg acgatatgaa gatgatcttg    133320
gtggtattct gggccaggaa ccccagaatg tgttgaagg cctctttctt gatgaagtgc     133380
gcctcgtcca ccagcagcaa gtggaagttt tgtcctcgga tgctctgtgt agagaggaga    133440
cagaaaaggg actcttataa ttacgcacgc tcggctggaa gcctacagag tcggggtggg    133500
gccggacagg tgagccaggt gagccgccag gtgaggcggg atcaccgtgt gccaaccggg    133560
ctgcgacctg aaaaccggaa ccaatccgcc gacaccggcg ccgcgtgacg cgcgcccata    133620
aaaacgaaag tgtcgtcgtc gcgacccgcc acagccgcca tgaactcgtt gctggcggaa    133680
ctcaaccgac tgggggtcgc gcacgccact acggaggatg tttttatctt tgtcgaccgc    133740
ctctttcaac acttttcctt ccttttccag gccgaggagt caggcccgcg ccgcttggaa    133800
ctggtcgcgt ccgtgttcga gcacctgacg gtggagtgcg tcaacgacat cctggacgcc    133860
tgcagccatc cggacgtgaa cgtcgcggag acaagcaaca cctgtcgtcc ctgcccttct    133920 cctgcccct ccgcccccaa aactgtcagc gacgctcaga cgtcatgtgc gacgcctcgg     133980
gcgcctgtga catgaggcac gtccagaacg cgtttaccga ggagatccag ttacattcgc    134040
tctacgcgtg cacgcgctgc tttcgcacgc acctgtgtga tctgggcagc ggctgcgcgc    134100
tcgtctccac gctcgagggc tccgtctgcg tcaagacggg cctggtatac gaggctctct    134160
atccggtggc gcgtagccac ctgttggaac ccatggagga ggcctcactg gacgacgtca    134220
acatcatcag cgccgtgctc agcggcgtgt acagctacct catgacgcac gcaggccgtt    134280
acgccgacgt gatccaagag gtggtcgagc gcgaccgcct caaaaagcag gtggaggaca    134340
gtatttactt cacctttaat aaggttttcc gttctatgca taacgtcaac cgtatttcgg    134400
tgcccgtcat cagccaactt tttattcagc ttatcatcgg tatctactca aagcagacca    134460
agtacgacgc gtgtgtcatc aaggttagtc gtaagaagcg cgaggacgcg cttctgaaac    134520
agatgcgttc cgaatatgga aacgcacctg tattcggatc tggcgtttga agcgcggttc    134580
gctgacgatg agcaattgcc tctacatctg gtgctcgacc aggaggtgct gagtaacgag    134640
gaggccgaga cgctgcgcta cgtctactat cgtaatgtag acagcgctgg ccgatccgcg    134700
ggccgcgctc cgggcggaga tgaggacgac gcaccggcct ccgacgacgc cgaggacgcc    134760
gtgggcggca tcgcgctttt tgatcgcgag cggcggactt ggcagcgggc ctgttttcgt    134820
gtattaccgc gcccactgga gttgcttgat tacctacgtc aaagcggtct cactgtgacg    134880
ttagagaaag agcagcgcgt gcgcatgttc tatgccgtct tcactacgtt gggtctgcgc    134940
tgccccgata atcggctctc aggcgcgcag acgctacacc tgagactggt ctggcccgac    135000
ggcagctatc gtgactggga gttttttagcg cgtgacctgt tacgagaaga aatgaagcg    135060 aataagcgcg accggcagca ccagttggcc acgaccacga atcaccgtcg gcggggcgga    135120
ctgcgtaata acttagacaa tgggtcggat cgccgtttgc ccgaagcggc tgtggcttct    135180
ctggagacgg ccgtcagtac tccatttttt gaaattccga acggagcagg aacctcctcc    135240
gcgaacggcg gcggcagatt cagtaacctg agcagcgggg tagcgcgttt gttgcgcggc    135300
gacgaggaat tcatctatca cgcgggtcca ttggagccgc cttccaagat acgcggtcat    135360
gagttggtgc agctgcgcct ggacgtaaat ccagacctca tgtacgccac cgatccgcac    135420
gaccgcgacg aggtcgcgcg tacggacgag tggaagggtg ccggtgtctc gcgtctccgc    135480
```

```
gaggtctggg atgtgcagca tcgcgtgcgc ctccgtgtgc tgtggtacgt caattccttt   135540
tggcgcagtc gcgagctgag ctacgatgac cacgaagtcg aactataccg ggcgttggac   135600
gcttatcggg cgcgcatcgc cgtcgagtac gtgctgattc gcgccgtgcg cgacgagatc   135660
tacgctgtac tacgacggga cagcggcgcg ttgccacagc gtttcgcctg ctacgtgcca   135720
cggaacatgt cctggcgcgt tgtttgggaa ctttgccgtc atgccttggc gctctggatg   135780
gatcgggcgg acgtgcgtag ctgtattatt aaggcgctaa cgcctcgtct gagccggggt   135840
gccgccgctg ccgctcagcg agctcgtcgc cagcgcgagc gctcggcgcc caaaccgcag   135900
gagctgcttt tcggaccgcg gaacgagagc ggtccgcccg ccgaacggac ttggtacgct   135960
gacgtggtgc gctgcgttcg cgcgcaagtg gatttgggcg tggaagtgcg cgcggcgcgt   136020
tgtcctcgca ccgggctttg gatcgtccgt gatcgtcgcg gacgcttgcg acgttggctc   136080
tcgcaggccg aggtgtgcgt gctctacgtc acgccagact tggactttta ctgggtgctg   136140
ccgggcggct ttgccgtctc ttcgcgcgtc actcttcatg gcttggcgca gcgggctttg   136200
cgagaccgat tccagaactt tgaagcagtt cttgcaagag gaatgcatgt ggaagctggt   136260
cggcaagagc cggaaacacc gcgagtatcg ggccgtcgct tgccgttcga cgatctttag   136320
tccggaggac gacggctcgt gtatcttgtg ccaattgctg ttgctctacc gcgacggcga   136380
atggatcctc tgtctttgct gcaacggccg ttatcaaggc cactatggcg tgggccacgt   136440
acatcggcgt cgtcgacgca tctgtcattt acctaccttg taccaactga gcttcggagg   136500
tcctttgggt ccagccagca ttgatttctt gccaagcttt agccaggtga ccagcagtat   136560
gacgtgcgat ggtattacgc ccgacgtgat ttacgaggtc tgcatgttgg tgccccagga   136620
tgaagccaag cgcatcctgg tcaagggtca cggtgccatg gacctgacct gtcagaaggc   136680
agtgacgcta ggcggcgccg gcgcctggtt gctgccgcgt cccgaaggct acacgctttt   136740
cttttacatt ctgtgctacg acctgtttac ctcatgcggc aatcggtgcg atatcccttc   136800
catgacgcgg ctcatggcgg cggccacggc ctgcgggcag gcgggttgca gcttttgcac   136860
ggatcacgag ggacatgtag atcccactgg caattacgtg ggttgcaccc ccgatatggg   136920
ccgctgtctt tgttacgtgc cctgtgggcc catgacgcag tcgctcatcc acaacgatga   136980
acccgcgact tttttctgtg agagcgatga cgccaagtac ctatgcgccg taggttctaa   137040
gaccgcggcg caggtcacac tgggagacgg cctggattat cacatcggtg tcaaggattc   137100
tgagggccga tggctgcccg tcaagaccga tgtgtgggac ctggtcaagg tagaggaacc   137160
tgtgtcacgt atgatagtgt gttcctgtcc ggtgcttaag aacctagtgc actaacgggg   137220
tctgacagtt cacggggaga agaaacaaga aataacaaaa aaaaaaagag gacatggact   137280
cgccacggtt tgtggcaagg cgtatgttat catcatggag ctactcacgt tggtgttgta   137340
gcaactggca aaaagcgccg tgctcttggc gccgcggtgg tcgatgctga tcacgttgtc   137400
cttgttctcg accacgtagt cgcgcgcgaa ggtgtggcgg cagcggaact cgacctcttt   137460
gagcacaaac tgcgacacgt gcttttggtg cgccacgtag ccgatgctga tgccgatcat   137520
gtgcttaagc agaaacgaga taatgggat gatgaaccaa gtcttgccgt gacgtcgcgg   137580
caccaggaac acggtggctt tctgcttaaa gatgtcgatg gaggtctgcg agaggaagtc   137640
gatctggaag gcgtggatga ggtactgcag cacgcgattg gccagcacgg ggatcttggt   137700
cacggctata aaaagatga cgtgtatcaa taaattcttt tgaaacggtt cgagtcggat   137760
ggcttttgcg tcgccctcga cggcggtact gaagccgccg tcgagccact ttttaaagtc   137820
```

```
ggtcatgaag ttgttgatct gctgaaactg cggatcgcgg tagagctcgg tcaacgcgtc   137880
cagcttctgg taggaggcgc gctgctcctc ggagcacggg cgaaacgtca gttcatcgag   137940
cgcgctcttg aggcgctcgt gaaacagcag ctcgcgctgg ctttcctcgg gcgagttgta   138000
gtcgcggtgg cggccgcaga aggccatgag cggcaggaag gcctcgttgc acgagtgggc   138060
cagcccgagt tcggggtgca tcatctggta gcgcttgcgg cacagcgccg ccacattggt   138120
gaaggccgtg gagatgcagg aggtgggtg gctcttgcgc ttctgcagct ccgcgtagcg   138180
ctcctggatc ttgcggccg aatctccgcg caacatgatg gcggcggcgg tggtgcgagc   138240
ggaggttagg cggcagcggc gagaggagag gaaaaagatg gcgtccgcga ggacgacgga   138300
ggatccaccc gaaaaccacg ttgtcgcgga cgtggcttgt gggacgggcg ccgtcactcg   138360
ttcgtcttcg tcgtccttag tggtgtcgtc ctcctcggcg tcaggctcag acgaatcttc   138420
atccgcctct cctctcagtt tccccgtctc ctccccctca actgccgtca ggtctccggg   138480
gtccgccggg gtttcaacgt ccctgtgctc ggtggaacgg atggtcgagc tgtcggcgca   138540
gtctccggcc gccgatttct cggtctccga ggcttggcgc ttcgaggagg ccgtaaatat   138600
ggcgctggtg gcctgcgagg ccgtgtcacc ttacgatcgc tttcgcctaa ttgaaacgcc   138660
cgacgagaat ttcttgttgg tcactaacgt aattccgcgc gagtcggccg aggtgccggt   138720
gttggatagc agtagcagcg gtggcgatag cgggccggag gacaaaaaga aaaacgtcgg   138780
gaataaaacc gcggggaaa agaacggcgg tgggtctcgg gccaaacgcc gtcgtagacg   138840
acgcgctccg aaaacgacg ccgccacgcc gtcttttcta cgtcgacacg acgtgctgga   138900
gcgtttcgcg gccgcggctg agcctttgcc gtcgctttgt gtgcgtgatt atgtgttacg   138960
caatgctgac cgtgttacct acgacggcga attaatctac ggcagttacc tgttgtatcg   139020
caaggctcac gtgagctgt cactctccag caacaaggtg caaacacgtgg aagccgtgct   139080 gcgacaggtg tacacgccgg gcttgttaga tcatcacaac gtgtgcgacg tggaggccct   139140
gctgtggctg ctgtactgtg gaccgcgaag cttttgcgcg cgtgacacct gtttcggtcg   139200
cgaaaagaac ggctgtcctt tccccgcgtt gttgcccaaa ctcttttacg aacccgtgcg   139260
ggactatatg acctacatga atctggctga gctgtacgtc tttgtttggt atcgcggcta   139320
cgaattccct gcgccgacgc cgcaggcgac gacggcgggt ggtggtggta gtggtggcgg   139380
cggcggggcc ggcgcttgtg cggtcgagac gagcgcgtca gcaggccggg tcgatgacgc   139440
cggcgacgag gtgcatttgc cttaaagcc cgtctcgctg gaccgtctca gagaggtatt   139500
gcaggcggtg cgcggccgct tctcggggcg cgaggtgccc gctggccgg cctcgtcgcg   139560 cacctgtttg ttgtgcgcgc tctacagtca gaaccgtctc tgtttagatc tcgcgcgtga   139620
cgaggcgcgg accgtgagtt atagccccat cgttatccaa gactgcgccg cggctgtcac   139680
cgacgtcact ttgagccaca tcttgcccgg ccagagcacc gtctcgcttt tccccgtcta   139740
ccacgtcggc aagttgctgg acgctctctc gctgaacgac gcgggtctca tcacgttgaa   139800
tctatgacgt cggtcaacaa acagctctta aaggacgtga tgcgcgtcga ccttgagcga   139860
cagcagcatc agtttctgcg gcgtacctac ggaccgcagc accggctcac cacgcagcag   139920
gctttgacgg tgatgcgtgt ggccgctcgg gaacagaccc gatacagtca gcgaacgacg   139980
cagtgcgtgg ccgcacacct gttggagcaa cgggcggccg tgcagcaaga gttgcaacgc   140040
gcccgacagc tgcaatccgg taacgtggac gacgcgctgg actctttaac cgagctgaag   140100
gacacggtag acgacgtgag agccaccttg gtggactcgg tttcggcgac gtgcgatttg   140160
gacctggagg tcgacgacgc cgtctaacag gtatagcaat ccccgtcacg cctctgttca   140220
```

```
tattttatta aaaaaaaaca caacataacg acagtgtcgg tgtggtagct agtgcagccc 140280
taggaacagg gaagactgtc gccactatgt cctccgcact tcggtctcgg gctcgctcgg 140340
cctcgctcgg aacgacgact cagggctggg atccgccgcc attgcgtcgt cccagcaggg 140400
cgcgccggcg ccagtggatg cgcgaagctg cgcaggccgc cgctcaagcc gcggtgcagg 140460
ccgcgcaggc cgccgccgct caggtcgccc aggctcacgt tgatgaaaac gaggtcgtgg 140520
atctgatggc cgacgaggcc ggcggcggcg tcaccacttt gaccaccctg agttccgtca 140580
gcacaaccac cgtgcttgga cacgcgactt tttccgcatg cgttcgaagt gacgtgatgc 140640
gtgacggaga aaaagaggac gcggcttcgg acaaggagaa cctgcgtcgg cccgtagtgc 140700
cgtccacgtc gtctcgcggc agcgccgcca gcggcgacgg ttaccacggc ttgcgctgcc 140760
gcgaaacttc ggccatgtgg tcgttcgagt acgatcgcga cggcgacgtg accagcgtac 140820
gccgcgctct cttcaccggc ggcagcgacc cctcggacag cgtgagcggc gtccgcggtg 140880
gacgcaaacg cccgttgcgt ccgccgttgg tgtcgctggc ccgcacccg ctgtgccgac 140940 gtcgtgtggg cggtgtggac gcggtgctcg aagaaaacga cgtggagctg cgcgcggaaa 141000
gtcaggacag cgccgtggca tcgggcccgg gccgcattcc gcagccgctc agcggtagtt 141060
ccggggagga atccgccacg gcggtggagg ccgactccac gtcacacgac gacgtgcatt 141120
gcacctgttc caacgaccag atcatcacca cgtccatccg cggccttacg tgcgacccgc 141180
gtatgttctt gcgccttacg catcccgagc tctgcgagct ctctatctcc tacctgctgg 141240
tctacgtgcc caaagaggac gatttttgcc acaagatttg ttatgccgtg acatgagcg 141300 acgagagcta ccgcctgggc cagggctcct tcggcgaggt ctggccgctc gatcgctatc 141360
gcgtggtcaa ggtggcgcgt aagcacagcg agacggtgct cacggtctgg atgtcgggcc 141420
tgatccgcac gcgcgccgct ggcgagcaac agcagccgcc gtcgctggtg ggcacgggcg 141480
tgcaccgcgg tctgctcacg gccacgggct gctgtctgct gcacaacgtc acggtacatc 141540
gacgtttcca cacagacatg tttcatcacg accagtggaa gctggcgtgc atcgacagct 141600
accgacgtgc cttttgcacg ttggccgacg ctatcaaatt tctcaatcac cagtgtcgtg 141660
tatgccactt tgacattaca cccatgaacg tgctcatcga cgtgaacccg cacaacccca 141720
gcgagatcgt gcgcgccgcg ctgtgcgatt acagcctcag cgagccctat ccggattaca 141780
acgagcgctg tgtggccgtc tttcaggaga cgggtacggc gcgccgcatc cccaactgct 141840
cgcaccgtct gcgcgaatgt taccaccctg cttccgacc catgccgctg cagaagctgc 141900
tcatctgcga cccgcacgcg cgtttccccg tagccggcct acggcgttat tgcatgtcgg 141960
agctgtcggc gctgggtaac gtgctgggct tttgcctcat gcggctgttg gaccggcgcg 142020
gtctggacga ggtgcgcatg gcacggagg cgttgctctt taagcacgcc ggcgcggcct 142080
gccgcgcgtt ggagaacggt aagctcacgc actgctccga cgcctgtctg ctcattctgg 142140
cggcgcaaat gagctacggc gcctgtctcc tgggcgagca tggcgccgcg ctggtgtcgc 142200
acacgctgcg cttttgtggag gccaagatgt cctcgtgtcg cgtacgcgcc tttcgccgct 142260
tctaccacga atgctcgcag accatgctgc acgaatacgt cagaaagaac gtggagcgtc 142320
tgttggccac gagcgacggg ctgtatttat ataacgcctt tcggcgcacc accagcataa 142380
tctgcgagga ggaccttgac ggtgactgcc gccaactgtt ccccgagtaa ccgggacgcg 142440
gaacgtgacg gttgctgagg ggaaaggcaa cagagaaggt acaaacccac cggcggggaa 142500
aataccgagg cgccgccatc atcatgtggg gcgtctcgag tttggactac gacgacgatg 142560
```

```
aggagctcac ccggctgctg gcggtttggg acgatgagcc cctcagtctc tttctcatga 142620
acaccttttt gctgcaccag gagggcttcc gtaatctgcc ctttacggtg ctgcgtttgt 142680
cttacgccta ccgcatcttc gccaagatgc tgcgggccca cggtacgcca gtagccgagg 142740
actttatgac gcgcgtggcc gcgctggctc gcgacgaggg tctgcgcgac attttgggtc 142800
agcggcacgc cgccgaagcc tcgcgcgccg agatcgccga ggccctggag cgcgtggccg 142860
agcggtgcga cgaccggcac ggcggctcgg acgactacgt gtggcttagc cggttgctgg 142920
atttggcgcc caactatcgg caggtcgagc tcttccagtt gctggaaaag gaatcgcgcg 142980
gacagtcgcg caactcggtg tggcatctgt tgcgtatgga cacggtctcg gccaccaagt 143040
tctacgaggc cttcgtcagc ggctgtctgc ccggcgccgc ggcggcggac ggttcgggtg 143100
gcggcggctc gcactacacg ggctcgcgcg ccggcgtctc gccgggcatc cagttcggta 143160
tcaaacacga gggcttagtc aaaacgctgg tggaatgtta cgtgatgcac ggacgcgagc 143220
cggtgcgcga cggcctcggt ctgctcatcg accccacgtc ggggctgctg ggcgcttcca 143280
tggacctgtg cttcggcgtg ctcaagcagg gcagcggtcg caccttgctg gtggaaccgt 143340
gcgcgcgcgt ctacgagatc aagtgccgct acaaatattt gcgcaaaaag gaggacccct 143400
ttgtgcagaa cgtgctgcgg aggcacgacg cggcggccgt ggcctcgctg ttgcagtcac 143460
acccggtgcc gggcgtggag tttgcggtg aacgcgagac cccgtcggca cgcgagtttc 143520
tgctttcgca cgacgcggcg ctcttcaggg ccacgctcaa gcgcgcgcgc ccgctcaagc 143580
cgcccgaacc gctgcgcgag tacctggccg atctgctgta tctcaataag gccgagtgtt 143640
cggaagtgat tgtgtttgac gccaagcacc tgaatgacga caacagcgac ggggacgcca 143700
cgaccactat taacgcgagt ctcgacctag ccgcgggcga cgccgctggc ggcggcgctg 143760
atcaccacct gcggggcagc ccgggcgatt cgccgccgcc gatacctttc gaggacgaaa 143820
acacgcccga gctgctgggc cggctcaacg tgtacgaggt agcgcgcttt tcactgccgg 143880
cttttgtcaa tccgcgtcac cagtattact ttcagatgct cattcagcag tacgtgctca 143940
gccaatacta tataaagaag catccggacc cggagcggat cgatttccgt gacctgccta 144000
ccgtctacct ggtctcggcc atcttccgcg agcgcgagga aagcgaactg gctgcgagt 144060 tgctggccgg cggtcgcgtt ttccactgcg accacattcc gctcctgctc atcgtcacgc 144120
ccgtggtctt tgaccctcag tttacgcgcc atgccgtctc taccgtgcta gaccgttgga 144180
gtcgcgacct gtcccgcaag acgaacctac cgatatgggt gccgaactct gcaaacgaat 144240
atgttgtgag ttcggtacca cgcccggtga gcccctgaaa gatgctctgg gtcgccaggt 144300
gtctctacgc tcctacgaca acatccctcc gacttcctcc tcggacgaag gggaggacga 144360
tgacgacggg gaggatgacg ataacgagga gcggcaacag aagctgcggc tctgcggtag 144420
tggctgcggg ggaaacgaca gtagtagcgg cagccaccgc gaggccgccc acgacagctc 144480
caagaaaaac gcggtgcgct cgacgtttcg cgaggacaag gctccgaaac cgagcaagcg 144540
gtcaaaaaag aaaagaaac cctcaaaaca tcaccaccat cagcaaagct ccattatgca 144600
ggagacggac gacctagacg aagaggacac ctcaatttac ctgtccccgc cccggtccc 144660 ccccgtccag gtggtggcta agcgactgcc gcggcccgac acacccagga ctccgcgcca 144720
aaagaagatt tcacaacgtc cacccacccc cgggacaaaa agcccgccg cctccttgcc 144780 cttttaactc ataaactttc aggtctcgcg tacgattcgc gagtcgggaa tgggacaccc 144840
gtgggtgttt ctccgtgtgt atattatttt tttttgtgtg tgtgtgtgtt tgcgcccccg 144900
tgtgtctaat gtgctgtttg aaacacgtaa agtagctggt ggaagaacag ataaaccttt 144960
```

```
aataaaaaaa aagtatgtgc tcccgaccca cggtctgcgt gtctcttttt tatgtccatg   145020
tctccaagtc tggtgcgggt ggcggcgggg tcaagcgtcc tcgaagtctt catcatcgtc   145080
gtcgtcctct tgttcgcgga ggcgacggct ttccaagctg tcgtggtgac tgagcgcagc   145140
gacttcttcg ccggaggctg tggccagcgc ctggtacttg acactgccgc taccgcgtcc   145200
gcgaaagtag cggacggcgc gacacgtcgt aaacatggcc catatgaaaa agagcatgcc   145260
gaacgaccag ctgatgccgg tgcggtattc gttgctgagg aaggtatcgt actgcacgat   145320
ggggtagatg aggccgcaga gtccaaagaa ggcgcccagg tggtagccga attgcacctt   145380
gacgtattga aaaagacgg cctcgatcag taaaaagtag atgatggaga tgatagcgta   145440
gaccacgaag acggctaaca ccatgtggcc tgtacgcacg aaaaagttgt tccgaagcc    145500 gtagcacagg gccatggcta ccacggtggt gttgaaacca agcgctacct ccaccaggtt   145560
gacgatgagc gtgcggaact gcaccgtacc tttgagcttg gggtgcagac gcgagaagaa   145620
aaagagtgag cgtttgtagc tgcggtactg cgtgaccatg ctcacgttga aaatggtcag   145680
gcagaaaaag tgcacggcgg ccatgaaggc gatcatgctg ggcagccgaa atgacatggt   145740
cagtgtgaat agttggaacg tgtccatgct gagaatgaag aggaaggctg tgaggctgtc   145800
gcccatgtac gaaatgtcgc gtgtcgactg gtttaggctc atgcctttgt ccttgcgcat   145860
gctgatcttg atccagcata ccaggtagta gatggtcacg gctaaaaaga cgagctgcat   145920
gaacacggcg tagcacacca actgcaccga gtctaagaaa agcataggcg tgtgcaggtg   145980
cattacgttg taggccgaca tgttgagcct ttcaaagtcc acgacgtgat agtgagcgca   146040
ggggtagccc aggtgcggaa aattgctcag cactagatgc acgctgacgt tgacaaaagt   146100
gagcaccatg aaaacgatag aagcgctcca tgtccgtgta ttcactttat ccacgtgcga   146160
gggggccatg gcgatagcgg cggcccgctc gctcgggagg cgatgggggc gcgccgatga   146220
cgacaggctc gcgggtcgtt aaatactacg atgggagccg ccgcggctca cgacgcggtt   146280
tgagcacgtc cgggcgatcg gtgaaaaaag accccgcggg ccttcgcgac tctcttctgt   146340
ccgaggatga ccgctcagcc gccgctgcac caccgccacc acccgtacac cctgttcggg   146400
accagctgtc atctcagctg gtacggcctt ctggaggcct cggtgcctat cgtacaatgt   146460 ctgttttttgg atctgggtgg cggccgtgcc gagccgcggc ttcacacgtt cgtggtgcgc   146520
ggtgaccgtc tgccgccggc tgaggtgcgt gctgtgcatc gtgccagcta cgccgcgctg   146580
gcctcggccg tgactacgga cgccgacgag cgccggcgcg gcctagagca gcgtagcgcc   146640
gtgttggcgc gcgtgttgct agaaggcagc gcgttaatcc gcgtgttggc gcgcaccttc   146700
acgccggtgc agattcagac ggacgctagc ggcgtggaga ttttggaggc cgcaccggca   146760
ctgggcgtgg aaaccgcagc gctatcgaac gcgcttagtc ttttccacgt agccaagcta   146820
gtggtcatcg gctcgtatcc cgaagtgcac gagccgcgtg tggtcacgca tgccgcggaa   146880
cgcgtctccg aagagtatgg cacccacgcg cacaaaaaat tgcgtcgcgg ttactacgcc   146940
tacgatttgg ccatgtcgtt tcgcgtcggc actcacaagt atgtgctgga gcgcgacgac   147000
gaggccgtcc tggcacgcct ctttgaggtg cgcgaggtgt gttttttgcg cacctgtctg   147060
cgtctggtca cgcctgtcgg tttcgtggcc gtggcagtga ccgacgagca gtgttgttta   147120
ttgctgcagt cggcctggac tcacctttac gacgtgcttt tccgtggttt cgctgggcag   147180
ccgccgttac gcgactacct ggggccggac cttttttgaga cgggcggcgc ccgttctttc   147240 tttttttccccg gtttcccacc cgtgcccgtc tacgcggtcc acggtctgca cacgttaatg   147300
```

```
cgcgagacgg cgttggacgc ggcggctgag gtgctctcgt ggtgcggcct gcccgacatc  147360
gtgggctcgg ccggcaagct ggaggtggaa ccctgcgcgc tctcgctcgg cgtgcccgag  147420
gatgagtggc aggtcttcgg caccgaggcc ggcggcggcg ccgtgcgtct caatgccacg  147480
gcttttcgcg agcgaccggc cggcggcgat cgtcgctggc tgttgccgcc gctgccgcgt  147540
gacgacggcg acggtgaaaa caacgtcgtg gaagtcagca gcagcaccgg cggtgcgcac  147600
ccgccgagcg acgacgctac tttcaccgtg cacgttcgcg acgccacgct acatcgagtg  147660
ctcatcgtgg atttggtcga gcgcgtgctg gccaagtgtg tacgcgcgcg cgacttcaat  147720
ccctacgtgc gttatagtca tcgactccac acttatgcgg tttgtgaaaa gtttattgaa  147780
aatctgcgtt ttcgctcgcg acgcgccttc tggcagatcc agagtctgct gggctacatc  147840
tccgagcacg ttacgtcagc ctgcgcttcg gccggccttt tgtgggttct gtcgcgtgga  147900
caccgcgagt tttatgtcta cgacggctat tcgggtcacg gacccgtctc ggccgaagtg  147960
tgcgtgcgga ctgtggtcga ctgttattgg cgcaaacttt ttggcggcga cgatccgggt  148020
cccacctgtc gtgttcaaga gagcgcgccc ggcgtgctgt tggtttgggg cgacgagcgg  148080
ttggtgggtc ccttcaactt cttctacggc aacggcggcg ccggtggtag tccgctccac  148140
ggggtggtgg gtggtttcgc ggcgggacat tgtggcggcg cttgttgcgc gggctgcgtc  148200
gtcactcacc gccattctag cggtggcggc ggcggtggtg gtggcgtggg cgacacggac  148260
cacgcgagtg gcggcggtct agatgccgct gccgggagtg gtcataacgg cggtagtgat  148320
cgggtttctc cctccacgcc gccgcggcg ttaggtggct gttgctgcgc ggccggtggc  148380
gactggctct cggccgtggg tcatgttctg ggccggctgc cggcgctgtt acgggagcgc  148440
gtgagcgtgt ccgagctgga agccgtgtac cgcgagatcc tctttcgctt cgtggctcgc  148500
cgcaacgacg tggactttg gttactgcgc ttccagcccg tgaaaacga agtaaggccg  148560 cacgccgggg tgattgactg cgcgcccttc cacggcgtgt gggccgagca gggccagatc  148620
atcgtacagt cacgcgatac ggcgttagcg gccgatatcg gctacggcgt ctatgtggac  148680
aaggcctttg ccatgctcac ggcttgcgtg gaggtctggg cgcgagagtt attgtcgtcc  148740
tccaccgctt ccaccaccgc ttgttcttct tcttccgttc tctcttccgc cttgccgtcc  148800
gtcacttcgt cctcttcggg cacggcgacg tgtgtcctc cgtcttgttc ttcttcgtcg  148860
gcgacttggc tcgaggagcg cgacgagtgg gtgcgttcgc tggcggttga cgcgcaacac  148920
gctgctaagc gggtggcttc cgagggcctg cggttttcc ggctcaacgc ttaacgagtc  148980
acgtagggga actacgtggg taagtgacgt ggatactagt aaaaaaagtg cgtcaaagtt  149040
ctcagcgtgt gacgtggata ctagtaaaag ggacgtcaaa gctcactacg tgttgcgtgt  149100
tttttttttt tctatgatat gcgtgtctag ttcgcttctc actcttcctc tccccgttcc  149160
cagcgcggtg gcagcttggg gggtgagggc aaattggggt agttggcgtt gagcacgtct  149220
agcaggccca ggcccacggg ccaaccgtcc acggtcttac gctcggtcag cttgaggcta  149280
aacgagtgtg cctcgtcttg accggtaagg cggaaaaaga agcgtgctac cagctgcagg  149340
caggtatgcc gcgtctgctg gaagagcacg aaggtagcgg gcacgtactg cacaatgtgc  149400
ggttcttttt cctcaaagag taggtagagc gcgctgcaga tcagccgccg ggcgctgtgg  149460
tgcagcagcc ggccgaagct ttcgcgcacg ttcactgcgt ccaggtactg gagcaggtcg  149520
tgcaggcact tgcgcgttaa gttgcaattt tccacgcatg aaataacggt acagagcgcg  149580
aagtgcagca ggttgtcggc cttgacgatg ccgcagcggt gtttgagccg cagatccgag  149640
agcctcacct gcgtgacgac gtcttcggtc tcgagcaaaa acacggcgga gtagcccaga  149700
```

```
aaggccgagg tgcacagcaa ctcgctgcgg tactcggcca tggaaaccag cagcccgtgc   149760
tccgtgtgca gccacagctt gtcgccgcgc accgtaaagt cgagcacttg cggctccatg   149820
atcatcacat tctgtctagt gaaatccgta tggacctcca gcacgccgcg gatcatcagg   149880
gcctccattt cgaaatcggc cgacacgctc tgggccgcgc cgctcctcgt ctgccgtgat   149940
caagcggcgc ggcgcggacc tttcaagcgt tcctgggccg ccgctcgagg cagttcccct   150000
ttctggcact ccgcccgccg cttcgcggct catttggcgc cggcgcgcct tctcgcggct   150060
gcaaatcagc tccacgtatc ggcaaaactt gctgtcgtcg taggcggcgg ccacgatctc   150120
gccgaaggag agctgcaggt aggcttcggg tacgggtcc agcgtgccta gcgccaggat   150180
gtgacacaga tagggcaggg tcacgcgctc taccgtgtaa ttggagtaga cgatggcctc   150240
ttcggcccct tgatgcgtga ccagacgccg taggcgaaag gtgcggaaat actcgttttc   150300
ccacaactgc gtgaggaagc gttctagcga ctcggtgcca ggcacgaact gcgagaagaa   150360
gctgttggcc accaggcggt tgtcttccac cgccagcgga cggaagggcg ccgcgtcgcg   150420
cgccttgcgc acggcctcca acacgggcag gtggtagagt tcggcgtcgc gcgcgcccag   150480
gctcatggag tcctcgcgcc gcgaggcgta gcgcgtgagc aggtcgcgca gctcgcgcac   150540
gcgattctcc caggtctggt tgagcgtgcg caggtcctgg atctcgtcca cctgcgactg   150600
gatctgctcc tccaggcact tgatgacctg cttcttaaac aggtcgcgga tgtcccgctc   150660
gggcgccgcc gggccgggtg gcggcggcag cagcccgacg tggcccgcgg gtcctcccac   150720 cacgcgccg ccgggtccca ccacgccggg tccaccccgga ccacgcgcgg gtagtagacg   150780
gttttggtcc accagcgagg gggtcaggtc ctgcagaaag gactcgacgc tgtcctcgat   150840
gccgatgcgc gatttgctgt ccgagacgtt aagcaaaaac ttcataatgg acttttggc    150900 gtcgctgccc cggtcgtgct gctccatcat ctccaccagc ttcttgcagt tgagctcgtg   150960
gcggctggcg gtcaccactt tcacaggaaa ggtattgagc agctggcaga tcttttggtg   151020
gcggcagagc ccgtcgtagc gcagaatctc ctcgtgcagg tgtgccaccg gcgtggtgaa   151080
cagcagcttg tcgcgctcat aagccagcgg ttcggccgcc acgtacaagc ggatgtgctt   151140
gccgcgcagc tgcgcctcca gccgctccga gcgcaccttc ttgaagacgc gtacctcggg   151200
cgcgttggct acgcgcacgg cgcccaggcg ctcggccacc tgcagcagca gcgccaggtt   151260
agcctgcagc aggtcctgcg ccagcgggtg tgtctcggtg gcccgctgca cggccgcgcg   151320
tacaaattgc gcccgctcgg ccgcctcgct cggcttggtt ttcacgtcca gcagcggtac   151380
cagtcccacc gttacgcacc aatccacgta gagaccatag tcgtcgttat cggcgtactg   151440
atataaaatg tcgcggagcg cgcccagcac gcccgtttgc acgctctggc gcaacgaggc   151500
gctccacacc aacagatact gctccaggtc ctcttcgtcc agcgcgcggt agggaaacag   151560
cgccgcgtgt aacttccact cctcggccac gcgccgcacc gtgatggtgt caaagagcgt   151620
cttgcacact ccgtagagca gctgcttgcg cagcacgcac gggtcgcgca gcacctggtg   151680
catgctctgg ccgcgacacg tccccagaaa gccgtgcagc aaccgcagga agctcatcgt   151740
ctggcccgtg gggaaaatgt cgatgacggc ctcgtcatcc acgccgcggc ccacgcccaa   151800
gtacgacgac gccttgatcc tcaacctctc gtcggctgcc aagatcgaac ggatcgtcga   151860
caaggtcaag tctctctcgc gcgagcgctt tgcgcccgag gattttcgt tccagtggtt    151920 tcgctccatc agtcgcgttg aacgaacgac agataacaac ccctctgccg caactaccgc   151980
cgcggcaacg acgaccgttc actcctccgc ctcctcttct gccgccgctg ccgcttcgtc   152040
```

```
cgaggccggc ggcacgcgcg taccctgcgt cgaccgttgg cccttctttc ccttccgcgc  152100
gctgctcgtc accggcacgg cgggcgccgg caagacttcc agcatccagg tgctggcggc  152160
caatctagat tgcgtgatca ccggtaccac ggtgatcgcc gcgcagaacc tcagcgcgat  152220
cctcaaccgc actcgctcgg cgcaggtcaa gaccatctac cgcgtcttcg gtttcgtcag  152280
caagcacgtg ccgctggctg atagcgccgt tagccacgag acgctggaac gctaccgcgt  152340
gtgcgagccg cacgaggaga ccaccatcca gcgcctgcag atcaacgatc tgctcgccta  152400
ctggccggtc atcgccgaca tcgtggacaa atgcttaaat atgtgggagc gcaaggccgc  152460
ttcggcctcc gccgcggccg cggccgccgc ctgcgaggac ctctcggagc tgtgcgagag  152520
caatatcatc gtcatcgacg agtgcggcct tatgctgcgc tacatgctgc aggtggtggt  152580
gttttttttac tacttttaca cgccctggg cgacacgcga ctttaccgcg aacgccgcgt  152640
gccctgcatc atctgcgtcg gttcgcccac gcagaccgag gcgctggaga ccgctacga  152700
ccactacacg caaaacaaga gcgtgcgcaa gggcgttgac gtgctctcgg cgctgattca  152760
gaacgaggtg ctcatcaact actgcgacat cgccgacaac tgggtcatgt ttattcacaa  152820
caagcgttgc accgacctgg actttggcga cctgctcaag tacatggagt tcggtatccc  152880
gctcaaggag gagcacgtgg cctacgtgga ccgcttcgtg cggccgccca gctccatccg  152940
caacccctcg tacgccgccg agatgacgcg gcttttctc tcgcacgtcg aggtgcaggc  153000
ttacttcaag cggctgcacg agcagatccg cctgagcgag cgccaccgtc tcttcgatct  153060
gcccgtctac tgcgtggtca acaaccgcgc gtaccaggag ctctgcgagc tggccgaccc  153120
gctgggcgac tcgccgcagc ccgtcgagct ctggttccgc cagaacttgg cgcgcatcat  153180
taactactcg cagtttgtcg accacaacct ctccagcgag atcaccaagg aggcgctgcg  153240
ccccgcggcc gacgtcgttg ccaccaacaa ctcctccgtc caggctcacg gagggggagg  153300
atctgtcatc gggagcaccg gcggcaacga cgagacggcg ttttccagg acgatgatac  153360
caccaccgcg cccgatagcc gtgagacgct gctcaccttg cgcattacct acatcaaggg  153420
cagttcggtg ggagtcaact ctaaggtgcg ggcctgtgtt atcggatacc agggcacggt  153480
cgaacgtttc gtggacatct tgcaaaagga cacgtttatc gaacgcacgc cctgcgagca  153540
ggcggcctac gcctactcgt tagtttcggg cctgctcttc tcggccatgt actacttcta  153600
cgtgtcgccc tacacgaccg aggagatgtt gcgtgagctg gcgcgcgttg agctgcccga  153660
cgtgagttcg ctctgcgccg ctgccgccgc cacggccgcc gctcccgctt ggagcggggg  153720
agagaatccg ataaataatc acgtcgacgc ggattcttct cagggcggcc agagcgtgcc  153780
ggtatctcaa cggatggaac atggccaaga ggaaacccac gacatcccct gcctgtccag  153840
ccaccatgac gactcggacg ccatcacgga cgccgaactc atggatcaca ccagtctgta  153900
cgcggatccc ttttttctca aatacgtcaa gccacctagc ctggcgctgc tttctttcga  153960
ggagacggtg cacatgtaca ctaccttccg cgacattttt ctcaagcgct accagctcat  154020
gcagcgtctc acgggcggtc gcttcgccac gttgccgctc gttacctaca atcgccgtaa  154080
cgtggtgttc aaggccaact gtcagatcag ctcgcaaacc ggctccttcg tgggcatgct  154140
ttcgcatgtg tcgccggcgc agacgtacac gctcgagggc tacaccagcg acaacgtgct  154200
cagtctgccc agtgaccgcc accgcatcca ccccgaggtg gtgcagcgcg tctttcgcg  154260
gctggtacta cgcgatgcgc tcgggttcct ctttgtgctc gacgttaacg tctcgcgctt  154320
cgtcgagtcg gcgcagggca agagtctgca cgtgtgcacc accgtggact acggcctcac  154380
ttcgcgcacg gccatgacca tcgccaagag tcagggcctg tcgctcgaga aggtggccgt  154440
```

```
ggactttggg gaccatccca agaacctcaa gatgagccac atctacgtgg ccatgtcgcg    154500
agtcacggac cccgagcacc tcatgatgaa cgttaacccg ttgcgactgc cctatgagaa    154560
gaacaccgct atcaccccct atatctgtcg cgcgctcaaa gacaaacgca ccacgcttat    154620
tttttgacac aacaccgtgt aagcaaaacg tgactttatt gagcagggta aaaaccacgt    154680
acaagaacca cgttgtctat cccccaaaa aaaaacacac cgtcagggaa cacatcgcct     154740
atagatagcg gcactttaca taaaaccacc gtacctgcat cacggtggct cgatacactg    154800
gaaattcaat aaaaaccacc gtgtccacgt tacggtactt gccgggtcag cgtccttctc    154860
ttgagatttc tgttcgcaaa cttatccgtt tccccggtcc gcggtgtctc ctcgcgaggc    154920
tgacagtcta cgagtggtat ctacaagaga aagaaacccg ggtgggagcg acgccgtcgc    154980
tgggtatcaa ccccgcggct gaccgtcgtc cggtaaagga acaacccgtc gtcgcaagcc    155040
gggttcgacc aagagaaaaa aacccgggtg cggggggaga cgggtcgtcc tttggtcgtt    155100
cgcggacggc gtacatgccg cgtgggtcag tcgacggcgt cgctccgtgc ggtcggtcat    155160
cattctgctt cacatatatg ggttgtttgt gttttttta taatgaatac gcactcatcc     155220
tatccgtgac tgcgcgtgtg gcagagagga tgccttataa catgtatttt gaaaaattgc    155280
caacagctat aatttctctc atgtagcaga atagagacct tttgtcgtct ttttgtttgt    155340
cattacttgt tttccaggga attagagaga gggaaccgcg cctccggcgg cggtgcccgc    155400 ggacccggc ccttctcgc gtgcgcggtg tgactggttg agcgaatgag cagctaggct      155460
tggtggtgct ccgcgtgcgg gggagaagac gattaacaac aaaaaataag tggaagtggc    155520
cggtgggtct ttgtccgcgt gcgcgcccat ccgtcgccgg gaccgagcag aaagtgatgt    155580
ggtggtacat tgattttttc cttgacagga aagaaaaaaa agagttttgt tttcctatgt    155640
gagaggagaa aggtatgtga ggagatgttc gatgatcgta tgttacagtt atgctgtaag    155700
gaagctttta tcgtgcgtcc tgttttttcat ttgatgtata tgacacaatt gaaacctatc    155760
gataggcgta tatcgaggat tcatcaattc ttagaatcgt cgtcttttg gctaattgga     155820 ctttgcccat gttggttgtc attcgtggcc tgaggtcatc gtcgtccacg acgacgtgtc    155880
tatagcgtgc ggtgtgatca ttgtgtcgag ccagagaaag cgcgcctcgc acgacgtttg    155940
cggatcggct cgcgggtgtg tggaattcct aagaacataa tcagctggtc gtctttcttt    156000
gatgtgttgt tgtcgtcgag gtcttgcttc gttttcttt ttcttttag tcgatggaac      156060 ttttcttcgg tacgggttct tgttatggaa gcttgtgttt tcgaacatga attcgaaaaa    156120 ataaaaggc ctatcttcgt ttcaaaaaaa ggacagatat caatcttctt aacttatatc     156180
atggtaaatt cagaatccta tggtgtctta ttatctctaa agtagtcaac attatggtct    156240
aacttgtatt tccctgacga gatatatatg atccttataa cctggctact atcatgaaca    156300
acaatatcct tacttacagt catcttcgtg agttaatgaa gtataatatc ggtcatctat    156360
caacttatct gctatgtaac gtacccttt aggtattttg cgtttcttaa cgagtgtacc     156420
cgcctgtgtg aggcgaaact ctgagaagtc taccgagtcg agttacaagt cactaaaaca    156480
cttacacgag ttatctatac taaaatcact atctatgttg tttgcttacc taattattat    156540
cctacatgac gaagctacct cccaacgtaa ggtaggggga gaggagacag aacaataaaa    156600
agtaactaat gtttcttaga acttacccgc taaggactta ccaaactata ttcaccaaaa    156660
aacaacagct acgtgtttca tttgttttaa tctaccgaag taaaaaaaaa aaagatgatt    156720
agctatccag aacctactta cttcttaatg tttaaactaa ggatgcctat gggattggaa    156780
```

```
aaaaaatcac agcaacttgc tactaatcag ttgacagcga agagactcat aacaaagatt  156840
tctgggtaat acggttataa taatgcttat ggactaaagg atacttggaa aaaaagaacg  156900
ggctatgact atagagattc gtcgagatat taaacttcaa ataggcggct atcattcatg  156960
gttgtggtga ctatatcgtg gagaaaaaat gtgatcgtta gttagctagg tgagacttac  157020
agctatccat ccgtctagtt tttcgttgta atgatgatag tacgtctatg gtggtgatcg  157080
attttggtta acaatttgtt cgtttaaagg cttaatgtac ttatgctaca tgatgtatta  157140
ttctttgatt catcgttcct cctaagggg tgtatgtatg tatgtactag tcgtatagtg  157200
ttcctaacat catgattatt cagactatgg cttcatctat cgtgtctaaa gttcacttat  157260
tctactatta ctatatatat gcactactat gtaactagga tatggtccta aaggtgtct  157320 tctatcacgg tggcttgttt atcgcttggc ggttacgagc aagagttcat cacggaccag  157380
ccgtgaggca gggcacacgc gggtcggcgg cgatgatgtc ccccgcgaag gggacaacaa  157440
aaacaagaca agaggccgcc ggccgcggcc acggacgcgt agcggttaca caatgtttgg  157500
ttgagcgttt tgtttcatcg tcgtggtggt ggttttgttg ttctctgtat atatcgtgtg  157560
gtggctttat cgtcatcatt attatcatca ttcttgtttc catcatcacg atgagttttc  157620 tccgtttttcc tctcctccag tggtagtcgt gtatcatcat caatcatcgt agtgacgtcg  157680
ttgctgctgc tgctcttgcc ttcatggcgg tatttctctt cctccccct aaccccatat  157740 taactcgtga gtgtgatggt tagagtggct gcttgttttt ttttcttttc tctttggaac  157800
aacaaaagag gataaagatg gtcggtgaat gtattattat tattatcatc attatgatac  157860
ggtcgcggtc ttcttctccg atgacgaaac ctgcgcacat cgaagaaaag acgagcgcgc  157920
gaaccgatag ccgtccgtct gggacgaagg agaagatgat ggggagagga ggagagcccc  157980
agaagccaga gcgagaaggg agacgacaga catacgtcgt caccgtcctc tggaggaggc  158040
acggcggcgc tgtttgttgt ttggatgctt gattatatcc tgttctatgg ggtagattat  158100
tatcaatagg cttggttttc aaaggtcagc ctgtgtattg tcgtgtcttt ttttcgttc  158160 tcatgatcgc ggagaccaca cagacgtgcg cgtctcccaa tggctaggcg ttctttttag  158220
gtagtaattt tttgatcttt tttttttctt aacaagtctg gcttgatttc ttttatctat  158280
gatcgattct tcttttttctc ggggttgca tcttccgtga agtaaagtg acactactct  158340 aaatggtaac catattatct gttgattagg agaaaaaata atttttttcgc acgaaatcga  158400 tcctaagtga ggtgatttac ttgctatcac acgaaatgat tatcttttgc tgctaacgta  158460
ctgaattttt taacagaatt gcttctccgt aactatttcc gcagattcag acagattgtc  158520
aaaaaaaaat acggcacaga aatagtgggt ctgtggcttt tggttcgtgt acattcgcgt  158580
ttgcgtgtcg agatttctac ggtatgttta ttcttcctgc gatgatgtag ggtccttggt  158640
gtaagtagga tttcgagtat ctctcttaga gcgaacaaaa taatcaaaaa acaacagcta  158700
ggaaatcgag ggttactcta cgataaagtg tctctacaaa gtgaagaatg ttacgttgtg  158760
gtggaataat aagactcgcg tgatcgatga gtgatcgaga gcggctcgaa ccttctttaa  158820
gagctttgtt tagtgcaact ttaaattaca aggagtagaa agctgaaatg aatctatgaa  158880
ggtgctattc tttgaatatc ttactttgta cgcttcacat tcgttatttg gatagagagt  158940
tgtctagaga aaatctgtga ttctctatga gtgttatttt tattatcctt tgggggacta  159000 cgattttttct tcttgttcta cataccacta ctactcgtaa tcacatacat ggacgaaaaa  159060
aaaattcgtc aggcagtaga taccagattc tccgacgtta cggcgtcttt ttttcttttg  159120
agagagtatc tgctgagatt gtccgtggtg tatctagtcg ctattttgt tgttactagt  159180
```

```
agttttgcac acagtttatt cagtataatt tttcttcttg ccatgatcaa ttgagcccac    159240
caccttttt ttttagagag gaggaatttc gtcttgatct ccagccggag acaacggcgg    159300
cggtggtggt ggcgggagag atttcaaggc aatgaaaaaa aaaatttcgt tttgccatca   159360
agtggtgacg ataacccgtc agattgataa ttggttccta cagaaactat tctaaccgcg   159420
gaagaaagaa attgaaaaaa aaattgaca aaacatcat aacataaagg accacctacc     159480
tgggacgcgc agttgggcgg cggactgggg cggcatgctg cggcgatgct gtcggtgatg   159540
gtctcttcct ctctggtcct gatcgtcttt tttctaggcg cttccgagga ggcgaagccg   159600
gcgacgacga cgacgacgat aaagaataca agccgcggt gtcgtccgga ggattacgcg    159660
accagattgc aagatctccg cgtcaccttt catcgagtaa aacctacgtt ggtaggtcac   159720
gtaggtacgc tttattgcga cggtctttct tttccgcgtg tcgggtgacg tagttttcct   159780
cttgtagcaa cgtgaggacg actactccgt gtggctcgac ggtacggtgg tcaaaggctg   159840
ttggggatgc agcgtcatgg actggttgtt gaggcggtat ctggagatcg tgttccccgc   159900
aggcgaccac gtctatcctg gacttaagac ggaattgcat agtatgcgct cgacgctaga   159960
atccatctac aaagacatgc ggcaatgcgt aagtgtctct gtggcggcgc tgtccgcgca   160020
gaggtaacaa cgtgttcata gcacggtgtt ttacttttgt cgggctccca gcctctgtta   160080
ggttgcggag ataagtccgt gattagtcgg ctgtctcagg aggcggaaag gaaatcggat   160140
aacggcacgc ggaaaggtct cagcgagttg gacacgttgt ttagccgtct cgaagagtat   160200
ctgcactcga gaaagtagcg ttgcgatttg cagtccgctc cggtgtcgtt cacccagtta   160260
ctttaataaa cgtactgttt aaccacgttg cgtcgtgacg ttgtttgtgg gtgttgctag   160320
gcgggctgga aagatgatgt ataaatagag tctgcgacgg ggttcggcgc tctgccggct   160380
gcggcggcac tcgctccacg gcctccgacg agcgttgcgc tcgcgctttg cgccgccgcg   160440
tcatggatct gcctactacc gtcgtgcgaa aatactggac ttttacgaat cctaaccgca   160500
tcctgcatca gagcgtcaat cagactttcg acgtgcgcca gttcgtcttt gacaacgccc   160560
gtctggtcaa ctgcgtggac ggcgatggca aggtgctgca ccttaacaag ggctggctct   160620
gcgctaccat tatgcagcac ggcgaggctt cggccggcgc caagacgcag cagggcttca   160680
tgtccattga cattacgggc gacggggaac ttcaggagca cctctttgta cgcggcggta   160740
tcgtctttaa caaatccgtc tcctcggtgg tgggctccag cggacccaat gagagcgcgc   160800
tgctcactat gatttccgag aacggtaatt gcaagtgac ttacgtgcgg cattacctga    160860
aaaccacgg cgaatcctcc agcggaggcg gtggttgcgg tgccgcgtct accgcctccg    160920
ccgtctgcgt gtcctcgctg ggtggcagcg gcgggactcg cgacggccct tctgcggagg   160980
aacagcaacg gcgaaggcag gaacagcgtc acgaagaacg gcgcaaaaaa tcgtcctcgt   161040
ctgccggtgg tggtggaggc ggcggcactg gtggtggcgg tggcggcggc gggagcggcg   161100
gtcagcactc ctcggactcc gccaacggac tgctgcggga tccccggttg atgaaccggc   161160
agaaggagcg gcggccgcct ccctcctccg agaacgacgg tgagtccgg ccctcctcgc     161220
gtcacggtgc tttccgagtg gactcgtgag cccccgtag cgcacgagcg agcaggcgag     161280
cggtgttggt gcgctggtgg ttgtgtggat gataaccatg tgcttttcg tgcgctatgt     161340
gtcgtcccgt ctgtaggctc tcctcccctc cgggaggcga agagacaaaa gaccaccgca   161400
cagcacgaag gccatggcgg cggcggcaag aacgagacgg agcagcagtc cggtggtgct   161460
ggcggtggtg gtggcggcgg cagcggccgc atgtcgctgc cgctggacac gtctgaagcg   161520
```

```
gtggcctttc tcaattactc gtcctcatcc tccgcggtct cttcttcctc caacaaccac  161580
caccaccatc atcaccacca taacgccgtg acggacgtgg ccgccggcac cgacggtgcg  161640
ttacttctac ccattgagcg cggagcggtg gtttcgtcgc cgtcgtcgac gtcgccgtcg  161700
tcacttcttt cgctccctcg acccagcagc gcccacagcg cgggcgagac ggtgcaggag  161760
tccgaggcgg cggcgacggc ggcggctgcg gggttaatga tgatgaggag gatgaggagg  161820
gctccggctg aggcggcgga ggcaccaccg cagtcggagg aggagaatga ttccaccact  161880
ccagtctcta actgccgtgt tcctccgaat tcgcaggaat ccgcggcgcc tcagcctcct  161940
cgcagtccgc gttttgatga cattatacag tcattgacca aaatgctcaa tgattgtaag  162000
gagaaaagat tgtgcgatct cccccctggtt tccagcagac tcttgccaga dacgtcgggc  162060
gggactgtcg tcgtcaacca cagcagcgtc gcgaggaccg ccgcagctgt ctccacagcc  162120
ggcgttggcc ccccagcagc cgcatgtccg ccactcgtca ccaccggtgt tgtaccctca  162180
ggttccgtcg ccggtgtcgc gcccgttgcc ccgcagtcg aaacaccagc tgctcctccc  162240
cggcccgtgt gtgaaatcaa gccctacgtg gtaaaccccg ttgtcgccac cgccgcggct  162300
gccagtaact cttcctcgtc ttcttcggct ccactgccgc cgccgccacc accgccgggc  162360
ggacgtcggg gtcgggcccg gaacaatacc cgaggaggcg gcggtggtgg cggtggtaga  162420
aacagccggc ggcaggccgc atcgtcgtcg tcctcctcct ctcggagatc gcgacggaga  162480
aacaaccgcc acgaggacga ggacaacgat cctctgctcc ggttgtcgca agtcgccggc  162540
agcggccgcc ggcgagggcc ctcgttcctc gaggacggac tcgaaattat cgatcccagc  162600
gaggaggctg cgatcgccgc cgcctcgatc gcggcgtttt tcgacgatta aaaaccgag  162660
ccgagaccgg aaaaattatg aaacaggacg cgcttggaca tttgggtttc caccccttc  162720
ggtgtgtgtc tatatatatt gtggtcactg attttttttt tacaataaag agatagacat  162780
cacagttcac catcttgtct ccccggtgtg tctattatca tcaatcaccc acagagtcgc  162840
cagtccatgg tctctcggta atgcgtgtcc agatacgcgt tggccagtat aaagtggtcg  162900
ttgcccacga aggcgcgggt ggtgttgcgc ggcgacgggt ggcaggactt aagtaccaag  162960
tgccgccgtc ggtcgatcag gtactcgcag gtgtgcgcgt cggcgcccca cagcatgaac  163020
accagatgct cccggcgctc tgacagcctc cggatcacat ggttactcag cgtctgccag  163080
cctaagtgac ggtgagatcc aggctgtccg tgcaccacgg tgaacacggt gttgagcagc  163140
agcacgccgc gtcgcgccca ggcgtccagg caacccgagg ccggacgctg aaacccgtcc  163200
accgtacgcg ccagttcgcg aaacacgttg ttgagggagg gcggcggcgg tcggcccgcc  163260
agcgtgccga aggccaggcc gctggcgctg ccgtcgcagt acgggtcctg gcccacgatc  163320
accacgcgca cctgctcggg cggacacaga tagctccagc ggtgtacgtg ctcgggtgcc  163380
gggtacacca tctcgagttg ccgcgcgcct tccaccgccg ccaccgtgtc gcgcagcagc  163440
accgtgtcgt ggtcgggcaa gctgaggaag cggatccagt cggcgctcag acaaaacacg  163500
cgagcctgct cgtcggggt taacagagag cctttattat cagcaatgtt agcgagcatc  163560
cactgcttga gggccatagc gcgagtgagc cggcaggttg acgcgcgtct gcttcagctc  163620
gggcggcagt ccggcgtagt atttatctag gtggcgtagc agcggcgggt ccagctggtg  163680
acgcaggcag aattccttca ccgcgttgta caggccgtaa aagagcgtga tgccctcggg  163740
cgcggcagcg gtgctcacgg gcagacgcac ggcgcggttg gtacgcgtgg cttcgttgcg  163800
tatgccacc accacgttaa agagagacgg tggcaccagc tcgaagccta acacgtgttc  163860
cgtgaagatg ctgcgcccgt atgacagtcg cgtgaggtcg tagccgcggc acaggtcgtc  163920
```

```
cacgcacgtg tacacggccg gcgagccatc gccgcactcg ctgtagccgc gcattaccgt   163980
catccagcgc ggcgctgtgt ccgagcttaa cagcgtcagc agggcccgca attgatccgg   164040
attgttgtac agcagggcca gagtgtccag gaaagcatcg tccaacagca cggagttggc   164100
ggcctccggc gtaacgggac ggtaacggat aagttgcgat agcgggccat cgcgcccggt   164160
aacattcacc aacgggcgca gccaactttc atacttgtca ccctgaaaca cctcacccaa   164220
caggcatcgg cgcgttagtt cggggcactc cgcggggact ttctcggcgg cggtaggagc   164280
gacgctgacg gcggctgagg aaacaatgga cagcagaagg caacaccaca gcagtatcac   164340
cggtccaggt gagaaagaga agccgcaatc cgggcggcgg cacatcaagt ctgcggcacg   164400
atgagagtgt gacggtaagg agccagttgg cgccgaaagt tggcactcag gtcttcgatc   164460
cctaaaacgt tatatattgc atccagcagg tgagccaggc taaacggatt cacgtaccag   164520
gtttggttac ccgcgacgat gacggccaga ccgtgggcgc tacagttgga gaggttcctg   164580
ggtacgaagg taactgagtc gatgtcgcgc acgggggga atgagacaga cgactggcgc   164640
acgctgtaat cacaactgtg attgacgtat tgtagcgtgt aatttaggtt gcactcagcc   164700
tcgaagtaga gggggaacca cagttcgtcg tactcgtcgt cgtcctccag ttctggctct   164760
tcttcatcca ccgcaatgtc tacgctgctt tgagattcct cttcgtacag gatgattgac   164820
aggttatggc tacaaaggtc ctgggcggga ggacgcgtgg gagcgcgggt ggtggtaatg   164880
ttttccagat caaaagttgg agtgtagtcg gatgttacat ccccgttgtt ggaggtggta   164940
gaagttgcgg ccggtgtcgc ggtggtaagt atggatacag aaggggaggg ggaagtagcg   165000
ttcgtaccga tggttgtggt attattattc cctgtgtttc ttgttccaga aaccgttgac   165060
gttgagatgg gaatcgacgt ggtgctggac gtcagattgc tgaccgagga aaccgtggtg   165120
ggagtggtga cggtgttact cgtggttgaa gtgacgttag gggaggtagt agtggtaccg   165180
gtggtggcga cggtagtgtt tgtcgtggcg gcggcagcgg tggtaccggt aacggtggtc   165240
gcgttggttt ccaccgcttc acacagtaag caaaagcaca gagccaggaa aagcaaccag   165300
ccccgccatc gccgccgccg cttcatgagg tgggcaggcg aaagctggtg aattcgttgt   165360
acagcggcaa gtggggcgcc gcgatcgaag ggtacgtcaa caagctgacg ttgatattaa   165420
atacgtctgg ctgcttttct acgatggaag cgcacagggt tacggcgtca aacaggtctt   165480
tcttggtggc gcccgagacc cacatctggt atacacccgt ctcgtggtac gaagtagagc   165540
gcggcaccac cggacggatg cagtccagaa cgcggttggg atcttggtga aagaatttga   165600
acgtggctac ggcctgtggc gtgtgcggca tcgtctgcgt gatgagctgc tggcccgcta   165660
acacggtgac gttgtgcaac ttgagcaggg cactcttgag ggcctggaaa gcgttgccgc   165720
acgaggcgct gatctgcagc tgcacggccg tggagtcgtg cagccgcatg agacgtgaca   165780
cctcttcgaa gacgtactta tacttactgg caaagagtgg cgcgtatcga cagtcggccg   165840
gcaaaatgta ggtggcgttg ccgccgttgg tagccacggc gggcgcagcg gccgcggagg   165900
ccggcgtaaa cagcgtcagc ggccggtggt ggctggtaag gtcgatcatg ggcggcgtgg   165960
tgaccgtggc ggtggcgggc atgacggggt ttgcggcgac gggcactccg gccacagcgg   166020
cggccgcggc ggccacggcg gcgctggccg agcccacacc cgccgcagt cctccgctac   166080 ccatgacgcc gccgggcaga gcgtcgccca gacagacttc cacagtggcg ggcgcgctct   166140
cggcggtcag tacggtttgc cgatcgacct cgcgacgaaa gctggtgagg aactcactat   166200
gatccatggc cgcagggccc gagatcccgg gattctgcgg gtgctgaccg agtgcgggcc   166260
```

```
gagttatatg gaagacgatt agcttggagc ggagttttgc gtccctagct gacctgcgga    166320
tcagcgacgt accataggga tagactgtga gcggcggccg caacggcggg gtcggccgcc    166380
gttcgtcgtc acgggcggc gcgagggagg aggaggtggt gggtacgatc ttgacgtggt     166440
tgacgtcctg cccgtccggg ggaatacgca aaaaaacccg tcgcggcgct accacgatgg    166500
tgcgatgggt ctttctcttg ttggccgggg ccagggactt gcagatgcgt gtggagccgt    166560
agacgatctg gacgtggtcc tgggagaaca tgaccatcgc cgccaacgct cagcgggggg    166620
acgtattggg aacacagagg atgagggaaa actccgtaga agtcagcgaa ataaagacaa    166680
cacagcagcc actcctctcg tctcgggccc taccactgct tgaagtaggg caccgggtgt    166740 ttctttttcct caacgggctc ctccagtctc ttataggacc agtcccgccg gcgcgccagc   166800
atgtaggtca cgtacaaaag aataatcacc atgaacacca ggaaagccag cacgccgtag    166860
gccagcagcc ggtcctcgaa cagcgggtcg ctcttgataa acacgtaggt ggtggtaaaa    166920
cttcggcccg cgatctgaac gtggagacgc acgacagtat acgtgccgtt gaggtagaag    166980
acaaactcgc gtaaccgttg tccgttatac gtcacgttac taatattcca cggcggaatg    167040
agctggttgc cctgatgcag atgcacggtg ctgttggggt gatagaggct gctaccgttg    167100
agcaagcagt gttcgtgttc ctgaagcagc acgcggaccc gcatcgtggt agcgttcaag    167160
cgagtcccgt acacggcgta gatgggatag gtgaaaaggt cccaagtggc gttgtgatgg    167220
cggccccagc tgaagaaaga gcacgtgtac tcagtggtct cctgcggcct gagtcccgag    167280
ataagcagct cttgagcagt agcgttgtag gagagatgta gttttcctgt ggaaaaaatt    167340
aatgagttgt ttattttgtt agcaggttgg cgagggagga aggagaacaa aacagaaagg    167400
tacgtgttac ttacctttat cgttggaggg aaaagcgcta agataccca cctgagtgaa     167460 gggacccttg cagtctgtcc gtgcataaca agtaactgat aaaatgtctg gattttttggt   167520 attattcaac aggattactt tgcaggtggc gtttagagac acttggtcgt agctgtagct    167580
ggcttcgcaa ttcacagtat acaggtgccc ctctttctgc gtcgtggcta tcacggaggt    167640
ggaggcggac gaggtagagg tttgtaccgt ggtggtgaca gcagaagtga cgttgttaga    167700
ggtacttatt gacgtagtag acgtgacggt ggtattacta ggggaagtga cggcgcttgt    167760
ggtgctactt ttcactctcg ggtgcatgtc gcccaagagc gcaactacga gcgcgatcgc    167820
cagcacggaa cacatgttgc cgtgtgacga acggcgtgt ggacgagcta tatgtggcag     167880
gaggtcgcgt cacctcttgt gacgcctaaa cgtccagctc cagataaaag aggcgttaat    167940
aatgaagacc acaaaaacca cttgcgtcag tatgacaatc ataaaggctc ggtgattgct    168000
acgcctaaag tacgcgggat tatccaccag ttcatcctgc tgaacaaagt ggatgattga    168060
cgtgctggtg ttaccggccg tcgtattgat catggatttt actaagaaag ttttggcacc    168120
aaaagtcccg ttagagcccc agcaggtaac gctgccgttc ataggctc ccggtgcccc      168180 tgtcagcatg cgtttcagtt catgagtata attttccta tcgttataca tatcatcact     168240
gtagttgact ttgctggtga gaaactgtgt gttctgtgga atactgatca tcatccccga    168300
ggccaaaaag ggcgaatcgc aagctgtagt gttacagaaa atagtcaggt tagtgtcatt    168360
atgctcatac atataagcca cgctaacctg gggctcatac cacccaatcg caaccgccag    168420
cacgtcccat ctcccgacat ttatcaccgc caccactaac aacgtcaccc ccgcacggta    168480
catagttacc ctctcgacgt cgccggctgt caatgacgtg cctgcgtcag tggctatgat    168540
ttatagcttt tggacacaac cgcaacggat ctgtcgtaat ctaccttcca cagggccgcc    168600
gcgacgatgc tgaacgacag gatcagacag acggcgtata ggagtcctag gtcggcgtcg    168660
```

```
acgcggcaag tgcggatgtc tcgcagggtg ggtagatggg cgatgcacaa ctctttctcc   168720
ccccgcacgt acatcccatc tcgtatcagc agccgtagcg tagcattaat ggtcagcggg   168780
gtaaccaaag aaatcacata gggatgtgta caggaagtac agtgacgggt atccgtgaga   168840
tgtaagtcat caccctttctc actgttatca tgaaagacca ggactcgggt aagacgaccc   168900
gatgaatact ggatctccca ccacagtctt tggtccaaca ccgagagggc acaagagatt   168960
ctaagtctcc ctgggttggg ggagcagatg taagccccgt gtgtgcccct cgccatcaga   169020
accatacaca tgaggggaa aaggacaagt atccgggacc accgcaccc ccacatcacg   169080 agaccagaga cggagatgta taaaaaaaag ctacttttat taaacagcat tctcaccaca   169140
cgttaatact gtcacgggga atcactatgt acaagagtcc atgtctcttt ccagtttttc   169200
acttactgag acttgttcct caggtcctgg atggctgcct cgatggctag gctcaggtg   169260 tccaggtctt cggagggggt ctcggtgggc tgctcaaact gccccacgtc gtaggccttc   169320
gcggccgtct cgtagatagg cagcatgaac ccacccggt tggtggagaa gatgcgcacc   169380
atgacctgtt tgggaaactt ttgcatcagg ggcaggcaca ggttgagagc gcccaacagg   169440
tccacggggg tggcagcgtg gatgatcatg ttgcggtaat cggaagaacg ggggcataat   169500
tggtgggtgt gcaattcttt gaggctccac gcggccttga cgccttcgtt acaagcatcg   169560
gccgtgcgct gcgccacttc gggtgggtgt gtcacaggca tggtgtgctc catgagaaag   169620
ggagtggaga gggccaggtt gcacatggtg cccaggcgac accgcaccgc atccacctca   169680
ctcttcacct catgattgcg ggtgtagatg atctggatgc ccttgttgtt cacctgcatg   169740
gttttgcaag ctttgatggc ctcatctaac acctggtgca tactgggaat catgaagggc   169800
aggttcttgt attcaagaga gcgattggtg ttgcggaaca tgcggctcac ctcgtcaatc   169860
ttgacgcgac cccgccgagt ctgcacgttg ggtgtgcaga aggggtgtt cttatctttc   169920 atgatattgc gcaccttctc gttgtccaac tcggagatgc gttgtgctctt cttcttgcgg   169980 ggtccggtgc tcgccccgcc gctgctctga tggccgcagc tcagcagaga ggaggaggcc   170040
gcgccaccaa aaccgccgcg cccatggtgg ctcgaggtca cggatgctcc tccgccactg   170100
ctgcatttca tctcctcgga ctcactctcc gagtccgaag ccgaactgca ggaggaggaa   170160
gacgaagagg aactatcttc atcgggccgg cccaagggat cgggaagagg agggtggttc   170220
atctgggaga gcgggtgcgt gggagaggtc actcgcggcg tgccgctgcc ggtggaaggg   170280
gaagacgcgg tagcaccgcg ggtttcgact tcttcaccct gttcttcctc gctatcagag   170340
atcacgatac agccggcggt atcgataatc ttgttgcggt actggatggt aaagtcggcc   170400
tcgggcttga tgtcttcctg tttgatgagg aggggcagca tgataggcgc gggaggcacg   170460
ggcggtttaa taatcacctt gaaaggacgc gtggttttgc gcggtttctt acgcgggctg   170520
agctcgggag tagcggatgc cccggggaga ggagtgttag taaccgcgac gctggtgggg   170580
gtcggcttgt taagaggggc gctgctaacg ctgcaagagt gggttgtcag cgtgtggccg   170640
gtgctactgg aatcgatacc ggcatgattg acagcctggg cgaggatgtc acctgatggt   170700
gataagaaga cacgggagac ttagtacggt ttcacaggcg taacacgttt attgagtagg   170760
attacagagt ataacataga gtataatata gagtatacaa tagtgacgtg ggatccataa   170820
cagtaactga tatatataca atagtttact ggtcagcctt gcttctagtc accataggt   170880 gggtgctctt gcctccagag gtggtggtt cctcagcacc atcctcttct tcctctgagg   170940
caacttcccc tatctcagac actggctcag acttgacaga cacagtgtcc tcccgctcct   171000
```

```
cctgagcacc ctcccctgt tcctcatcac tctgctcact ttcttcctga tcactgttct 171060
cagccacaat cactgaggac agagggatag tggcgggtac aggggactct gggggtgaca 171120
ccagagaatc agaggagcta gcaccagcgg tggccaaagt gtaggctgca atagcatctt 171180
cctcatctga ctcctcagcg atggcccgta ggtcatccac actaggagag cagactctca 171240
gaggatcggc ccccagaatg tactgggcaa agaccttcat gcagatctcc tcaatgcggc 171300
gcttcatgac attgataacc tcaggcttgg ttatcagagg ccgcttggcc agcatcacac 171360
tagtctcctc taagatatag cagcacagca cccgacaaaa ctcacttaag agagagatgg 171420
acccgtacat ggtcatcatg caagcgtcac tggtgacctt gtactcatta cacatggttt 171480
ccacacatgt agtgaggata tccataaata tgtgatcaat gtgcgtgagc accttgtctc 171540
tctcctcatc caaaatctta aagatttttct gggcataagc tataatctca tcaggggagc 171600
actgaggcaa gttctgcaat gccgccatgg cctgactgca gccattggtg gtcttaggga 171660
aggctgagtt cttggtaaag aactctatat tcctgtagca catataaatc atttttctct 171720
taagttcatc cttcttagca cgggcttag ccttcagtgc accccctaac ttgttagcgg 171780 cgccccttggt cacatcatgc agctccttaa tacaagccat ccacatctcc cgcttatcct 171840
cgggtacaat gtagttctca tacatgctct gcatagttag cccaatacac ttcatctcct 171900
cgaaaggctc atgaacctta tctaagatat ctaaggcatt ctgcaaacat cccccccatca 171960 tattaaaggc gccagtgaat ttctcttccg tctgggtata tttttttcagc atgtgctcct 172020 tgattctatg ccgcaccatg tccactcgaa ccttaatctg tttgactgta gaggaggata 172080
acaacacata taagtatccg tcctcctgac tcatttatcg ctatctcgat gccccgctca 172140
catgcaagag ttaatcttca ctctatctga catacacaag taaatccacg tcccatgcag 172200
gttagtatat atcacataca tgtcaacaga cttaccgagt tctgccagga catctttttc 172260
ggggttctcg ttgcaatcct cggtcacttg ttcaaaggtt ttgagagatt cttcggccaa 172320
ttctgggaac agcgggtctc ccaggctcag ctgactgtta acctccttcc ttaacatagt 172380
ctgcaggaac gtcgtggcct tggtcacggg tgtctcgggc ctaaacacat gataaacaaa 172440
gtcataagca catgggtcac atacaggaaa tatgtatata acattaaaga tataactttt 172500
tattaaaaaa aggggaacac aagtcccgac acgtaccgtg gcaccttgga ggaagggccc 172560
tcgtcaggat tatcagggtc catctttctc ttggcagagg actccatcgt gtcaaggacg 172620
gtgactgcag aaaagaccca tggaaaggaa cagtctgtta gtctgtcagc tattatgtct 172680
ggtggcgcgc gcggcagcaa cgagtactgc tcagactaca ctgccctcca ccgttaacag 172740
caccgcaaca ggagttacct ctgactctca acagaacaca actcagctgc ctgcttcttc 172800
tgctgctgct gccttaaatc ttccatctgc gtcagcggtg caagcccatt ccccgagctc 172860
attttcagac acatacccta ccgccacggc cttgtgcggc acactggtgg tggtgggcat 172920
cgtgctgtgc ctaagtctgg cctccactgt taggagcaag gagctgccga gcgaccatga 172980
gccgctggag gcatgggagc agggctcgga tgtagaagct ccaccgctac cggagaagag 173040
cccatgtccg gaacacgtac ccgagattcg cgtggagatc ccacgctatg tttaataaaa 173100
actgcgggca ctgggacgg tggtgttgta tatgtgaatt tgtaaataat aaatgagacc 173160
ccatcctgta aaaatacaga gtccgtgtca gtctctgaag gacagagtat tggcatatag 173220
ccaataaaga tagttgtggc aaagagccat gttatggatt agtaatggaa agtatcgtca 173280
ccaatagggg agtggtcaat aatggtcaat aaaccacacc tataggctaa gctataccat 173340
cacctatagc ataaggaagc ggggggtgtat agaccccaag ccaaaaacag tatagcatgc 173400
```

```
ataagaagcc aagggggtgg gcctatagag tctataggcg gtacttacgt cactcttggc   173460
acggggaatc cgcgttccaa tgcaccgttc ccggccgcgg aggctggatc ggtcccggtg   173520
tcttctatgg aggtcaaaac agcgtggatg gcgtctccag gcgatctgac ggttcactaa   173580
acgagctctg cttatataga cctcccatcg tacacgccta ccgcccattt gcgtcaatgg   173640
ggcggagtta ttacgacatt ttggaaagtc ccgttgaatt tggtgccaaa acaaactccc   173700
attgacgtca atggggtgga gacttggaaa tccccgtgag tcaaaccgct atccacgccc   173760
attgatgtac tgccaaaacc gcatcaccat ggtaatagcg atgactaata cgtagatgta   173820
ctgccaagta ggaaagtccc gtaaggtcat gtactgggca taatgccagg cgggccattt   173880
accgtcattg acgtcaatag ggggcgtact tggcatatga tacacttgat gtactgccaa   173940
gtgggcagtt taccgtaaat actcctccca ttgacgtcaa tggaaagtcc ctattggcgt   174000
tactatggga acatacgtca ttattgacgt caatgggcgg gggtcgttgg gcggtcagcc   174060
aggcgggcca tttaccgtaa gttatgtaac gcggaactcc atatatgggc tatgaactaa   174120
tgacccgta  attgattact attaataact agtcaataat caatgtcacc atggcggtca   174180
tattggacat gagccaatat aaatgtacat attatgatat ggatacaacg tatgcaatgg   174240
ccattagcca atattgattt atgctatata accaatgact aatatggcta atggccaata   174300
ttgattcaat gtatatatcg atatggattg gccatgtgcc aacttgatgt cgcctctatc   174360
ggcgatatgg cctcatatcg tctgtcacct atatcgaaac tgcgatattt gcgacacaca   174420
gaatcgccca ggtcgccaaa gtcgtctatc gccatccccc gtaaacgata taagcgctat   174480
cgccagatat cgcgtatgcc caaaaatcac ttttggaaaa atggcgatat cagttacaca   174540
gagactcaca tcggcgacat tttcaatatg ccatatttc  aaatatcgat ttttccaata   174600
tcgccatctc tatcggcgat aaacaccact atcgcgcgac atgaatttag tcggcgacag   174660
aaatctcaaa acgcgtattt cggacaaaca cacattttat tattcactgc agcatatagc   174720
ccatttagc  gcggcacaca tccagccgtt tgtgtttctt aacgctctcc aggtactgat   174780
ccaggcccac gatccgggtt atcttgtcgt attccaggtt gatccatcga tagggaacgc   174840
tgccagcggc gcccagcagg tactgcgcct tgtcgttcac tttgccgcag cgtattcgcc   174900
cgtcagcttc gaggtataac ctacaacacg gaagggaagg ggggtacaaa acgtgaaatt   174960
agacttttt  tttaatgatg ttttgtccct ctctgtctta ctctcccata ggctgtaagg   175020
ccctcgagga agagacttac ggattgtagt tgcagctcgt cagtttgttg tgtacgacct   175080
ggcgtgtcaa tgaatgggtc atggtggtga tgatcccgcg aatctcagcc gttttctcgg   175140
gactgtagca gacttcgccg tccggacacc gcagcctgtg gattcatgaa aatctactct   175200
ggcattcccg aggatcgtcg atggaacatg gctatcagaa acgtcgagag acagatccag   175260
acgcaccaca gaacgcagac aatcatgaaa atacgtacgc gacggtgaag cgattgcaca   175320
tttgaaatc gtaacagcgt tccggcgggt ggttgacgtt tatgaattcg caacattctt   175380
ctgcgcgtac ccgcggcacg cggctgtgac ccagtagcaa ccacaacgtc gtcaagaacg   175440
gcgtcaggtc tttgggactc atgacgcgcg gttttcaaaa ttccctgcgc gcgcgacggg   175500
ctcaaacgat gagattggga tggtgcagaa ggtgtaagt  ctggttattg gcctcggtga   175560
acgtcaatcg cacctgaaaa gacacgctgt agtcccggaa gacgtgggcc cagctctcca   175620
gtttcatcac acacatctga taacgtgtgc catcgttgac gacgaagcgt agcagcttgg   175680
tctgcttggg caccatgtgc gctccaaaaa tcttggcgtc ttccacgctg atctgcacgt   175740
```

```
ttccgtcgct cggtttcgaa gccgttcggg gcatccgttg gaggatggtc tggttgcgac   175800
cgctcagata ccagatcacc ttttcaccc aggtggagct tttctccacc aaggtctggc    175860
cttcccggtt gtacagcaga tacagggtct cgttgcgaca ctcgggaccc gttgataccc   175920
gctggaaccc cgagaattgc gaggggggacc gtggggcga gggatagaga aaaggacagt   175980
aaaacgtcgc cgcgtcatgc ggtttggaat acgtcagttt agaccatggc ggggacggat   176040
tctggttcgc cgttagcgtc gaccacgaag acgccagaca gggcgttgcc caaaccgcgc   176100
acagaagcag gcagtgaaag tagtgacgaa gcagaagccg cagcatatta tttcccgtga   176160
cgcaggctag ttggcaaaga gccgcacgct gaactcgagg ctccgggcgt gcggcgccag   176220
cgaaccggcg gcgttgaacg tggtcctttt gttggtgccg ccgcgacggt tctgacgtct   176280
aaagtcgctg atgagcaacg acacctcggt cacgttgatt ctgcaagcac aggttccgaa   176340
cgtcatttca caccccatgc ggttacctac ccgttacccg ttcgcccta ccttcccgtt    176400 gtcatacacc tttagcgcgt accctcacct cttgagcacg tcaaagttgt ccaagccgtg   176460
gctcgcatcg tagtggtagt tcaacgtgag gtccacgagc tgttccacat acttgtaacg   176520
ggtttggtcg ggcagcgcgc gagagcacgc gtcccagtaa tgcggtactc ggtaataatc   176580
gtttttttct gcggtctccc gctggcactg acccagcacc acggcgcaca gacaaacaga   176640
cagccacacc cgatacagcc gcatgttgca gactgagaaa gagagcttta ttatgagaca   176700
tcatacacat agtataggcg aggtaatggg gcggggaaag agttggaacc gaaagacaaa   176760 aaaaaagcc tagtcgtact cgggatctct gagcgagacg gattgcgtag caactttcat    176820
tagtttggga atctgccagc tggtgctgtt ggaaggttct tccatttccg aggcggtcag   176880
ttcatcgtac accgagacgt agtacctgat ggggtcctcc tcattgtccg agaggtgaga   176940
ttcgatggtc aaaggcgagc ctctcccata attgggattc acgaacgacg tgtccaagtt   177000
gccatccttt ctgaaataga tgacgttctc aggatcatgt ttcatgcgct cgcgggccgc   177060
ggacgcctcc tcctcctcgt cccagtcccg agtttccaac cgctgataag ggctcgagga   177120
acaaaatccg gcggggatct gagaacctcg tcgggaaccg ctgccaaacg ggctgctgcc   177180
gccactatcg tccgtgtcgt ccaacaggtt gacggcctct tcgtcggcga aacgaaagcg   177240
gcccgggtgc ttgcaacacg aggagtaaac taccgcgatg agtaccgcta tgaagctgaa   177300
aatggaggtg cctgtcacaa tgtagaagag gatagccagc actttcatga tttcgtcatt   177360
gcgcgcgtcg tgaacggaag attcgcgggc ggtggtcatg ttggtttcgg ttgtaggttc   177420
gctactcgta gtgctctcga cggtatttct gctgctggtg ctagtaggga cgtttgtgct   177480
gctggtcata tttgtagcgt cgctgaagtc catgtgaagc agcaacccga acgcgaccag   177540
gaccaggaat gttgcgcgaa ggagaccccg cggggccggc attcttgaga cgtggcgacg   177600
tggatttctt gttatgtccg cgaacgacgt gtgacgagga cgtggtttcc gcaagcctct   177660
accgacgccg cgacaccagg taggttatga aaacgcgagc ccatatcgcc gccatcattg   177720
taatcagcaa tgtgttgagg tactgcacga tgaatctgtc tagtgacacc agccaaccct   177780
ctgcttttgc gggcaagcgc gctttcggtg acagggtgta tcgtacgtag ccgcgggtca   177840
ggcgcgcgtt gtagcggtac acgcagaaat ctatccacag gccaacgccc ggctgtagct   177900
tcggatggtg gataatagcg cggtgacgta cgccgcgggg ctttagaatc tccacctgta   177960
aggccatctc ctccaggtag tgggtctgac tgcgacgcag cgtccagttc atgtaaaagt   178020
cggtctcgcc gtgtccggcc acgaagaggc tgcttactaa atcgggcgcc agagctaggt   178080
caggcgtatc aaattccact gccaggcgac ctgattctaa cggttccacg atccgggaga   178140
```

```
gcgtttctag atatagagca aagcgtacca cgtctacctg cggtgtaaaa aactgttgtg  178200
ggcgttcacc gtcgttgacc acgtaggcca cgtagaggcc aacatttcc accacgggtt   178260 ctagctgcag gcggcacgta aagcttagaa acgacggctg tacggtttgg ttcccgtgaa  178320
gctgaagcgt cacttccttg ccggggctca ccgtgctgta acgtcgcacc gagtcggtca  178380
tctgctccag atcggtagac cagaaaggcg tgcaatgcat actgtcccag tcgcgacaca  178440
cagcccagcc tagctcggtg aagggtcgac gcacacccga aaaagtgtgc ttgaagacca  178500
gggggtcgcc tcggtagctc agtagccgaa catgcacata gtcgcggcta gcgttgacag  178560
acggcccgtg gagggccagt aggacgagcg tgaacagcaa gcgcaacatg ctgcgcgggt  178620
taggaaatgc ggcgtgccgg ccaccgcccg actcataaac gctaccagca tgacgtctca  178680
gatcacacaa gtgacgagga gcgtaccgca aatcactagg gaaaaggcca gcagagcccg  178740
atagtcttgc tcttcgcgaa cgatctcgtc cggttcctcg cagtcttcgt ggtccacaga  178800
agatgaggag caggattctt cgttaatctc tgccaggata ctagtgctat accacaccag  178860
agcgctcagc gtgcccaggg ctaccgcacg gtaaaatagg gacatgatca ccagcgcagt  178920
ctaaagtagt ggtaattaag tttcttggcg tatttccaga gaaaggcttt gtaggccgta  178980
gggactggcc aggcaccgaa ctcaatattg gtagacacta cgtcgtaaat gcgttgttcc  179040
tcatctaaga ttaaccgaaa aaatagccgg ttgatgtgac ggcgcacggc ttgcgcgtta  179100
ggattgagac acttggtgcc cttgtccttt aaaatagcca gcacttcctg acgattgcag  179160
ctttcgctcg ctgcgattgg cttaagcagt tgagttccga ctggcagggt attcaacaga  179220
atttggttgt tgcaacggca gcgcctgtcg taatcttcta gttctaaaac atggacggct  179280
aggggacata tggtaagtaa catatatgcg attaatgaca ggtatcgtac cgataacaga  179340
ttgatatgcg agtttgaaac cggatggtgc aaccatgtta gtaccatatt aaacacatac  179400
tgtaatattt tgttttaacg aacttgtctg tttgaaaaca tacattaaat attatcctct  179460
aacacctatc aaggttatat ttattcgtct cggttctggt gatttcgtta tgttaacatt  179520
ataccaccta ttatcgttgc gtttgtctaa ccattttgag aagaggtgat cgggcgataa  179580
acatactcca tgtccaggcg gcttccttcc gtctggatac aataaatgtt cattttatc   179640 gcatccgggc cctctgggat cgcgatgaag ccaataatta cccaatataa ttttattagg  179700
cggccatttt ctatgaagac atctgcagcg taattctgtt ccattcacct cataatgata  179760
cacatatgct aaaaaaataa tcaacgcacc aaaaattaat cgcattataa ttttattatc  179820
tacgtcacta ccagtaattc gtaatatccg gtattcccgg aaaatcactc aaaactgcgt  179880
ccatgacaca tcaattcccg ataagtaccc cctttgaaa tcggatcccc ccacatacca   179940
atcaatcaca caacacacag gtttaaaaat cgatcacacg tcaattaggt ttcaaaatcg  180000
atactgttta ttatcaggaa tctagactaa ttctacaatg acagctctga atttctctct  180060
tgtctttctt gtcaggttct catcatcagt catcacttcc acccatcgag gagtcatcgt  180120
cgctccaaaa tccctttgggg tcgctagttg gaaaagtctc tgacacgatc caggcacccc  180180
gcacccagtc cgactgatct agcttgcgga gcatctcaac aggcatgagc tgcagggcca  180240
cggctgtcac ggcactgtat cgatgtaaca ctagggactt tctttgcgat gtagccatca  180300
acacggcgta tgccccatag ttcgcgtgat acgacgcatg atgggttaaa cgttcccatc  180360
cggcagtgcc gtctcgggtc cgtgcacaca acagctgcac agcgttatga tgcttaaaat  180420
taaccataac gctgggacta ctgatgaagg agtagtaatg agccaggacg ccgtacatcg  180480
```

```
aaggcaacaa gaaagagtga cagcacgata gcaccgggct cttatgtagg cgacagctta  180540
ttttcctga  cgtcggcaaa aagtacctaa attccccaca gatattcaga cacggttccg   180600
taaagtgctt ctttttttag tgcaggaatt ggaaaaaata ataaaaaata tgaacagctc   180660
atctgtaatt atctgtgtga cttcatcgta ccgtgatgta aaacaacaa  caggaagctt   180720
acagggtgcg gtagaaaaat tgccgattg  tgcaacactg ttggcatctc tcactccgat   180780
aggcggctat aagatagaga attaaaagta tgatacccac aagaaagatg aagagggaca   180840
accaggctag agtatgacga ccgcttttcc tttgtttgac ggttacatgt gcggtatgat   180900
tttgctgtcg ttgcttgtga tgttggacac ctggagtgga aaacgacgta tgattcttag   180960
atgcgcatat ggtgttatta gtggaagtgc agttacgaac cgtgatctga gtgtcgttac   181020
attgagtaca attagtacag ttgtaaagcc ctgtgagata agtaccgttt gggcacagtg   181080
tacacgttat gccactattc tctgtacaca cttttgtaac ttttgtcct  gatccgcatg   181140
gcggcaaca  ttgattaccc agcttcacct catcgggctt acacatttta cttcccccaa   181200
gctgtagtaa aaacataccg aagcagatga gcatcaccag aggcttcatg cctcctaccg   181260
gaagaataaa aataactcat agggccgaac ggtgtcatcc tctccgcggt ttgtaatacg   181320
agattgcaaa cgtaaataaa tgacataact tcactaacac gcatactaca aagtccacct   181380
acgacgctga aagttcttcc aggacagaac aggatagtca gccatcttca cagtctacct   181440
cttaggccgt atccaggagc ataggtaatc agtttccagc cacagtacag cgagcccagg   181500
aaaccgcaca cggtccctgc cgggaacacg taccaccaca tcgattcgtc gtgccgtaga   181560
accgtagagt tttccgaact tttatacacg ccggtggcgt tagggccgtg tgtgctgctg   181620
tgattggagg ttttgtgagc taggtaacag ctgtgatttc acctgtcgcc aacactgaca   181680
gcgattaccc aggtggagca caatcacata gctgatggac gttggttgat ccgttgattc   181740
ccatggacat tttaacggcg acagtacagc tcccgttaaa cattagaata atagacgtta   181800
gtggataaca gcatgttatt cgcccaagtg tgatcgtggt tatacacttt cttgtttttt   181860
gctcatatgc tgtaaggtgt tcgaggatcg tggggagtat atgtgttgaa tcggaatcat   181920
gtttactgac cgcgccatac ttcgtatacg aacctaaccg gcgtaaagtg ttttccgata   181980
tataaactgg cgcctattgt ggctgtagcg cccataggta tggcgtatac ccacggtgat   182040
gttgtgttat tcgttttttg tgataaaacg tagcttatgt ttaacgtgtg ttccgtcacg   182100
ttatgtgtgt cgttaaaaga cggcgcctgt acagtatggc tttgagttgt atcttgaatt   182160
gttattgcat ctggaggtgt tgtgtacaga gtggttgttg cgtgttgagg tgttgttacg   182220
ttttgaggca cagttgcggt gtacacgggc tccaaggtgt agttacggag tctttctatg   182280
caggtagtgt tgagatattt ttgaatgctg gttatgttcg attctgtgag gttaaagtgt   182340
gtactattta tgacggtgta atttagacgg tcttgccatc ccgaggatat tagtgttagg   182400
taattcgtgt tgttcacgtt tgcttgatat gtataggtag gtgtactgtt tgtgaggtcg   182460
caagtgtgat tttcttgcag agattttatc catcttgtgt gaaaatattg agatacgcga   182520
tgaatgtttt cgctatctat attataaagc gtttcagtgt cacctagggg ttgtttgttg   182580
taacttttat tttggaccct gggtgtgaac catgattcca atgtttgtat agtaaggtgt   182640
cctactaata aagacgaact gattcctacc gtaatgttat accgcacacc cagggtgccg   182700
tttacaaaca cggaaatgtt tccgttacaa accacgttgg cagatgaatt agattccagg   182760
tggtaacgat aggataatga ccgttcgctc ccaacggatg acacaaagta tccgaataac   182820
caacacgccc attcaatccg catattttaa tcacactatt cacacctcac acactgcatt   182880
```

```
ttttaacatc ttattttttt attttatgcg tgttctcacc tcttcatctt tttaacaccg    182940
gggtaactat cgtaagtcgg taggcgtcga tagccctcac cacctcgtcg tcccctcccc    183000
ggcgtggggc accagcgtcc acagcactgc aggtaacaca ggtagcatag gaaacatacg    183060
gtgaaaatac tccaaaatcc caaaaatgcc gcgattcccc gagtggccca gggagacatc    183120
ccggtgtcta tgtcggccgg cggtgctggc gtcaccggta aaaatttcgg cgggtgtggc    183180
tgcgaacggt agcagtcgcc ggggagccgg taacgctgta tcactgtcca acagcggtcg    183240
ggttcctcgt ccggacatgc gggtttccag caatcctcgg cgtcggcgcg tccgatatag    183300
aagtagttgc gctgaaaacc gcggtacatc ccgcagtcgt gattccgtag acgccagggc    183360
gtcggcgacc agatctggtc tcccagcgag tagcgaccta acgccggcgt gcagcaaggt    183420
tcgtcgggcc ggctgagcgt ctccagttgc gtgagaatta cgaagcgttg catgatgagg    183480
ccgtggctgt agttgcgcag cacgcattcg tacatgccgg ccgtgtccgt cgatacgttg    183540
aaagtcagcg agaatatttg gccgagatgc aattgcgaga aattccaagt ggcgtacggc    183600
aggcggtact ggagtccgtt catcagccga tggcctttga cggcgtccag gatgagctcg    183660
tcgctgccgt cgtgggaacg acagaaacgt gcgcgaatgg agaccatggg ccaggagtgt    183720
gtcatgaccg tgcaggggat ggtaacttgc tctccctcgg cgaccaacac cggcgccggc    183780
gacgtggtct cataattctc ggcccacatc ttttcggcaa tgtcagcggt ggcgaagggg    183840
aacgaagagg aagaatattc gaggagtcgc gggcagctca acagcaccca gaacagccac    183900
ggcagagttc ggagcgactc ccggcggcac atgatgattc tttccttccc tttttcgcag    183960
agacgctgcg cgcctgctcc tgctccgtgt gtcggccgct caaacgtcgg gccggcgtgg    184020
tggtgaccac cgtgcgacgc agcttctcgc ccgggatgcc cgcgactgag cgtccggttt    184080
ttttgcaggt cttttttgct gcctcctcct cgccgtcgcc gtcgcggccg acgtggtgga    184140
ccagcaccgc gcaggaactc tcgcgtcgcc ggcggtacgc gacctgtctc attgctacct    184200
cggatgttta agaaggaacg ttcatctgcg tcacagggtc tgatgaagct gccaagagtc    184260
gtggctgtgg cgcagcgcgt tctgtacggc gcgtttcacc gctttctgca tggccgctac    184320
cacgtcgggg gggagcggct ccggcggaag ctcgatgagc agttgctgcg agtctcggcg    184380
ctcggcgtcc gccgtttcgt cggacgtggc gtagaaaacc gaggtggtcg cccagtcgtc    184440
cacgctgtcg acggcctctg tcagtgccgg gttgtcaaaa ccgccatcgg acgcgggtga    184500
taaaagaacg tacgatgaca cgctgttagt acgattctcg tcgtcgctct gggaacgacg    184560
tgatggacga cggtagatga cctcgtcttg ccacgcgtcg aagcgatcgc agcagcgctg    184620
gatccaagcg cagcgaagca gcttacggaa cacgtcgttg ttccaaaagt agagcataaa    184680
gagaaagaaa agtagcgtaa cgatgaagcc gaaaacgacg agggtcggca gggcactacc    184740
gccgctgccg ttttttgtgt cgtgcgggtg cacggtggta gtggcgttag tctgagctgg    184800
ggtcatgaca agtctgaaga gatgagagcg tgggtgctca tcagggacag ttgaggtctc    184860
tccctaccga agccttagcc tctacggtgt tttatgatca acgtgtctac gaacgtcatt    184920
gtgaaagtga cgtctcaggc tttccgaaac cgcgtcagat tcaacgtggg tttcggttta    184980
gcctgcgtca ccgaggcgga ggtggaaatg agccgtcctg tggggagtg tacgaccctg    185040
tagtgcccat gggtaacgtc gcgtcggaag aagtgaatgc ggcattggtg tacgcgtggg    185100
ttgttttgct ctctgactcg gaggagttgc cgcagcagct gcagatttta cgtactagcc    185160
aaaagcagca aaagcagcag gtaaataaga gaaggagtcc agataatgtc cagccgctag    185220
```

```
cggcaaacag cgcaagttgc gcgactgtcc aattactacc accaaaactc tcaacacatt   185280
gaatcgacgc tgaggttggt gttgcagtgc tgttgctact agtggatgaa gacgaagtag   185340
attgactgga attagagctg gtacctgtag tggtttcact tgccgatgcg gcaagtgcaa   185400
ataaaactaa tatccacagc atgttcgtta ctatataatt gatatacgaa cccgtttgtc   185460
gtaacaatca gcgttatata cgctgtatcg gcatcgtttt accggaaagt ttatcgtaat   185520
gtaacccgcg ttgtgtacat tcgtactgaa agggaacccc cggtgatgtg cacattatac   185580
tctttcattc tggggtttcc caatgacgta aaaatttcca ctatacaata aaattacgga   185640
atcatgtgaa aagtgtgctt tttattaaca gagcagaggg tttacagtag atatatgttt   185700
gccagggcca ctgttttcta acaccgatca ccgccaccat taccacccgt tgaactccac   185760
acccgggagc cgcctgatcg ccagggactc ctcaccgtcc atcgtccgaa caagctcccg   185820
ccaccgatgc tgccaccatc accgagagaa agaaccgctt gctgcagata cgcttgggct   185880
cgcctccgtg cggacgccgt ttcgtgcaga cgctgagtag atcgagcaga gaatgtcaaa   185940
acgacattac cgcgatccgc tcccctcttt tttcttttc tcattcacgt gtattcttga    186000
tgataatgta ccatggctac ggtggtgaac tgcgtcgcgg atcccgtcac gggtttcaac   186060
agatcgacgt cggtcagcgg cgccgtcacc gccatgtccg gcggaggcac gctgtttctc   186120
tggttagcga cgtggaccga cgacgaagac gatgaacccg cgcggcggtc tgttatccgc   186180
gacgacgcgt agctgcactg gaagacact tcctcccaac ggaccaagat ctcatcgggc    186240
cgttcggaga aacggtatcg tctgtccgac tcccgccgta cggcgccgag gcccagcgac   186300
gacaggtccg cgaaccggcg ctcgtattcc ccgtacagct cgcaacagcg gatcagccag   186360
cggtagctca aaaacatgcg caccagtttg aaggtgtcgt gccaatggta agctagatag   186420
cagagaatgg ccacgatcag cacgagcatc acgccgatga tgggtaaccc gacgttcagc   186480
ggcagatcgt ccatggtgac cgtcctctgt ccggatctac gtcccagtct ctctcttttg   186540
tacagcactc gcgcgggaac ggccccctca accctcttac gtagcgggag atacggcgtt   186600
ctcccgcggg ccacttactt gcacggtcgc ttgaacggcg gcttggactg ccacatgcac   186660
cgcatccatc catttcggca gcagcgcgtt cgacgatgtc gtacgagtcg cggatgatgt   186720
taccccgcca gcacctccgc cggcaaccgc gtcgtcgttg ctatcgtcgc cggtttcggg   186780
cgatgacagc gccggcggcg cgggtctcgt tcgtccacc atttccaccg tgtcgaagcg    186840
acagccgctg ccgtagtaca tagctccgtt caacggccgg cgggccgggt cgccgagttc   186900
cgggtcgggc acatccatgg ctcgccgtct ccttctttgc cgctcgtggt gccgacggca   186960
cttctcggga taatgacagc cgcaaaatag atcgtggagc atgtctcgcc aactgtcctg   187020
gtgataatat cttaagtacg cgatgagcgc gccgatggcc ataatcataa gcgtaagcaa   187080
aacggcacag ataacgtgaa acaccgcggt catccaagtc gggcggcgtc ggggacgcgg   187140
tgggtcggtt tctcttacgc cggcgtcact cagccaccac acccgtagcc gacattccca   187200
gaatcggtga atgcgactca aggcctttcg acgccgccat ttatttccaa cgtccaagtc   187260
ccacgtcatt tctggcatct ccacgccctt gactgacata ctctctttct ctctcttagc   187320
tgcggtgaaa aagagggaag gcgtgtgctg ctatacaact gtacaacgga cgcgctcgct   187380
ctttcggtct caggtcatct gcatcgactc ggcgtccttc atgacgctct gcaccgcctt   187440
ttccaacagt tcctcgatgt ccgaccatcg aggaggcggg gctaactcgg aaaccgacac   187500
gataggcagc gtggtcggct ccgttggtgt gcggggtcgg ggacagggac acgagagtcc   187560
caccttcgag agattctcca gcccgacggt gcgcggcagt ctcggattcc gcggcggctt   187620
```

```
ttgcggcgtc ggcgttttcg ggaagggcct gggcgtcacc ggcggtgtcc agccgaccgg   187680
cttgggtttc gtgggcggcg gtgttttctt ggtgagcggc gtgctcaggt tcttacgcgg   187740
cgcgggtatc ggcgtcgggg gcctgtgcga cgacagccgc gtggtgggg cccggaccgg    187800
cggcgtaggc ggccgcttct tgcgcccggg cggcggaggt ggcttccagg atggtggcgg   187860
ctgatgcagc accgtgtcga cgctggtcga ggacgacaaa gagctcgacg aggaacaatg   187920
cgacggagat cggccgatgc tggttggcgt tcccggagtg gatacgtcgg ggatctcgaa   187980
ccgcgccgga ggaaactcgg gtttatctat cggcagacca tcctctccta tgtagagcga   188040
cgtacaccgc ggcacctgcg gcgtcggcgg gtgggtggcc accccgcatga gccccagttc   188100
cagatccagc ggctcgacga cgtcttcttt cggattgcga tagcagcacg cgcaggcacc   188160
acgcttatca gaagcagcac ccgggagccg gcctcgcgac gaagtctcgt cggatcgctt   188220
gcggcctcgg cgctgggtaa ataaggaaat ggccaggacc agggaagcca gtccggtacc   188280
gccgaggagc ccgacgccga gccacagcca caccatgatc ttctctcctg cttggaatct   188340
caaactccgt gtcgggaagg gccggtgtac ggacatttat gccttggatt tctggaaacg   188400
tcattttttg gcaaggaatg tgtttattgt ccaaacactg aggaaggaga tgtgggccaa   188460
gtcggaaaat tccttatcac accggggcg ggttacgttc cggtctgatg ctgctgctgt     188520
tgttgtagag ccgcggccac ggccgtctgc acggcagctt gtaccgcctc ggccacgccg   188580
ggtggcatct gcggcatggc gggggaggc gcgtcgggcg gaccgccggg catcgccgtc    188640
ggctgtgacg gtggttgtga actcaccgtc ggctcgcacg gaggtttgtt cttcggtcta   188700
cccctcggtt tgtctttcgc cctaccttc ttcggtttgg gttccgatgt cggtgttggc    188760
ggctgcggtg ggatgacggg ctggtgggac tcctccgacg gcgggggac gaacaccgtc   188820
ggcgccgaaa ccgggggact ctcgactatc tcgcagatca ccctgtcagg atcgtcgccg   188880
tgcccgggac gccgtcgatg accgtattgg accatgtcgt aaatcatcgt ctccttgtaa   188940
cacgctgaac agcagcggct gcaggggccc gagatgcatt tacagctgca cttacagctg   189000
cagctgcagt agcgcaccca tcggcaagtt aaaatgtcga ttatggaatc tttgaaaaat   189060
tcccggtagc ggatgaggta cgcgcagagg aaaatcatga aaacggaaca gacgaccaca   189120
gccgcgatgc caggtccaga aaaaatattc gctgatgaac ccgccaaaca ccaaattccc   189180
aaggccgcgc atatcatcca gatcacaatg atcgcgggga cgccccattg gcattggcac   189240
gaaggatctt gcacatcgca acccatcgct actgcgttct cccacaaacg ccatcgcact   189300
atttatccct acagcggctg ccgagtcacg tccgccggcg cccatcggcc gcggcgatct   189360
cctagtaaca ctcgtccgac acttccacca tctccagctc ggccggcggt tcggcatcct   189420
ccaccagcgg cgtcgtctca tctttgccgc agcagcggac gcacaccttc tccaggcaga   189480
acgccaccag ctgccgccga acgtaccaca ggtacacgtg cagacctgcg aacaggacta   189540
cggaggtcat gaccaccacg acgcacacgg gaatccaagg atcgagattg tcgctggaac   189600
tcatggctat cgccaccgac gtgcccgcgt ctgtctcacc gccgctcgcc cgatgtcgca   189660
cggcttgtta tacgctagcc cgtcgccgcc tcggggcacg gtgccctcct acccacgtaa   189720
cttcctccgt gacttaaagt cgcgtgtggt agatctcctg ctccgtggac gaaccgttcg   189780
gcaggatagc ggttaaggat tcggtgctaa ggccgtgtcg ccaacgtcga atgctacgtt   189840
gcaatagctt cgacggacgg ccatcctccc tctcatcgca ataataaaac accagcagcg   189900
cacacgacgc gatcacggtg accccatga ctagacccac gcagatagcc agcccgcta    189960
```

```
gcgtatccag cgccatcccg ttcgctcccg tcgtcgtctc ctgaacaaag caactccgca  190020
gtccccgttt tcaaccgttt tcaaccgttt ttgtttcctt ctccgcgact agatgttaac  190080
gcccgcggtc tttccggccg tgctctacct cctggcgctt gtcgtctggg ttgagatgtt  190140
ctgcctcgtc gccgtagccg tcgtcgagcg cgagatcgcc tgggcgctgc tgctgcggat  190200
gctggtcgtt ggcttgatgg tggaagtcgg cgccgccgcc gcttggacct tcgtgcgttg  190260
cctcgcctac cagcgctcct ttcccgtgct tacagccttc ccctgaaacc cgcgtcaatc  190320
gactgtcccg aaaacgccgg cgttaacaca ggaaaaaaaa accacgcagg aaccgcgtag  190380
gaaccacgcg gaacatggga cactatctgg aaatcctgtt gaacgtcatc gtcttcactc  190440
tgctgctcgg cgtcatggtc agcatcgccg cctggtactt cacgtgaacc accgtcgtcc  190500
cggtttaaaa accatcatcg acggccgtta taaagccacc cggacacgtg ccgcggcact  190560
tgcctacggc gctgctccag ggaaactcct cttccttctg ctcttcctcc ttcaccgcag  190620
ggaccgtctc cctcgaccag ggacccgccg aagcaaccgc cggaacaacc tggaggaggc  190680
gcggcatgac ggcacccaag tgtgttacga ccactactta tctggtcaag accaaggaac  190740
agccctggtg gcccgacaac gccatcagga gatggtggat cagcgttgcc atcgtcatct  190800
tcatcggagt ctgtctggtg gccctgatgt actttacgca gcagcaggca cgcaacggga  190860
gcggcagcgg ctagataagt ctctggcggc tacagctcca agcgccgtag ccggcccgcc  190920
tgccgatcgc gacgtcgtgg accatcgaac agagactcac cgtacgaga ccccgaggta  190980 cgccacgcgg tgcctaacgc ggtataccac acccgtacgg tctgcagtgc ggcgtacaac  191040
gtgtggaaaa cgcgttgcgt cgcagagtca gccacgtccc cgtcttgtcg ctccccaatc  191100
ggctcccgca caccccccgc ggcacccaga gggcgggtga gccaagtatt cttaaggccg  191160
ttctctgttc catatcccat aaattgttta ttccggagct cgttggcgcg gaaatagccg  191220
gataagggga gcaacaaccg tcggcgaaag ccgtcccgct cattcagtcc gggtttcgcg  191280
tctagtcgga ggtgtgaccg ttggccaacg gaacggcgtt tcacgatcaa aatcgtatcg  191340
ggtagtgtag gagacgtcgg cggtgcagaa tgcgactcgc ggcgtagctc gccgtcgcta  191400
tgcggctcgt cgccgtgtgg cgcggcctgg ccggctgtct gcgcccagat ctgttggcct  191460
tttgggtcct ctggctgctg ctgcgtgtgt gctttggcag acgcggtggc aatttgcggt  191520
ctgcggtaag tgaggatatc gccgagcaag cgcatttgcg gcacgtgggc ggcacgcgtg  191580
ttattgttcg ttcgttgcca gatagcaagt gctgtcgaca gcagacgttg tgggcggttg  191640
gtgtattttt gcgggttgcg gtgaaagtcg gcagccggcg tcttgtgaag tatcttaacc  191700
atctgtgttg cttttttgcag cgtccagaaa agcgacgcga ctttggggat ggcctcgtgc  191760
tcaccttcgc ggagagcgcc gccggacctg ctcgtcagca gcgagctacg cagacggaat  191820
atctggagga gagttacgtg tgtcacaggg gagcgcgggt ctccggcggt aacgacggcg  191880
gtatcgtcga cacgtgtgcg gcctgctgtg ctctgcggaa aagcgccggt ctcggagacc  191940
gtggacgaaa aagagaacgc agcagctacc gctggcggcg gcgtcgttaa tgctgccgtt  192000
gatgatcgac gttgtgagta ctcggaaaca gcggtgaggc agaagctcgg ttctccaggg  192060
aacgaccgtc gatgcgtggt aggcgcagca ggtgaggttg gggcggacaa cgtgttgcgg  192120
atcgtggcga gaacgtcgtc ctccccttct tcaccgcccc acccaccctc ggttggtgtt  192180 tcttttcct tgtgttctgc agatagttcc acggacagcg acggcaagtc cataagcacc  192240
ggtgtgcaag tggtggagca cgacgaagat atcaccgcgc cgcagagttt gtggtgcacg  192300
gcgttcaagg aagccctgtg ggatgtggcc ctgctggaag tgccgcgttg ggtgtggcag  192360
```

```
ggctggaaga ggtggcgcaa cagcgagtcc gggcgtcgat ggagtgctgg gtctgcgtcg 192420
gcttccagct tgtctgactt ggcgggcgag gccgtgggag aattggtggg ctcgctcgtc 192480
gcgtacgtca tcctcgaacg gctgtggttg gcggcccgag gctgggtgtg cgaaacgggt 192540
gtgcaagccg aggaggccat ggcgcgacgg cgacagcgca tgctgtggcg gatgttctct 192600
cgtggaggcg acggcgaatg cagcacacgg tgtgcgatgg agatggcgtg cgaggaagaa 192660
agcgccgtgt tgtgagccga cggcgcggga cgcgggccgg cgcagcgcgt gggccacgtg 192720
tggtggcagg cggcgtcgtc cgcttgcggc cgtcgccgcg ccgcacagac gcaaacacat 192780
gtcgccgtca agagaaacag tctgagcata gccgtctgca gcggtccgcg tgtagaagcg 192840
gggggagaac gacgttaata aagaatagcg gcggtgccga tagggcgacc gctgaagcga 192900
gctgcgtgtg cgtgcctgtt ttgttcccccg tcgccgccga aaagctacgc gcggcccccg 192960
tccctagcct tgagcgcgcc acagcacgcc gcaaactcgg cgtcgcgctt acgtcccgca 193020 aaccccctc agcctcgtcc cgccaaccaa taccgtggca cgcagtgcca tagcgccgcg 193080
cgtcaaggcg cttacacccc cctcagcccg gtcccgcacc ggcgtcggtc tgggtgtggc 193140
gggggtgcgg ctgggtgggt gtgtgccggg tgcggctggg tgtggcgggt gtgtcgcggg 193200
tgtgtcggct ggctgtgtgg cgggcgcgtg ccgggtgtgt cgcgggcgtg tgccgggtgt 193260
gtcgcgggtg tgtcaggggt gtgtcggcgg ggtgtgcgcg cggccagatg gaagcagtgt 193320 gccccgggc ccgcgatccc cccccccgcc ccggcgcggg cgcttcttct gcgtgtgtcc 193380
tcgacgcggg tctgtgcgcc tgcctgccgg tcccggcaga ctgggctgcg gcttcctcgt 193440
tttttttttc cgcctgtggc cgtccccggg gacttcctct tttccgcgtc cgatcttcgc 193500
gtccccaggg agtcgcgccg ccgtcccctc gggaccgctt cctctttcc ccggggactc 193560 aaagacacgc aagacagacg cgcgactgaa agagacgcaa gacacacgcg cgtctgggtt 193620
tcgccgtgcg cgccgcacgg cgcttttatt cgccgtcgcc gtcccccgcc accgccaact 193680
tcccaaattc ccacatttca cccccccgat gaaaacaccc ccccgcccct cggggaccca 193740
gcacacggcc cggaatggag gtcaggcgtc cacctaggtg tgcgcgcgct cggcggcccg 193800
ttgttggtgg cttgtcgcgc atcttctttc ggttttttca cggccttcca gactgcgcgg 193860
cggcaaggcg gcgccagcaa gcgccgtgca cgtcgctgcc tataaaagcc aggtgcgtgt 193920
cgcccgcggc acacgggcga cggaggcgtc cgcgtgtgta acggcgtggt cgctgacgc 193980 gggtttgctt cctatatata cagagtggac gtcggaggcg tccggcggcc atggcccagc 194040
gcaacggcat gtcgccgcgc ccccgcccc tcggtcgcgg ccgcggagcc ggagggcctt 194100
cgggggttgg ttcctctcgt tcttcttctt tggaagcgac gtcaacagcg gggactagta 194160
cgagtactgc gggtacggcg acgccggccc acgccgtcca ccgggtagaa ccccgcggc 194220 cgccgggcgc cctccgggt agcggcaaca acagcacctt ttggcacggc ccggagcgct 194280
tgctgctgtc tcagattccg gtggagcgcc aggcgctgac ggagctggaa taccaggcca 194340
tgggcgccgt gtggcgcgcc gcgttttttgg ccaacagcac gggccgcgcc atgcgcaagt 194400
ggtcgcagcg cgacgcgggc acgctgctgc cgctcggacg gccgtacgga ttctacgcgc 194460
gagtgacgcc gcgcagccag atgaacgcg tgggcgccac ggacctgcgt cagctgtcgc 194520
cgcgggacgc gtggatcgtg ctggtggcga ccgtggtgca cgaggtggac cccgcgccg 194580 acccgacggt gggcgacaag gccggccatc ccgagggtct gtgcgcgcag gacgactgt 194640 acctggcgct gggcgccggg ttccgcgtgt tcgtgtacga cctggcgaac aacacgctga 194700
```

```
tcctggcggc gcgcgacgcg gacgagtggt ttcggcacgg cgcgggcgag gtggtgcgcc    194760
tgtaccgctg caaccggctg ggcgtgggca ccccgcgcgc gacgctgctg cctcagccgg    194820
cgcttcgcca gacgttgctg cgcgccgagg aggcgacggc gctcggacgg gagctgcgcc    194880
ggcggtgggc cggcacgacg gtggcgctgc agacgccggg caggcgactg cagccgatgg    194940
tgctgctggg cgcgtggcag gagctggcgc agtacgagcc gttcgcgtcg cgccgcacc     195000 ccgcgtcgct gctgacggcc gtgcgtcggc acctgaacca gcgtctgtgc tgcggctggc    195060
tggcgctggg cgcggtgctg ccgtcgcggt ggctgcgctg cgcggcaggg ccggcgacag    195120
ggacgacggc ggggacgacg acgacgatga cggcggggac gacggcgatg gcgacgggga    195180
cgacgttgct gccggggggcg agcggcacgg agacggaggc cgccggcggg gacgcgccgt    195240
gcgcgatggc gggagccgtg gggtctgctg tgactttacc tccgcagccg tacgcgcccg    195300
ccggcgggag cgcgatttgc gtgccaaacg cggacgcgca cgcggtggtc ggaacggatg    195360
cggcagcggc agcagcggcg cgccgacgg tgatggtggg tccgacggcg atggcgggtc     195420
cggcggcgtc ggggaccgtg ccgcgcgcca tgctggtggt ggtgctggac gagctgggcg    195480
ccgtgttcgg gtactgcccg ctggacgggc acgtgtaccc gctggcggcg gagctgtcgc    195540
actttctgcg cgcggggcgtg ttgggcgcgc tggcgctggg gcgcgagtcg gcgcccgccg    195600
ccgaggccgc gcggcggctg ctgcccgagc tggaccgcga gcagtgggag cggccgcgct    195660
gggacgcgct gcacctgcac ccgcgcgccg cgctgtgggc gcgcgagccg cacgggcagt    195720
gggagttcat gtttcgcgaa caacgcggtg accccataaa tgatcccgtc gcatttcgtc    195780
tttcggacgc tcgaactctc ggtctcgacc tcaccaccgt catgacagag cgtcaaagtc    195840
aattgcccga aaagtatatc ggtttctatc agattaggaa acctccttgg ctcatggaac    195900
aacctccacc cccatctcgc caaaccaaac cggacgctgc aactctgccc ccaccgctca    195960
gtgctcaggc aagcgtcagc cacgcactcc gatacgatga cgagttgtgg cgcccgctca    196020
gtacagttca cgaccacaaa gcctggttgg atctcgacga atcacactgg gtcctcggag    196080
acagccgacc cgacgatata aggcaacgca gactgctgaa ggccactcaa cgacgaggcg    196140
ccgaaatcga cagacccatg cctgtcgtgc ccgaagaatg ttacgaccaa cggttcacta    196200
ccgaaggcca ccaggtcatc ccgttgtgcg cgtccgaacc cgaggatgac gacgaagatc    196260
ctacctacga cgaattgccg tcgcgcccac cccagaaaca taagccgcca gacaaacctc    196320
cgcgcttatg caaaactggc cccggcccac ctccgctgcc gccaaagcaa cggcacggtt    196380
ccaccgacgg aaaagtttct gcgccccgac agtcggagca tcataaaaga cagacccgac    196440
cgccaaggcc gccaccgccc aaattcgggg atagaaccgc ggcccatctc tcgcaaaata    196500
tgcgagacat gtacctcgat atgtgtacat cttcggccca caggccacgg ccgccagcac    196560
ctccgcggcc gaaaaaatgt caaacacacg cccctcacca cgttcatcat tgaaagtctc    196620
tccagtccat atgttgtcag gacgtgctgt cgttctccgc ttgctgcgaa gcccgttctt    196680
ccgagtcgtg tcgctgcgtc cagcgtcgcg cccaagatgg gaatttgggt ctcttcacgc    196740
gtagcctcct ccaccacggc tgctgatcgc cgtcactaag gaccgacacg gaggatgacg    196800
aggagcttct ccccgactcc gcggtccgcg accggctacg tagcgcgtgt ccctgccagt    196860
ctccgcagtt acaccacacg tcgtgagcag cgtgcacctg ctgccgccac tgggcctcgg    196920
cgtgctcggg ccaccgccg gagcccggtc tgagctccga cgcaggatgc gcgtactcaa    196980
cgtgcgcctt ccagtccata cagcaacacc ataggtcgtg cgagtcgtcg gctacccgcc    197040
gccaggccag ttcccgcatg ggaaggctgg acacgccgac cgagaggtca ccgagcccgg    197100
```

```
acgccatctc ttcttcctct ccgtcgctgt cattaagcag ccaggtcacc tcctccgctc  197160
cgcggtccgc cggtctcgac ggaccgcgcc gccgtcggca acacggaaaa cagtacgcca  197220
gcccgagccg ctaaggccgc atgcccctgc cgcccaactg aacacgcata tcccgctcaa  197280
ctgcgttttg ccaccctgc cagtgctccc gctcgagcac caccccgcat ctcccaacct  197340
ttttccaata aacgaaaccg acatgacaca cgtaatgggt actcgtggct agatttattg  197400
aaataaaccg cgatcccggg cgtctcagca cacgaaaaac cgcatccaca tcatagacaa  197460
gttacagtcc acagtcacat acacgataaa caataccaac agggtaatgt ttatggagta  197520
aaacactatt gtccaggcca catgcgtgta tgacttccgc accatcccgt actgcatgtt  197580
ccacatgtac gcgctagacg tgtaatccac tcgcagttcg gggacgcaac gcagccagat  197640
cacatcccct tgcagtacca gacgcagggc tagcgtctcg aagatcggca tcacatctaa  197700
gttccgcacg ttccacttta acgactcccc gggaacgaac tccacgtcgt cggcgtgtac  197760
gtacaggttc tctcccacgc cgccataatc ggccttcgga tcgaagacga accgactcat  197820
gttgcccacg atgctccccc gagcaaacaa cttgccgttg tcaatgtagc accggttgtc  197880
ctcgatttga aaccagggat gcttggccgt ggacttccag ggccggagcg cgtcttcccc  197940
ggctttagtg attccatcgg gcaggcggat caagggaccc atggaggtcc aaagacccac  198000
ccaggctttc cagagattgt tcatggtgaa acagcgtgtg gactgtacgc tctttcccaa  198060
tttatatccc agagtagtga cgtgagccca gccacctccc agattcctga cgttttggtt  198120
gtctttcctg ccaattcctc ccgtaaactt atgattatcc tagcccattc ccgataaaaa  198180
tacacggaga cagtagatag agttacgaat aaaccggttt atttattcaa gtgtctcagg  198240
agattattga cgagcgtgg ataccacgcc gtcgtcagtt catggtggca ttgagcagcc  198300
atagcaccag agtcccggcg cccggtatca gacacgctga cctaccgggc gccttcgagt  198360
ccgtaccccg cggcctgggt gttagagtcc gtaccttgca gcccaggtag gtttcaggta  198420
ccagctggtt cgtacctgtt aaataaatcg cagacgggcg ctcaccccta cggtcaggag  198480
cacaagaaca accagagaga acagatatac gagcagggtt ctgaacagca gaccccaatt  198540
gtcgtctctc atgcttcgct gaaggtacca gttgatggtc tgagagctat agtccatcct  198600
cacctgagga acacacgcgg catatttctt ggggtctccc cacctcgtag acaacgtgat  198660
gtccaccata tccacggtgt gcgtcaccgg gtgcccaccg atgttccact cgaaataggc  198720
tccgcgctca tcatggtggt actgctcacc ggacacctgc agtctgtcca tgtaagattg  198780
agagacgata cccacgttca caaagtgttt ctcggtgaag ttgcccgaca tcctccccctt  198840 gaagtacagc atgcccatat ggaaccagca ttggttctcc tccactcgaa agtgggccga  198900
tctgatctcc gataccacca catccagggg ccggggcacc gagtccgcga gtctcaggaa  198960
caagacggcc aggatcgcga gcaccaacac cggcttcatg gctccgaagg tccgctgctc  199020
ggctccgctc accgctccgg tctggctgca gcagtgcttc gctgagaagt agcgtgtgga  199080
ctgaacggtg ttttgaata tatagcgttt cttggtgacg ttgtttcccc tacgtagtag  199140
gcaactacgt gccaaaagag gcgttacggt actttccgta ctgggatttc caaaccggga  199200 cttccacac ggcggtttca acaccgggac ttttcacacg gtgatttcgg caccgggact  199260
ttccgcacgg cggtttcgcc accgctgacg ttctcatcgc cgcccacgtc aacggtggcg  199320
acaccgtact ttcccatgcg gtttataaac gtcaagagtc acgtcagtcg cccaccccca  199380
ttacacggcg atatcccgat agggcatgag gggacccggg tgtcgcgaca tgtcgacgac  199440
```

```
aggtgcggat tagtggtcgt gtcgcgacat ggacgtgcag ggggatgtct gtcgcgatag    199500
agttgatgtg acagcccgct acacctctct gtcgcgacat gcatacacaa cgggccggct    199560
tgtcggcgat tgtcgcgaca tatcgttatc agttagcgac cggagttgtc tatcgcgaca    199620
tatcgtcgac tatcgcgaca gaaaaaatac cgttcgtaga gaatgccgtg ttgaaggaac    199680
gcgcttttat tgagacgata aaacagcatc aggagccaca acgtcgaatc ccacgtccag    199740
tcgattcgta tgttatgctg cacagcaatg ctagaataac aaccagcagg gtaatcccgc    199800
aacataaata caaagtcaca gcgaagaatc cgtgtcgttc tatcaagcga aacgcgttcc    199860
aaacggcccc gtcacagacg cagttattca taagcgttaa caaccggtgg ctaggatgaa    199920
tatccaaatc acagggcagt agccgacgga ctcgttgaca ggtcagccta ccctcaaggt    199980
tcctatcgtt cggacgggat tgtgcgtttt taggcctctt tttcgccgcc tgcaagcatt    200040
ggtgcgcaaa gtcctcaccc agctgtttcc agctatcatc tgcatctgtg cagtcccctg    200100
tatcgttgta acaaacgggt ctgtgcgact tcgttctcgg aacacaagct tgttgtcgcg    200160
gagacagaga gagaagggtt ttcgggtcac gcgaagaccg ctcaccgggg gtcggcaacg    200220
cacacatcaa cagaaaaccg agacgaatca agagatccat agtgaaggag tgatatcgac    200280
gtgcttacga aacggcgatt atatatgttc tcaacaatac cgccctacgt tgtatgatgt    200340
aacgtgtgac gtgagtctga tccaacactg aacgctttcg tcgtgttttt catgcagctt    200400
ttacagacca tgacaagcct gacgagagcg ttcatcgggg catgaagtac gcattacaca    200460
aactccatat atttgttacg atagaatacg gaacggagga ggctttcgcc acacctatcc    200520
tgaaagcgtt gcattcttta tgataggtgt gacgatgtct ttaccattcc cacggctgct    200580
ttgcgtgatg atgacattca tcatgtattt ccattcacac ataccttttg tgcatacggt    200640
ttatatatga ccatccacgc ttataacgaa cctaacagtt tattagccct tgacaggata    200700
ggtcaaaaga ttatatgtag gttttccggt aaaccgaatt gtgatatttc tctgcaggaa    200760
atagaacagc ctggtaccta taaaacggac aatgcagtac tgtagcagcg taaccaagta    200820
ggtccacatg aacacgtaca aaattatggt aagccatcgt ttttcatacc acagcctgta    200880
gctgtcgtac atgaatgagg acggtcgagg aacccagggt agttgtaatt gggggcgaca    200940
ttcgtactgt ccagaagaca attgcacggg tttcagtgag atgagtactt tagcgatgtc    201000 ggcggggggcg ctacgtttca ccgtgacggt gagaacttga ccgtcgtttt gtatttcatg    201060
aggcacgtta tacaagccac tggtatcatg aaggatgacc tctgatgcga tgtgaggatt    201120
aaattgtccc tcaaaccgcc aaacgctggt catgtttcca ccgtcaatta cgcagctgac    201180
ggtgtgagat accacgatgt tggacttagg tttgggggct aattgccttt ttacaaattc    201240
ccttctgtat tgcaggtcct gctgccactg ctttttccgtg cggaaagtcg ccatgtcttc    201300
cacacgtgtg gcgacgatag acgccaccaa ggtagctacc agaagcagct ggatccgcat    201360
ggcattaccg tatgtcaatt agaaagttga gcggacacgg ttatcgttcc tggcggatat    201420
aagtatataa acgcgagtta gcctttcccg tccgttttgt acaccccgttc cccacacaaa    201480 tgacgaatac gaccttttt tttataaaaa taaaccacgt gtattatata aaacattta    201540 catagaaaag agacacactc tagattaatt aagggccggc cgcatcagct tgatatcgaa    201600
ttcctgcaga tctgctagat aacttcgtat aatgtatgct atacgaagtt atgcggccac    201660
ggatgcatgt ttaaactcga cagcgacaca cttgcatcgg atgcagcccg gttaacgtgc    201720
cggcacggcc tgggtaacca ggtatttttgt ccacataacc gtgcgcaaaa tgttgtggat    201780
aagcaggaca cagcagcaat ccacagcagg catacaaccg cacaccgagg ttactccgtt    201840
```

```
ctacaggtta cgacgacatg tcaatacttg cccttgacag gcattgatgg aatcgtagtc 201900
tcacgctgat agtctgatcg acaatacaag tgggaccgtg gtcccagacc gataatcaga 201960
ccgacaacac gagtgggatc gtggtcccag actaataatc agaccgacga tacgagtggg 202020
accgtggtcc cagactaata atcagaccga cgatacgagt gggaccgtgg ttccagacta 202080
ataatcagac cgacgatacg agtgggaccg tggtcccaga ctaataatca gaccgacgat 202140
acgagtggga ccatggtccc agactaataa tcagaccgac gatacgagtg ggaccgtggt 202200
cccagtctga ttatcagacc gacgatacga gtgggaccgt ggtcccagac taataatcag 202260
accgacgata cgagtgggac cgtggtccca gactaataat cagaccgacg atacgagtgg 202320
gaccgtggtc ccagtctgat tatcagaccg acgatacaag tggaacagtg gcccagaga 202380
gaatattcag gccagttatg ctttctggcc tgtaacaaag gacattaagt aaagacagat 202440
aaacgtagac taaaacgtgg tcgcatcagg gtgctggctt ttcaagttcc ttaagaatgg 202500
cctcaatttt ctctatacac tcagttggaa cacgagacct gtccaggtta agcaccattt 202560
tatcgccctt atacaatact gtcgctccag gagcaaactg atgtcgtgag cttaaactag 202620
ttcttgatgc agatgacgtt ttaagcacag aagttaaaag agtgataact tcttcagctt 202680
caaatatcac cccagctttt ttctgctcat gaaggttaga tgcctgctgc ttaagtaatt 202740
cctctttatc tgtaaaggct ttttgaagtg catcacctga ccgggcagat agttcaccgg 202800
ggtgagaaaa aagagcaaca actgatttag gcaatttggc ggtgttgata cagcgggtaa 202860
taatcttacg tgaaatattt tccgcatcag ccagcgcaga aatatttcca gcaaattcat 202920
tctgcaatcg gcttgcataa cgctgaccac gttcataagc acttgttggg cgataatcgt 202980
tacccaatct ggataatgca gccatctgct catcatccag ctcgccaacc agaacacgat 203040
aatcactttc ggtaagtgca gcagctttac gacggcgact cccatcggca atttctatga 203100
caccagatac tcttcgaccg aacgccggtg tctgttgacc agtcagtaga aaagaaggga 203160
tgagatcatc cagtgcgtcc tcagtaagca gctcctggtc acgttcatta cctgaccata 203220
cccgagaggt cttctcaaca ctatcacccc ggagcacttc aagagtaaac ttcatccc 203280
gaccacatac aggcaaagta atggcattac cgcgagccat tactcctacg cgcgcaatta 203340
acgaatccac catcggggca gctggtgtcg ataacgaagt atcttcaacc ggttgagtat 203400
tgagcgtatg ttttggaata acaggcgcac gcttcattat ctaatctccc agcgtggttt 203460
aatcagacga tcgaaaattt cattgcagac aggttcccaa atagaaagag catttctcca 203520
ggcaccagtt gaagagcgtt gatcaatggc ctgttcaaaa acagttctca tccggatctg 203580
accttaccca acttcatccg tttcacgtac aacattttt agaaccatgc ttccccaggc 203640
atcccgaatt tgctcctcca tccacgggga ctgagagcca ttactattgc tgtatttggt 203700
aagcaaaata cgtacatcag gctcgaaccc tttaagatca cgttcttga gcagatcacg 203760
aagcatatcg aaaaactgca gtgcggaggt gtagtcaaac aactcagcag gcgtgggaac 203820
aatcagcaca tcagcagcac atacgacatt aatcgtgccg atacccaggt taggcgcgct 203880
gtcaataact atgacatcat agtcatgagc aacagtttca atggccagtc ggagcatcag 203940
gtgtggatcg gtgggcagtt taccttcatc aaatttgccc attaactcag tttcaatacg 204000
gtgcagagcc agacaggaag gaataatgtc aagccccggc cagcaagtgg gctttattgc 204060
ataagtgaca tcgtcctttt ccccaagata gaaaggcagg agagtgtctt ctgcatgaat 204120
atgaagatct ggtacccatc cgtgatacat tgaggctgtt ccctggggt cgttaccttc 204180
```

```
cacgagcaaa acacgtagcc ccttcagagc cagatcctga gcaagatgaa cagaaactga   204240
ggttttgtaa acgccacctt tatgggcagc aacccccgatc accggtggaa atacgtcttc   204300
agcacgtcgc aatcgcgtac caaacacatc acgcatatga ttaatttgtt caattgtata   204360
accaacacgt tgctcaaccc gtcctcgaat ttccatatcc gggtgcggta gtcgccctgc   204420
tttctcggca tctctgatag cctgagaaga aaccccaact aaatccgctg cttcacctat   204480
tctccagcgc cgggttattt tcctcgcttc cgggctgtca tcattaaact gtgcaatggc   204540
gatagccttc gtcatttcat gaccagcgtt tatgcactgg ttaagtgttt ccatgagttt   204600
cattctgaac atcctttaat cattgctttg cgtttttta ttaaatcttg caatttactg    204660
caaagcaaca acaaaatcgc aaagtcatca aaaaaccgca aagttgttta aataagagc    204720
aacactacaa aaggagataa gaagagcaca tacctcagtc acttattatc actagcgctc   204780
gccgcagccg tgtaaccgag catagcgagc gaactggcga ggaagcaaag aagaactgtt   204840
ctgtcagata gctcttacgc tcagcgcaag aagaaatatc caccgtggga aaaactccag   204900
gtagaggtac acacgcggat agccaattca gagtaataaa ctgtgataat caaccctcat   204960
caatgatgac gaactaaccc ccgatatcag gtcacatgac gaagggaaag agaaggaaat   205020
caactgtgac aaactgccct caaatttggc ttccttaaaa attacagttc aaaaagtatg   205080
agaaaatcca tgcaggctga aggaaacagc aaaactgtga caaattaccc tcagtaggtc   205140
agaacaaatg tgacgaacca ccctcaaatc tgtgacagat aaccctcaga ctatcctgtc   205200
gtcatggaag tgatatcgcg gaaggaaaat acgatatgag tcgtctggcg gcctttcttt   205260
ttctcaatgt atgagaggcg cattggagtt ctgctgttga tctcattaac acagacctgc   205320
aggaagcggc ggcggaagtc aggcatacgc tggtaacttt gaggcagctg gtaacgctct   205380
atgatccagt cgattttcag agagacgatg cctgagccat ccggcttacg atactgacac   205440
agggattcgt ataaacgcat gggcatacgg attggtgatt tcttttttgtt tcactaagcc   205500
gaaactgcgt aaaccggttc tgtaaccccg ataaagaagg gaaatgagat atgggttgat   205560
atgtacactg taaagccctc tggatggact gtgcgcacgt ttgataaacc aaggaaaaga   205620
ttcatagcct ttttcatcgc cggcatcctc ttcagggcga taaaaaacca cttccttccc   205680
cgcgaaactc ttcaatgcct gccgtatatc cttactggct tccgcagagg tcaatccgaa   205740
tatttcagca tatttagcaa catggatctc gcagataccg tcatgttcct gtagggtgcc   205800
atcagatttt ctgatctggt caacgaacag atacagcata cgttttttgat cccgggagag   205860
actatatgcc gcctcagtga ggtcgtttga ctggacgatt cgcgggctat ttttacgttt   205920
cttgtgattg ataaccgctg tttccgccat gacagatcca tgtgaagtgt gacaagtttt   205980
tagattgtca cactaaataa aaagagtca ataagcaggg ataactttgt gaaaaaacag    206040
cttcttctga gggcaatttg tcacagggtt aagggcaatt tgtcacagac aggactgtca   206100
tttgagggtg atttgtcaca ctgaaagggc aatttgtcac aacaccttct ctagaaccag   206160
catggataaa ggcctacaag gcgctctaaa aagaagatc taaaaactat aaaaaaaata    206220
attataaaaa tatccccgtg gataagtgga taaccccaag ggaagttttt tcaggcatcg   206280
tgtgtaagca gaatatataa gtgctgttcc ctggtgcttc ctcgctcact cgagggcttc   206340
gccctgtcgc tcgactgcgg cgagcactac tggctgtaaa aggacagacc acatcatggt   206400
tctgtgttca ttaggttgtt ctgtccattg ctgacataat ccgctccact tcaacgtaac   206460
accgcacgaa gatttctatt gttcctgaag gcatattcaa atcgttttcg ttaccgcttg   206520
caggcatcat gacagaacac tacttcctat aaacgctaca caggctcctg agattaataa   206580
```

```
tgcggatctc tacgataatg ggagattttc ccgactgttt cgttcgcttc tcagtggata  206640
acagccagct tctctgttta acagacaaaa acagcatatc cactcagttc cacatttcca  206700
tataaaggcc aaggcattta ttctcaggat aattgtttca gcatcgcaac cgcatcagac  206760
tccggcatcg caaactgcac ccggtgccgg gcagccacat ccagcgcaaa aaccttcgtg  206820
tagacttccg ttgaactgat ggacttatgt cccatcaggc tttgcagaac tttcagcggt  206880
ataccggcat acagcatgtg catcgcatag gaatggcgga acgtatgtgg tgtgaccgga  206940
acagagaacg tcacaccgtc agcagcagcg gcggcaaccg cctccccaat ccaggtcctg  207000
accgttctgt ccgtcacttc ccagatccgc gctttctctg tccttcctgt gcgacggtta  207060
cgccgctcca tgagcttatc gcgaataaat acctgtgacg gaagatcact tcgcagaata  207120
aataaatcct ggtgtccctg ttgataccgg gaagccctgg gccaactttt ggcgaaaatg  207180
agacgttgat cggcacgtaa gaggttccaa cttcaccat aatgaaataa gatcactacc  207240
gggcgtattt tttgagttat cgagattttc aggagctaag gaagctaaaa tggagaaaaa  207300
aatcactgga tataccaccg ttgatatatc ccaatggcat cgtaaagaac attttgaggc  207360
atttcagtca gttgctcaat gtacctataa ccagaccgtt cagctggata ttacggcctt  207420
tttaaagacc gtaaagaaaa ataagcacaa gttttatccg gcctttattc acattcttgc  207480
ccgcctgatg aatgctcatc cggaattccg tatggcaatg aaagacggtg agctggtgat  207540
atgggatagt gttcacccTT gttacaccgt tttccatgag caaactgaaa cgttttcatc  207600
gctctggagt gaataccacg acgatttccg gcagtttcta cacatatatt cgcaagatgt  207660
ggcgtgttac ggtgaaaacc tggcctattt ccctaaaggg tttattgaga atatgttttt  207720
cgtctcagcc aatccctggg tgagtttcac cagttttgat ttaaacgtgg ccaatatgga  207780
caacttcttc gcccccgttt tcaccatggg caaatattat acgcaaggcg acaaggtgct  207840
gatgccgctg gcgattcagg ttcatcatgc cgtttgtgat ggcttccatg tcggcagaat  207900
gcttaatgaa ttacaacagt actgcgatga gtggcagggc ggggcgtaat tttttaagg  207960 cagttattgg tgcccttaaa cgcctggttg ctacgcctga ataagtgata ataagcggat  208020
gaatggcaga aattcgatga taagctgtca aacatgagaa ttggtcgacg gcccgggtcg  208080
acagttaggg tgtggaaagt ccccaggctc cccagcaggc agaagtatgc aaagcatgca  208140
tctcaattag tcagcaacca ggtgtggaaa gtccccaggc tccccagcag gcagaagtat  208200
gcaaagcatg catctcaatt agtcagcaac catagtcccg cccctaactc cgcccatccc  208260
gcccctaact ccgcccagtt ccgcccattc tccgccccat ggctgactaa ttttttttat  208320
ttatgcagag gccgaggccg cctcggcctc tgagctattc cagaagtagt gaggatcgat  208380
ccaccggtct cgaggaagat gtccaattta ctgaccgtac accaaaattt gcctgcatta  208440
ccggtcgatg caacgagtga tgaggttcgc aagaacctga tggacatgtt cagggatcgc  208500
caggcgtttt ctgagcatac ctggaaaatg cttctgtccg tttgccggtc gtgggcggca  208560
tggtgcaagt tgaataaccg gaaatggttt cccgcagaac ctgaagatgt tcgcgattat  208620
cttctatatc ttcaggcgcg cggtctggca gtaaaaacta ccagcaaca tttgggccag  208680 ctaaacatgc ttcatcgtcg gtccgggctg ccacgaccaa gtgacagcaa tgctgtttca  208740
ctggttatgc ggcggatccg aaaagaaaac gttgatgccg gtgaacgtgc aaaacaggct  208800
ctagcgttcg aacgcactga tttcgaccag gttcgttcac tcatgaaaaa tagcgatcgc  208860
tgccaggata tacgtaatct ggcatttctg gggattgctt ataacaccct gttacgtata  208920
```

```
gccgaaattg ccaggatcag ggttaaagat gtaagtatca aggttacaag acaggtttaa    208980
ggagaccaat agaaactggg cttgtcgaga cagagaagac tcttgcgttt ctgataggca    209040
cctattggtc ttactgacat ccactttgcc tttctctcca cagatctcac gtactgacgg    209100
tgggagaatg ttaatccata ttggcagaac gaaaacgctg gttagcaccg caggtgtaga    209160
gaaggcactt agcctggggg taactaaact ggtcgagcga tggatttccg tctctggtgt    209220
agctgatgat ccgaataact acctgttttg ccgggtcaga aaaatggtg ttgccgcgcc     209280 atctgccacc agccagctat caactcgcgc cctggaaggg attttttgaag caactcatcg   209340 attgatttac ggcgctaagg atgactctgg tcagagatac ctggcctggt ctggacacag    209400
tgcccgtgtc ggagccgcgc gagatatggc ccgcgctgga gtttcaatac cggagatcat    209460
gcaagctggt ggctggacca atgtaaatat tgtcatgaac tatatccgta acctggatag    209520
tgaaacaggg gcaatggtgc gcctgctgga agatggcgat tagcggccgc gactctagat    209580
cataatcagc cataccacat ttgtagaggt tttacttgct ttaaaaaacc tcccacacct    209640 cccccctgaac ctgaaacata aaatgaatgc aattgttgtt gttaacttgt ttattgcagc   209700
ttataatggt tacaaataaa gcaatagcat cacaaatttc acaaataaag catttttttc    209760
actgcattct agttgtggtt tgtccaaact catcaatgta tcttaagctt ataacttcgt    209820
ataatgtatg ctatacgaag ttatggatca acataaggac ttttcacact tttgggtac     209880 acaggcgtgc caccgcagat aataagcgct ggatacacgg tacacagtcc tggccagcac    209940
gtatcccaac agcagcacca tcgccatctg tatggcgatc acgaccccga gctctaagtg    210000
tctgtattca tagtgtagtc gtcgcaggtt atccactgaa ttcccgtagc tgaaataacg    210060
tatatggtac cgaggctggc accacatggg tttgcatttg gagcacggca ccaaatgcag    210120
agtgagatgg tccaagtccg tgggcaccca ctggcgcaaa cggaatacgg cttcggtggt    210180
ctccacgagg cactccgggg cttgcagacg gccccacttt cgtccgtgac ggcccgacca    210240
gccgacccga gccactatcc ctttctcggg atagaacgta ccctgtacac gccatacagc    210300
gtccaacacg ccgtctttga cgacgcagct ggcctgatag ctggacacgt tgttaagcgg    210360
cggaaagcga aactgacgtg ccggcggagc cacatagttc ggttcaccgt gttgtcgcgg    210420
ttcgtcctcc ctatagtaat agtagtcgtc gtcctcatag gggttgccgg cgtgagccag    210480
cgttacccaa cagcagccca ggccgacgag gaggcgcagc caccgcctca tggcggcttc    210540
gccagtcaat cgtctttagc ctcttcttcc cgtgaggtcc ttccggtggc gcggtgccga    210600
cctcggaccc agggacgtat ccacctcagg tacacacagt aggctacctg gacaccgaag    210660
ctgaacaagg ctacatgttt cacaaactgc accagtacca catagaggaa tgtcaggtag    210720
cgtctctccg caaacagccg ttccaagtct gagggcgtta cccgcagcgg caaccagggc    210780
agcctggacg ccggccggca atggagcacg ctccggttac aggcactgca ggggtaaacg    210840
gttaacatca cgtaagagag tcgagcgtcc acctgtggga gctcagtttc gtaacgtaga    210900
gccccgtcat tttccagctg gggtgcgccg accttgaaat gggtcgcgct ccgttcgtta    210960
ccccaggtgc cgtaggctct cggggccgta tcggagaagt tgccgtgcac aagccaggcg    211020
gccacgagta ccccgtgctg gacgtaacat tcggacacgg aactggagac acggtagccg    211080
gacacgtccc caaacccgcg agggtactgg ggcagacgga cggacttgct atttgacaac    211140
ggacagatac gagacgacga ggacgcagac gactcgtcgc tggaccacga caaccggagc    211200
gactccttgg agcggctcga gagtacactt actgcgatca gacaccagtg ccagaagaag    211260
gaacaggtgg acggggacca caggatcata gccgccggca ccgcggccgg ccgcaggaag    211320
```

```
ccgcccggcg cgtcgtctgt gtgcgggagc cgaaacaccg tgcctcttta tatcgtcccg  211380
acgtgacgcg agtattacgt gtcaggggaa aaccccgtca tgacgaacgt gattcgtaag  211440
tgacgcgggg tgctgacggg gttcggctcg agaagtgacg gagcgcctca cgtcagtatg  211500
atgtccgatc cgcgtcagcc ccgacgtggt tatggtcacc gaaacccacg tttatatgga  211560
cgttgagaac agcgcctgac cacatgattc atcataccat ttctcggaat cgggcccatg  211620
ccgggaaagc acattccttt tcagtaaaca acaatgacat cataacaaat cattttattc  211680
gcgaggtgga taataaccgc atatcaggag gagggatcgg gtgatgacgc aggccccgca  211740
aaacagtccg aaataaattt ttagtatcgc cccgtagtcg cctagatacc agaggtacgt  211800
caagttcatc aaaacgccca tcggcgtccc ggaatcgtat accgggcaca cgaagcgttc  211860
ataacaatcc cgggaggcga gtgttagggt agcagaatag tttcggggtc ggtttccttc  211920
cggcgacgac agctccgtgg gcagcagaat gtagagcgcc tcggtagccg tcgcggtgcc  211980
ttccacgagg atgggctgcc ggtgcctttc gtgattttct ccgtcgtgta gccaagccga  212040
ggcccgcaaa gtcttaggcg agggggaattg tccatagact ttcaccgcac ccttcagtac  212100
atggttctga ataacacagc cgcacgtgaa gtaggtcggt tctctcgtct cctccgtggc  212160
tgccgccacc actcccagcc accacaacag gcaggtcgcg agagggttcc ggaggcttcc  212220
ccggcgtagc atggtttcgg gttaaagcaa aaagtctggt gagtcgtttc cgagcgactc  212280
gagatgcact ccgcttcagt ctatatatca ccactggtcc gaaaacatcc agggaaaatg  212340
tcggtgcagc caacctttca catacagccc ccaaaacact tgaatcactg ccaccatcat  212400
cagcgtatac tgcgccgact taatcgtgag cgcgtagtac gccattagac ggcgatcttc  212460
gaacaatagt cgttcgatgt cctctaacga gctccacaga ggaacccaag gcacgaggca  212520 ccgggggttcg cactctacat aataagtttg gcattggtgg caggggggaaa agtagaacaa  212580 cacgagttttt gtgcgttggg gaacacgata gtcccggagc cagtagcgtt ttgcgacgag  212640
gctttcggag acgtcctcca ccggcgtcgg cactcgatcc gcgtagccct ccagcgtctg  212700
gtagtacacc cggggtgtcg gcgtgggcac ggacaggttc ccgcgcaggg tccacagagc  212760
ctccagtcga ccgcccgatc ggagcacgca gcgcgcctcg gaatactcta ctcggtactc  212820
cgaaacatcg ggcagaggcg gtaacggctc cgtctccacc aagggcggag gttcatcgaa  212880
aagagtcaag gataattcag gcatactacc tgcgaccggg gcccagaggg ctaggataag  212940
cattacaaga ttcattctgt cttacaaggg aaggctgttc ccctgtctag actcaaaagc  213000
tgtaaggctg tcttatagca tgtagtcttg cacgtcacgg ggaacagggt ggtgatctag  213060
tgacgtcggg agaacacggt gttttagggt gcggggaca aaggacagta cgacagatta  213120
ggtgatagaa acgttttttt ttatttatga aaaagccagt gtgccgtgcg gcctagggcc  213180
ccggcgtagt ttggatacca gatgggggcc gtcagggta ctaccacgag cagaaacata  213240
ataacttggt ccatgtatag cagcatagcg gtgcgtagca ggtcgccgtc cgtgtagcaa  213300
tttgacggtg agcgataaag caccgttaat gtgtcgcgga taagcacgat cttgaggccg  213360
tagatgaagc tcacagtcag tgctaaaatg atgcgttggt atggttccca ggactgcacg  213420
gcgatgaaga gccagagtat gggaagcatg aagcttagca aacagaggat ggctaaccgt  213480
cgttgcatgt tccaggccat gagccaggct aggcccgtac accagacgca gagcatggat  213540
gacaggacat aggcctggat taccacggtg cgatcgaaac acagcccgat ggtggacacg  213600
gatatcgtag tgagggtggt ataccatg accagcatca gggtcccggg taggcgccga  213660
```

-continued

```
cgttccagcc agtacgcgtg gcaacgcaga gcgcagggta gcagtgtgct ccagaagggc   213720
agtgtatcgc gcaggtaggg ggtcgtcacg cgccacggta tgagcatgaa aaggatggta   213780
gtggctatgg tggcgctggt ctggaacacg acggtgccgt agagacgtac catccagaga   213840
aagtgttgaa cgctccgcag ggtgtcttca tctttggtga ttacggtgac tcgacggatc   213900
ggcggtggtg acggcggcga cacgggtggg ggtttctctt tcttatggcc gagtggctcg   213960
ccttggtgaa actggatctg taccatgacg ggtgctcgac gaacagtcgt cggggcttta   214020
ggtacccggc aagttttata gagaaagggg gacgatgggt ggtggctacg agccaccgcc   214080
accttcgcaa tacgaggatc tgaaggcggc aaagacggtc gtccaggca ggtgccagag    214140
gttgggactg agcacgatca gcgtgatttt aaacatggtc accagtccta cgtagatcag   214200
cagcgagcca cgtaacgtct gagcagccgg cagttcgtcg cggatgtaac gcgtgccgta   214260
gaaagtcacg gtcatcataa ggaagacgat ggcgccgtag ccgtagagta gaatacgctg   214320
atgatggaac acggtctggt cgccgataac ccagagcgtg atgaaaaaaa cgctggtgag   214380
caccccgtgtg catatgagct cccaacgctt agcgcgaaag ctgtccccaa ccatgacagc   214440
gccggtgcaa gctatccaca cgtgaggac cagtgtgtag tcgatgagga tggcgggcag    214500
gtcggagcac caggtgtaga aaccgtggt aacgagagg aggcctacgt agcccatggt     214560
caataccacg tcgtcggggt gcctttcgcc ctgtatcaag accaaacacc agagaaggga   214620
gggggcaaaa accagcagca gaggggaaga ttcatgttga catatgttgt gggaatcggg   214680
gatgcccagc caaatcattc gcagaaagc cgtactgatg gcgatgtgaa agaccactag    214740
ggcgtagacc cggacgagga cagcaaaacg gcgcagccac ataaggccgt ggtgcagctg   214800
caggagagaa gcccattgcg gcgaatgtag cgacggcagc ggcgggtcca tgaggcgggt   214860
gatgcacccg agtgaacggg tgagcgtctc ggtggagtct tcttataaac cagcggagct   214920
caggcagtct tgctctggag cgtcgcagtg gtggtgttga ggatgacgct gagcgtgccg   214980
ttgtcaatcc ggtaatgatg ataggtgcca agcttggcca ggtagctgaa catttggtcc   215040
cagcgtgccg accacaccac gggcgtgagc atcaggagtg tggtgtgata aatgagtgtt   215100
tcggtggcgt aaagtatcag cgagctgcgg atgatgtggc tcacgggcat tttggtggcg   215160
atgtagcgca cgtcttggaa aagaacggcc aggatgcagc ccacgaacac ggtatagaga   215220
cacagcagag tcttatgcaa ccaggtgtaa gtagaagcca ggacgctgac catcaccgtc   215280
aaaagtgtgg aggtaaaaag cgcgtcacgc cacacggagc tgagacggtg ctcccaagcc   215340
acgccgttgc aggccacgaa caacgtccac gttaagatga ggctgaaaac gccaatgggc   215400
gctgtggcgc acaggttgag cccggcggtg gtgaacgaca aagcgccac atacagcgca    215460
aacaccaggc cgttgctggg gtgtctatga tcggtaagct ccagcgcgcc cagaaccaac   215520
accggtgtgc agctaagcaa taacggcgaa ggatcgtcgc ggcactcgta gcccagcgag   215580
gggtaaccca gccaaaccag cgcgctaatg agcacgctaa aagcggtttc cagcgtcagc   215640
aatccgtaga cacgcatgac gatcgcggtc cgccgtagcc aacacaccgc atcttcggaa   215700
gctgtggacg ctgtttccga ataccggag gagatcgtgc ttccctcttc caaggatcgg    215760
aaagtagcgt ccgtcgtttc cgcagacgcg gcttccctgg tacgctccgt ttccgacgac   215820
gcggtttccc gctgcgtgga aactgtctcc atgtcgggac cgcagcgccc ggcggcgtat   215880
ccgcaaggtc tcgaagctac agcttgtcag aggaaaagta ggtttgcaaa aggtgcgca    215940
gggtcatgat tctcagcacc atcagcagag tgaaaaccag gctgagaaac accttgacgg   216000
ccgccaaaag cgcgcgttcc agcggcgtct cgtagcgtac agccagggcc gcttcgtgga   216060
```

```
aatgcgagac ggctagacag gtaatgagca cgctgaagga caagacgatc ttaaagcacc   216120
aggaccaacc acgcctcaag atgaccacca cgattgccgt gaaggtcaac gtgatcaaag   216180
catggatgac cacgatctga cggcggacgg tacgttcggg agccaacaac gctacgccgg   216240
tgcagctgag aaaggccagt aaggtgaaca acgcggccga gatgaccaac gtaccgtcca   216300
ggcagagaca tatcacgatc aacggcggca cgtgaagcag cgtgtaaaag agcagaacgc   216360
cgatattgct gggatgcgat gtttcgtaac agtgaatgaa gatcaccgac gtgacgggta   216420
tgataaagac gaggctgggc gaggactccg tgagacacag acgggaatgg tgaaaccacg   216480
tcgcgggcgc cgcgtagcag aaggcgctca acaacgcggt caagccggcc agctgccaac   216540
ccacggcgcc ataggtgtgc agcgccacgc ggcaacagtc gacccaagcc agactgcggg   216600
tcgccagccg ggtctcttgg atcccggggg gcacgtagat gaccgtgcca tcggtgggta   216660
cctgaaaccc ttttctctt ctcatggtgc gctgcgttct ctggaaacgg ctgctctgtc   216720
cgaaaaccag ttccgaacga aaatctaggg cgagagggtg acaacggcg tcgacgacga   216780 agcatgggac aggtcgttcg gcgttaacgt catcgcgtcg gacgacggta gttctaagag   216840
acgtagatcg ctcagcaggt cctgacagtt gcggattcgc aagatcagaa aaaaagggga   216900
aatgaacgta ataaagagct gtagcgacgt atgcgctaca tcgcgtggca taagaacgtg   216960
acggacgaaa aggacctgct gcgaaaagtg gccggcaaag ataaggccca ccgtgctgta   217020
gaagcccaaa agcagccgca ggggccaagt ccagggccgc gtaaagacga tgagaacgtt   217080
aaccagaaag accacgaccc agacgccgtt gatgagggta aattgatcgg acagggtgca   217140
gttgtcgcga cagatgaaga ctacttccgc gcagagcaag gtgatgacca atgtgagcac   217200
aaacgacgtc aacacctcgc ggggctcctg gcaggcacac gtgacaccta gcgccgggat   217260
gtgcgccagg aggccggcga gtaatagcac cagctgtcgg aacggacgac ggcagcgcgg   217320
gtgccggttt cgctgagcga gaaccggtcg ctcataacgg aaatacacga agagcgcgga   217380
ggccacaggc accaggagga gcacctcggg cgcccagacg acgtgacaag gaaagcctgg   217440
acgcgactta agagtcgctg tagggaagac cagagagaag ctacccaaga cggccaccgc   217500
cgcggagatt tggaagagga gcaagccggc gattcggacg acaacctcga agcgatgcac   217560
ccagcccagc acggccacca cggccgcttc atcatagtcg tcgttgttgc cgctgtcgaa   217620
cagccgccga aacacgatct gtcgctgggt cgcggtggga agcgcagac ccatgacagc   217680 cggaggctat atgaccgcgc gtctaaggcg cgagatccgt gggggggactt ttagatgttt   217740 gggcggcccg cggttctaac aggcttgatt ggtggagacg gccggcgcgg cgggtggggg   217800
aaacgacgag ttttccgtt acgccatggt tcgcgtgagg tttctctgta cctcccgcaa   217860
aaggtcacag cccgaaatgg aggccgcgtt ggtggcccg gtggcgcgtg acgataacca   217920
ggtcatccaa gtgatgagtt tgtctaatga gtcctcggtg gtgaagagga taagaatgag   217980
caggtacaag tacaccaggt tctcatagag acacaaggtg agcaggtcgg cctcggacca   218040
cgcgatctca acaggcgtg tggtgtcaaa gaccgtaacg accagcatga agctgagcgc   218100
catggcgtaa tagcccaaaa aaagtttgtg ccccaacggt acgggctgca ggtaaagtgc   218160
gatcaagaac gcgataacgc cgatcacaaa cagcgtgacg atgacctgcc atcgacgcg   218220 attatggccg gctagacccg tgacgcagct gcagaggcta aaaagcacgc aagccaagag   218280
gcccgagaag gtcaccagcg tagaggagga gcaggcgctg gccacgatca ccgaaagcgt   218340
cgtgagcacg ctataaatgg tgagcaggcc cgggctcggc ggcgacgtaa acgatccttc   218400
```

```
atcgcgtttg ccatgcagca gggccaaaca gatggtgggc accatcaaac tcaagggcgg  218460
cataaagccg gtgcaacaga gaaagacggt gcctttaaga tgcggaaaag ccagcaccag  218520
gcccagacag agcaagaagg tgcaggtgcc ctgcacggcc acggtgctgt agacccgcat  218580
acaaagtaaa aagcgacgta cgtcgttcgt cgagacggag gaaatcataa tgactccgcg  218640
cgagggtcgc gggggtgggg gcgcccaggc cgtcccggtg gcctctgagt tcggagacat  218700
gacggcggtg gctatcaaaa ggcgcgtatg agaaaccgtt tatagagtgt aatagaatca  218760
ccgtcattcc cacacggcgt tcccccataa agtcacgtca cactcgagta agcgtgaaaa  218820
agctttatta ttgaataaaa aacacgagta caacaccgag ttgcggtgtc ctgtctactg  218880
ggtgggggag gtttatcgtc tgtctctaga gggaaggtgg ggaacgtcta agcgagcggg  218940
agcgtgtcat ctcccccatc tttttacaac aagctgagga gactcacgcc gtcgatgcgt  219000
ccgccgtgtt tctcggcgta ctgctgcacc cagacgtggc cgctaaagat ggcgacgctc  219060
atgtttagga gactcatgac gatggtgtac aacacgacgc tgacacagac gctgttttta  219120
gacagcgttc cacgctggta gatgagatcc agggtctcgt aaataagcac ggccgaagcg  219180
gcggtcacca ccaggacgta gagtccgctg tagatcttgc tgaccacag cacgggcgaa  219240 aagtaaagca ataggtaaaa gacgatgacg gaccagccgt agccaatccc gatgactttc  219300
cagcgcgtgg gattgttgcc ggccaggtag gtgagaccgc tgcagagaac gaaaagacc  219360 atcaccaggg caaacgacag accgatgacg cgcctttctc cgcaaaagcc cgtgcacacg  219420
gtgatgccgg tgttgatcag caggcatgcc accgtgagat gagcaaaatt ggtggtgtgt  219480
gggcgaaact cggcgaaacc gcgtagcatg gccagcgtgg acacgggcac gatggaggac  219540
agggctggca ctatgccgtt ggcgcactgt ccctgcacat cggggaaggc gagccaagcc  219600
agcaggcaga ccgtgagggt acaagccagc tgccacacga gcccgtgata gacctccatg  219660
agcagcttga agcgtttcaa ccactggaag agctgctgtt cggccaccag cgcgtggctg  219720
cgatggagcg gcacgatggt gaccgtcggc gactcatggt gttcggaaac cgaggcggtg  219780
tcgcccatgc tgccgcttac gaccgctgtc ggtctaaggt aggcgtcgat gaaacagtcc  219840
gtcttatcag cacccggtta ccgcggattt gattgacgtc acgagtgtgg tcaaaccgtg  219900
gcggcaccct gtatccgacc cgtcgtcatg ggctccacaa ccagagcctc agaagatggt  219960
acatgccgat gaataaagcc acattttcga catagaggcg tagcgagggc tgaaaactct  220020
ccgggaaaga actctgacag gtgatcaggg acagatcgtg aattagcatc agcgtcaccg  220080
tcaacagcgt cgtcgcgtgt aaaccgagaa agaacggggc gcggcccgc agcagccaaa  220140 gtcccagcgc cgtagcgcag agcagagaca ggaccgacgg tagccacagc cgccggagag  220200
acgcgccagg atcgcaaccc aaaagcgagg cccccaggca gccgagatct accgccaggg  220260
cgagaagagc cgcgccgaga aaggcctgcg gcgacggctg gcacatcagc aaggtcagaa  220320
aggctagcgc gtgcggcagg cagtaagcca acaggagtgg gagtttgcgg ggacaacggt  220380
cgatagacgg accgcgtagc agcaggaaca ggcagccgac gggcacgacg aggctgagat  220440
gagaaagcgg cggtgggtcg tcgtcccgtc cccgctcgca tagctcggcc accggtggcg  220500
gcatgagcca ccagctgagc acgctgaggg cgacggtggc ggtaagctgg aaggcgacga  220560
ggacggaggc gcgcagccat accgccagcc tctctaagta ggggactacc tcctcgacgg  220620
tccattctag cgggacgaca tgaagcatgg cgacaagcgc ggctgctgtg aaaatgagcg  220680
cggttttata ggcattagga cttcccgatc gtactggcgg ctgtcaaagt cccgttgtcc  220740
aaagacgcgc cgtccgaaag actaatccaa cggggacccg agagcatgag caacaacgtg  220800
```

```
agaaagatgg ccatgctgtc caggtagaga cagacggcat gacggatgca ctggttaggt 220860
gggcagaaaa agatgaccat gagactgtcg taggccagaa tacccaaaaa gaagctgatg 220920
gagaaggcgc acaacgtcac cactatcttc tgcagccagt cggcgtcgct tagcagagcg 220980
agcgtgagga acgaaagcag catcaccacg tagacgcagc tgatgcattt ccaacgacgt 221040
cggtcacggc cacctagaaa cgccagcccc gtaaaggaga taaacaacgc cagggtcatc 221100
acgtaggaac ctactagtac gcggctttca gagcacattt ggaagatggc cgccgtcagg 221160
ctgttggcca acagatagat gaaaagcacc gtggcgttac tagggtgctc gttgcccaaa 221220
gtgtacgtga tgaacatgca gacgatgggc acgagcacgg tgagaaagaa gctgtagttc 221280
tcgacgcaaa agttgcggtt ttgtgggaac cccaaccaaa aaacgcttcc caagccgaag 221340
ctgaaagcca actgaaagat gaagatggcg tacacacgca gccatacggt gaactttttg 221400
aaccactcga gagcctccat gcgggagagc agcagcgcgt tagcctcctg cgcctgcatg 221460
gtggcgacgg tctcggcaca aagccgctgc ggcgcaccta cccttctctt atacacaagc 221520
gagcgagtgg ggcacggtga cgtggtcacg ccgcggacac gtcgattagg agacgaactg 221580
gggcgacgcc gctgctgtgg cagcgaccgt cgtagcgacc gtcgtctgag cagtgtgggc 221640
gctgccgggc tcggagggca tgaagtagag cacggagaca aagaggtaca tgaggtccat 221700
gtacaagcag agcgcgcccg ggatataact ctcatactcg atgtcgtgca ggatgtcctg 221760
cgtatcgcac accaccgagg tcacgatgac ggccaaaccg gctatcatca ccaggatctc 221820
acttaccgcc tcgggaaaaa gagaaaatac ggcgaacagt aagagaatca gcgtggatgc 221880
gcccgtcaat agggaacgct gtaattccac gtcgcgggca aacagatacg tagcgagcgt 221940
aaggaaacaa aatagcgtta ctgtggccac catggcataa atgactgaac gatgactaaa 222000
atggaagcct gacgccgtga cagccacgct ggtaagcaac gtgtacgtca gtaagatcca 222060 tacgttttg ggaaagttgg gctcggccca acgcaacaga cctaggcaca cgatggagat 222120
cattaagcaa gacagcgtca gacgcacgct ggaaaagagc tgctccagcc ggtgcggcaa 222180
caccagccag caaaaggcgc agacgctcat aaggatgagg cattgcaccc agataaggat 222240
gtagatgcgc agcaggaaga ccgaccgggc tatctggacc tgaccgcgga gcgacatggc 222300
ggcaacgccg gcggttatcg ccgagattcg tctaaataca cgaagcgaac tagaaaacgc 222360
acacacgtta tttgcaaaaa gaaagcagct gccggcttat tattttatta aaaatttatc 222420
tgtgcagaat cataagttta tgatgaataa aaacgggaa agggaatctg cttttaggga 222480
cccgggtctg gtccgtcgtc tcccatctgg tcgggttcgg ggatggggac ctgtttcagc 222540
gtgtgtccgc gggcgtgcat ggcttttgct cgccggccgc gctgtaacca ggcctctttc 222600
tctgtggtcg gcgagtcttc cgacgggtag ggagtctggg agtccatcgc ttcaggccca 222660
ccgctcgttc cctcgaccgt cgtgtcgtcc tcgttttcgc tattacacgg ggtttctgga 222720
gtatcgccta tacggttggc gattctccgg gggtggccgc tctcgtcctc gtcgctgcta 222780
tcgccgcccg gtaattcgac gccgcattcg ttgtacggag cgcggcacat gggcggcgga 222840
aagaacttgg gcatgcgaaa gcagcgttgt ccatccacgg tctgcgtggt ttcatcatta 222900
tcctcccata atcccccctg tagcgccggc agcgtttcga cgctgtgaga ggggaaggcc 222960
cagttctggt tgtcttgcag cgcgcccgtg ggcagtaggt ccgtgcggcc ccaggcgctg 223020
ctgttgttgg gtaccttgtc agtgccgcga gtaggtcgca gaaaccagtc cagagcgctc 223080
tctagctgcg agcgtgtgat ggtgcccagt gcgccgtgcc agcgcagcac gtctcttttc 223140
```

```
agcgtgtggt gacagacggg cagctcctcc aaccgacact cgccgcgcaa tccgcggtcg 223200
aagcggcaga gaccacgcaa tttaagcaga ccgcacttga gaaacatgtg aaaattatcg 223260
gcaatgcgat acaggtctga gtcctcgatc ttgtgtaggt agaccacgcc aaacttgtcg 223320
agcagcacca ggccgctggg cacaaaaggc ccgtaggcca ggtaatagcc cacgaggccg 223380
acgacgtacc actcgcagca caagcgttga cgaataaagt tcagaagatc gcgaaagtcc 223440
gcggccggca tgtggtcaaa aggccggcag gcgcgcaggc cctcgatgga gcccagcatg 223500
agcaacggct ccacctcggt gcgacccggc gtgcggatga ccaggttgag accgctcatt 223560
tcgcgggccg tcttggccac ggccgcagcg tcagtgggt cggtgcagag gaattttttgc 223620 acatgatagc gcggttcggt ggtggcgaac ggcgtttgtg ggtgccgata cacatattcg 223680
caccagagta ggccgttctt ggaaaaggct ttgatatcac tggccacctc gtagagcccg 223740
tcggtctccc agtcgtagac gtagacggtg ccgtaatgac ttagcatgag cacgcagggc 223800
agttcctgcg cctgcttggt gtttcgtgtt agatcgctgt cgggtggacg cacggctagt 223860
acaccgacgg cttccagggt gtcatcgcag cagagatagt cggcggccag agaacgtgcg 223920
taaatctgcg ggatggcggc ctgttcgcgc atcactagga accagttggc ggggttgcgc 223980
agtgctacgg tggttccttg gtggcgctgc acgtaggttc tcagcgccgg aggatcgtac 224040
tggcgcagat agaggccttg cagcatcgat aacgtctttt gaaagacggt gtttctaaat 224100
tggaaaacgc cgtagtcgca gcggatagca tcttcgcagc gctcgtcgcg ctgtcggaga 224160
taggtgcccc aggcttcggc ggcggctttg gtgagtaggg acatgccggc ggagccgtct 224220
cgacagcgag tcggataaag cgcgctgcgc gaaagcttaa tataggagca gcgtcagacg 224280
aatcgcggct ggtggcccgg ggggtgggac gcgccgccta cacaaaatgc tcccgaaaat 224340
cgaaactctt gacccactcc ggagacaaat ccgtattcag attgatgcgt cgcgcttcca 224400
cttcggcttc cgaaacctcg gcctccgtcc ggtaggcgtt aacaatacgc tgacccaggt 224460
gccaacgctc tttctctgcc aaacgccgtt gctcaaacca ctcgtctacg tccttgaggt 224520
caaagacagt gtcctcctca aggtcaaagc ctaggtcttc ccactcgtcg tcatcgctct 224580 cgtgccggc ggccatacgc gcggcaaccg cgtcttcccc tcctcttctt tcaacgttgg 224640
gtaccacgtt gttttcttcg ggttccatgg gttctgcgcc actatcgtca tcgtcctctc 224700
cctgctcctc atcgtccgcc aaggcgtcgt ggatcacctc caggttctga ttgtcgggta 224760
cgacgtggtt atcttcgtcg tcgtcgcgtg gcatgggcgg cggccgacgg cggacgaccg 224820
gcatggcgcg gccgtcgttt ccttcgtctt cctcttcacc gtctcccaag gaacgcggtc 224880
gacgacgttc cgcgaagtcg ccgcggacca cgcgcgcctg ccaaatggta aacgcgtccc 224940
aaccgtccca gttattgagc atttcggcgc gaaaacggtc gcctcgacag agccagcgaa 225000
actgccgcgc gtagtcgcgg tctacgccgc tgtcgaacat ggtaaagtgc agacgcgccg 225060
cctcgcccat gtgtacgcag cctccattgc gttccagcct ggccgcgcgc cgcagaccgt 225120
gttcgtagcg gcgacgcacg tacaccttca tgaggccggc gcgaaaaagt tcctctaggc 225180
tgtcggccag acggtagatt tcaccggcta gacgctgcag gggcggcgag cggtccagat 225240
gcgacttgac aatcaccacg taaaaacgac agaaacggtc gaagatgatg aggaaggacg 225300
tgtcaaagaa accaccggcg cggtaggagc ccacggcgcc tagcaggtac cagcggcaac 225360
gcagttgcag cgtgacgtac atttcgcact cggccaagcg ggcggctggc gctacctcga 225420
agggccagca atccgtcaag cagccgaaac tggtcaggag tttcaacgtt ttggcatggc 225480
gcccaggtgt gtgaaagttc acgtcgcgtc cgtggtgttc gccaacgcag gcggccaacg 225540
```

-continued

```
cgtcggcgtc atgagcgtga cgcagcagca tcgctaccac gtcgtgcggt acccgcgtag 225600
caaacggcgt ctgtggctga cggtatacgg cttcggtgta catcataccg taacgtgcca 225660
gctcgtccag atgacgcgcg cacagcagca gaatctcttg cgagggttcg tagatgtaga 225720
ggcgcgtacc gccccccatg cagagcacca gctccgtctc ttcgtagtga tcttccacca 225780
tgatcacgca cttgcctagc acgataaggc gttcggggca acaaatcacg tcgtccagca 225840
gttggtcgcg cagctccggc atggtgctgc caggccgcac ctgcaggaac cagttgtgcg 225900
gaatgccgag cgacaacacc tggtcgacgt ggttacggac ccagtcgcga agcacgtcgg 225960
cgctgtactg gcactcaaag atgccctgaa agtcgctcat gacccgcaga aaagtttcgt 226020
agcgcgtgtg gcaatagagg aattcatcgt ttcgcgtgaa cgtgggagct ccgtcttccc 226080
aacgtgtacg ccacatgtca aaagaggccg ccagctagac accccagaaa agaagcagag 226140
aaagagagtt ctttgtgcga cacgttttat tccgcgtcct ccgctcgacg ctcaaatctg 226200
gatgtactcg cgcacacccg tcaggctctt taagggaaaa gggtccgagt acgtcactaa 226260
ccgcgactga tgcaccaggg cggtaatcac ccgctctgcg ccctcgcgcg tcgacgaacg 226320
cgtcgtcacc aggcagtgca gccgcgggcc cgtatcgtcc tgatgaccag cggcctcgcg 226380
ctcggctgct tccacaccga caatgtcggg atccaacacg tagctctgcg agttggtgtc 226440
gtagcggtgt aacaccaacg tgttggggtc cagacgctcc cacgcgccct cgtgcgggtc 226500
aaaacgctcc gttaaacaga gccagtcata ctgctgctgc agaatacgcc gctcgcgctc 226560
gcgtcgctca tcgggcaacg cagcgtcttc gttgaagaga atgtcccgct tgtggtctac 226620
ggcacgctcg tggtggtgcg ggcacagatg acggtgttcc atacgcgtct gacgctgacg 226680
ctcgcgttcg aagcgccggt gtcgaaagac cattttcagc aacccatgc ggaaaaactc 226740 cgtgatggtg ttggcaacgc gccgcacata gtggttgggg tcgtccatct ggatggcgta 226800
cacggcaccg aaccagtcca gcagtaccag cacttcggcc acaaagttgc gtcccggtcg 226860
cggacgtccc gtcacgccta gcacatacca cggcgtggcc agattagcac ggacagccca 226920
ccaccaacga cggctctcca cctcggtgag cgcacagaag ggccaaatgc ggtgtaactg 226980
ctgcaccgtt ttcatcagcc gcataatcac cgtaccgtaa cccggtgtat gcaacttcac 227040
gtcgcaaccc aggattcgtt cggccgtggc gtacgagccc tcgggcgtgg tgtcattgag 227100
aaacaaaaca tgcatggtac gcgcgccctt agggtatcgt cgcggaacag gtaccgtcat 227160
tctccgcaga gtggtgtgaa tcacgtcgcg atacgcaatc tccgaacgcg acacaccgta 227220
acgtgccagt tcatccaagt tgtgcgatac taacaccatg tacttttcac gagtgtcgta 227280
ggcgtagacg cgagaaaagc gacccataaa accacgtac ggggtagcca ccatgccatc 227340
atggtgatcg cgacgtggct cgggcaacaa aataacagcg tatcccaacg gcgtcagcgg 227400
ctcgcggcaa cagatgagct ttgacgccgc ctgtctggcg gcggtaatga tcccgtcctc 227460
cgtacgtaac atcacatgcc agcccttggg gggacccaag acagacaac gtccctcgtt 227520 acgatgaacg taacgcgtga tttccattgg ctccaggcaa agaacagtt ccttaaaatc 227580 ccgcaacact tgtcggtata acgccatggg atcctcggcc gccacaggca gcgcggggag 227640
ctccggcggc acaactgcag cgccgtcagg gccagaaccc gcagcggat ccatcattac 227700 gcgacactct cagccggaca accggcgtca ctgacagaag ccgagccaaa tacagagaaa 227760
gcaacgctac accgtcaccc cgctcccaag cgccgcggaa agtgctccga ttttcaccg 227820 tcgttcgcga cgttgatttg cctcggtctg agaaccgacc tagcgttcgg accggtgcgc 227880
```

```
agaaacagcc ggcggtccga gccactgagc ggttcacagc cccggccgcc gatagttacc   227940
ggagagacgt tcgagctgca ggtacatcgg cgctccccgc ttcgccaccc cgcgcccgcc   228000
ccagtttata ctctccgacg ccccgtccaa cgcgcctgtg gagggccaat cggaccgcgg   228060
gagctctcca agtggatgac aggcacagcc gggtgcccga ccgtgaagag ccctcatcca   228120
cctgaacaga ccgctaaccg aaggaccccg agtcgcgtcc gtcggtcccg acgtccgtcg   228180
ccatctggct ccctgctgtt ggctacctct cggatttcaa aaagagcac gtgccgatga    228240
cggtgcacag gaaagagcca aagtgtcacg gcgtcttttt ttatttgtat tccttcctg    228300
ttttgtactc gtaaactgtt gacgttgttt ttacatccaa aagggcaagt aagaaacagg   228360
atgaggcatg gtaggtttgg gcgtggggcg gccctccagc acggcggccc gggccgcccg   228420
gcgggtgagc accccggcgtt gcgccgtatc tatcttgtgt ttcttctgtg tcttttcct   228480
atcttgttcc gcgacggcct cttcatcac gttcagcatg cgttcctcga cgccctccag    228540
ggatcctggg gaggagggag tcctagtgag gcttccaatg ttgttttgtg gattttcggt   228600
ttcctcttct tggtcgtcat cgtcggacgt gtcgtcttcc tcttgatcct cttcttcgtc   228660
cgagtagtag acgcatagtc cctggttcat caggctggga ttcatcaggt tctgacgggg   228720
aatccgctgt tgtagacgtt taaccgcccg ttccaggcga gagctcatgc cgcaccgac    228780
gctgtaacgc cgcacgggcc cgtagcgggc tgtttgttcg cgtacatgat cgttgagctc   228840
ttgccaatat tgtttggcac actccagatc ggaggtttgt ggatagtcgg gtcggatccg   228900
cggatcccaa ctgacatcgg cggtgccaga gacttcgtcc agactgttac gcatagagca   228960
ccagtcgggt cggacgataa acctgtcctt gcggattaac catttataac gtagttcgtg   229020
atggcgtgta gaggcccgta cacgctccac ggtcccaaag cggtcccaga agggaaagtt   229080
ttcgtggggg cagcgacccg gcacttccaa acgttcggcg tcgtccacgg cgtagtggaa   229140
acgccggccg gcctggtaaa ttttgagcag acccacggtt aacaacatat ccacgctgtc   229200
agccaaccgc cagatctcgc gccgagatac gtcaaaatag aaaaattcgc aggctcggtc   229260
gaccaggatc acgaaatcgg cgtgaaaaac gccggagggt agcgactcgc ccaccacacc   229320
cattatcatg gtttcacagc ataagcggtc cacaaagaac ttcaacaggt cgttgaattg   229380
ctccgtctcc atacagatga agggccagac gcctttgagg ttctcggcct ggccgcagag   229440
cagcaacgga cgcgtcatct cgcctggagt gcgcagaggc acgcattcgc cgcgataacg   229500
acaggtcaca cgctgcagtt cgctgatgct gttgtcgtgc aggcgaaggt cgcagataat   229560
atgatccggt tgcgtggtta gcagcggcgt gcgcatttgc tcgccgtaga tggcctcgca   229620
gtgcaatagc ccgtgtcgtg caaaatcgtc cagactgtgc gccaggtagt aaagcacccc   229680
gcgatcgcgg tctagacacc acacggtttc gtaacgtcct agcagaagca ccagacgggc   229740
ctggctaggt ggctcaattt cctctacata cacgaaaaag tcgtcatcgt ccgagtcctc   229800
gtcctcagaa gaggaccgcg gcccgtgtac tctgggcaac acggtggtag agaactgcag   229860
gacgcccaga gactcgagcg actcttcgca gcagatgagc tgaccccagg gcgtttctgg   229920
cccgtcggtg acagccgcgc tgccaaagat gtcctcaaac tctacaaaat ctagacgcca   229980
tccgggtggc gctgaaacgg gaaggctaat gttcatatca gcatagctac gaactaagtg   230040
gcggatgtcc tgccgcaagt cttggcagag aatgagcttt cgtaaaccct tgagggtcct   230100
ccgaacaacg gccccagacg cgtagcgata ggactggcgc atggtgccgc ggcgtggagc   230160
ggcacttggc agcctatttt atggagtttc ttcagtgacg tggcttgttc acgtcgttcg   230220
tgggctgcgg ttggcagctc cggtctgtaa accacccgaa aagactgaca tcgacgtcaa   230280
```

```
agacccacgt aatttggaac atgtgcgacc gcaaagtgcg tcagaataac acgtggcttt   230340
aggacataaa aagtaccgtg aggtccagac gtggtttttg tgattgacac ttacaccagg   230400
taagccaagg gacggtgaaa ctgtatgtga ggaacctggg tgcttagacg actaacgtgt   230460
aatgctttt acaggactgt tcgacaggtg atagtacctg taaggtgatg accacctcta    230520
caaataatca aaccttaaca caggtgagca acatgacaaa ccacaccta aacagcaccg    230580
aaatttatca gttgttcgag tacactcggc tcggagtatg gttgatgtgc atcgtgggca   230640
cgtttctgaa cgtgctggtg attaccacca tcctgtacta ccgtcgtaag aaaaaatctc   230700
cgagcgatac ttacatctgc aacctggctg tagccgatct gttgattgtc gtcggcctgc   230760
cgttttttct agaatatgcc aagcatcacc ccaaactcag ccgagaggtg gtttgttcgg   230820
gactcaatgc ttgtttctac atctgtcttt ttgccggcgt ttgttttctc atcaacctgt   230880
cgatggatcg ctactgcgtc atcgtctggg gtgtagaatt gaaccgcgtc cgaaataaca   230940
agcgggctac ctgttgggtg gtgattttt ggatactagc cgtgcttatg gggatgccac    231000
attacctgat gtacagccat accaacaacg agtgtgttgg tgaattcgct aacgagactt   231060
cgggttggtt ccccgtgttt ttgaatacca aagttaacat ttgcggctac ctggcgccca   231120
ttgcgctgat ggcgtacacg tacaaccgta tggtgcggtt tatcattaac tacgttggta   231180
aatggcacat gcagacgctc cacgttcttt tggttgtggt tgtgtctttt gccagttttt   231240
ggtttccttt caacctggcg ctatttttag aatccatccg tcttctggcg ggagtgtaca   231300
atgcacacact tcaaaacgtt attatcttct gtctatacgt cggtcagttt ttggcctacg   231360
ttcgcgcttg tctgaatcct gggatctaca tcctagtagg cactcaaatg aggaaggaca   231420
tgtggacaac cctaagggta ttcgcctgtt gctgcgtgaa gcaggagata ccttaccagg   231480
acattgatat tgagctacaa aaggacatac aaagaagggc caaaacacc aaacgtaccc    231540
attatgacag aaaacatgca cctatggagt ccggggagga ggaatttctg ttgtaattcg   231600
atcctctctc acgcgtccgc cgcacatcta tttttgctaa ttgcacgttt cttcgtggtc   231660
acgtcggctc gaagaggttg gtgtgaaaac gtcatctcgc cgacgtggtg aaccgctcat   231720
atagaccaaa ccgacgctg cctcagtctc tcggtgcgtg gaccagacgg cgtccatgca    231780
ccgagggcag aactggtgct accatgacgc cgacgacgac gaccgcggaa ctcacgacgg   231840
agtttgacta cgatgaagcc gcgactcctt gtgttttcac cgacgtgctt aatcagtcaa   231900
agccggtcac gttgtttctg tacggcgttg tctttatctt cggttccatc ggcaactttt   231960
tggtgatctt caccatcacc tggcgacgtc ggattcaatg ctccggcgat gtttacttta   232020
tcaacctcgc ggccgccgat ttgctttcg tttgtacact acctctgtgg atgcaatacc    232080
tcctagatca caactcccta gccagcgtgc cgtgtacgtt actcactgcc tgtttctacg   232140
tggctatgtt tgccagtttg tgttttatta cggagattgc actcgatcgc tactacgcta   232200
ttgtttacat gagatatcgg cctgtaaaac aggcctgcct tttcagtatt ttttggtgga   232260
tctttgccgt gatcatcgcc attccacact ttatggtggt gaccaaaaaa aacaatcaat   232320
gtatgaccga ctacgactac ttagaggtca gttacccgat catcctcaac gtagaactca   232380
tgctcggtgc tttcgtgatc ccgctcagtg tcatcagcta ctgctactac cgcatttcca   232440
gaatcgttgc ggtgtctcag tcacgccaca aggtcgcat tgtacgggta cttatagcgg    232500
tcgtgcttgt ctttatcatc ttttggctgc cgtaccacct gacgctgttt gtggacacgt   232560
tgaaactgct caaatggatc tccagcagct gcgagttcga aaaatcactc aagcgcgcgc   232620
```

```
tcatcttgac cgagtcactc gccttttgtc actgttgtct caatccgctg ctgtacgtct  232680
tcgtgggcac caagtttcgg caagaactgc actgtctgct ggccgagttt cgccagcgac  232740
tcttttcccg cgatgtatcc tggtaccaca gcatgagctt ttcgcgtcgg agctcgccga  232800
gccgaagaga gacgtcttcc gacacgctgt ccgacgaggt gtgtcgcgtc tcacaaatta  232860
taccgtaata aaaagcgct acctcggcct tttcatacaa accccgtgtc cgccccttt  232920
ttccccgtgc ccgatataca cgatattaaa cccacgacca tttccgttcg attagcgaac  232980
cggaaaagtt tatggggaaa aagacgtagg aaaggatcat gtagaaaaaa catgcggtgt  233040
ttccgatggt ggctctacag tgggtggtgg tggctcacgt ttggatgtgc tcggaccgtg  233100
acggtgggtt tcgtcgcgcc cacggtccgg gcacaatcaa ccgtggtccg ctctgagccg  233160
gctccgccgt cggaaacccg acgagacaac aatgacacgt cttacttcag cggcacctct  233220
ttccattctt ccgtgtcccc tgccacctca gtggaccgtc aatttcgacg gaccacgtac  233280
gaccgttggg acgtcgacg ttggctgcgc acccgctacg ggaacgccag cgcctgcgtg  233340
acgggcaccc aatggagcac caactttttt ttctctcagt gtgagcacta ccctagtttc  233400
gtgaaactca acggggtgca gcgctggaca cctgttcgga gacctatggg cgaggttgcc  233460
tactacgggg gttgttgtat ggtggcgggg ggtaatcgtg cgtatgtgat actcgtgagc  233520
ggttacggga ccgccagcta cggcaacgct ttacgcgtgg attttgggcg cggcaactgc  233580
acggcgccga aacgcaccta ccctcggcgc ctggaactgc acgatggccg cacagaccct  233640
agccgttgcg atccctacca agtgtatttc tacggtctgc agtgtcctga gcaactggtt  233700
atcaccgccc acgcggcgt gggtatgcgc cgctgtccta ccggctctcg tcccaccccg  233760
tcccggcccc accggcatga cttggagaac gagctacatg gtctgtgtgt ggatcttctg  233820
gtgtgcgtcc ttttattagc tctgctgctg ttggagctcg ttcccatgga agccgtgcgt  233880
cacccgctgc ttttctggcg acgcgtggcg ttatcgtcgt ccacttccaa ggtggaccgc  233940
gccgtcaagc tgtgtcttcg gcgcatgctg ggtctgccgc cgccaccgtc agtcgcacca  234000
cctggggaaa agaaggagct accggctcag gcggccttgt cgccgccact gaccacctgg  234060
tcactaccgc cgtttccgtc cacgcggata cctgacagtc cgccgccacc gtaccagctt  234120
cgtcacgcca cgtcactagt gacggtaccc acgttgctgt tatatacgtc atccgacatc  234180
ggtgacacag cttcagaaac aacgtgtgtg gcgcacgcta cttatgggga acccccggag  234240
cccgctcgat cgacggctac ggttcaggaa tgtaccgttc ttaccgctcc aaattgcggc  234300
atcgtcaaca acgacggcgc ggtctctgaa ggccaagacc atggagatgc ggttcaccat  234360
agcctggatg tggtttccca gtgtgctgct gatactgggg ttgttgacgc ctccgagtaa  234420
cggctgcact gttgatgtcg gacgaaacat gtccattcga gaacagtgcc gccttcgaaa  234480
cggtgcgacg ttctccaagg gagacatcga aggtaacttc agtgggcccg tcgtcgtgga  234540
gttggactac gaagacatcg atattactgg cgaacggcag cgacttcggt tccacctcag  234600
cggactcggg tgtcctacaa gggagaaaat aagaaaagat aatgaaagcg acgtcaacgg  234660
tggaattcgc tgggctctat atatacaaac cggcgacgcc aagtacggta ttcgtaatca  234720
gcatttgagt atacgttaa tgtatcctgg ggaaaaaaat acacaacagc tgttgggttc  234780
tgatttcagt tgcgaacgtc accggagacc gtccacgccg ttgggaaaga acgccgaagt  234840
gcctcccgcg acccgcacgt cttctacata cagcgtcctc agcgcttttg tagtgtggat  234900
cggatccggc ctcaatatca tctggtggac cggcatcgtg cttctggcgg tggacgctct  234960
cggacttggc gagcgttggc tgaggttagc actgtcccac cgggacaaac atcacgcatc  235020
```

```
gcgaaccgcg gcgctccagt gtcaacgcga catgttactt cggcaacgtc gacgggctcg  235080
gcggctgcat gccgtttctg aaggcaaact gcaggaagag aagaaacgac agtctgtctc  235140
ggtctggaac gttgaggcgc gacccttccc gtccacacat cagctgattg tgctgccccc  235200
tcctgtagcg tcagctcctc ctgcagttcc ctcgcagccc cccgagtatt cgtctgtgtt  235260
tccgcctgta taaaaataaa gagacgggag gctgatcgcg gccttcagcg tctcatttgt  235320
ctttactctc gagtgcggtc ggtgtctcgt cggtgagacg aggccgccgc ccgacaagtt  235380
cgatctcatg tcgctcttgg agcgcgaaga gagttggcgt cgcgtagtcg actactcgca  235440
caacctgtgg tgtacgtgcg gtaactggca gagccacgtt gagattcagg acgaagagcc  235500
caactgcgag cagccggagc ccgcacactg gctggaatac gtggcggtcc agtggcaggc  235560
ccgggttcgc gattctcacg atcgctggtg tctctgcaac gcctggcgtg atcacgcttt  235620
gcgcggccgt tggggtacgg cgtattcctc gggttcctcg gcctcttcct ccggtttcgt  235680
cgccgagagc aagttcacct ggtggaaacg actgcgccac agtacccggc gctggttgtt  235740
tcgccgccgg cgagctcgat acactccatc taactgtggg gaaagtagca ctagcagcgg  235800
ccagagtagc ggtgacgaga gtaactgcag tctacgcacc cacggcgtgt acacacgggg  235860
tgaacaacac taatcgataa gtcgcgtgta ggcgactggc tacatcaacc ggatatctgc  235920
ggggatttaa aaagacgacc cgttgtcatc cggcttagag caaaccgtcc ttttatcatc  235980
ttccgtcgcc atggctatgt acacatccga atccgaacgc gactggcgtc gtgtaatcca  236040
cgactcgcac ggcctgtggt gcgactgcgg cgactggcga gagcacctct attgtgtgta  236100
cgacagccat tttcagcgac gacccacgac ccgagccgaa cggagggccg ccaattggcg  236160
gcgacagatg cggcggttac accgtctgtg gtgttttgt caggactgga agtgtcacgc  236220
gttatacgcc gagtgggacg gcaaagaatc cgacgacgag tcgtcggcgt cttcctcggg  236280
cgaagcgcca gagcaacagg tccccgcttg gaagaccgtg cgggccttct cgcgggccta  236340
ccaccaccgc attaaccggg gtctgcgggg cacgccccca ccgcgcaact gccgggata  236400 cgagcacgcc tccgagggct ggcggttttg cagtcgacgg gaacggcgag aggacgatct  236460
tcgcacgcgg gctgagccgg accgcgtggt gttccagtta gggggagtac ctcctcgtcg  236520
tcaccgagaa acttacgtgt aagaacacgg cgtgacaata aacaacatag cgtaaatccc  236580
cgtgtgatgt gtgtgattga cgttcggaa acatgtcccc atcatcagcg tcacaactga  236640
cgtgggttgg tcactgacgt gcaggatgtt gcgcgagtca gagaatcgca taagaacggg  236700
gtggtgagcg ggttcccaca ggagtctctg gcgcaaaagc accatgagcc tcaggttccc  236760
cgagagggcg ggttacgaga aactgggata ccgcccgcat gccaaacgcg tgcgggtgca  236820
tgacccgttg ggattgacgc ggtttatcat gaggcaactc atgatgtacc cgctggtgtt  236880
gccgttcacc tttccgtttt acgtgccgcg gtcctagcac gtcagtggtg atgctgataa  236940
ttgcaacatg gccatgacg aaccgcttg ggacgaacgt caataccacg tcaaaccacc  237000
gtgacttggc tgaacgttga aacataaagc caaagcgccg tcggcacttg gcttcagagc  237060
agcgcctcgg ggcgatgcga cggcgatgaa cttagagcaa ctcatcaacg tccttggtct  237120
gctcgtctgg attgccgctc gtgctgtcag ccgcgttggt ccgcatggct ccggactcgt  237180
ttatcgtgag cttcatgatt tctacgggta tctgcagctg gaccttctgg gaccagtggt  237240
ggcggggaat cgctcagtcc ggacctgaa agagcaggcg gaccgagcca gagggacctt  237300
cgttcggcgt tcaggcctta atactagcta catcttacct gtcggcggcc tgtctggggg  237360
```

```
ctccggtacc ttacccgtcg gcctgtatcg tcccgaagaa gaggtgttcc tcctcttgaa   237420
ccgctgccat gggccactgt caacgccgaa aaatgcttgt ctggctgagg tcggtgtcgc   237480
taatgccact ttttttgtctc gcttcaatgt cggtgatttt cacggagcgt catgggaaaa   237540
cggtaccgct cccgatggag agcccggggt atgctgaaat tcctcttaag attccgtaaa   237600
cgacgttgtc cagtcgttgt gccgcgattc gtacggttca tcgtctacgt cgttttgttc   237660
accgtcgctg tgcaacgcgt gaaacaagag cgtgatgcgc accttcggcg gtatgaagaa   237720
cggttacgga aaaccgcgc acggcgtcgg cagtcttttc cgtgacttgg ggcgatgggt   237780
ccgagctgcg gtatgggtca cggcggcgtg tgttttattg acgaagatgc cgatgtgtga   237840
ctaaaaacgt cccagcccta gagcgatgtg tttcaataaa aattatgtcg tatcatagta   237900
tgcgtgtcct ggttttttcat ttttggatgt atttgtgaca taaaaggcga tagaatgtgg   237960
ggacgaaaca tatccagata cacagttttg ttattcgaac aaaacccgtg tgatgcagaa   238020
aacagtactg caggatgaaa gtcccatggg gggggggggg cagacagtag tcgttttttgc   238080 cgctgggcgt acgctatgct tgtatttatg actataatat gtgcactcgt gtgtcgatgt   238140
tcctattggg aagggtgtca atgtaggagg tataaagaat ggtgggatgc ggagaggcat   238200
cgctagacac aggttgatcg ctgtgctagc cccacctgat cagcgtcatg ggtaaagcgg   238260
tgattaagcg tgaaaacacc gtaagggggg ggggcagac aggaagcttg gtggcagtgg   238320
ccgttagatg cattacgtgt ctgtattggt acatttgcaa accgtcgggt gtggcggtat   238380
agtttagcga tgattatatt atgtatgtgc cgtatagaat ggcctaaaac attgtaacac   238440
gaaacgttac aatgatggga aagatgccga taaaaacac ataaaaggca tatacacgaa   238500
ttactagtta cacgtttgtc tatgtgcgag tttaaggacg cttgtataat gcgtatgacg   238560
gcaaacggcc gcggaaacga tggggggggg gggtagtaac tgtattaatt atacgtcttg   238620
cagtacacgg tattgtgtgc tggtgcgcgt attacgacac gaacggcata gcgctataac   238680
cgggtgtatg gtatttatat gtgcgtctag catccttgcg agattctgaa agtcttcttg   238740
taagcgtaat taaacggtg tatgttctgc gtaaagtgca ttcaaacaac gtaacagtat   238800
gggatgaatg ccaataaata acatataaaa gcgagaagta tacatataag ggttgctaga   238860
cacaggtttg tttctgtgct agcccaatgg cacttgtaca atccatgcaa gcaaaaaag   238920 gatgcgaaac caacatcgtg gggtggggg ggggtaaaag caatgttaat cattggtctc   238980
gcggtgcaag ttgctgcgtt ttacgtgtat tgttacacgg gttgcgtatc ggtataatcg   239040
gatgtgtgtt actcattcgt ggcgttgtta tagtattgtg aaaagaatt ctcgtaagca   239100 tgttgacaac tgcaaaataa aaccatttta ttgagcattg taatggtagt gtgtcgctac   239160
attagaaaac gtgacgcgtc gcatgtcgcg gcacaatctg gcagcggggt cggggtaggg   239220
tacggtggga ggcatgtaca cagatggaac aaaagcagaa gtaacgtgag acggagcata   239280
tagtccagta tccagcggtt cctgagtagc accacccatc aactgaatgc cctcatgagt   239340
aaaagtctgc gggcggcagc ccttggggac cgttggcatg gacgatcga tctccaaacc   239400 acagcgtaac acggtttct tccaacgtcg ttgatacacg tcgttttttac ggttactccc   239460 cagaacccag aaagtctcgt ccaagtcgta ccaggagtct tccccaggga gacgtggcgg   239520
tttccaatcc tcatcgtccc gtcgcaaagc acgtcccaaa ctggcttggg gagtcaacgg   239580
tggttctgtg ggtcgggtgt agcgcgagtg ttttccgttc atgagcgatt cgtcctcctt   239640
gcctttaggc ttttttggcct ttttgtgtat catctggccg ccggcctcca taaccaccgt   239700
ggccaagtcc agtcccagag cttgagcgtc ggcgcggcgt cgggcgtctt gcaggtagtc   239760
```

```
ttccacattt gcacagatgg ccgggtgttt ggtggctagg gtgaggacct cagcctcgcc    239820
gcggcccgga cgtagcaaaa aagctaactg cccgtgcggc tcgcgcgccc acagcgcggc    239880
gcgcgggtgc aggtgcagcg cgtcccagcg cggccgctcc cactgctcgc ggtccagctc    239940
gggcagcagc cgccgcgcgg cctcggcggc gggcgccgac tcgcgcccca cgcgcagcgc    240000
gcccaacacg cccgcgcgca gaaagtgcga cagctccgcc gccagcgggt acacgtgccc    240060
gtccagcggg cagtacccga acacggcgcc cagctcgtcc agcaccacca ccagcatggc    240120
gcgcggcacg gtccccgacg ccgccggacc cgccatcgcc gtcggaccca ccatcaccgt    240180
cggcgccgcc gctgctgccg ctgccgcatc cgttccgacc accgcgtgcg cgtccgcgtt    240240
tggcacgcaa atcgcgctcc cgccggcggc gccgtacggc tgcggaggta aagtcacagc    240300 agacccacg gctcccgcca tcgcgcacg cgcgtcccg ccggcggcct ccgtctccgt    240360
gccgctcgcc cccggcagca acgtcgtccc cgtcgccatc gccgtcgtcc ccgccgtcat    240420
cgtcgtcgtc gtccccgccg tcgtccctgt cgccggccct gccgcgcagc gcagccaccg    240480
cgacggcagc accgcgccca gcgccagcca gccgcagcac agacgctggt tcaggtgccg    240540
acgcacggcc gtcagcagcg acgcggggtg cggcgccgac gcgaacggct cgtactgcgc    240600
cagctcctgc cacgcgccca gcagcaccat cggctgcagt cgcctgcccg cgtctgcag    240660 cgccaccgtc gtgccggccc accgccggcg cagctcccgt ccgagcgccg tcgcctcctc    240720
ggcgcgcagc aacgtctggc gaagcgccgg ctgaggcagc agcgtcgcgc gcggggtgcc    240780
cacgcccagc cggttgcagc ggtacaggcg caccacctcg cccgcgccgt gccgaaacca    240840
ctcgtccgcg tcgcgcgccg ccaggatcag cgtgttgttc gccaggtcgt acacgaacac    240900
gcggaacccg gcgcccagcg ccaggtacag tccgtcctgc gcgcacagac cctcgggatg    240960
gccggccttg tcgcccaccg tcgggtcggc gcgggggtcc acctcgtgca ccacggtcgc    241020
caccagcacg atccacgcgt cccgcggcga cagctgacgc aggtccgtgg cgcccacgcc    241080
gttcatctgg ctgcgcggcg tcactcgcgc gtagaatccg tacggccgtc cgagcggcag    241140
cagcgtgccc gcgtcgcgct gcgaccactt gcgcatggcg cggccgtgc tgttggccaa    241200 aaacgcggcg cgccacacgg cgcccatggc ctggtattcc agctccgtca cgcctggcg    241260 ctccaccgga atctgagaca gcagcaagcg ctccgggccg tgccaaaagg tgctgttgtt    241320
gccgctaccc ggaggggcgc ccggcggccc gcggggttct acccgtgga cggcgtgggc    241380 cggcgtcgcc gtacccgcag tactcgtact agtccccgct gttgacgtcg cttccaaaga    241440
agaagaacga gaggaaccaa cccccgaagg ccctccggct ccgcggccgc gaccgagggg    241500 cgggggggcgc ggcgacatgc cgttgcgctg ggccatggcc gccggacgcc tccgacgtcc    241560
actctgtata tataggaagc aaacccgcgt cagcgaccac gccgtttaca cacgcggacg    241620
cctccgtcgc ccgtgtgccg cgggcgacac gcacctggct tttataggca gcgacgtgca    241680
cggcgcttgc tggcgccgcc ttgccgccgc gcagtctgga aggccgtgaa aaaaccgaaa    241740
gaagatgcgc gacaagccac caacaacggg ccgccgagcg cgcgcacacc taggtggacg    241800
cctgacctcc attccgggcc gtgtgctggg tccccgaggg gcgggggggt gttttcatcg    241860 gggggggtgaa atgtgggaat ttgggaagtt ggcggtggcg gggacggcg acggcgaata    241920 aaagcgccgt gcggcgcgca cggcgaaacc cagacgcgcg tgtgtcttgc gtctcttcca    241980
gtcgcgcgtt tgtcttgcgt gtctttgagt ccccggggaa aagaggaagc ggtcccgagg    242040
ggacggcggc gcgactccct ggggacgcga agatcggacg cggaaaagag gaagtccccg    242100
```

-continued

```
gggacggcca caggcggaaa aaaaaaacga ggaagccgca gcccagtctg ccgggaccgg    242160
caggcaggcg cacagacccg cgtcgaggac acacgcagaa gaagcgcccg cgccggggcg    242220 gggggggggga tcgcgggccc cggggcacac tgcttccatc tggccgcgcg cacacccgc    242280 cgacacaccc ctgacacacc cgcgacacac ccggcacacg cccgcgacac acccggcacg    242340
cgcccgccac acagccagcc gacacacccg cgacacaccc gccacaccca gccgcacccg    242400
gcacacaccc acccagccgc accccgcca caccccagacc gacgccggtg cgggaccggg    242460
ctccattccg ggccgtgtgc tgggtccccg aggggcgggg gggtgttttc atcggggggg    242520
tgaaatgtgg gaatttggga agttggcggt ggcgggggac ggcgacgcg aataaaagcg    242580 ccgtgcggcg cgcacggcga aacccagacg cgcgtgtgtc ttgcgtctct ttcagtcgcg    242640
cgtctgtctt gcgtgtcttt gagtcccgg ggaaaagagg aagcggtccc gaggggacgg    242700
cggcgcgact ccctggggac gcgaagatcg gacgcggaaa agaggaagtc cccggggacg    242760
gccacaggcg gaaaaaaaaa acgaggaagc cgcagcccag tctgccggga ccggcaggca    242820
ggcgcacaga cccgcgtcga ggacacacgc agaagaagcg cccgcgccgg ggcggggggg    242880
gggatcgcgg gccccggggc acactgcttc catctggccg cgcgcacacc ccgccgacac    242940 accccctgaca caccccgcgac acaccgcgca cacgcccgcg acacacccgg cacgcgcccg    243000
ccacacagcc agccgacaca cccgcgcacac cccgccaca cccagccgca cccggcacac    243060 acccaccccag ccgcaccccc gccacaccca gaccgacgcc ggtgcgggac cgggctccat    243120
tccgggccgt gtgctgggtc cccgaggggc ggggggggtgt tttcatcggg ggggtgaaat    243180
gtgggaattt gggaagttgg cggtggcggg ggacggcgac ggcgaataaa agcgccgtgc    243240
ggcgcgcacg gcgaaaccca gacgcgcgtg tgtcttgcgt ctctttcagt cgcgcgtctg    243300
tcttgcgtgt ctttgagtcc ccggggaaaa gaggaagcgg tcccgaggg acggcggcgc    243360 gactccctgg ggacgcgaag atcggacgcg gaaaagagga agtcccccggg gacggccaca    243420 ggcgggaaaaa aaaaacgagg aagccgcagc ccagtctgcc gggaccggca ggcaggcgca    243480
cagacccgcg tcgaggacac acgcagaaga gcgcccgcg ccggggcggg ggggggatc    243540 gcgggccccg gggcacactg cttccatctg gccgcgcgca caccccgccg acacaccccct    243600 gacacacccg cgacacaccc ggcacacgcc cgcgacacac ccggcacgcg cccgccacac    243660
agccagccga cacacccgcg acacacccgc cacacccagc cgcacccggc acacacccac    243720
ccagccgcac ccccgccaca cccagaccga cgccggtgcg ggaccgggct gagggggtg    243780 taagcgcctt gacgcgcggc gctatggcac tgcgtgccac ggtattggtt ggcgggacga    243840
ggctgagggg ggtttgcggg acgtaagcgc gacgccgagt ttgcggcgtg ctgtggcgcg    243900
ctcaaggcta gggacggggg ccgcgcgtag cttttcggcg gcgacgggga acaaaacagg    243960
cacgcacacg cagctcgctt cagcggtcgc cctatcggca ccgccgctat tctttattaa    244020
cgtcgttctc ccccgcttc tacacgcgga ccgctgcaga cggctatgct cagactgttt    244080
ctcttgacgg cgacatgtgt tgcgtctgt gcggcgcggc gacggccgca agcggacgac    244140
gccgcctgcc accacacgtg gcccacgcgc tgcgccggcc cgcgtcccgc gccgtcggct    244200
cacaacacgg cgctttcttc ctcgcacgcc atctccatcg cacaccgtgt gctgcattcg    244260
ccgtcgcctc cacgagagaa catccgccac agcatgcgct gtcgccgtcg cgccatggcc    244320
tcctcggctt gcacccccgt ttcgcacacc cagcctcggg ccgccaacca cagccgttcg    244380
aggatgacgt acgcgacgag cgagcccacc aattctccca cggcctcgcc cgccaagtca    244440
gac                                                                  244443
```

<210> SEQ ID NO 2
<211> LENGTH: 21
<212> TYPE: RNA
<213> ORGANISM: Artificial Sequence
<220> FEATURE:
<223> OTHER INFORMATION: siRNA

<400> SEQUENCE: 2
gcuacaagcu ggagaaugau u                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA

<400> SEQUENCE: 3
ucauucucca gcuuguagcu u                                              21

<210> SEQ ID NO 4
<211> LENGTH: 498
<212> TYPE: PRT
<213> ORGANISM: Artificial Sequence
<220> FEATURE:
<223> OTHER INFORMATION: HIVgag

<400> SEQUENCE: 4

Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Tyr Thr Leu Lys
            20                  25                  30

His Leu Val Trp Ala Ser Arg Glu Leu Asp Arg Phe Ala Leu Asn Pro
        35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240

-continued

Ser Thr Pro Gln Glu Gln Leu Gln Trp Met Thr Gly Asn Pro Pro Ile
            245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
            275                 280                 285

Pro Lys Glu Pro Phe Arg Asp Tyr Val Asp Arg Phe Phe Lys Ala Leu
            290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
            325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Ala Gln Gln Thr Asn Ile Met Met Gln Arg Gly Asn Phe Arg Gly
            370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
            405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
            435                 440                 445

Ser Arg Pro Glu Pro Thr Ala Pro Pro Ala Glu Leu Phe Gly Met Gly
            450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
            485                 490                 495

Ser Gln

<210> SEQ ID NO 5
<211> LENGTH: 498
<212> TYPE: PRT
<213> ORGANISM: Artificial Sequence
<220> FEATURE:
<223> OTHER INFORMATION: #3D6 p4

<400> SEQUENCE: 5

Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Asp Arg Phe Ala Leu Asn Pro
            35                  40                  45

Ser Leu Leu Glu Thr Thr Glu Gly Cys Gln Gln Ile Met Asn Gln Leu
            50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
            85                  90                  95

```
Thr Lys Glu Ala Leu Asp Lys Ile Glu Ile Gln Asn Lys Ser Lys
                100                 105                 110

Gln Lys Thr Gln Gln Ala Ala Asp Thr Gly Asp Ser Ser Lys Val
        115                 120                 125

Ser Gln Asn Tyr Pro Ile Ile Gln Asn Ala Gln Gly Gln Met Ile His
130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
                180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
210                 215                 220

Pro Gly Gln Ile Arg Glu Pro Arg Gly Ser Asp Ile Ala Gly Thr Thr
225                 230                 235                 240

Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
                260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
        290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Ala Gln Gln Thr Asn Ile Met Met Gln Arg Gly Asn Phe Arg Gly
370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
                420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Pro Ala Glu Leu Phe Gly Met Gly
450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln

<210> SEQ ID NO 6
```

<211> LENGTH: 498
<212> TYPE: PRT
<213> ORGANISM: Artificial Sequence
<220> FEATURE:
<223> OTHER INFORMATION: #3D6 p5

<400> SEQUENCE: 6

| Met | Ala | Ala | Arg | Ala | Ser | Ile | Leu | Ser | Gly | Gly | Lys | Leu | Asp | Ala | Trp |
|---|---|---|---|---|---|---|---|---|---|---|---|---|---|---|---|
| 1 | | | | 5 | | | | | 10 | | | | | 15 | |

| Glu | Lys | Ile | Arg | Leu | Arg | Pro | Gly | Gly | Lys | Lys | Lys | Tyr | Arg | Leu | Lys |
| | | | 20 | | | | | 25 | | | | | 30 | | |

| His | Leu | Val | Trp | Ala | Ser | Arg | Glu | Leu | Asp | Arg | Phe | Ala | Leu | Asn | Pro |
| | | | 35 | | | | | 40 | | | | | 45 | | |

| Ser | Leu | Leu | Glu | Thr | Thr | Glu | Gly | Cys | Gln | Gln | Ile | Met | Asn | Gln | Leu |
| | 50 | | | | | 55 | | | | | 60 | | | | |

| Gln | Pro | Ala | Val | Lys | Thr | Gly | Thr | Glu | Glu | Ile | Lys | Ser | Leu | Phe | Asn |
| 65 | | | | | 70 | | | | | 75 | | | | | 80 |

| Thr | Val | Ala | Thr | Leu | Tyr | Cys | Val | His | Gln | Arg | Ile | Asp | Val | Lys | Asp |
| | | | | 85 | | | | | 90 | | | | | 95 | |

| Thr | Lys | Glu | Ala | Leu | Asp | Lys | Ile | Glu | Glu | Ile | Gln | Asn | Lys | Ser | Lys |
| | | | 100 | | | | | 105 | | | | | 110 | | |

| Gln | Lys | Thr | Gln | Gln | Ala | Ala | Ala | Asp | Thr | Gly | Asp | Ser | Ser | Lys | Val |
| | | | 115 | | | | | 120 | | | | | 125 | | |

| Ser | Gln | Asn | Tyr | Pro | Ile | Ile | Gln | Asn | Ala | Gln | Gly | Gln | Met | Ile | His |
| | 130 | | | | | 135 | | | | | 140 | | | | |

| Gln | Asn | Leu | Ser | Pro | Arg | Thr | Leu | Asn | Ala | Trp | Val | Lys | Val | Ile | Glu |
| 145 | | | | | 150 | | | | | 155 | | | | | 160 |

| Glu | Lys | Ala | Phe | Ser | Pro | Glu | Val | Ile | Pro | Met | Phe | Ser | Ala | Leu | Ser |
| | | | | 165 | | | | | 170 | | | | | 175 | |

| Glu | Gly | Ala | Thr | Pro | Gln | Asp | Leu | Asn | Val | Met | Leu | Asn | Ile | Val | Gly |
| | | | 180 | | | | | 185 | | | | | 190 | | |

| Gly | His | Gln | Ala | Ala | Met | Gln | Met | Leu | Lys | Asp | Thr | Ile | Asn | Glu | Glu |
| | | | 195 | | | | | 200 | | | | | 205 | | |

| Ala | Ala | Glu | Trp | Asp | Arg | Leu | His | Pro | Val | Gln | Ala | Gly | Pro | Ile | Pro |
| 210 | | | | | 215 | | | | | 220 | | | | | |

| Pro | Gly | Gln | Ile | Arg | Glu | Pro | Arg | Gly | Ser | Asp | Ile | Ala | Gly | Thr | Thr |
| 225 | | | | | 230 | | | | | 235 | | | | | 240 |

| Ser | Thr | Pro | Gln | Glu | Gln | Leu | Gln | Trp | Met | Thr | Gly | Asn | Pro | Pro | Ile |
| | | | | 245 | | | | | 250 | | | | | 255 | |

| Pro | Val | Gly | Asn | Ile | Tyr | Lys | Arg | Trp | Ile | Ile | Leu | Gly | Leu | Asn | Lys |
| | | | 260 | | | | | 265 | | | | | 270 | | |

| Ile | Val | Arg | Met | Tyr | Ser | Pro | Val | Ser | Ile | Leu | Asp | Ile | Lys | Gln | Gly |
| | | | 275 | | | | | 280 | | | | | 285 | | |

| Pro | Lys | Glu | Pro | Phe | Arg | Asp | Tyr | Val | Asp | Arg | Phe | Phe | Lys | Ala | Leu |
| | 290 | | | | | 295 | | | | | 300 | | | | |

| Arg | Ala | Glu | Gln | Ala | Thr | Gln | Asp | Val | Lys | Gly | Trp | Met | Thr | Glu | Thr |
| 305 | | | | | 310 | | | | | 315 | | | | | 320 |

| Leu | Leu | Val | Gln | Asn | Ala | Asn | Pro | Asp | Cys | Lys | Ser | Ile | Leu | Lys | Ala |
| | | | | 325 | | | | | 330 | | | | | 335 | |

| Leu | Gly | Ser | Gly | Ala | Thr | Leu | Glu | Glu | Met | Met | Thr | Ala | Cys | Gln | Gly |
| | | | 340 | | | | | 345 | | | | | 350 | | |

| Val | Gly | Gly | Pro | Gly | His | Lys | Ala | Arg | Val | Leu | Ala | Glu | Ala | Met | Ser |
| | | | 355 | | | | | 360 | | | | | 365 | | |

| Gln | Ala | Gln | Gln | Thr | Asn | Ile | Met | Met | Gln | Arg | Gly | Asn | Phe | Arg | Gly |
| | 370 | | | | | 375 | | | | | 380 | | | | |

```
Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln

<210> SEQ ID NO 7
<211> LENGTH: 498
<212> TYPE: PRT
<213> ORGANISM: Artificial Sequence
<220> FEATURE:
<223> OTHER INFORMATION: #3D6 p6

<400> SEQUENCE: 7

Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Tyr Arg Leu Lys
            20                  25                  30

His Leu Val Trp Ala Ser Arg Glu Leu Asp Arg Phe Ala Leu Asn Pro
        35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240
```

-continued

```
Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
    290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Gln Gln Thr Asn Ile Met Met Gln Arg Gly Asn Phe Arg Gly
    370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln
```

HUMAN CYTOMEGALOVIRUS COMPRISING EXOGENOUS ANTIGENS

CROSS REFERENCE TO RELATED APPLICATIONS

The present application is a national phase entry under 35 U.S.C. § 371 of International Application No. PCT/US2015/040807, filed Jul. 16, 2015 entitled "HUMAN CYTOMEGALOVIRUS COMPRISING EXOGENOUS ANTIGENS," which designated, among the various States, the United States of America, and claims priority to U.S. Provisional Patent Application No. 62/025,348, filed Jul. 16, 2014, entitled "HUMAN CYTOMEGALOVIRUS COMPRISING EXOGENOUS ANTIGENS," the entire disclosures of which are hereby incorporated by reference in their entirety.

REFERENCE TO SEQUENCE LISTING SUBMITTED ELECTRONICALLY

The content of the electronically submitted sequence listing, (file name: 41530060001_Sequence_Lising.txt; size: 336,021 bytes; and date of creation: Jan. 29, 2019), filed herewith, is incorporated herein by reference in its entirety.

FIELD

Generally, the field involves vaccine platforms. More specifically, the field involves recombinant human cytomegalovirus vectors expressing exogenous antigen.

BACKGROUND

Animal experiments have demonstrated that cytomegalovirus (CMV)-vectored vaccines are unique in that they: a) induce and maintain high frequencies of extralymphoid T cell responses (so called effector memory T cells); b) superinfect CMV-positive hosts; and c) maintain immunogenicity even when rendered deficient in host-to-host spread. Furthermore, experiments in animal models have shown that vaccine vectors derived from animal CMVs induce a protective immune response against infectious diseases and cancer (US 20080199493; US 20100142823; US 20130136768; and US 20140141038; all of which are incorporated by reference herein). Particularly striking is the finding that a rhesus CMV (RhCMV)-vectored simian immunodeficiency virus (SIV)-vaccine was able to not only prevent AIDS in non-human primates, but ultimately cure these animals from SIV (Hansen S G et al., Nature 502, 100-104 (2013); incorporated by reference herein).

It is important to use an attenuated strain in the development of a cytomegalovirus vaccine because an unattenuated strain could spread from host to host and potentially be pathologic at least in immunocompromised individuals. Previously, attenuated human CMV (HCMV) strains have failed to a) establish latent infection (Plotkin S A and Huang E S, *J Infect Dis* 152, 395-397 (1985); incorporated by reference herein); b) induce long-lasting immunity (Jacobson M A et al., *J Clin Virol* 35, 332-337 (2006); incorporated by reference herein); c) reinfect the significant proportion of the population that has been previously naturally infected with CMV (Heineman T C et al., *J Infect Dis* 193, 1350-1360 (2006); incorporated by reference herein); or d) produce persistent infections (WO2013/036465; incorporated by reference herein.) Furthermore, clinical strains of HCMV genomes are highly unstable in vitro when grown in fibroblasts, resulting in fibroblast adaptations such as deletion of UL131A.

The impact of such adaptations to tissue culture for the ability to perform vector functions in vivo is mostly unknown. In addition to the need for attenuations to be stable in vitro and in vivo, it is important that these vectors can be manufactured with reproducible results. The most stable attenuation strategy is gene deletion. However, this generally requires the generation of complementing cell lines which is difficult to achieve for primary cells used to grow cytomegalovirus.

SUMMARY

Disclosed herein are severely attenuated, spread-deficient (i.e., deficient in cell to cell spread) vectors derived from HCMV-TR3, which is a genetically modified version of the HCMV TR strain. The disclosed vectors establish and maintain persistent infections, induce and maintain effector memory T cells against heterologous antigens, and re-infect CMV-seropositive hosts. Said vectors comprise heterologous antigens such as non-CMV pathogen specific antigens or tumor antigens.

Specifically, TR3 was engineered to be ganciclovir-sensitive. In one example, this is due to the addition of an active UL97 gene (which was mutated in the original clinical isolate of TR3). TR3 was further engineered to include active US2, US3, US6, and US7 genes which were removed during BAC cloning of the original clinical isolate of TR3. Additional versions of TR3 include a deleterious (i.e., inactivating) mutation in the pp71-encoding UL82 gene—which can be termed TR3Δpp71 or, alternatively TR3ΔUL82 herein.

In further examples of the vectors, the expression of a gene encoding a heterologous antigen can be driven by the UL82 promoter or another viral promoter such as the UL7, UL38, UL45, or US13 promoter. In still further examples, multiple genes encoding heterologous antigens can be inserted in place of UL82 and another viral gene such as UL7, UL38, UL45, or US13 such that the viral gene promoter drives expression of the heterologous antigen gene.

Also disclosed herein is a method of producing an HCMV lacking a functional pp71 protein (encoded by the UL82 gene). The method involves infecting a cell with the HCMV lacking a functional pp71 protein, wherein the cell contains an siRNA that silences the DAXX gene. In other embodiments, the method involves infecting a cell with the HCMV lacking a functional pp71 protein, wherein expression of the DAXX gene in the cell is downregulated at the protein or RNA level by other techniques known in the art, for example by RNA interference (e.g., microRNA targeting and short hairpin RNA (shRNA) targeting), ribozyme cleavage, regulated expression by a conditional or inducible promoter, expression of DAXX binding proteins, or targeting DAXX or DAXX protein complexes for ubiquitination and degradation. Using these methods, the HCMV is produced efficiently without complementation. The cell can be any cell, including a human fibroblast.

BRIEF DESCRIPTION OF THE SEVERAL VIEWS OF THE DRAWINGS

Some of the drawings herein are better understood when presented in color, which is not available in patent application publications. However, Applicants consider the color drawings to be part of the original disclosure and reserve the right to present color versions of the drawings herein in later proceedings.

FIG. 1A is a map of the genome organization of the HCMV clones used in FIG. 1B. HCMV genomes are flanked by terminal repeats (TRL and TRS as indicated) and internal repeats (IRS) that separate the unique long (UL) and unique short (US) regions. The location of the BAC cassette in each construct is indicated by the region indicated as B. The US region of HCMV TR lacks US2-7 due to insertion of the BAC-cassette. TRΔ4 lacks the genes UL128-UL150 in addition to lacking US2-7. The UL131A gene is deficient in AD169 but repaired in AD169 BAD UL131A (Wang and Schenk, 2005 infra). Toledo has an inversion of the UL133-128 region with a deletion in UL128 (Murphy et al., 2003 infra). FIG. 1B is a plot summarizing the results of NOD/SCID/IL2Rγ-null (NSG) mice engrafted with human CD34+ stem cells and inoculated intraperitoneally with human fibroblasts infected with the indicated HCMV strains. Four weeks after infection, human hematopoietic stem cells were mobilized by granulocyte colony-stimulating factor (G-CSF) treatment, and the viral load was measured in the liver by quantitative PCR.

FIG. 4A is an image of a gel showing the following: HCMV-TR3 BAC was reconstituted on MRC-5 cells and then passaged 20 times in vitro on primary human fibroblasts. At passage 1, 5, 10, 15, and 20, viral DNA was extracted from infected cells and subjected to restriction digestion analysis and PCR sequencing of the UL128-131 region, a region that is frequently mutated as a result of multiple passaging (Dargan et al., 2010, infra). FIG. 4B is a plot showing the infectivity of TR3 in human umbilical vein endothelial cells (HUVECs) after multiple passages on MRC-5 cells. A purified stock of virus was made at passage 10 and used to infect HUVECs at MOI=0.5. At the same time, HUVECs were also infected with the HCMV lab adapted strain AD169 as control. Supernatants and cells were harvested at 5, 10, 15, and 20 days post infection (pi) and titrated by plaque assay on MRC-5 cells. The increase in titers over time indicates that HCMV TR3 was able to grow on HUVECs, consistent with an intact UL131A-128 region, whereas HCMV AD169 does not grow.

FIGS. 17a and 17b confirm the gag insert expression and homogeneity over several infectious cycles. FIG. 17a depicts a composite Western blot confirming the absence of pp71 protein expression in the ΔUL82(pp71) constructs and the presence of HIVgag(p24) expression. A positive control for HCMV expression (pp28) and a loading control to beta-Actin are included. FIG. 17b shows the sequence of the gag inserts (SEQ ID NO:4, SEQ ID NO:5, SEQ ID NO:6, and SEQ ID NO:7) are stable through these early passages with no polymorphisms detected by Sanger sequencing.

FIG. 18 is a plot showing an example of how alternative insertion sites and promoters can affect insert stability. In this example, the EF1a promoter driving the SIVgag insert has been placed into the UL36 locus. This construct shows the emergence of polymorphisms above the background level. In this case, the emergence of a G>T substitution generates a stop codon, thereby truncating the vectored antigen.

SEQUENCE LISTING

Figure 1A:
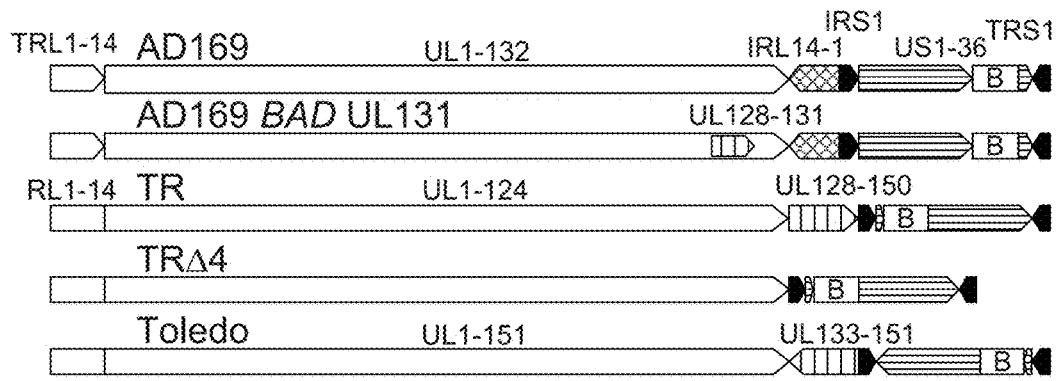
FIGS. 1A and 1B collectively show that HCMV TR is superior in establishing latency and in reactivating from latency (+G-CSF) compared to other HCMV strains.

SEQ ID NO: 1 is the nucleic acid sequence of HCMV TR3ΔUL82 BAC SEQ ID NO: 2 is the nucleic acid sequence of the sense strand of an siRNA that silences DAXX.

SEQ ID NO: 3 is the nucleic acid sequence of the antisense strand of an siRNA that silences DAXX.

SEQ ID NO: 4 is the amino acid sequence of the HIVgag insert.

SEQ ID NO: 5 is the amino acid sequence of the HIVgag insert from #3D6 at passage 4.

SEQ ID NO: 6 is the amino acid sequence of the HIVgag insert from #3D6 at passage 5.

SEQ ID NO: 7 is the amino acid sequence of the HIVgag insert from #3D6 at passage 6.

*Homo sapiens* DAXX mRNA includes a number of splice variants. Examples of the splice variants include the following GenBank entries: AB015051; CR457085; AF006041; NM_001254717.1; NM_001350; NM_001141969; NM_001141970; HQ436529; HQ436528; all of which are incorporated by reference herein.

DETAILED DESCRIPTION

Terms:

As used herein, the term "antigen" refers to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

As used herein, the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein, the term "small interfering RNA" ("siRNA") (also referred to in the art as "short interfering RNAs") refers to an RNA agent, preferably a double-stranded agent, of about 10-50 nucleotides in length (the term "nucleotides" including nucleotide analogs), preferably between about 15-25 nucleotides in length, e.g., about 20-24 or 21-23 nucleotides in length, more preferably about 15, 16, 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The terms "protein", "peptide", "polypeptide", and "amino acid sequence" are used interchangeably herein to refer to polymers of amino acid residues of any length. The polymer can be linear or branched, it may comprise modified amino acids or amino acid analogs, and it can be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein the term "recombinant" means a nucleotide or protein molecule that has been generated through the use of recombinant DNA technology, resulting in a nucleotide or protein molecule that does not occur in nature. One example or a recombinant nucleic acid is a nucleic acid encoding an HCMV vector that expresses a heterologous (non-CMV) antigen.

As used herein, the term "vector" encompasses any biological molecule that allows or facilitates the transfer of nucleic acid molecules from one environment to another, including a virus such as a CMV virus.

It should be understood that the proteins and the nucleic acids encoding them may differ from the exact sequences illustrated and described herein. Thus, the invention contemplates deletions, additions, truncations, and substitutions to the sequences shown, so long as the differing HCMV vectors are still capable of generating immune responses to the heterologous antigen while, a) inducing and maintaining high frequencies of extralymphoid effector memory T cell responses (so called effector memory T cells); b) reinfecting CMV-positive individuals; and c) maintaining immunogenicity while remaining spread-deficient (i.e., deficient in spread from one subject or host to another subject or host).

In this regard, substitutions may be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the activity of the vector are therefore, within the scope of the invention.

Alternatively, homologs can be expressed in terms of the percent homology relative to a described protein or nucleic acid sequence. Homologs can have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the HCMV vectors and/or heterologous antigens described herein.

Sequence identity or homology can be determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, *Proc. Natl. Acad. Sci. USA* 87, 2264-2268 (1990), modified as in Karlin & Altschul, *Proc. Natl. Acad. Sci. USA* 90, 5873-5877 (1993).

Another example of a mathematical algorithm used for comparison of sequences is the algorithm of Myers & Miller, *CABIOS* 4, 11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, *Proc. Natl. Acad. Sci. USA* 85, 2444-2448 (1988).

Other examples of methods used to compare biological sequences, including those using the BLAST algorithms are readily available at the US National Center for Biotechnology Information website.

HCMV Vectors

Disclosed herein are human cytomegalovirus (HCMV) vectors. The vectors are engineered to prevent viral spread from subject to subject (i.e., cell to cellspread), yet still persistently infect subjects who have previously been infected naturally with HCMV. The vectors generate a persistent immune response to the heterologous antigen and are sensitive to the drug, ganciclovir.

In specific examples, the vectors are derived from the HCMV TR strain and have been engineered to include an active UL97 gene (not present in the original TR clinical isolate) as well as an active US2, US3, US6, and US7 gene (removed from the original TR-BAC during cloning). One example of a vector of the TR strain with these changes is referred to as TR3 herein. TR3 comprises UL97 as well as US2, US3, US6, and US7 genes from the AD169 strain. In some embodiments, the vectors derived from the HCMV TR strain further comprise an active UL131A gene. TR3 comprises an intact UL131A gene.

Additional TR3 variants have deleterious or inactivating mutations in one or more other viral genes including UL82 (which encodes the pp71 protein), UL7, UL45, UL78, and/or US13. The deleterious or inactivating mutation can be any mutation that results in a lack of function of the protein encoded by the gene, including a mutation that involves a partial or entire deletion of the coding sequence and/or the promoter of the gene. Deleterious or inactivating mutations also include point mutations and frameshift mutations of the coding sequence and/or the promoter of the gene that result in a lack of function of the protein encoded by the gene.

TR3 variants can also express heterologous antigens such as pathogen specific antigens or tumor antigens. These heterologous antigens can be expressed by any promoter including an endogenous HCMV promoter, including the UL82, UL7, UL45, UL78, and/or US13 promoters or the HCMV immediate-early promoter. In related TR3 variants, the heterologous antigen replaces the viral UL82, UL7, UL45, UL78, and/or US13 genes. In still other related TR3 variants, a first heterologous antigen replaces the UL82 gene and a second heterologous antigen replaces the viral UL7, UL45, UL78, or US13 gene.

In other examples of TR3 variants, the heterologous antigens are provided with a promoter from a CMV other than HCMV (such as MCMV-IE or RhCMV-IE), with a promoter from a herpesvirus other than CMV, from a virus other than herpesvirus, or with a non-viral promoter such as EF1a.

In some embodiments, the promoter comprises an association of DNA sequences corresponding to the minimal promoter and upstream regulatory sequences. A minimal promoter includes a CAP site plus a TATA box. These are the minimum sequences for basic, unregulated of transcription. Upstream regulatory sequences include upstream elements such as enhancer sequences. A truncated promoter is a promoter from which some portion of the full-length promoter has been removed.

Also disclosed herein are nucleic acids encoding any of the HCMV vectors described herein. While exemplary nucleic acid sequences are provided, one of skill in the art can understand that due to degeneracy in the genetic code, many different nucleic acid sequences can encode identical protein sequences. Also disclosed are cells comprising the HCMV vectors and/or nucleic acid sequences encoding the HCMV vectors. Such cells can be mammalian or human cells, such as human fetal fibroblasts and other cells. In some examples, the cells can be engineered to express an siRNA that silences the expression of a particular gene such as the DAXX gene.

Additionally disclosed herein are methods of producing an attenuated HCMV vector in a cell (e.g., an isolated cell). The methods involve infecting a cell with the attenuated HCMV vector. The cell is transfected with or expresses an siRNA that silences a gene that would otherwise prevent the attenuated HCMV vector from growing in the cell. In one example, the HCMV vector comprises a deleterious or inactivating mutation such as a deletion in pp71, and the siRNA silences expression of the DAXX gene. Also disclosed is a method of producing an attenuated HCMV vector lacking a functional pp71 protein in a cell (e.g., an isolated cell), wherein expression of the DAXX gene in the cell is downregulated at the protein or RNA level by other techniques known in the art, for example by RNA interference (e.g., microRNA targeting and short hairpin RNA (shRNA) targeting), ribozyme cleavage, regulated expression by a conditional or inducible promoter, expression of DAXX binding proteins, or targeting DAXX or DAXX protein complexes for ubiquitination and degradation.

Site-directed mutations of the type described here can be introduced using synthetic oligonucleotides. These oligonucleotides contain nucleotide sequences flanking the desired mutation sites. A suitable method is disclosed in Morinaga et al., Biotechnology 2, 646-649 (1984). Another method of introducing mutations into enzyme-encoding nucleotide sequences is described in Nelson and Long, *Analytical Biochemistry* 180, 147-151 (1989). Site directed mutagenesis methods for BACs are described in Chadburn A et al., *Histopathology* 53, 513-524 (2008); Lee E et al., *Genomics* 73, 56-65 (2001); and Yu D et al., *Proc Nat Acad Sci USA* 97, 5978-5983 (2000); all of which are incorporated by reference herein.

RNA interference (RNAi) is a method of post transcriptional gene silencing induced by the direct introduction of double-stranded RNA (dsRNA) and has emerged as a useful tool to knock out expression of specific genes in a variety of organisms. RNAi is described by Fire et al., *Nature* 391, 806-811 (1998) (incorporated by reference herein). One such method involves the introduction of siRNA (small interfering RNA) into cells by transfection. Other systems, such as specific plasmid vector systems result in stable siRNA expression in a cell (for example, the pSUPER system—Brummelkamp T R et al., *Science* 296, 550-553 (2002); incorporated by reference herein). Methods of designing siRNAs that can efficiently silence any gene are known in the art.

Heterologous Antigens

A heterologous antigen can be derived from any protein that is not natively expressed in HCMV and includes pathogen specific antigens, tumor antigens, markers (such as fluorescent proteins or enzymes), growth factors, fusion proteins, or any other protein or fragment thereof to which an immune response can be generated (such as an MHC class I or class II restricted peptide).

The heterologous antigens in the HCMV vectors described herein can be pathogen specific antigens. For example, a protein from a viral pathogen can be used. Viral pathogens include, but are not limited to Adenovirus, coxsackievirus, hepatitis A virus, poliovirus, rhinovirus, Herpes simplex, type 1, Herpes simplex, type 2, Varicella-zoster virus, Epstein-Barr virus, Kaposi's sarcoma herpesvirus, Hepatitis B virus, Hepatitis C virus, yellow fever virus, dengue virus, West Nile virus, Human immunodeficiency virus (HIV), Influenza virus, Measles virus, Mumps virus, Parainfluenza virus, Respiratory syncytial virus, Human metapneumovirus, Human papillomavirus, Rabies virus, Rubella virus, Human bocavirus, and Parvovirus B19. In some embodiments, the heterologous antigens in the HCMV vectors can be HIV antigens, including gag, pol, env, rev, tat, and nef. Advantageously, the HIV antigens include but are not limited to the HIV antigens discussed in U.S. Pub. Nos. 2008/0199493 A1 and 2013/0136768 A1, both of which are incorporated by reference herein.

Alternatively, the heterologous antigen can be a protein from a bacterial pathogen. Bacterial pathogens include: *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnet Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholera*, and *Yersinia pestis*.

Alternatively, the heterologous antigen can be a protein from a parasitic organism. Parasitic organisms include but are not limited to protozoans that cause diseases such as Acanthamoeba, Babesiosis, Balantidiasis, Blastocystosis, Coccidioides, Dientamoebiasis, Amoebiasis, Giardia, Isosporiasis, Leishmaniasis, Primary amoebic meningoencephalitis (PAM), Malaria, Rhinosporidiosis, Toxoplasmosis, Parasitic pneumonia, Trichomoniasis, Sleeping sickness, and Chagas disease.

Alternatively, the heterologous antigen can be a protein from a helminth organism. Helminth organisms include but are not limited to: hookworms, roundworms, tapeworms, guinea worms, liver flukes, intestinal flukes, lung flukes, *Schistosomosa*, and whipworms.

Alternatively, the heterologous antigen can be a protein derived from a tumor.

Heterologous antigens can be codon optimized. Many viruses, including HIV and other lentiviruses, use a large number of rare codons and, by altering these codons to correspond to codons commonly used in the desired subject (for example, humans), enhanced expression of the antigens can be achieved. For example, rare codons used in HIV proteins can be mutated into those that appear frequently in highly expressed human genes (Andre et al., J Virol 72, 1497-1503, (1998). Additionally antigens can be consensus sequences or mosaic antigens containing sequence fragments from different strains of pathogens.

Immunogenic Compositions:

Disclosed herein are immunogenic compositions containing the disclosed recombinant HCMV vectors, and a pharmaceutically acceptable carrier or diluent. An immunogenic composition containing the recombinant HCMV vector elicits an immunological response. The response can, but need not be, protective. A vaccine composition elicits protective response, generally involving the development of immunological memory.

Methods of inducing an immunological response in a subject are also disclosed. Such methods involve administering to the subject an immunogenic or vaccine composition comprising the disclosed recombinant HCMV vectors and a pharmaceutically acceptable carrier or diluent. For purposes of this specification, the term "subject" includes all animals and humans.

The immunogenic or vaccine compositions can be administered via a parenteral route (intradermal, intramuscular, or subcutaneous). Other administration can be via a mucosal route, e.g., oral, nasal, genital, etc.

The immunogenic or vaccine compositions can be formulated and administered in accordance with standard techniques well known to those skilled in the pharmaceutical arts. The compositions can be administered alone, or can be co-administered or sequentially administered with other HCMV vectors or with other immunogenic, vaccine, or therapeutic compositions.

Examples of such compositions include liquid preparations such as preparations for injectable administration—for example, parenteral, subcutaneous, intradermal, intramuscular or intravenous administration—such as sterile suspensions or emulsions. In such compositions the HCMV vector is in admixture with a suitable carrier, diluent, or excipient such as sterile water, physiological saline, glucose or the like.

Immunogenic or vaccine compositions can contain an adjuvant. Alum (aluminum phosphate or aluminum hydroxide) is a typical adjuvant. Saponin and its purified component Quil A, Freund's complete adjuvant, Freund's incomplete adjuvant and other adjuvants are often used in research and veterinary applications.

The composition can be packaged in a single dosage form for injectable administration or other administration with the effective dosage and route of administration determined by the nature of the composition, by the nature of the expression product and other factors. The dosage of the disclosed HCMV vectors can be expressed in plaque forming units (pfu) including a dosage of more than $10^2$ pfu, more than $10^3$ pfu, more than $10^4$ pfu, more than $10^5$ pfu, more than $10^6$ pfu, or more than $10^2$ pfu.

EXAMPLES

The following examples are illustrative of disclosed methods. In light of this disclosure, those of skill in the art will recognize that variations of these examples and other examples of the disclosed method would be possible without undue experimentation.

Example 1—the HCMV-TR3 Vector Platform

Clinical use of effector memory T cell-inducing CMV vectors requires vectors that are genetically stable and maintain a persistent infection, but lack the ability to spread to immunocompromised subjects in which HCMV can be pathogenic. Previous attenuation strategies for HCMV variants that entered clinical trials relied on serial passaging of virus in fibroblasts (Plotkin S A et al., J Infect Dis 134, 470-475 (1976); incorporated by reference herein), recombination of attenuated with non-attenuated HCMV strains (Heineman J et al. 2006 supra) or generation of replication-deficient recombinant vectors (WO2013/036465; incorporated by reference herein). However, the resulting viruses either retained pathogenicity or lost beneficial features such as the ability to establish latent infections or secondary infections in subjects previously infected naturally with CMV.

Disclosed herein is an HCMV vector platform—HCMV-TR3—that overcomes these limitations. HCMV TR3 is a modified version of the molecular clone HCMV-TR (Murphy E et al., *Proc Nat/Acad Sci USA* 100 14976-14981 (2003); incorporated by reference herein). HCMV TR is superior to other HCMV strains in establishing latency and persistence in vivo. HCMV-TR is also superior to other clinical isolates of HCMV in vitro since it does not display the HCMV-typical fibroblast-adaptations upon multiple passages. TR3 was altered in order to make it ganciclovir-sensitive, to make it able to reinfect previously infected subjects, and to facilitate the recovery of CMV vector from the bacterial artificial chromosome (BAC) system.

Specifically, deletion of the UL82 gene (which encodes the pp71 protein) from TR3 results in the generation of a spread-deficient (i.e., defective in cell to cell spread) vector. However, previously viruses that lack pp71 expression were shown to require complementation for growth in vitro (Bresnahan, W. A., and T. E. Shenk. *Proc Nat/Acad Sci USA* 97:14506-11 (2000); incorporated by reference herein). UL82 virion protein activates expression of immediate early viral genes in human cytomegalovirus-infected cells, which in turn results in the risk that the virus will revert to a wild type with active pp71. As a result, a new method of growing HCMV vectors lacking pp71 was developed and described in detail below.

A non-human primate model further demonstrates that pp71-deleted HCMV-TR3 maintains the ability to induce and maintain effector memory T cell responses while tropism-deficient versions of HCMV-TR3 that recapitulate viral adaptations that commonly result from passage through fibroblasts do not.

Additionally, pp71-deleted HCMV-TR3 vectors maintain latent infections but lack the ability to reactivate in humanized mice.

Further, internal expression sites that can be used to insert and express heterologous antigens are disclosed. These can be used to produce HCMV vectors that include multiple heterologous antigens.

Figure 1B:
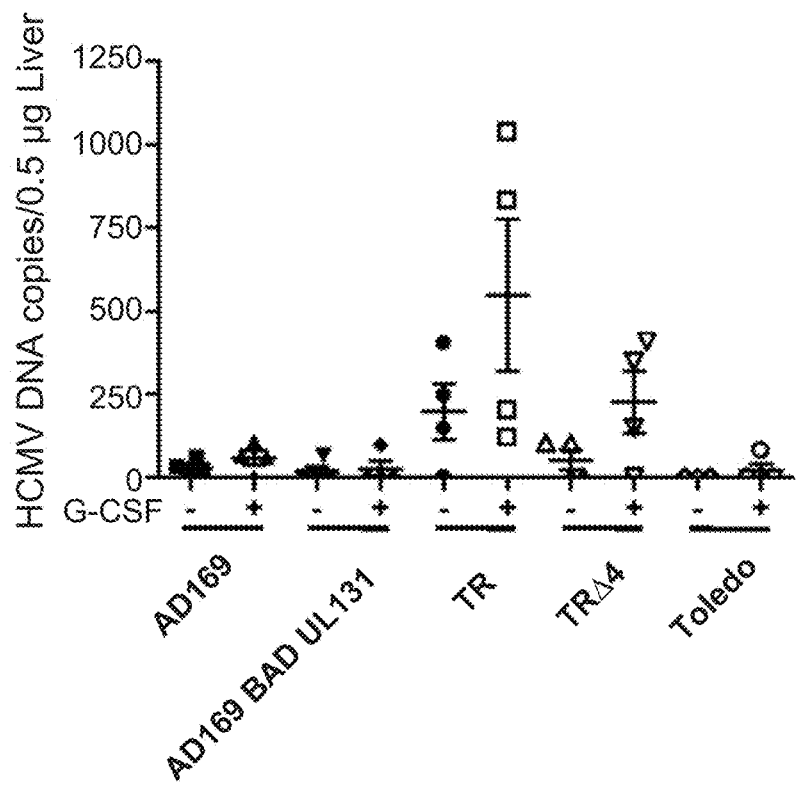

Example 2—HCMV-TR is Superior to Other HCMV Strains in Establishment of Latent Infection A humanized mouse model that permits studying HCMV latency and reactivation is described in Smith M S et al., *Cell Host Microbe* 8, 284-291 (2010) (incorporated by reference herein). This model was used to demonstrate that HCMV-TR is superior to other HCMV strains (AD169, Toledo) in establishing persistent infection. Persistent infection is important for the induction of effector memory T cells. The ability to generate a persistent infection is independent of the UL128-150 region, which is mutated in many HCMV strains including all strains previously used in clinical trials of HCMV vaccine (AD169, Towne and Toledo). The repair of UL131A in the AD169 strain does not restore the ability to establish latency, but the HCMV-TRΔ4 strain that lacks UL128-150 maintains the ability to establish latency (FIG. 1B). Note that these previous clinical trials did not involve HCMV comprising heterologous antigens. Genetic maps of these strains are shown in FIG. 1A.

Figure 3:
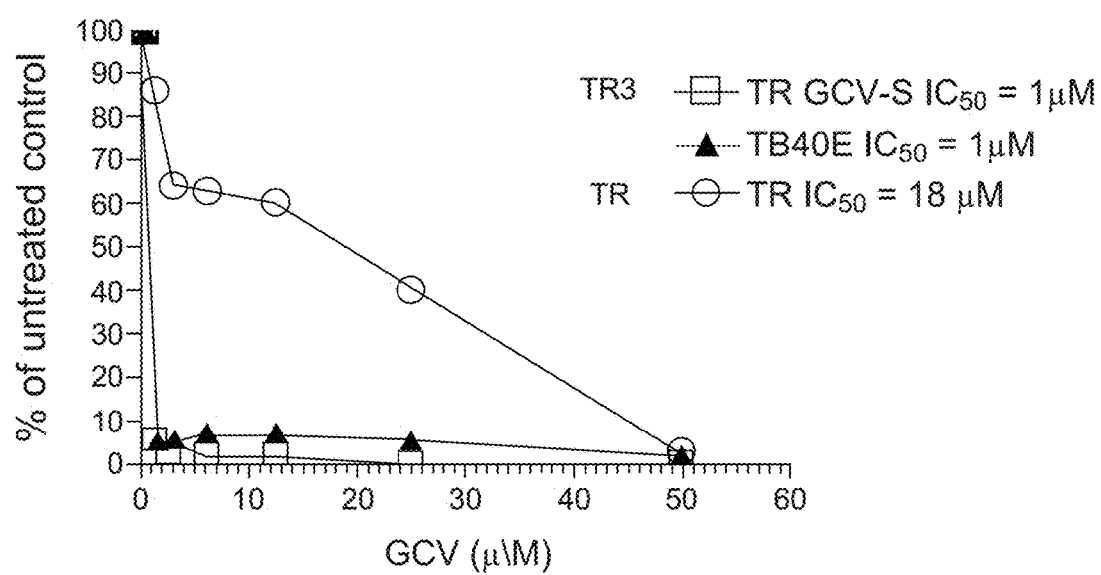
FIG. 3 is a plot showing that HCMV-TR3, but not HCMV-TR, is sensitive to ganciclovir (GCV). Growth-arrested human fetal fibroblast MRC-5 cells were infected with HCMV TR3, HCMV TB40E, and original HCMV TR (MOI of 1 PFU/cell) or mock infected. Where indicated, cells were treated with increasing concentrations of GCV 90 min after infection until an extensive viral cytopathic effect was observed in the untreated control (4 days post-infection). Supernatants of cell cultures were then assayed for infectivity by standard plaque reduction assay on MRC-5 cells. The number of plaques was plotted as a function of drug concentration, and the $IC_{50}$ was determined. Values are the means of two independent determinations.

Example 3—HCMV-TR3 is Sensitive to Ganciclovir and Includes the US2-7 Region Whereas the Original HCMV-TR does not HCMV TR was cloned by BAC recombineering from a viral isolate that is resistant to the antiviral drug ganciclovir (Smith I L et al., *J Infect Dis* 176, 69-77 (1997); incorporated by reference herein). ganciclovir resistance is not a desirable trait in a HCMV vector because treatment with ganciclovir would be important in the event of CMV-associated disease caused by HCMV-based vectors. Confirmation of ganciclovir resistance is shown in FIG. 3.

Figure 2:
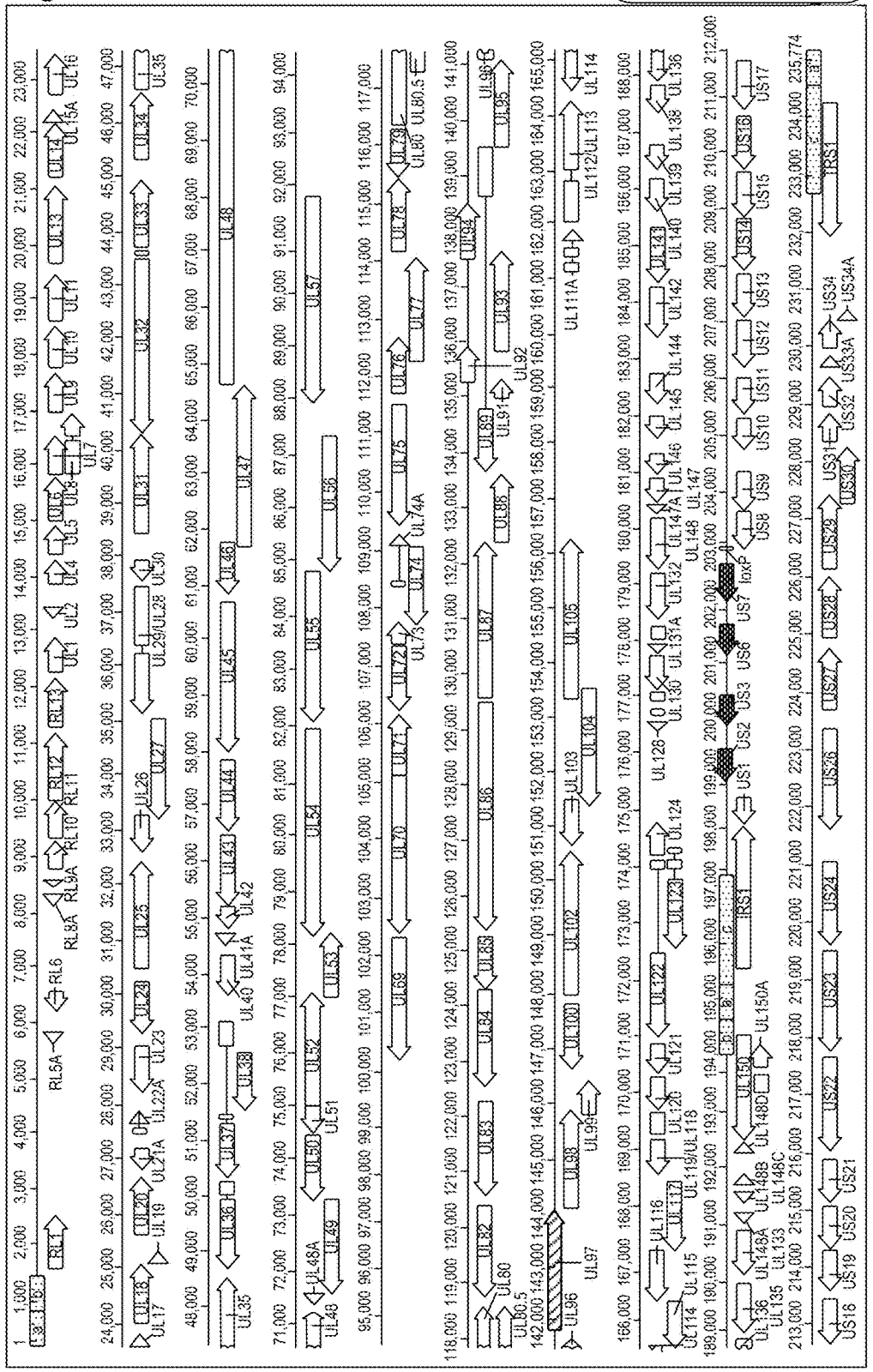
FIG. 2 is a graphical representation of the HCMV-TR3 genome showing alterations to the open reading frames (ORFs) present in the original HCMV TR strain. To confer ganciclovir sensitivity, UL97 of HCMV TR was replaced with that of HCMV AD169. The BAC cassette is flanked by loxP sites, and, after cre-mediated self-excision, a single loxP site remains in the genome. Since the HCMV-TR BAC lacks US2-7, the corresponding genes from HCMV AD169 were inserted. The terminal (ab and c'a) repeats and internal repeats (b'a'c) are shown.

An intact UL97 gene was inserted into HCMV TR (FIG. 2) to generate a ganciclovir-sensitive vector. The molecular clone of HCMV-TR was further modified. Insertion of a BAC cassette during the original cloning of HCMV TR resulted in a deletion of the US2-7 region (Murphy et al. 2003 supra). US2-7 was later determined to be a region that is essential for the reinfection of CMV-positive individuals (Hansen S G et al., *Science* 328, 102-106 (2010); incorporated by reference herein. A modified version of HCMV-TR was generated in which the US2-7 region of HCMV strain AD169 was inserted to modify the BAC cassette. This modification was made because in the original HCMV TR clone that BAC cassette could not be removed when virus is reconstituted by transfection of fibroblasts (Lauron E et al., *J Virol* 88, 403-416 (2014); incorporated by reference herein). HCMV-TR3, therefore also includes the US2-7 region of AD169 and a loxP site between US7 and US8 upon viral reconstitution as shown by full genome sequencing (FIG. 2).

Figure 4A:
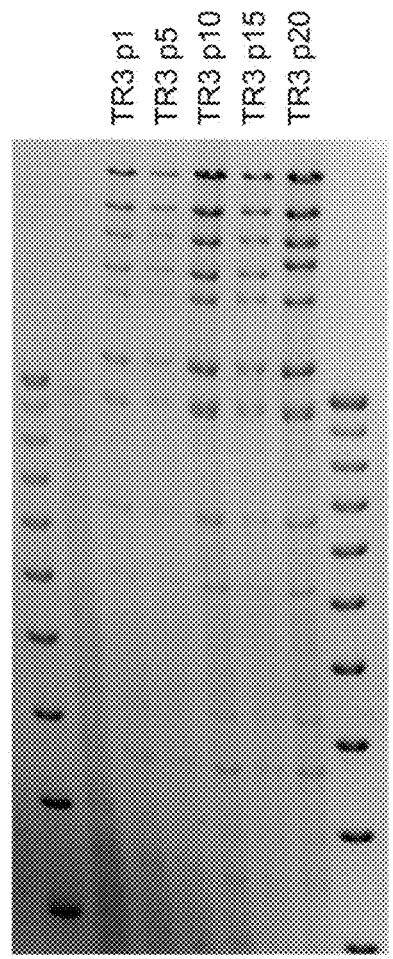
FIGS. 4A and 4B show that HCMV-TR3 surprisingly maintains the ability to infect endothelial cells and maintains genome stability after multiple passaging.
Figure 4B:
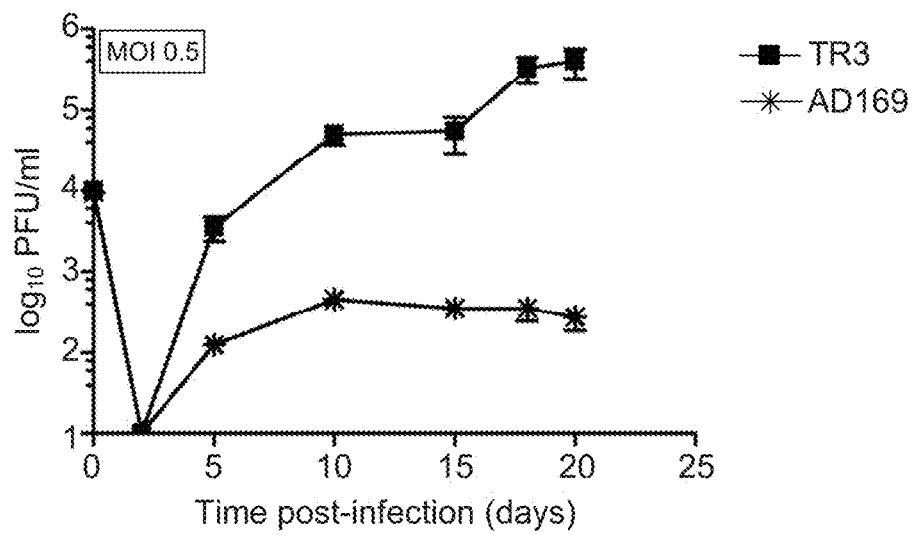

Example 4—HCMV-TR3 Displays Superior Genome Stability Upon Multiple Passages Through Fibroblasts Passaging of HCMV in fibroblasts results in the preferential selection of vectors with deleterious (i.e., inactivating) mutations in the UL128-131A region (Dargan D J et al., *J Gen Virol* 91, 1535-1546 (2010); incorporated by reference herein) and the RL13 gene (Stanton R J et al. *J Clin Invest* 120, 3191-208; (2010); incorporated by reference herein). However, passaging through fibroblasts results in the highest viral yields when producing vaccine. FIG. 4A shows that, surprisingly, the genome of HCMV-TR3 remains stable even after 20 passages in fibroblasts.

Figure 5:
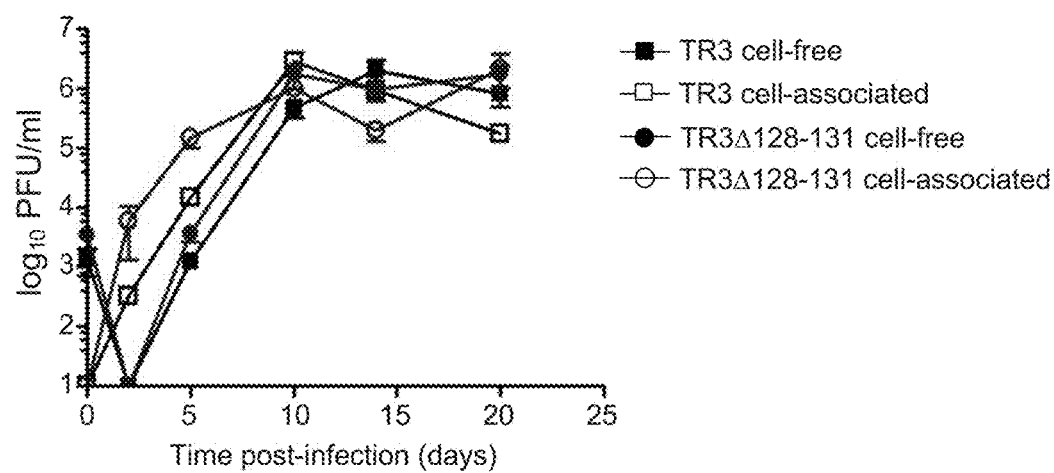
FIG. 5 is a plot showing that the presence of UL128-131 does not reduce the yield of cell-free HCMV-TR3. A multiple-step growth curve analysis was conducted using MRC-5 cells infected at MOI 0.01 with HCMV-TR3 and a strain identical to TR3 but with the UL128-131 deleted (HCMVΔUL128-131). Titers of infected cells and supernatants were measured at 2, 5, 10, 15 and 20 days post infection by standard plaque assay on MRC-5 cells.

Example 5—the Presence of UL128-131A does not Reduce the Yield of Cell Free HCMV-TR3 Unlike Other Strains of HCMV For vaccine manufacturing, cell supernatants, rather than cell pellets, are preferred to isolate vaccine vectors. In most HCMV strains, the yield of cell free virus from fibroblasts is drastically reduced when the genes UL131A, UL130 and UL128 are intact (Wang D and Shenk T, *J Virol* 79, 10330-10338 (2005); incorporated by reference herein). Surprisingly, removal of UL131A-128 does not affect the ratio of cell-free versus cell associated virus for HCMV-TR3 (FIG. 5).

Figure 6A:
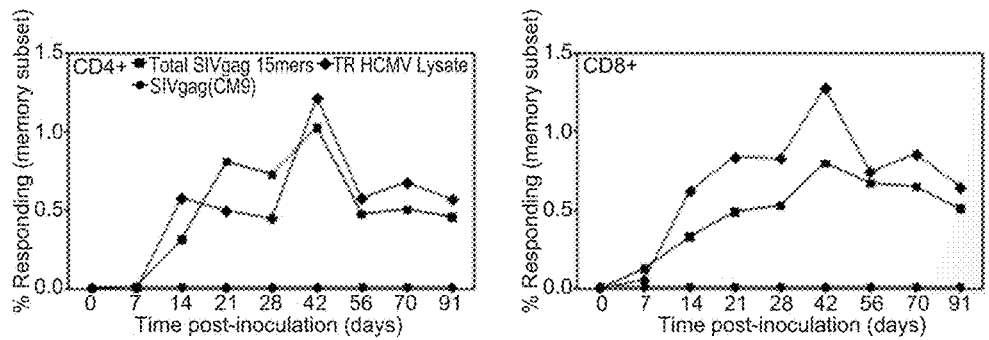
FIG. 6A is a set of two plots showing the results when SIVgag under control of the EF1α promoter was inserted into the HCMV-TR3 genome using BAC mutagenesis as described in Hansen S G et al., Nat Med 15, 293-299 (2009) (incorporated by reference herein). Rhesus macaques (RM) sero-positive for CMV were inoculated with $10^5$ plaque-forming units (PFU) of HCMV-TR expressing SIVgag. Shown is the % memory T cells in peripheral blood mononuclear cells (PMBC) responding to HCMV lysate (diamonds) or over-lapping SIVgag (squares) peptides. Note the absence of T cells to the canonical CM9 peptide (circles), indicating that the T cell response induced by HCMV is different from that of other vectors as described for RhCMV (Hansen et al., Science 2013 infra). The plot on the left shows $CD4^+$ T cell responses. The plot on the right shows $CD8^+$ T cell responses.
Figure 6B:
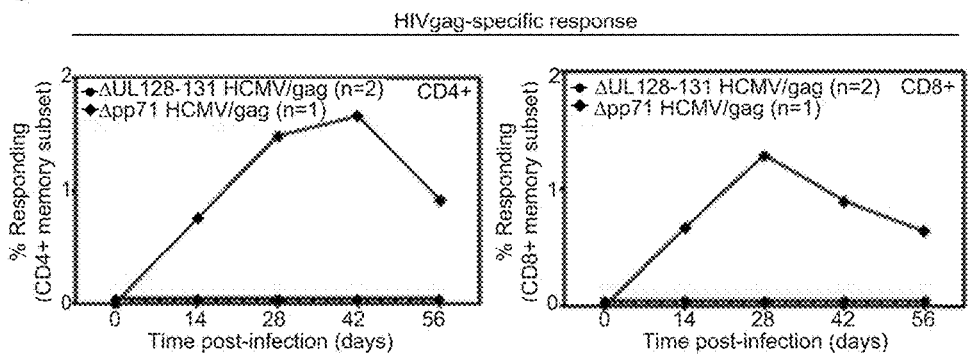
FIG. 6B is a set of two plots showing the HIVgag-specific T cell responses in RM inoculated with HCMV expressing HIVgag under control of the UL78 promoter with UL128-131 deleted (ΔUL128-131 HCMVgag) or HCMV expressing HIVgag under control of the UL82 promoter with UL128-131 intact (Δpp71 HCMVgag). When $10^6$ PFU of the ΔUL128-131 vector were inoculated into RM, no $CD4^+$ or $CD8^+$ T cell response to HIVgag was observed. In contrast, HIVgag-specific T cell responses were observed with Δpp71 HCMVgag vectors. The plot on the left show $CD4^+$ T cell responses, the plot on the right shows $CD8^+$ T cell responses.
Figure 11:
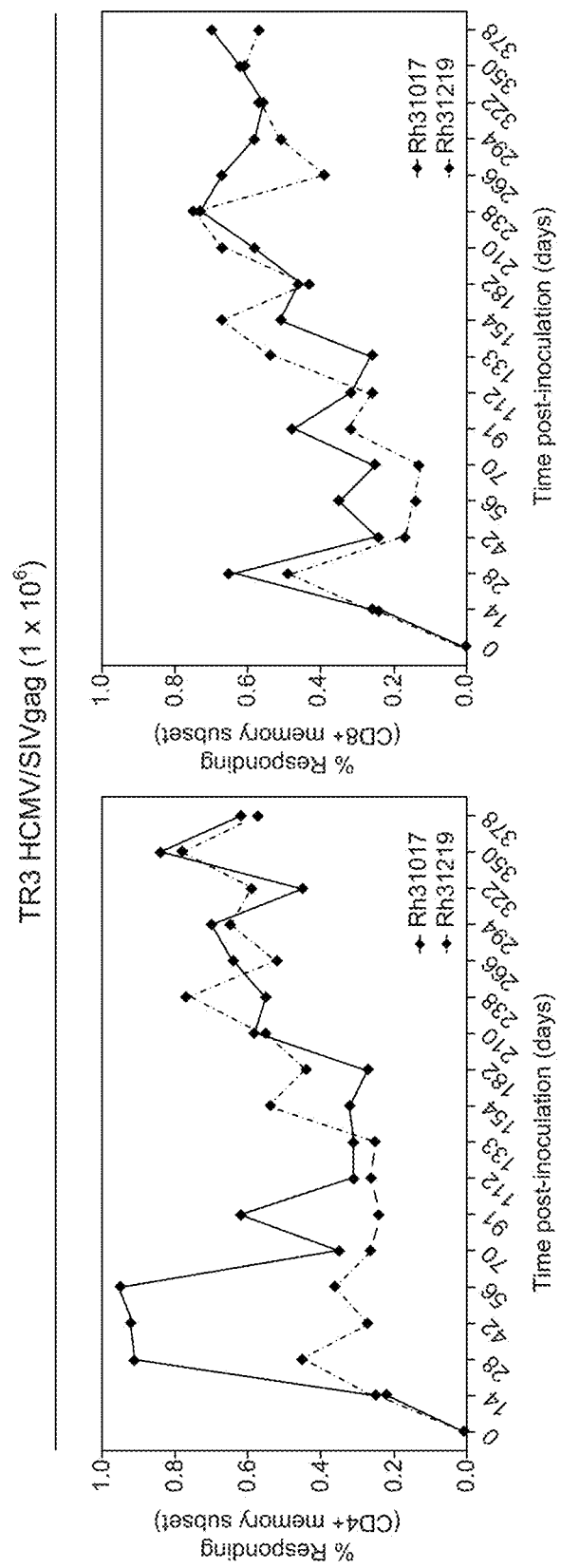
FIG. 11 is a set of two plots showing results with SIVgag under control of the EF1a promoter. SIVgag was inserted into the HCMV-TR3 genome using BAC mutagenesis as described in Hansen S G et al., Nat Med 15, 293-299 (2009) (incorporated by reference herein). Rhesus macaques (RM) sero-positive for CMV were inoculated with 10$^5$ plaque-forming units (PFU) of HCMV-TR3 expressing SIVgag. Shown is the % CD4+(left panel) and % CD8+(right panel) T cells in peripheral blood mononuclear cells (PMBC) responding to over-lapping SIVgag peptides. Note that the plot shows a stable immune response for two rhesus monkeys (Rh31017, Rh31219) beyond 378 days post inoculation.
Figure 12:
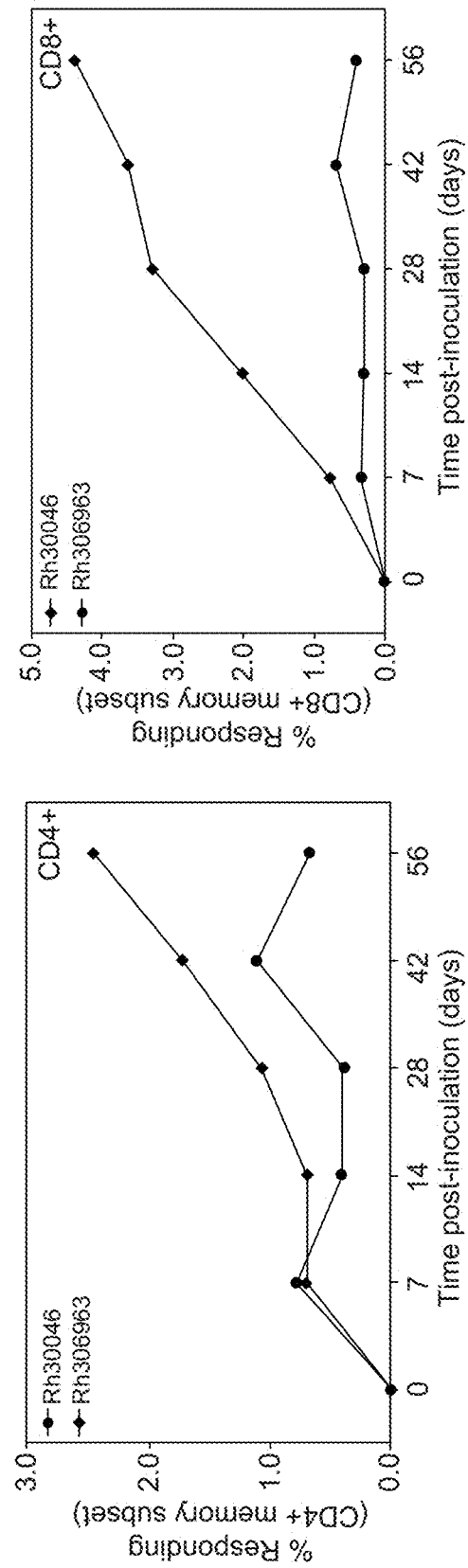
FIG. 12 plots the T cell immune response of two RM inoculated with the TR3ΔUL78 HCMV/HIVgag ΔUL128-130. Unlike constructs that included deletion of UL131A, limiting the deletion to UL128-130 results in sustained CD4+ and CD8+ T cell responses.

Example 6—HCMV-TR3 Induces Effector Memory T Cells in Monkeys Whereas HCMV Mutants Lacking the UL128-131 Region are Unable to do so HCMV-TR3 expressing the Gag-antigen of SIV is capable of inducing an effector memory T cell response against Gag in non-human primates (NHP; FIG. 6A). Importantly, this effector memory T cell response is maintained over time (FIG. 11). In contrast, HCMV-TR3 lacking the genes UL128-131, a gene region that is frequently mutated in HCMV strains attenuated by serial passaging in vitro, is unable to do so (FIG. 6B). This is also the first known demonstration of an HCMV vector inducing an immune response to a heterologous antigen in a non-human primate model. Further deletions in this genomic region demonstrated that viruses that lack UL128 and UL130 are able to elicit immune responses to heterologous antigens in vivo similar to the parental vectors (FIG. 12). Therefore, we conclude that UL131A is essential for infection by HCMV.

Example 7—Generation of Uncomplemented Pp71-Deleted HCMV-TR3 Using DAXX siRNA. A Method to Grow Attenuated Virus without Complementation or FKBP-Fusion A major limitation for the manufacturing of HCMV lacking essential genes, or genes that are required for optimal replication in vitro, is the need for complementation—that is, the exogenous expression of the deleted gene in a producer cell line. Producer cell lines are well known to be difficult to make and maintain, particularly in the context of GMP vaccine manufacturing.

One approach used in complementation is to fuse the essential gene to a degradation domain (such as FKBP), a strategy described in WO2013/036465 (incorporated by reference herein). While FKBP-fusions might be useful for the manufacturing of non-persistent vaccines that are replication deficient in vivo, in the case of the mutant HCMV described herein there is a risk that the degradation domain will be mutated and the attenuation will thus be lost, rendering the HCMV able to spread from host to host.

Figure 7A:
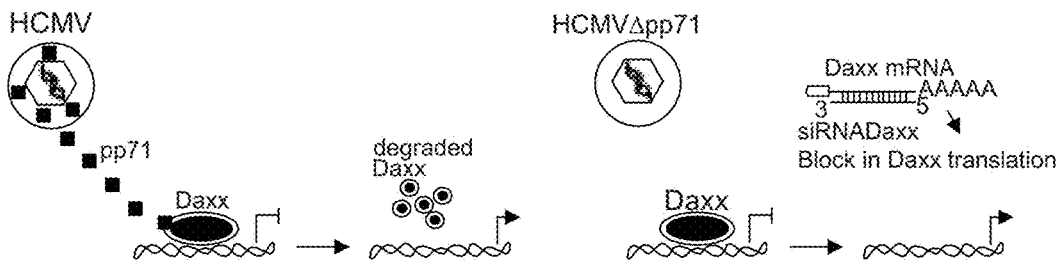
FIG. 7A is a drawing illustrating how, during infection with wildtype HCMV, the tegument protein pp71 degrades the cellular corepressor DAXX. In the absence of pp71, DAXX represses viral gene expression and thus lytic replication. However, viral gene expression can proceed normally even in the absence of pp71 when DAXX mRNA is eliminated by gene knockdown with DAXX-specific siRNA.
Figure 7B:
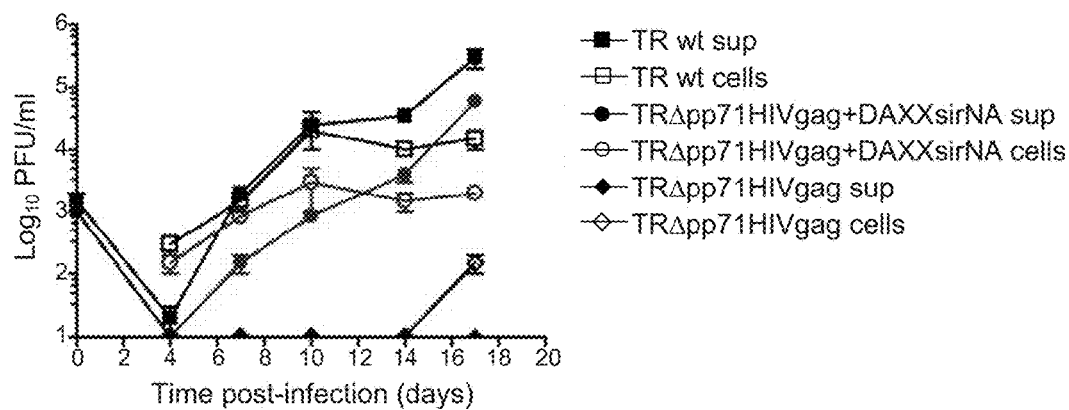
FIG. 7B is a plot of MRC-5 cells transfected with DAXX-specific siRNA and infected 24 hours (h) post-transfection with TR3 and TR3Δpp71HIVgag at MOI=0.05. At the indicated times post-infection, cells and supernatants were harvested separately and titered on complementing cells expressing pp71.
Figure 13:
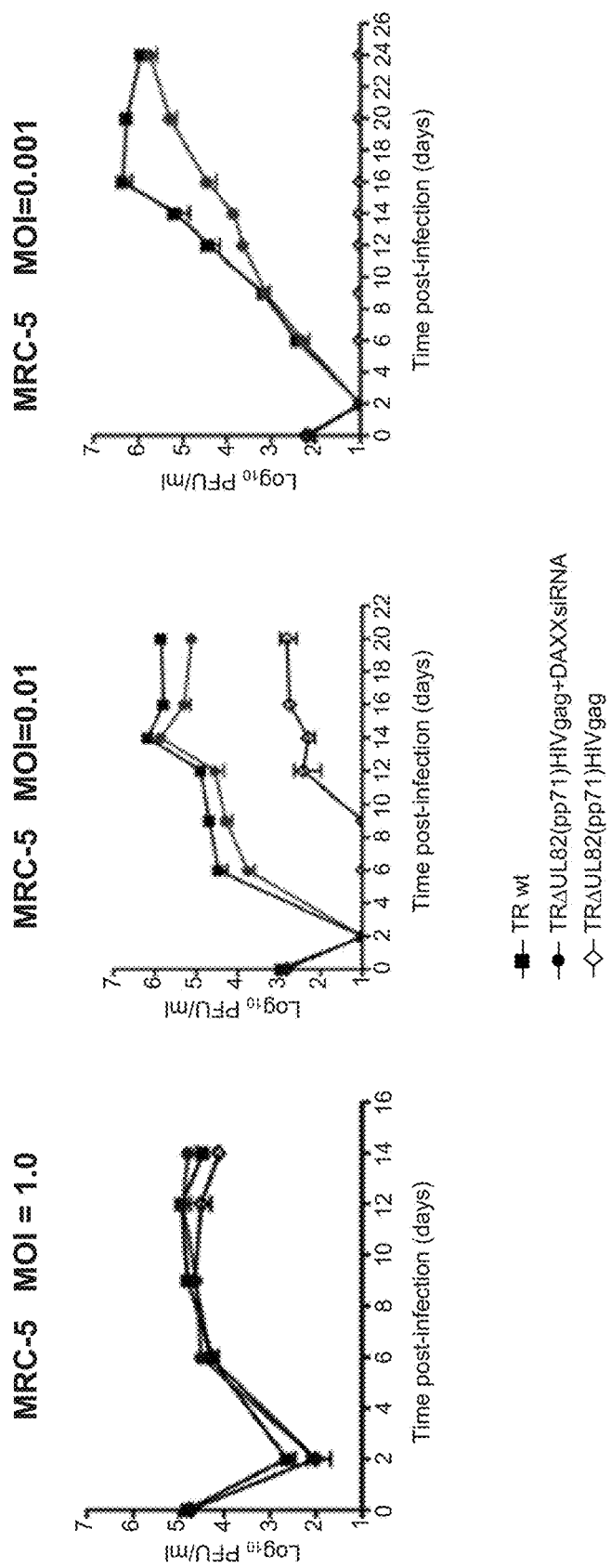
FIG. 13 is a plot comparing the growth kinetics of wild-type TR3 (squares) vs. ΔUL82(pp71)HIVgag in the presence (circles) or absence (diamonds) of DAXX siRNA over a range of infectious particles per cell. The growth defect becomes visible at clinically relevant low MOI, where MRC-5 cells transfected with DAXX-specific siRNA and infected 24 h post-transfection with TR3 and TR3Δpp71HIVgag are functionally complemented by siRNA or fail to replicate in the absence of DAXX siRNA. The lack of replication at low MOI indicates tha the virus is deficient in cell to cell spread. At the indicated times post-infection, supernatants were harvested and titered under pp71 complementing conditions (DAXX siRNA transfected MRC-5 cells).

Disclosed herein is an approach involving silencing an antiviral host cell factor using, for example, siRNA. The result is a cell line that does not require complementation because the mutant HCMV can be grown in vitro, even though it remains attenuated in vivo. An example of this process is illustrated in FIG. 7A. As described above, HCMV-TR3 lacking the UL82 gene that encodes phosphoprotein 71 (pp71) is unable to grow in fibroblasts. However, when expression of the antiviral protein DAXX is silenced by siRNA expressed in fibroblasts, HCMV-TR3ΔUL82 can be grown at high yield (FIG. 7B and FIG. 13).

Figure 8A:
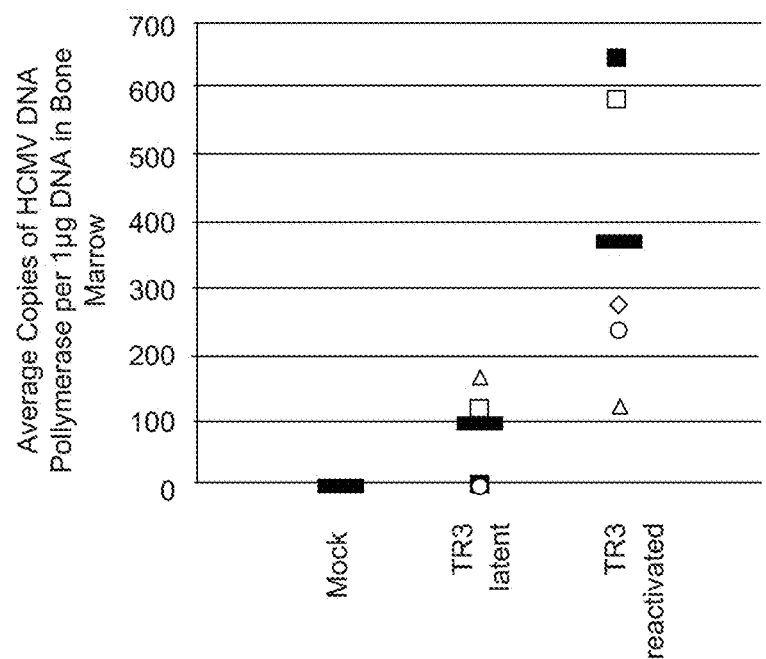
FIGS. 8A and 8B are plots showing that HCMVTR3ΔUL82 (Δpp71) establishes latency in humanized mice but is deficient in its ability to reactivate and disseminate. For both plots, NOD/SCID/IL2Rγ-null (NSG) mice engrafted with CD34+ stem cells were inoculated intraperitoneally with fibroblasts infected with TR3 or TR3ΔUL82 virus. Four weeks post-infection, human hematopoietic stem cells were mobilized by G-CSF treatment, and the viral load was measured in bone marrow (TR3, FIG. 8A) and liver (TR3ΔUL82, FIG. 8B) by quantitative PCR.
Figure 8B:
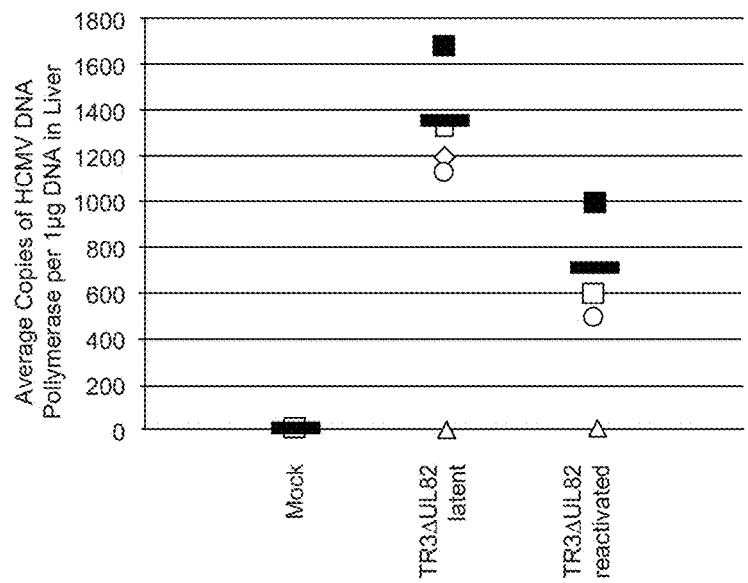
Figure 14:
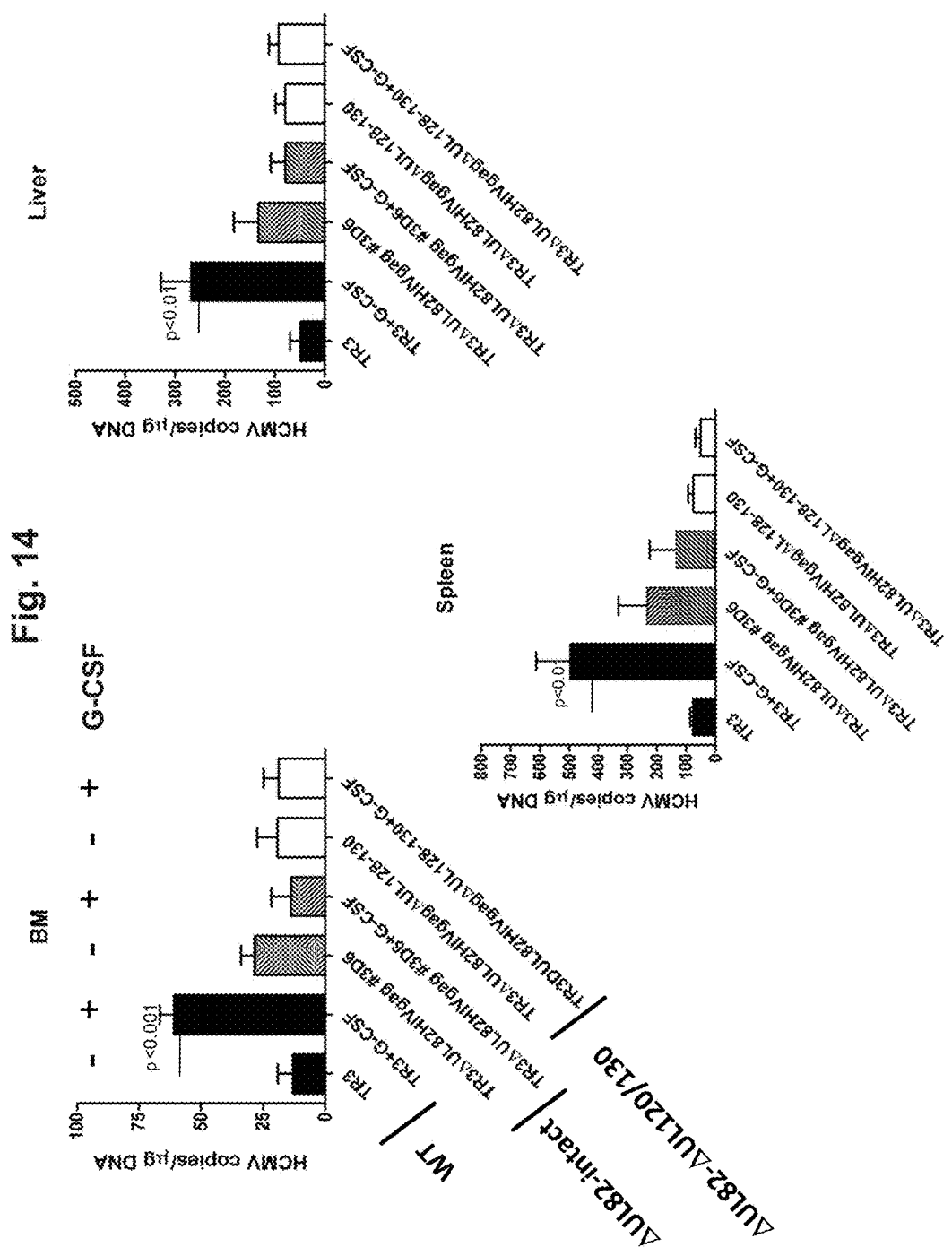
FIG. 14 is a set of three graphs demonstrating that HCMVTR3ΔUL82 (Δpp71) establishes latency in humanized mice but is deficient in its ability to reactivate and disseminate. NOD/SCID/IL2Rγ-null (NSG) mice engrafted with CD34+ stem cells were inoculated intra-peritoneally with fibroblasts infected with TR3, TR3ΔUL82, or TR3ΔUL82ΔUL128-130 virus. Four weeks post-infection, human hematopoietic stem cells were mobilized by G-CSF treatment and the viral load was measured in bone marrow (upper left panel), liver (upper right panel), and spleen (bottom panel). The relative virus copy number as a function of total micrograms of DNA are plotted based on quantitative PCR. Values in the absence of granulocyte colony stimulating factor (G-CSF) represent the latent viral load and values after G-CSF stimulation represent the reactivation of virus emerging from latency. Constructs deleted for pp71 establish latent infection but fail to respond to G-CSF stimulation as measured by copies of virus genomic DNA.

Example 8—HCMV-TR3 Lacking UL82(Pp71) Maintains Persistence In Vivo but is Deficient in its Ability to Reactivate from Latency Human cytomegalovirus (HCMV) establishes latent infection in host cells that is regulated via temporal expression viral genes. HCMV pp71 is a tegument protein that counteracts the host intrinsic immunity degradation of the cellular protein Daxx (death domain associated protein) (Penkert, R R, and R F Kalejta, *Future Virol* 7, 855-869 (2012); incorporated by reference herein). Degradation of Daxx by pp71 is necessary for optimal immediate early gene expression and lytic replication. In vitro data suggests that HCMV prevents pp71-mediated degradation of Daxx during establishment of latency by sequestering pp71 in the cytoplasm of infected cells. However, the in vivo role of pp71 in HCMV persistence, maintenance of latency and reactivation remains unknown. We have previously shown that HCMV infection of human hematopoietic stem cells (HSCs) engrafted in immune deficient mice (HU-NSG) results in viral latency that can be reactivated following G-CSF treatment. While this model is important, HU NSG mice lack mature human T-cells. In contrast NSG mice transplanted with HSCs in conjunction with human fetal liver and thymus (BLT mice) develop all the human hematopoietic cell lineages necessary for a functional human immune system, including mature CD4 and CD8 T-cells. In this new humanized mouse model it is demonstrated that HCMV establishes latency and reactivation similar to HU-NSG mice. Latently infected mice also generate human IgG as well as HCMV-specific T-cell responses. Importantly, infection of BLT mice with a conditionally expressing pp71 (TR UL82-FKBP) or a pp71 knockout (TR(delta)UL82) resulted in the establishment of infection but failed to reactivate. These data indicate that pp71 plays an important role in HCMV reactivation and that replication deficient virus can generate a T-cell response. The ability to replicate in vitro is not a good predictor of whether a virus can establish latency, as shown in FIG. 1B. For example, AD169 replicates well in vitro, but cannot establish latency, as shown in FIG. 1B. However, HCMV-TR3ΔUL82 grown on DAXX siRNA expressing MRC-5 cells establishes latency in humanized mice, but does not reactivate or disseminate (FIG. 8). Similar results were obtained in NSG mice for HCMV-TR3ΔUL82 and HCMV-TR3ΔUL82ΔUL128-130 (FIG. 14).

Example 9—Pp71-Deleted HCMV-TR3 Expressing HIVgag Maintains the Ability to Induce HIVgag Specific Effector Memory T Cells in In Vivo Due to its large genome, HCMV offers the opportunity to insert multiple heterologous antigens into a viral vector. The expression of multiple heterologous antigens by HCMV requires the identification of endogenous genes that can be used to insert foreign sequences without affecting vector function. Previously, transposon analysis identified all non-essential genes in the HCMV genome in vitro (Yu D et al., *Proc Natl Acad Sci USA* 100, 12396-12401 (2003); incorporated by reference herein.

Figure 9:
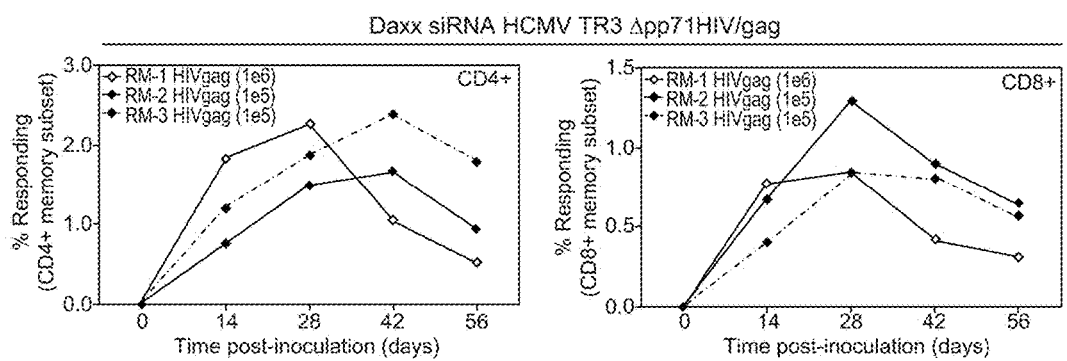
FIG. 9 is a set of plots showing that pp71-deleted HCMV-TR3 expressing HIVgag maintains the ability to induce HIVgag-specific effector memory T cells in non-human primates. HCMV expressing HIVgag but lacking pp71 was constructed by replacing the UL82(pp71) gene with HIVgag. The resulting virus was recovered using DAXX siRNA. $10^6$ or $10^5$ PFU of the resulting virus was inoculated subcutaneously into RM, and the T cell response to HIVgag was determined at the indicated days by intracellular cytokine staining. Shown is the percentage of CD4$^+$ (left) and CD8$^+$ (center) memory T cells in peripheral blood mononuclear cells (PMBC) responding to over-lapping HIVgag peptides. The right panel shows that the responding T cells display effector memory phenotype.
Figure 15:
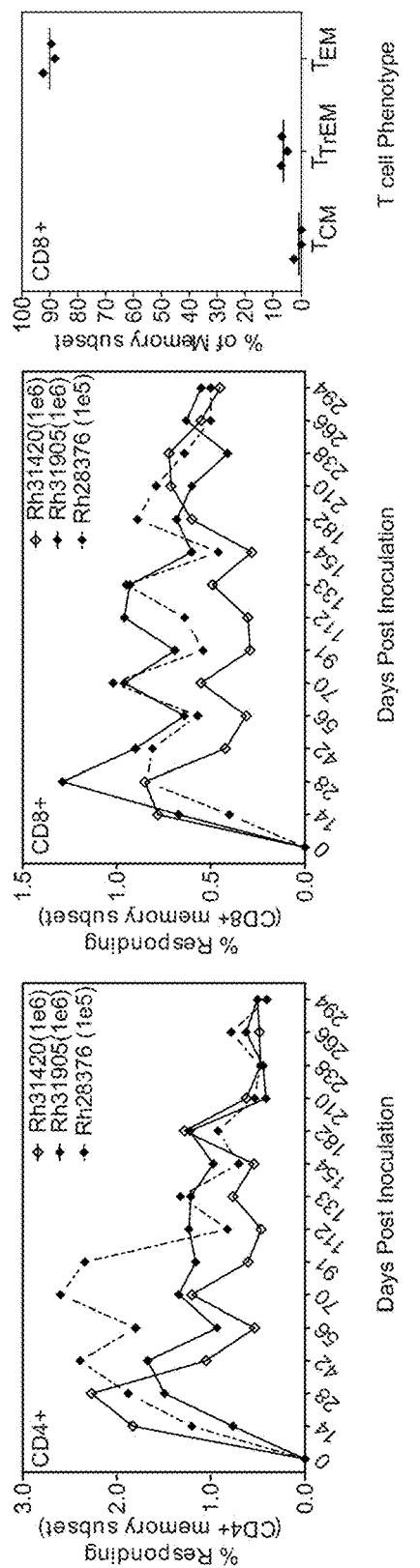
FIG. 15 is a set of three plots characterizing the immune response of three RM inoculated with the TR3/HCMV Δpp71(HIVgag) construct. The vector was grown and titered in the presence of siRNA and concentrated for subcutaneous inoculation. Shown is the percentage of CD4$^+$ (left panel) and CD8$^+$ (middle panel) memory T cells in peripheral blood mononuclear cells (PMBC) responding to over-lapping HIVgag peptides. Responses to different doses of the construct are graphed to 294 days post inoculum. The right panel demonstrates the CD8+ response of the Δpp71(HIVgag) TR3/HCMV to be consistent with the T-effector memory phenotype.

However, this does not provide a prediction as to which non-essential genes in vitro would be non-essential in vivo and, further, whether or not the replacement of a viral gene with a gene encoding a heterologous antigen would induce an immune response when the expression of the heterologous antigen is driven by the promoter of the replaced gene. FIG. 9 and FIG. 15 show that replacement of UL82(pp71) with HIVgag elicits and maintains an effector memory type T cell immune response in vivo.

Figure 10A:
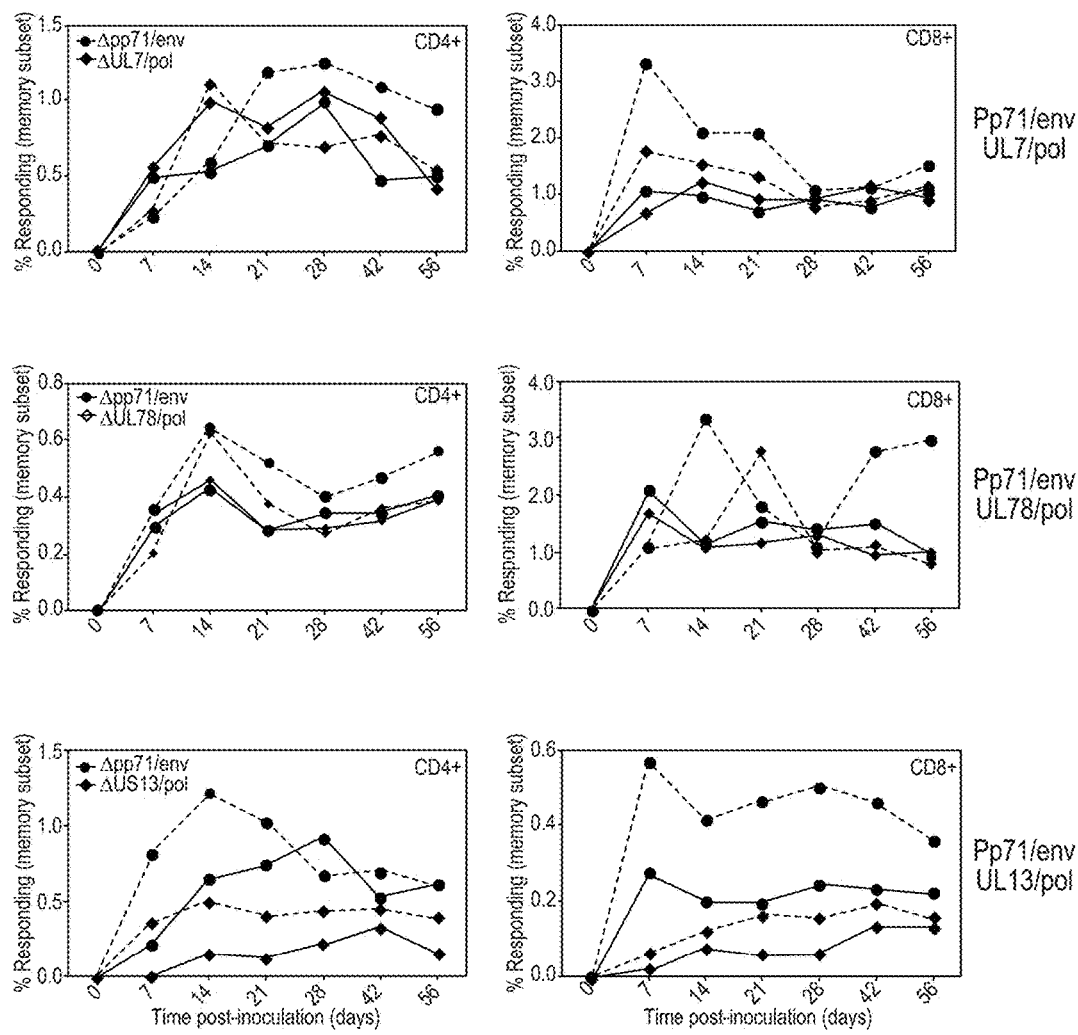
FIG. 10A is a set of six plots showing the results of dual RhCMV vectors expressing both SIVenv and SIVpol. The dual expression vectors were constructed by first replacing Rh110 (the RhCMV homologue of pp71) with SIVenv. Next, the homologs of HCMV genes UL7 (Rh19), UL78 (Rh107) or US13 (Rh191) were replaced with SIVpol. The resulting vectors were recovered in pp71-expressing rhesus fibroblasts. 5×10$^6$ PFU of each vector was inoculated into two RM each (one RM is shown as solid line, the other RM is shown as stippled line). The CD4$^+$ and CD8$^+$ T cell response was measured in PBMC at the indicated days using overlapping 15mer peptides corresponding to either SIVpol or SIVenv. The percent SIV-specific T cells within the T cell memory pool is shown.
Figure 10B:
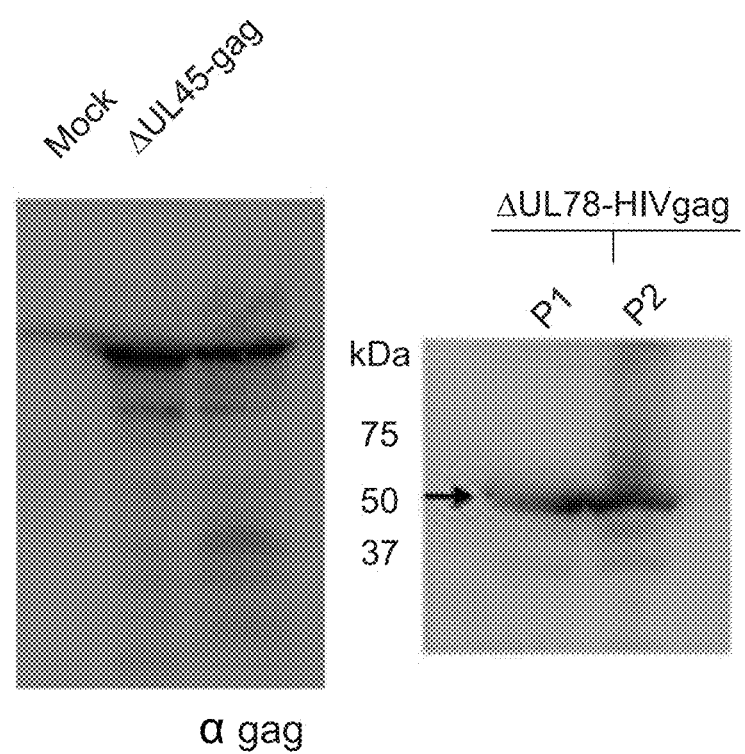
FIG. 10B is an image of an SDS-PAGE gel showing the results when MRC-5 cells were mock-infected or infected with TR3ΔUL7HIVgag, TR3ΔUL45HIVgag, or TR3ΔUL78HIVgag at MOI 0.5. Protein extracts were prepared 96 hours post-infection (hpi). 20 micrograms of proteins were separated on 10% SDS-PAGE, and the immunoblot was decorated with an anti-Gag (p24) antibody.

Additional sites for replacement with a heterologous antigen include HCMV UL7, UL78 and US13. When each of these is replaced with a heterologous antigen (SIVpol) in vectors that already carry a replacement of the pp71-ORF with antigen (SIVenv), immune responses were generated each time. The results are summarized in FIG. 10A. FIG. 10B shows that replacement of UL7, UL45 and UL78 with HIVgag in HCMV results in HIVgag expression in vitro.

Example 10—Stability of Pp71 Deleted HCMV-TR3 Through Growth and Production Under Conditional Complementation Previous work demonstrated that clinical isolates of HCMV undergo rapid adaptation in vitro when grown in fibroblasts. In particular, generation of frameshift mutations leading to premature stop codons in RL13 and loss of expression of one or more of the pentameric complex proteins (UL128, UL130 and UL131A) can occur after even a low number of passages in tissue culture (Stanton R J et al. *J Clin Invest* 120(9), 3191-3208 (2010); incorporated by reference herein). Reconstruction of the complete human cytomegalovirus genome in a BAC reveals RL13 to be a potent inhibitor of replication (Id.). As a consequence, all HCMV strains previously used in clinical studies (AD169, Towne, Toledo) display multiple rearrangements and deletions (Murphy, E D et al. *Proc Natl Acad Sci U.S.A.* 100(25), 14976-14981 (2003); incorporated by reference herein). These fibroblast-adaptations might result in the deletion of UL131A, as observed in AD169, thus rendering the virus non-infectious in vivo. To determine whether UL82-deleted HCMV-TR3/HIVgag grown in fibroblast cells treated with DAXX siRNA would similarly display instability upon multiple passages, we analyzed the viral genome by next generation sequencing (NGS).

Specifically, the recombinant bacterial artificial chromosome DNA was sequenced prior to introduction into fibroblasts, and, upon reconstitution in fibroblasts, viral DNA was isolated at passage 5 and passage 9. Genomic DNA was isolated from the supernatant of infected human fibroblasts by Hirt extraction (Hirt B. *J Mol Biol.* 26(2):365-369 (1967); incorporated by reference herein) after virus purification through a 20% sucrose cushion. DNA libraries were generated using the TruSeq DNA Sample Preparation kit and adapters with known primer binding sites were ligated to each end of the DNA fragments. Paired end sequencing, analyzing 150 bp on each end of the unknown DNA, was performed on an Illumina MiSeq NGS sequencer using the MiSeq Reagent Kits v2 for 300 cycles. The resulting sequence reads were imported into Geneious 8.1.4 and trimmed with the lowest possible error probability limit of 0.001, meaning that every base pair with a higher error probability of 0.1% is deleted. De novo sequence assembly was performed with 250.000 to 1.000.000 reads to determine the DNA sequence in an unbiased fashion. No major insertions, deletions or genomic rearrangements were observed compared to the predicted sequences. Next, a reference-guided assembly of all reads was performed using the de novo sequence as the reference to determine the full and correct majority sequence. The mean minimum coverage was >150 fold.

Figure 16:
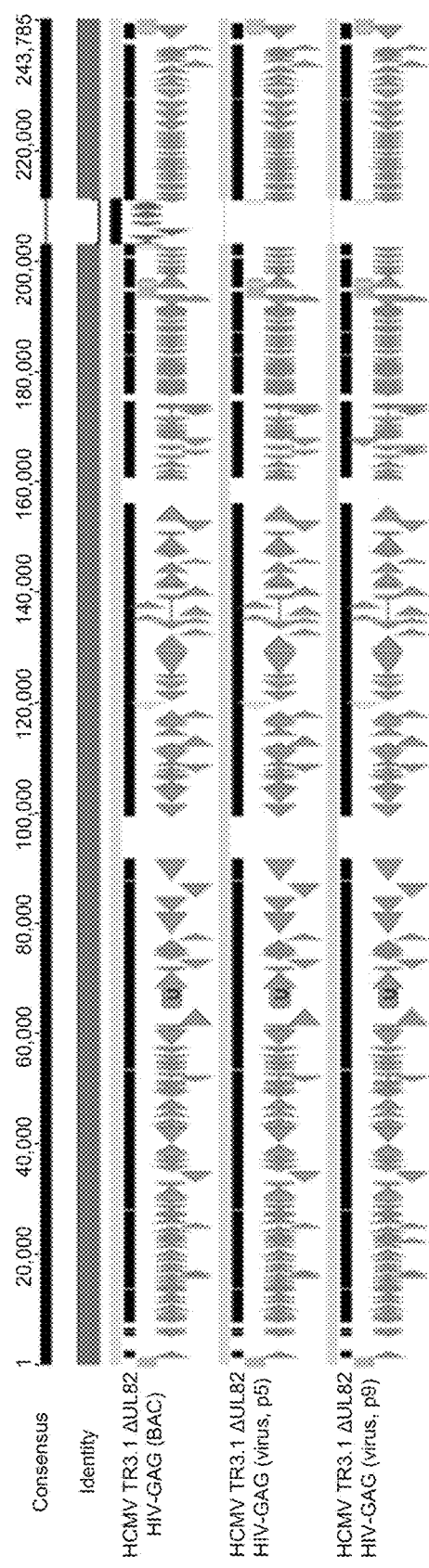
FIG. 16 graphically depicts the sequence alignment of HCMV/TR3 ΔUL82(pp71)HIVgag through passage 9 compared to the BAC clone sequence. The open reading frames (ORFs) are depicted as arrows, where the self-excising BAC is depicted with white arrows, the viral ORFs are depicted with grey arrows, and the HIVgag insert replacing the UL82 ORF is depicted with black arrows. Internal and terminal repeats are depicted with grey ovals. No significant polymorphisms were observed LOD 1%.

FIG. 16 shows an alignment of the resulting sequences. Open reading frames (ORFs) encoded in the self-excising BAC cassette are depicted with white arrows, and viral ORFs are depicted with grey arrows. Yellow arrows depict the HIVgag ORF replacing the UL82 ORF. Grey ovals depict internal and terminal repeats. Non-coding regions are shown as interruptions of the coding regions shown as black bars. As expected, the BAC cassette was excised upon viral reconstitution in tissue culture. However, all other nucleotides in the majority sequence were identical to the predicted sequence (consensus). Importantly, no changes of any amino acids were observed in the ORFs even through nine passages. This includes ORFs encoding the UL128-131A genes, RL13 as well as the AD169-derived genes UL97 and US2-7. These observations suggest a surprising stability of UL82-deleted HCMV-TR3 despite multiple passages in fibroblasts in the presence of DAXX siRNA.

Figure 17A:
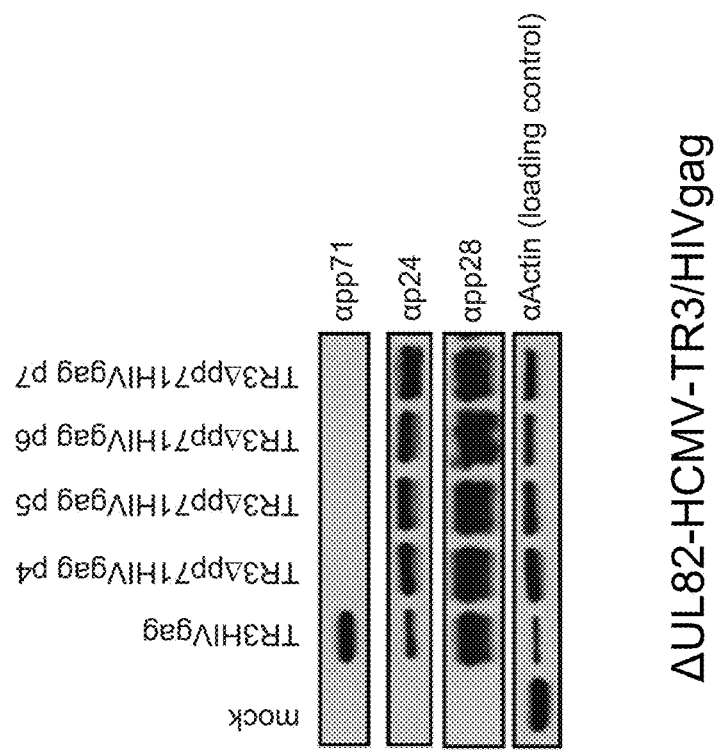

Importantly, there were no changes in the ORF encoding HIVgag expressed by the UL82 promoter. This was independently confirmed by immunoblot and Sanger-sequencing of the HIVgag insert at passages 5, 6 and 7 after reconstitution of UL82(pp71)-deleted HCMV-TR3. FIG. 17A shows an immunoblot of lysates from fibroblasts infected with the indicated viruses. Lysates were separated by SDS-PAGE, transferred onto nylon membranes and reacted with antibodies specific for pp71, HIVgag (p24) and the viral protein pp28 and the cellular protein actin. As expected, pp71 was present in the parental TR3 virus, but not in HIVgag-expressing vectors due to replacement of UL82 with HIVgag. Importantly, HIVgag was stably expressed upon each passage. FIG. 17B shows an alignment based on sequences analysis of PCR-fragments spanning the HIVgag gene and obtained from viral DNA at the indicated passage. No nucleotide changes were observed.

In contrast to the surprisingly stable expression of HIV-gag expressed by the endogenous UL82 promoter, expression of heterologous antigens by heterologous promoters are routinely unstable upon multiple passages. For example, SIVgag expressed by the heterologous EF1α promoter in the RhCMV 68-1.2 vector displayed a premature disruption of the coding region due to a point mutation. FIG. 18 shows the frequency of single nucleotide polymorphisms (SNPs) compared to the reference sequence from a next generation sequencing analysis of a UL36-deleted RhCMV vector derived from a clone of RhCMV 68-1.2 that expresses SIVgag using the EF1α promoter. Approximately 38% of the genomes demonstrate a premature stop codon in the SIVgag sequence.

The invention claimed is:

1. A recombinant human cytomegalovirus (HCMV) comprising:
(1) a nucleic acid encoding at least one heterologous antigen,
(2) an inactivating mutation in the UL82 gene, and
(3) active US2, US3, US6, US7, UL131A, and UL97 genes;
wherein the recombinant HCMV is a genetically modified TR strain of HCMV; and the recombinant HCMV is Ganciclovir sensitive.

2. The recombinant HCMV of claim 1, wherein the UL97 gene is derived from the AD169 strain of HCMV.

3. The recombinant HCMV of claim 1, wherein the active US2, US3, US6, and US7 genes are derived from the AD169 strain of HCMV.

4. The recombinant HCMV of claim 1, wherein expression of the at least one heterologous antigen is driven by the UL82 promoter, the UL7 promoter, the UL45 promoter, the UL78 promoter, or the US13 promoter.

5. The recombinant HCMV of claim 1, wherein the inactivating mutation in the UL82 gene is a deletion of all or part of the UL82 gene.

6. The recombinant HCMV of claim 5, wherein the at least one heterologous antigen replaces all or part of the UL82 gene.

7. The recombinant HCMV of claim 6, wherein expression of the at least one heterologous antigen replacing all or part of the UL82 gene is driven by the UL82 promoter.

8. The recombinant HCMV of claim 1, further comprising an inactivating mutation in a HCMV gene selected from the group consisting of: UL7, UL38, UL45, and US13.

9. The recombinant HCMV of claim 8, wherein the inactivating mutation in the UL7 gene is a deletion of all or part of the UL7 gene.

10. The recombinant HCMV of claim 9, wherein the at least one heterologous antigen replaces all or part of the UL7 gene.

11. The recombinant HCMV of claim 10, wherein expression of the at least one heterologous antigen replacing all or part of the UL7 gene is driven by the UL7 promoter.

12. The recombinant HCMV of claim 8, wherein the inactivating mutation in the UL38 gene is a deletion of all or part of the UL38 gene.

13. The recombinant HCMV of claim 12, wherein the at least one heterologous antigen replaces all or part of the UL38 gene.

14. The recombinant HCMV of claim 13, wherein expression of the at least one heterologous antigen replacing all or part of the UL38 gene is driven by the UL38 promoter.

15. The recombinant HCMV of claim 8, wherein the inactivating mutation in the UL45 gene is a deletion of all or part of the UL45 gene.

16. The recombinant HCMV of claim 15, wherein the at least one heterologous antigen replaces all or part of the UL45 gene.

17. The recombinant HCMV of claim 16, wherein expression of the at least one heterologous antigen replacing all or part of the UL45 gene is driven by the UL45 promoter.

18. The recombinant HCMV of claim 8, wherein the inactivating mutation in the US13 gene is a deletion of all or part of the US13 gene.

19. The recombinant HCMV of claim 18, wherein the at least one heterologous antigen replaces all or part of the US13 gene.

20. The recombinant HCMV of claim 19, wherein expression of the at least one heterologous antigen replacing all or part of the US13 gene is driven by the US13 promoter.

* * * * *